(12) United States Patent
Liedtke

(10) Patent No.: US 11,229,628 B2
(45) Date of Patent: Jan. 25, 2022

(54) TRPA1 AND TRPV4 INHIBITORS AND METHODS OF USING THE SAME FOR ORGAN-SPECIFIC INFLAMMATION AND ITCH

(71) Applicant: Duke University, Durham, NC (US)

(72) Inventor: Wolfgang Liedtke, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/993,010

(22) Filed: Jan. 11, 2016

(65) Prior Publication Data

US 2016/0199363 A1 Jul. 14, 2016

Related U.S. Application Data

(60) Provisional application No. 62/101,883, filed on Jan. 9, 2015.

(51) Int. Cl.
*A61K 31/426* (2006.01)
*A61K 31/4406* (2006.01)

(52) U.S. Cl.
CPC ........ *A61K 31/426* (2013.01); *A61K 31/4406* (2013.01)

(58) Field of Classification Search
CPC .............................. C07D 277/20; A61K 31/426
See application file for complete search history.

(56) References Cited

U.S. PATENT DOCUMENTS

| | | | |
|---|---|---|---|
| 4,921,333 A | 5/1990 | Brody et al. | |
| 7,459,450 B2 | 12/2008 | Zhu et al. | |
| 7,639,365 B2 | 12/2009 | Herring | |
| 9,290,489 B2 | 3/2016 | Liedtke et al. | |
| 10,329,265 B2* | 6/2019 | Liedtke ................ | A61K 31/426 |
| 2004/0198649 A1 | 10/2004 | Davis et al. | |
| 2006/0089351 A1 | 4/2006 | Zhu et al. | |
| 2007/0161560 A1 | 7/2007 | Davis et al. | |
| 2007/0259856 A1 | 11/2007 | Kumar et al. | |
| 2008/0039466 A1 | 2/2008 | Moussy et al. | |
| 2011/0009430 A1 | 1/2011 | Moran et al. | |
| 2011/0130400 A1 | 6/2011 | Bury et al. | |
| 2013/0310345 A1 | 11/2013 | Moran | |
| 2015/0105406 A1 | 4/2015 | Gullapalli et al. | |
| 2016/0194312 A1 | 7/2016 | Liedtke et al. | |
| 2019/0091206 A1 | 3/2019 | Liedtke | |
| 2019/0112301 A1 | 4/2019 | Liedtke et al. | |

FOREIGN PATENT DOCUMENTS

| | | |
|---|---|---|
| CN | 101747330 | 6/2010 |
| WO | WO 93/12227 | 6/1993 |
| WO | WO 00/45635 | 8/2000 |
| WO | WO 2005/000298 | 1/2005 |
| WO | WO 2005/073225 | 8/2005 |
| WO | WO 2005/111031 | 11/2005 |
| WO | WO 2006/122011 | 11/2006 |
| WO | WO 2006/122156 | 11/2006 |
| WO | WO 2007/026251 | 3/2007 |
| WO | WO 2007/095124 | 8/2007 |
| WO | WO 2007/118137 | 10/2007 |
| WO | WO 2009/002534 | 12/2008 |
| WO | WO 2009/010529 | 1/2009 |
| WO | 2010/109334 | 9/2010 |
| WO | WO 2012/084870 | 6/2012 |
| WO | WO 2014/008477 | 1/2014 |
| WO | 2016/028325 | 2/2016 |

OTHER PUBLICATIONS

King Jr. et al., "Idiopathic Pulmonary Fibrosis", 2011, Lancet, vol. 378, pp. 1949-1961.*
Zhan etal, "The role of TRPV4 in fibrosis", 2018, Gene, vol. 642, pp. 1-8. (Year: 2018).*
ScienceDaily Article, UC San Diego, "Researchers identify a new culprit behind fibrosis", 2015, https://www.sciencedaily.com/releases/2015/10/151015114803.htm, accessed Oct. 1, 2018, 3 pages. (Year: 2015).*
Andrews et al. Keloids:The paradigm of Skin Fibrosis—Pathomechanisms and treatment, 2016, Matrix Biology, vol. 51, pp. 37-46. (Year: 2016).*
European Patent Office Extended Search Report for Application No. 13813477.0 dated Aug. 25, 2016 (10 pages).
Adapala et al., "Activation of mechanosensitive ion channel TRPV4 normalizes tumor vasculature and improves cancer therapy," Oncogene, 2016. 35(3): p. 314-22.
Ahn, G.Y., Butt, K.I., Jindo, T., Yaguchi, H., Tsuboi, R., and Ogawa, H. (1998). The expression of endothelin-1 and its binding sites in mouse skin increased after ultraviolet B irradiation or local injection of tumor necrosis factor alpha. J Dermatol 25, 78-84.
Albers, K.M., and Davis, B.M. (2007). The skin as a neurotrophic organ. Neuroscientist 13, 371-382.
Albert et al., "TRPV4 channels mediate the infrared laser-evoked response in sensory neurons," J Neurophysiol, 2012. 107(12): p. 3227-34.
Alenmyr L, Hogestatt ED, Zygmunt PM, & Greiff L (2009) TRPV1-mediated itch in seasonal allergic rhinitis. Allergy 64(5):807-810.
Alessandri-Haber et al., "Hypotonicity induces TRPV4-mediated nociception in rat," Neuron, 2003. 39(3): p. 497-511.
Alessandri-Haber, N., Dina, O. A., Yeh, J. J., Parada, C. A., Reichling, D. B., and Levine, J. D. (2004) Transient receptor potential vanilloid 4 is essential in chemotherapy-induced neuropathic pain in the rat, J Neurosci 24, 4444-4452.

(Continued)

*Primary Examiner* — Rei Tsang Shiao
(74) *Attorney, Agent, or Firm* — Michael Best & Friedrich LLP

(57) ABSTRACT

Provided are methods of treating and/or preventing dermatological disorders. Provided are methods of reducing skin inflammation, reducing pain, and/or reducing itch in a subject in need thereof. The methods may include administering to the subject an effective amount of a TRPA1 and/or TRPV4 inhibitor. Further provided are compositions including a TRPA1 and/or TRPV4 inhibitor compound in combination with a carrier, vehicle, or diluent that is suitable for topical application.

16 Claims, 62 Drawing Sheets
Specification includes a Sequence Listing.

(56) References Cited

OTHER PUBLICATIONS

Alessandri-Haber, N., Joseph, E., Dina, O.A., Liedtke, W., and Levine, J.D. (2005). TRPV4 mediates pain-related behavior induced by mild hypertonic stimuli in the presence of inflammatory mediator. Pain 118, 70-79.

Alptekin, N. O., Ari, H., Ataoglu, T., Haliloglu, S., Alptekin, T., and Serpek, B. (2005). Neutrophil elastase levels in periapical exudates of symptomatic and asymptomatic teeth. Journal of endodontics 31, 350-353.

Andoh, T., T. Yoshida, J.B. Lee, and Y. Kuraishi, Cathepsin E induces itch-related response through the production of endothelin-1 in mice. Eur J Pharmacol, 2012. 686(1-3): p. 16-21.

Andrade et al., "TRPV4 channel is involved in the coupling of fluid viscosity changes to epithelial ciliary activity," J Cell Biol, 2005. 168(6): p. 869-74.

Atoyan, R., D. Shander, and N.V. Botchkareva, Non-neuronal expression of transient receptor potential type A1 (TRPA1) in human skin. J Invest Dermatol, 2009. 129(9): p. 2312-5.

Aycock, R. et al., "Development of UV-Induced Squamous Cell Carcinomas is Suppressed in the Absence of SPARC," Journal of Investigative Dermatology, 2004, vol. 123, No. 3, pp. 562-569.

Balonov, K., Khodorova, A., and Strichartz, G.R. (2006). Tactile allodynia initiated by local subcutaneous endothelin-1 is prolonged by activation of TRPV-1 receptors. Exp Biol Med (Maywood) 231, 1165-1170.

Baum et al. Antimicrobial Agents and Chemotherapy 2006, 50(1), 230-236.

Bellono NW, Kammel LG, Zimmerman AL, & Oancea E (2013) UV light phototransduction activates transient receptor potential A1 ion channels in human melanocytes. Proc Natl Acad Sci U S A 110(6):2383-2388.

Benemei et al., "TRPA1 and other TRP channels in migraine," J Headache Pain, 2013. 14: p. 71.

Benfenati et al., "An aquaporin-4/transient receptor potential vanilloid 4 (AQP4/TRPV4) complex is essential for cell-volume control in astrocytes," Proc Natl Acad Sci U S A, 2011. 108(6): p. 2563-8.

Benfenati et al., "Expression and functional characterization of transient receptor potential vanilloid-related channel 4 (TRPV4) in rat cortical astrocytes," Neuroscience, 2007. 148(4): p. 876-92.

Bernard JJ, et al. (2012) Ultraviolet radiation damages self noncoding RNA and is detected by TLR3. Nature medicine.

Bersinger, N.A., Gunthert, A.R., McKinnon, B., Johann, S., and Mueller, M.D. (2011). Dose-response effect of interleukin (IL)-1beta, tumour necrosis factor (TNF)-alpha, and interferon-gamma on the in vitro production of epithelial neutrophil activating peptide-78 (ENA-78), IL-8, and IL-6 by human endometrial stromal cells. Arch Gynecol Obstet 283, 1291-1296.

Bessac et al.,"TRPA1 is a major oxidant sensor in murine airway sensory neurons," J Clin Invest, 2008. 118(5): p. 1899-910.

Bishop, T., Hewson, D.W., Yip, P.K., Fahey, M.S., Dawbam, D., Young, A.R., and McMahon, S.B. (2007). Characterisation of ultraviolet-B-induced inflammation as a model of hyperalgesia in the rat. Pain 131, 70-82.

Bonvini et al., "Targeting TRP channels for chronic cough: from bench to bedside," Naunyn Schmiedebergs Arch Pharmacol, 2015. 388(4): p. 401-20.

Bonvini et al., "Transient receptor potential cation channel, subfamily V, member 4 and airway sensory afferent activation: Role of adenosine triphosphate," J Allergy Clin Immunol, 2016.

Bosch, U., "Arthrofibrosis," Orthopade, 2002. 31(8): p. 785-90.

Boulais, N., and Misery, L. (2008). The epidermis: a sensory tissue. Eur J Dermatol 18, 119-127.

Brandli, P., B.M. Loffler, V. Breu, R. Osterwalder, J.P. Maire, and M. Clozel, Role of endothelin in mediating neurogenic plasma extravasation in rat dura mater. Pain, 1996. 64(2): p. 315-22.

Brierley et al., "Selective role for TRPV4 ion channels in visceral sensory pathways," Gastroenterology, 2008. 134(7): p. 2059-69.

Brierley et al., "The ion channel TRPA1 is required for normal mechanosensation and is modulated by algesic stimuli," Gastroenterology, 2009. 137(6): p. 2084-2095 e3.

Burkhart, C.G. and H.R. Burkhart, Contact irritant dermatitis and anti-pruritic agents: the need to address the itch. J Drugs Dermatol, 2003. 2(2): p. 143-6.

Butenko et al., "The increased activity of TRPV4 channel in the astrocytes of the adult rat hippocampus after cerebral hypoxia/ischemia," PLoS ONE, 2012. 7(6): p. e39959.

Buzzi et al., "Peripheral and central activation of trigeminal pain pathways in migraine: data from experimental animal models," Cephalalgia, 2003. 23 Suppl 1: p. 1-4.

Cai X (2008) A new tr(i)p to sense pain: TRPA1 channel as a target for novel analgesics. Expert review of neurotherapeutics 8(11):1675-1681.

Cao, D.S., Yu, S.Q., and Premkumar, L.S. (2009). Modulation of transient receptor potential Vanilloid 4-mediated membrane currents and synaptic transmission by protein kinase C. Molecular pain 5, 5.

Cattaruzza et al., "Transient receptor potential ankyrin 1 mediates chronic pancreatitis pain in mice," Am J Physiol Gastrointest Liver Physiol, 2013. 304(11): p. G1002-12.

Cenac et al., "Transient receptor potential vanilloid-4 has a major role in visceral hypersensitivity symptoms," Gastroenterology, 2008. 135(3): p. 937-46, 946 e1-2.

Ceppa et al., "Transient receptor potential ion channels V4 and A1 contribute to pancreatitis pain in mice," Am J Physiol Gastrointest Liver Physiol, 2010. 299(3): p. G556-71.

Chang CY, et al. (2013) NFIB is a governor of epithelial-melanocyte stem cell behaviour in a shared niche. Nature 495(7439):98-102.

Chang, M. S., Mcninch, J., Basu, R., and Simonet, S. (1994). Cloning and characterization of the human neutrophil-activating peptide (ENA-78) gene. J Biol Chem 269, 25277-25282.

Charrua, et al. "Co-administration of TRPV4 and TRPV1 antagonists potentiate the effect of each drug in a rat model of cystitis," BJU Int, 2014.

Chen et al., "Marked attenuation of inflammatory mediator-induced C-fiber sensitization for mechanical and hypotonic stimuli in TRPV4-/-mice," Mol Pain, 2007. 3: p. 31.

Chen et al., "Selective blockade of TRPA1 channel attenuates pathological pain without altering noxious cold sensation or body temperature regulation," Pain, 2011. 152(5): p. 1165-72.

Chen et al., "The modulation of voltage-gated potassium channels by anisotonicity in trigeminal ganglion neurons," Neuroscience, 2008. 154(2): p. 482-95.

Chen et al., "TRPV4 is necessary for trigeminal irritant pain and functions as a cellular formalin receptor," Pain, 2014, 2662-2672.

Chen Y, et al. (2013) Temporomandibular joint pain: A critical role for Trpv4 in the trigeminal ganglion. Pain.

Chen, Y., Willcockson, H.H., and Valtschanoff, J.G. (2009). Vanilloid receptor TRPV1-mediated phosphorylation of ERK in murine adjuvant arthritis. Osteoarthritis Cartilage 17, 244-251.

Cheng, X., Jin, J., Hu, L., Shen, D., Dong, X. P., Samie, M. A., Knoff, J., Eisinger, B., Liu, M. L., Huang, S. M., et al. (2010). TRP channel regulates EGFR signaling in hair morphogenesis and skin barrier formation. Cell 141, 331-343.

Chung et al., "Role of TRP channels in pain sensation," Advances in experimental medicine and biology, 2011. 704: p. 615-36.

Chung, M.K., Lee, H., and Caterina, M.J. (2003). Warm temperatures activate TRPV4 in mouse 308 keratinocytes. The Journal of biological chemistry 278, 32037-32046.

Clay et al., "Ozone-Induced Hypertussive Responses in Rabbits and Guinea Pigs," J Pharmacol Exp Ther, 2016. 357(1): p. 73-83.

D'Aldebert et al., "Transient receptor potential vanilloid 4 activated inflammatory signals by intestinal epithelial cells and colitis in mice," Gastroenterology, 2011. 140(1): p. 275-85.

Davar, G., Endothelin-1 and metastatic cancer pain. Pain Med, 2001. 2(1): p. 24-7.

Dawes, J.M., Calvo, M., Perkins, J.R., Paterson, K.J., Kiesewetter, H., Hobbs, C., Kaan, T.K., Orengo, C., Bennett, D.L., and McMahon, S.B. (2011). CXCL5 mediates UVB irradiation-induced pain. Sci Transl Med 3, 90ra60.

De Jongh, R.F., Vissers, K.C., Meert, T.F., Booij, L.H., De Deyne, C.S., and Heylen, R.J. (2003). The role of interleukin-6 in nociception and pain. Anesth Analg 96, 1096-1103, table of contents.

(56) References Cited

OTHER PUBLICATIONS

Del Rosso, J., "Update on Rosacea Pathogenesis And Correlation With Medical Therapeutic Agents," Cutis, 2006, vol. 78, pp. 97-100.
Demehri, S., M. Morimoto, M.J. Holtzman, and R. Kopan, Skin-derived TSLP triggers progression from epidermal-barrier defects to asthma. PLoS Biol, 2009. 7(5): p. e1000067.
Denda, M., Sokabe, T., Fukumi-Tominaga, T., and Tominaga, M. (2007). Effects of skin surface temperature on epidermal permeability barrier homeostasis. The Journal of investigative dermatology 127, 654-659.
Dhand, A. and M.J. Aminoff, The neurology of itch. Brain, 2014. 137(Pt 2): p. 313-22.
Ding et al., "Involvement of TRPV4-NO-cGMP-PKG pathways in the development of thermal hyperalgesia following chronic compression of the dorsal root ganglion in rats," Behav Brain Res, 2010. 208(1): p. 194-201.
Domon et al., "Mass spectrometry and protein analysis," Science, 2006, 312(5771):212-7.
Dunn et al., "TRPV4 channels stimulate Ca2+-induced Ca2+ release in astrocytic endfeet and amplify neurovascular coupling responses," Proc Natl Acad Sci U S A, 2013. 110(15): p. 6157-62.
Dussor et al., "Targeting TRP channels for novel migraine therapeutics," ACS Chem Neurosci, 2014. 5(11): p. 1085-96.
Dussor, G., Zylka, M.J., Anderson, D.J., and McCleskey, E.W. (2008). Cutaneous sensory neurons expressing the Mrgprd receptor sense extracellular ATP and are putative nociceptors. Journal of neurophysiology 99, 1581-1589.
Dymecki, S.M. (1996). Flp recombinase promotes site-specific DNA recombination in embryonic stem cells and transgenic mice. Proc Natl Acad Sci U S A 93, 6191-6196.
Edelmayer et al., "Activation of TRPA1 on dural afferents: a potential mechanism of headache pain," Pain, 2012. 153(9): p. 1949-58.
Edwards RR, et al. (2008) Association of catastrophizing with interleukin-6 responses to acute pain. Pain 140(1):135-144.
Eid, S.R., "Therapeutic targeting of TRP channels—the TR(i)P to pain relief," Curr Top Med Chem, 2011. 11(17): p. 2118-30.
Elias, P.M., and Steinhoff, M. (2008). "Outside-to-inside" (and now back to "outside") pathogenic mechanisms in atopic dermatitis. The Journal of investigative dermatology 128, 1067-1070.
Elmariah, S.B. and E.A. Lerner, The missing link between itch and inflammation in atopic dermatitis. Cell, 2013. 155(2): p. 267-9.
Engel et al., "TRPA1 and substance P mediate colitis in mice," Gastroenterology, 2011. 141(4): p. 1346-58.
Eriksson, E., "Arthrofibrosis," Knee Surg Sports Traumatol Arthrosc, 1996. 4(4): p. 193.
Everaerts et al., "Inhibition of the cation channel TRPV4 improves bladder function in mice and rats with cyclophosphamide-induced cystitis," Proc Natl Acad Sci U S A, 2010. 107(44): p. 19084-9.
Feetham et al., "The depressor response to intracerebroventricular hypotonic saline is sensitive to TRPV4 antagonist RN1734," Front Pharmacol, 2015. 6: p. 83.
Feldmeyer, L., Keller, M., Niklaus, G., Hohl, D., Werner, S., and Beer, H.D. (2007). The inflammasome mediates UVB-induced activation and secretion of interleukin-1beta by keratinocytes. Curr Biol 17, 1140-1145.
Fernandes et al., "IP3 sensitizes TRPV4 channel to the mechano- and osmotransducing messenger 5'-6'-epoxyeicosatrienoic acid," J Cell Biol, 2008. 181(1): p. 143-55.
Fichna et al., "Transient receptor potential vanilloid 4 blockade protects against experimental colitis in mice: a new strategy for inflammatory bowel diseases treatment?" Neurogastroenterol Motil, 2012. 24(11): p. e557-60.
Filosa et al., "Astrocyte regulation of cerebral vascular tone," Am J Physiol Heart Circ Physiol, 2013. 305(5): p. H609-19.
Forsmark et al., "The challenging task of treating painful chronic pancreatitis," Gastroenterology, 2012. 143(3): p. 533-5.

Franzen, L., C. Mathes, S. Hansen, and M. Windbergs, Advanced chemical imaging and comparison of human and porcine hair follicles for drug delivery by confocal Raman microscopy. J Biomed Opt, 2013. 18(6): p. 061210.
Fuchs, E. (2009). Finding one's niche in the skin. Cell stem cell 4, 499-502.
Geppetti et al., "Cough: The Emerging Role of the TRPA1 Channel," Lung, 2010. 188 Suppl 1: p. S63-8.
Gilchrest, B. A., Park, H. Y., Eller, M. S., and Yaar, M. (1996). Mechanisms of ultraviolet light-induced pigmentation. Photochemistry and photobiology 63, 1-10.
Gomes, L.O., D.B. Hara, and G.A. Rae, Endothelin-1 induces itch and pain in the mouse cheek model. Life Sci, 2012. 91(13-14): p. 628-33.
Gonczi, M., Szentandrassy, N., Fulop, L., Telek, A., Szigeti, G.P., Magyar, J., Biro, T., Nanasi, P.P., and Csernoch, L. (2007). Hypotonic stress influence the membrane potential and alter the proliferation of keratinocytes in vitro. Exp Dermatol 16, 302-310.
Grant et al., "Protease-activated receptor 2 sensitizes the transient receptor potential vanilloid 4 ion channel to cause mechanical hyperalgesia in mice," J Physiol, 2007. 578(Pt 3): p. 715-33.
Grant, A.D., Cottrell, G.S., Amadesi, S., Trevisani, M., Nicoletti, P., Materazzi, S., Altier, C., Cenac, N., Zamponi, G.W., Bautista-Cruz, F., et al. (2007). Protease-activated receptor 2 sensitizes the transient receptor potential vanilloid 4 ion channel to cause mechanical hyperalgesia in mice. The Journal of physiology 578, 715-733.
Gunthorpe MJ & Chizh BA (2009) Clinical development of TRPV1 antagonists: targeting a pivotal point in the pain pathway. Drug discovery today 14(1-2):56-67.
Haeberle H, Bryan LA, Vadakkan TJ, Dickinson ME, & Lumpkin EA (2008) Swelling-activated Ca2+ channels trigger Ca2+ signals in Merkel cells. PLoS ONE 3(3):e1750.
Hargreaves, K., Dubner, R., Brown, F., Flores, C., and Joris, J. (1988). A new and sensitive method for measuring thermal nociception in cutaneous hyperalgesia. Pain 32, 77-88.
Harrison, G.I., Young, A.R., and McMahon, S.B. (2004). Ultraviolet radiation-induced inflammation as a model for cutaneous hyperalgesia. J Invest Dermatol 122, 183-189.
Hartmannsgruber et al., "Arterial response to shear stress critically depends on endothelial TRPV4 expression," PLoS ONE, 2007. 2(9): p. e827.
Hill K & Schaefer M (2009) Ultraviolet light and photosensitising agents activate TRPA1 via generation of oxidative stress. Cell calcium 45(2): 155-164.
Hurd et al., "A mutation in TRPV4 results in altered chondrocyte calcium signaling in severe metatropic dysplasia," Am J Med Genet A, 2015. 167A(10): p. 2286-93.
Imamachi N, et al. (2009) TRPV1-expressing primary afferents generate behavioral responses to pruritogens via multiple mechanisms. Proc Natl Acad Sci U S A 106(27):11330-11335.
International Search Report and Written Opinion for Application No. PCT/US13/49457 dated Feb. 24, 2014 (13 pages).
International Search Report and Written Opinion for Application No. PCT/US14/52394 dated Feb. 24, 2015 (21 pages).
Joachim, R. A., Handjiski, B., Blois, S. M., Hagen, E., Paus, R., and Arck, P. C. (2008). Stress-induced neurogenic inflammation in murine skin skews dendritic cells towards maturation and migration: key role of intercellular adhesion molecule-1/leukocyte function-associated antigen interactions. Am J Pathol 173, 1379-1388.
Kanju et al., "Small molecule dual-inhibitors of TRPV4 and TRPA1 for attenuation of inflammation and pain," Nature Scientific Reports, 2016, 1-12.
Katugampola R, Church MK, Clough GF. The neurogenic vasodilator response to endothelin-1: a study in human skin in vivo. Exp Physiol. Nov. 2000;85(6):839-46.
Keller, M., Ruegg, A., Werner, S., and Beer, H. D. (2008). Active caspase-1 is a regulator of unconventional protein secretion. Cell 132, 818-831.
Kennedy Crispin M, et al. (2013) Gene profiling of narrowband UVB-induced skin injury defines cellular and molecular innate immune responses. J Invest Dermatol 133(3):692-701.
Khan et al., "Animal models of orofacial pain," Methods Mol Biol, 2010. 617: p. 93-104.

(56) References Cited

OTHER PUBLICATIONS

Khodorova, A., Montmayeur, J.P., and Strichartz, G. (2009). Endothelin receptors and pain. J Pain 10, 4-28.
Kim et al., "Astrocyte contributions to flow/pressure-evoked parenchymal arteriole vasoconstriction," J Neurosci, 2015. 35(21): p. 8245-57.
Kim SJ, et al. (2011) Analysis of cellular and behavioral responses to imiquimod reveals a unique itch pathway in transient receptor potential vanilloid 1 (TRPV1)-expressing neurons. Proc Natl Acad Sci U S A 108(8): 3371-3376.
Kimball et al., "Stimulation of neuronal receptors, neuropeptides and cytokines during experimental oil of mustard colitis," Neurogastroenterol Motil, 2007. 19(5): p. 390-400.
Kligman LH & Murphy GF (1996) Ultraviolet B radiation increases hairless mouse mast cells in a dose-dependent manner and alters distribution of UV-induced mast cell growth factor. Photochemistry and photobiology 63(1): 123-127.
Knock, G.A., Terenghi, G., Bunker, C.B., Bull, H.A., Dowd, P.M., and Polak, J.M. (1993). Characterization of endothelin-binding sites in human skin and their regulation in primary Raynaud's phenomenon and systemic sclerosis. J Invest Dermatol 101, 73-78.
Knowlton WM & McKemy DD (2011) TRPM8: from cold to cancer, peppermint to pain. Current pharmaceutical biotechnology 12(1):68-77.
Köhler et al., "Continuous cultures of fused cells secreting antibody of predefined specificity," Nature 1975, 256, 495.
Kohler et al., "Evidence for a functional role of endothelial transient receptor potential V4 in shear stress-induced vasodilatation," Arterioscler Thromb Vasc Biol, 2006. 26(7): p. 1495-502.
Koivisto et al., "TRPA1: a transducer and amplifier of pain and inflammation," Basic Clin Pharmacol Toxicol, 2014. 114(1): p. 50-5.
Koltzenburg, M. (2004). The role of TRP channels in sensory neurons. Novartis Foundation symposium 260, 206-213; discussion 213-220, 277-209.
Kou et al., "Periostin levels correlate with disease severity and chronicity in patients with atopic dermatitis," Br J Dermatol, 2014. 171(2): p. 283-91.
Kowal et al., "ATP release, generation and hydrolysis in exocrine pancreatic duct cells," Purinergic Signal, 2015. 11(4): p. 533-50.
Krause et al., "Transient receptor potential ion channels as targets for the discovery of pain therapeutics," Curr Opin Investig Drugs, 2005. 6(1): p. 48-57.
Kunkler et al., "TRPA1 receptors mediate environmental irritant-induced meningeal vasodilatation," Pain, 2011. 152(1): p. 38-44.
Kupper TS & Groves RW (1995) The interleukin-1 axis and cutaneous inflammation. J Invest Dermatol 105(1 Suppl):62S-66S.
Kupper, T.S., Lee, F., Birchall, N., Clark, S., and Dower, S. (1988). Interleukin 1 binds to specific receptors on human keratinocytes and induces granulocyte macrophage colony-stimulating factor mRNA and protein. A potential autocrine role for interleukin 1 in epidermis. J Clin Invest 82, 1787-1792.
Lanciotti et al., "Megalencephalic leukoencephalopathy with subcortical cysts protein 1 functionally cooperates with the TRPV4 cation channel to activate the response of astrocytes to osmotic stress: dysregulation by pathological mutations," Hum Mol Genet, 2012. 21(10): p. 2166-80.
Lapointe TK & Altier C (2011) The role of TRPA1 in visceral inflammation and pain. Channels (Austin) 5(6):525-529.
Lazar J, Gharat L, Khairathkar-Joshi N, Blumberg PM, & Szallasi A (2009) Screening TRPV1 antagonists for the treatment of pain: lessons learned over a decade. Expert opinion on drug discovery 4(2): 159-180.
Lechner, S.G., Markworth, S., Poole, K., Smith, E.S., Lapatsina, L., Frahm, S., May, M., Pischke, S., Suzuki, M., Ibanez-Tallon, I., et al. (2010). The molecular and cellular identity of peripheral osmoreceptors. Neuron 69, 332-344.
Lee, H., and Caterina, M. J. (2005). TRPV channels as thermosensory receptors in epithelial cells. Pflugers Arch 451, 160-167.
Lee, K.T., M.J. Byun, K.S. Kang, E.W. Park, S.H. Lee, S. Cho, H. Kim, K.W. Kim, T. Lee, J.E. Park, W. Park, D. Shin, H.S. Park, J.T. Jeon, B.H. Choi, G.W. Jang, S.H. Choi, D.W. Kim, D. Lim, H.S. Park, M.R. Park, J. Ott, L.B. Schook, T.H. Kim, and H. Kim, Neuronal genes for subcutaneous fat thickness in human and pig are identified by local genomic sequencing and combined SNP association study. PLoS ONE, 2011, 6(2): p. e16356.
Leung, D.Y., Atopic dermatitis: new insights and opportunities for therapeutic intervention. J Allergy Clin Immunol, 2000. 105(5): p. 860-76.
Levine et al., "TRP channels: Targets for the relief of pain," Biochim Biophys Acta, 2007, 989-1003.
Li, J., Ghio, A.J., Cho, S.H., Brinckerhoff, C.E., Simon, S.A., and Liedtke, W. (2009). Diesel exhaust particles activate the matrix-metalloproteinase-1 gene in human bronchial epithelia in a beta-arrestin-dependent manner via activation of RAS. Environ Health Perspect 117, 400-409.
Li, J., Kanju, P., Patterson, M., Chew, W.L., Cho, S.H., Gilmour, I., Oliver, T., Yasuda, R., Ghio, A., Simon, S.A., et al. (2011). TRPV4-mediated calcium influx into human bronchial epithelia upon exposure to diesel exhaust particles. Environ Health Perspect 119, 784-793.
Li, L., Liu, C., Chen, L., and Chen, L. (2010). Hypotonicity modulates tetrodotoxin-sensitive sodium current in trigeminal ganglion neurons. Molecular pain 7, 27.
Liang J, Ji Q, Ji W. Role of transient receptor potential ankyrin subfamily member 1 in pruritus induced by endothelin-1. Neurosci Lett. Apr. 4, 2011;492(3): 175-8.
Liang J, Kawamata T, Ji W. Molecular signaling of pruritus induced by endothelin-1 in mice. Exp Biol Med (Maywood). Nov. 2010;235(ll):1300-5.
Liddle et al., "Neurogenic inflammation and pancreatitis," Pancreatology, 2004. 4(6): p. 551-9; discussion 559-60.
Liddle, R.A., "Pancreatitis: the acid test," Gastroenterology, 2010. 139(5): p. 1457-60.
Liddle, R.A., "The role of Transient Receptor Potential Vanilloid 1 (TRPV1) channels in pancreatitis," Biochim Biophys Acta, 2007. 1772(8): p. 869-78.
Liedtke et al., "Functionality of the TRPV subfamily of TRP ion channels: add mechano-TRP and osmo-TRP to the lexicon!" Cell Mol Life Sci, 2005. 62(24): p. 2985-3001.
Liedtke et al., "Mammalian TRPV4 (VR-OAC) directs behavioral responses to osmotic and mechamcal stimuli in Caenorhabditis elegans," Proc Natl Acad Sci U S A, 2003. 100: p. 14531-6.
Liedtke, W., "Molecular mechanisms of TRPV4-mediated neural signaling," Ann N Y Acad Sci, 2008. 1144: p. 42-52.
Liedtke, W., and Friedman, J.M. (2003). Abnormal osmotic regulation in trpv4-/-mice. Proc Natl Acad Sci U S A 100, 13698-13703.
Liedtke, W., Choe, Y., Marti-Renom, M.A., Bell, A.M., Denis, C.S., Sali, A., Hudspeth, A.J., Friedman, J.M., and Heller, S. (2000). Vanilloid receptor-related osmotically activated channel (VR-OAC), a candidate vertebrate osmoreceptor. Cell 103, 525-535.
Liu, B., J. Escalera, S. Balakrishna, L. Fan, A.I. Caceres, E. Robinson, A. Sui, M.C. McKay, M.A. McAlexander, C.A. Herrick, and S.E. Jordt, TRPA1 controls inflammation and pruritogen responses in allergic contact dermatitis. Faseb J, 2013. 27(9): p. 3549-63.
Liu, T., van Rooijen, N., and Tracey, D.J. (2000). Depletion of macrophages reduces axonal degeneration and hyperalgesia following nerve injury. Pain 86, 25-32.
Lu, C. P., Polak, L., Rocha, A. S., Pasolli, H. A., Chen, S. C., Sharma, N., Blanpain, C., and Fuchs, E. (2012). Identification of Stem Cell Populations in Sweat Glands and Ducts Reveals Roles in Homeostasis and Wound Repair. Cell 150, 136-150.
Luccarini et al., "Remind him to cut the existing cabinet covers to the size of our kitchen cabinets in the garage," J. Pain, 2006, 7(12):908-914.
Luck, J.V., "Traumatic arthrofibrosis; the fibroplastic response of joints to trauma," Bull Hosp Joint Dis, 1951. 12(2): p. 394-403.
Luvisetto et al., "Analgesic effects of botulinum neurotoxin type A in a model of allyl isothiocyanate- and capsaicin-induced pain in mice," Toxicon, 2015. 94: p. 23-8.
Magit et al., "Arthrofibrosis of the knee," J Am Acad Orthop Surg, 2007. 15(11): p. 682-94.

(56) References Cited

OTHER PUBLICATIONS

Maricich SM, et al. (2009) Merkel cells are essential for light-touch responses. Science 324(5934):1580-1582.
Maricich SM, Morrison KM, Mathes EL, & Brewer BM (2012) Rodents rely on Merkel cells for texture discrimination tasks. J Neurosci 32(10):3296-3300.
Martinez-Levasseur, L. M., Gendron, D., Knell, R. J., O'Toole, E. A., Singh, M., and Acevedo-Whitehouse, K. (2011). Acute sun damage and photoprotective responses in whales. Proc Royal Soc B 278, 1581-1586.
Masuoka et al., "Periostin promotes chronic allergic inflammation in response to Th2 cytokines," J Clin Invest, 2012. 122(7): p. 2590-600.
Matthews et al., "Ultra-rapid activation of TRPV4 ion channels by mechanical forces applied to cell surface beta1 integrins," Integr Biol (Camb), 2010. 2(9): p. 435-42.
McGrath, J.A., and Uitto, J. (2008). The filaggrin story: novel insights into skin-barrier function and disease. Trends in molecular medicine 14, 20-27.
McMahon SB & Wood JN (2006) Increasingly irritable and close to tears: TRPA1 in inflammatory pain. Cell 124(6):1123-1125.
McNulty et al., "TRPV4 as a therapeutic target for joint diseases," Naunyn Schmiedebergs Arch Pharmacol, 2015. 388(4): p. 437-50.
McQueen DS, Noble MA, Bond SM. Endothelin-1 activates ETA receptors to cause reflex scratching in BALB/c mice. Br J Pharmacol. May 2007;151(2):278-84.
Merrill et al., "Intravesical TRPV4 blockade reduces repeated variate stress-induced bladder dysfunction by increasing bladder capacity and decreasing voiding frequency in male rats," Am J Physiol Regul Integr Comp Physiol, 2014. 307(4): p. R471-80.
Merrill et al., "Transcriptional and translational plasticity in rodent urinary bladder TRP channels with urinary bladder inflammation, bladder dysfunction, or postnatal maturation," J Mol Neurosci, 2012. 48(3): p. 744-56.
Mishra SK & Hoon MA (2010) Ablation of TrpV1 neurons reveals their selective role in thermal pain sensation. Molecular and cellular neurosciences 43(1): 157-163.
Mishra SK & Hoon MA (2013) The cells and circuitry for itch responses in mice. Science 340(6135):968-971.
Mishra SK, Tisel SM, Orestes P, Bhangoo SK, & Hoon MA (2011) TRPV1-lineage neurons are required for thermal sensation. The EMBO journal 30(3):582-593.
Modir, J.G., and Wallace, M.S. (2011). Human experimental pain models 1: the ultraviolet light UV-B pain model. Methods in molecular biology (Clifton, NJ 617, 159-164.
Mogil et al., "The necessity of animal models in pain research," Pain, 2010. 151(1): p. 12-7.
Mogil, J.S., "Animal models of pain: progress and challenges," Nat Rev Neurosci, 2009. 10(4): p. 283-94.
Moilanen et al., "Monosodium iodoacetate-induced inflammation and joint pain are reduced in TRPA1 deficient mice—potential role of TRPA1 in osteoarthritis," Osteoarthritis Cartilage, 2015. 23(11): p. 2017-26.
Moore, C., F. Cevikbas, H.A. Pasolli, Y. Chen, W. Kong, C. Kempkes, P. Parekh, S.H. Lee, N.A. Kontchou, I. Yeh, N.M. Jokerst, E. Fuchs, M. Steinhoff, and W.B. Liedtke, UVB radiation generates sunburn pain and affects skin by activating epidermal TRPV4 ion channels and triggering endothelin-1 signaling. Proc Natl Acad Sci U S A, 2013. 110(34): p. E3225-34.
Moqrich, A., Hwang, S. W., Earley, T. J., Petrus, M. J., Murray, A. N., Spencer, K. S., Andahazy, M., Story, G. M., and Patapoutian, A. (2005). Impaired thermosensation in mice lacking TRPV3, a heat and camphor sensor in the skin Science 307, 1468-1472.
Moran, M. M., McAlexander, M. A., Biro, T., and Szallasi, A. (2011). Transient receptor potential channels as therapeutic targets. Nature reviews Drug discovery 10, 601-620.
Morita et al., "HTR7 Mediates Serotonergic Acute and Chronic Itch," Neuron, 2015. 87(1): p. 124-38.

Motta, E.M., Calixto, J.B., and Rae, G.A. (2006). Mechanical hyperalgesia induced by endothelin-1 in rats is mediated via phospholipase C, protein kinase C, and MAP kinases. Exp Biol Med (Maywood) 231, 1141-1145.
Mueller-Tribbensee et al., "Differential Contribution of TRPA1, TRPV4 and TRPMB to Colonic Nociception in Mice," PLoS ONE, 2015. 10(7): p. e0128242.
Mutai, H., and Heller, S. (2003). Vertebrate and invertebrate TRPV-like mechanoreceptors. Cell calcium 33, 471-478.
Muto et al., "Development and histologic characteristics of synovitis induced by trauma in the rat temporomandibular joint," Int J Oral Maxillofac Surg, 1998. 27(6): p. 470-5.
Nakatsuka et al., "Identification of molecular determinants for a potent mammalian TRPA1 antagonist by utilizing species differences," J Mol Neurosci, 2013. 51(3): p. 754-62.
Namer, B., Hilliges, M., Orstavik, K., Schmidt, R. Weidner, C., Torebjork, E., Handwerker, H., and Schmelz, M. (2008) Endothelin 1 activates and sensitizes human C-nociceptors. Pain 137, 41-49.
Nassini et al., "The 'headache tree' via umbellulone and TRPA1 activates the trigeminovascular system," Brain, 2012. 135(Pt2):p. 376-90.
Nassini et al., "The TRPA1 channel in inflammatory and neuropathic pain and migraine," Rev Physiol Biochem Pharmacol, 2014. 167: p. 1-43.
Nemes, Z., and Steinert, P.M. (1999). Bricks and mortar of the epidermal barrier. Experimental & molecular medicine 31, 5-19.
Nilins, B., Vriens, J., Prenen, J., Droogmans, G., and Voets, T. (2004). TRPV4 calcium entry channel: a paradigm for gating diversity. American journal of physiology 286, C195-205.
Peier, A. M., Reeve, A. J., Andersson, D. A., Moqrich, A., Earley, T. J., Hergarden, A. C., Story, G. M., Colley, S., Hogenesch, J. B., McIntyre, P., et al. (2002). A Heat-Sensitive TRP Channel Expressed in Keratinocytes. Science 296, 2046-2049.
Phan, M.N., Leddy, H.A., Votta, B.J., Kumar, S., Levy, D.S., Lipshutz, D.B., Lee, S.H., Liedtke, W., and Guilak, F. (2009). Functional characterization of TRPV4 as an osmotically sensitive ion channel in porcine articular chondrocytes. Arthritis Rheum 60, 3028-3037.
Porro, C.A., and Cavazzuti, M. (1993). Spatial and temporal aspects of spinal cord and brainstem activation in the formalin pain model. Progress in neurobiology 41, 565-607.
Pradhan et al. Journal of Environmental Research and Development, 2006, 1(1), 16-21.
Rabbani P, et al. (2011) Coordinated activation of Wnt in epithelial and melanocyte stem cells initiates pigmented hair regeneration. Cell 145(6):941-955.
Rahaman et al. "Role of Cation Channel TRPV4 in Mechanosensing, Myofibroblast Differentiation, and Pulmonary Fibrosis." Annals of the American Thoracic Society, Mar. 1, 2015, vol. 12, supplement 1, pp. S74-S75.
Rahaman et al. "TRPV4 mediates myofibroblast differentiation and pulmonary fibrosis in mice." The Journal of Clinical Investigation, Dec. 2014, vol. 124, pp. 5225-5238.
Rahaman et al., "Trpv4 Channel Regulates Tgfbeta-Induced Myofibroblast Differentiation By Activation Of Pi3k/akt Pathway," Am J Respir Crit Care Med 187, 2013:A3838.
Rausch, L., E.C. Bisinger, Jr., A. Sharma, and R. Rose, Use of the domestic Swine as an alternative animal model for conducting dermal irritation/corrosion studies on fatty amine ethoxylates. Int J Toxicol, 2003. 22(4): p. 317-23.
Rauschmayr T, Groves RW, & Kupper TS (1997) Keratinocyte expression of the type 2 interleukin 1 receptor mediates local and specific inhibition of interleukin 1-mediated inflammation. Proc Natl Acad Sci U S A 94(11):5814-5819.
Ren, K., and Torres, R. (2009). Role of interleukin-1beta during pain and inflammation. Brain Res Rev 60, 57-64.
Riccio MM, Reynolds CJ, Hay DW, Proud D. Effects of intranasal administration of endothelin-1 to allergic and nonallergic individuals. Am J Respir Crit Care Med. Dec. 1995; 152(6 Pt 1):1757-64.
Roosterman, D., Goerge, T., Schneider, S.W., Bunnett, N.W., and Steinhoff, M. (2006). Neuronal control of skin function: the skin as a neuroimmunoendocrine organ. Physiological reviews 86, 1309-1379.

(56) References Cited

OTHER PUBLICATIONS

Rustagi et al., "Antioxidant therapy for pain reduction in patients with chronic pancreatitis: a systematic review and meta-analysis," Pancreas, 2015. 44(5): p. 812-8.
Sacerdote P, Bianchi M, Ricciardi-Castagnoli P, & Panerai AE (1992) Tumor necrosis factor alpha and interleukin-1 alpha increase pain thresholds in the rat. Ann N Y Acad Sci 650:197-201.
Schwartz et al., "TRPV1 and TRPA1 antagonists prevent the transition of acute to chronic inflammation and pain in chronic pancreatitis," J Neurosci, 2013. 33(13): p. 5603-11.
Schweizer A, Feige U, Fontana A, Muller K, & Dinarello CA (1988) Interleukin-1 enhances pain reflexes. Mediation through increased prostaglandin E2 levels. Agents and actions 25(3-4):246-251.
Shibasaki et al., "A novel subtype of astrocytes expressing TRPV4 regulates neuronal excitability via release of gliotransmitters," J Biol Chem, 2014, vol. 289, No. 21, p. 14470-14480.
Shibasaki et al., "Effects of body temperature on neural activity in the hippocampus: regulation of resting membrane potentials by transient receptor potential vanilloid 4," J Neurosci, 2007. 27(7): p. 1566-75.
Shigetomi et al., "TRPA1 channels are regulators of astrocyte basal calcium levels and long-term potentiation via constitutive D-serine release," J Neurosci, 2013. 33(24): p. 10143-53.
Shigetomi et al., "TRPA1 channels regulate astrocyte resting calcium and inhibitory synapse efficacy through GAT-3," Nat Neurosci, 2012. 15(1): p. 70-80.
Shiraishi et al., "Periostin contributes to the pathogenesis of atopic dermatitis by inducing TSLP production from keratinocytes," Allergol Int, 2012. 61(4): p. 563-72.
Simon et al., "How irritating: the role of TRPA1 in sensing cigarette smoke and aerogenic oxidants in the airways," J Clin Invest, 2008. 118(7): p. 2383-6.
Sipe, W., Brierley, S. M., Martin, C. M., Phillis, B. D., Bautista Cruz, F., Grady, E. F., Liedtke, W., Cohen, D. M., Vanner, S. J., Blackshaw, L. A., et al. (2008). Transient Receptor potential Vanilloid 4 Mediates Protease Activated Receptor 2-Induced Sensitization of Colonic Afferent Nerves and Visceral Hyperalgesia. American Journal of Physiology 294, G1288-1298.
Situm, M. et al., "The Role of UV Radiation in the Development of Basal Cell Carcinoma," Coll. Antropol., 2008, vol. 32, Suppl. 2, pp. 167-170.
Sokabe, T., and Tominaga, M. (2011). The TRPV4 cation channel: A molecule linking skin temperature and barrier function. Communicative & integrative biology 3, 619-621.
Sokabe, T., Fukumi-Tominaga, T., Yonemura, S., Mizuno, A., and Tominaga, M. (2010). The TRPV4 channel contributes to intercellular junction formation in keratinocytes. The Journal of biological chemistry 285, 18749-18758.
Soter, N.A. (1990). Acute effects of ultraviolet radiation on the skin. Seminars in dermatology 9, 11-15.
Soya et al., "Plasma membrane stretch activates transient receptor potential vanilloid and ankyrin channels in Merkel cells from hamster buccal mucosa," Cell Calcium, 2014. 55(4): p. 208-18.
Stotz et al., "Citral sensing by Transient [corrected] receptor potential channels in dorsal root ganglion neurons," PLoS ONE, 2008. 3(5): p. e2082.
Strotmann et al., "OTRPC4, a nonselective cation channel that confers sensitivity to extracellular osmolarity," Nat Cell Biol, 2000. 2(10): p. 695-702.
Sulk, M., Seeliger, S., Aubert, J., Schwab, V.D., Cevikbas, F., Rivier, M., Nowak, P., Voegel, J.J., Buddenkotte, J., and Steinhoff, M. (2012). Distribution and Expression of Non-Neuronal Transient Receptor Potential (TRPV) Ion Channels in Rosacea. The Journal of investigative dermatology, 132(4): 1253-1262.
Sullivan, T.P., W.H. Eaglstein, S.C. Davis, and P. Mertz, The pig as a model for human wound healing. Wound Repair Regen, 2001. 9(2): p. 66-76.
Svensson CI (2010) Interleukin-6: a local pain trigger? Arthritis Res Ther 12(5): 145.

Tai C, Zhu S, & Zhou N (2008) TRPA1: the central molecule for chemical sensing in pain pathway? J Neurosci 28(5):1019-1021.
Taniguchi et al., "Periostin controls keratinocyte proliferation and differentiation by interacting with the paracrine IL-1alpha/IL-6 loop," J Invest Dermatol, 2014. 134(5): p. 1295-304.
Terada et al., "Roles of Cav3.2 and TRPA1 channels targeted by hydrogen sulfide in pancreatic nociceptive processing in mice with or without acute pancreatitis," J Neurosci Res, 2015. 93(2): p. 361-9.
Thodeti et al., "TRPV4 channels mediate cyclic strain-induced endothelial cell reorientation through integrin-to-integrin signaling," Circ Res, 2009. 104(9): p. 1123-30.
Tominaga, M., and Caterina, M. J. (2004). Thermosensation and pain. J Neurobiol 61, 3-12.
Trentin PG, Fernandes MB, D'Orléans-Juste P, Rae GA. Endothelin-1 causes pruritus in mice. Exp Biol Med (Maywood). Jun. 2006;231(6):1146-51.
Trevisan et al., "TRPA1 mediates trigeminal neuropathic pain in mice downstream of monocytes/macrophages and oxidative stress," Brain, 2016, 139:1361-1377.
Tsuboi, R., Sato, C., Oshita, Y., Hama, H., Sakurai, T., Goto, K., and Ogawa, H. (1995). Ultraviolet B irradiation increases endothelin-1 and endothelin receptor expression in cultured human keratinocytes. FEBS Lett 371, 188-190.
Turner, M.J. and B. Zhou, A new itch to scratch for TSLP. Trends Immunol, 2014. 35(2): p. 49-50.
Van Keymeulen A, et al. (2009) Epidermal progenitors give rise to Merkel cells during embryonic development and adult homeostasis. J Cell Biol 187(1):91-100.
Vasioukhin, V., Bauer, C., Degenstein, L., Wise, B., and Fuchs, E. (2001a). Hyperproliferation and defects in epithelial polarity upon conditional ablation of alpha-catenin in skin. Cell 104, 605-617.
Vasioukhin, V., Bowers, E., Bauer, C., Degenstein, L., and Fuchs, E. (2001b). Desmoplakin is essential in epidermal sheet formation. Nat Cell Biol 3, 1076-1085.
Vasioukhin, V., Degenstein, L., Wise, B., and Fuchs, E. (1999). The magical touch: genome targeting in epidermal stem cells induced by tamoxifen application to mouse skin. Proc Natl Acad Sci U S A 96, 8551-8556.
Vergnolle et al., "A role for transient receptor potential vanilloid 4 in tonicity-induced neurogenic inflammation," Br J Pharmacol, 2010. 159(5): p. 1161-73.
Vergnolle, N., "TRPV4: new therapeutic target for inflammatory bowel diseases," Biochem Pharmacol, 2014. 89(2): p. 157-61.
Verhoeven, E.W., S. de Klerk, F.W. Kraaimaat, P.C. van de Kerkhof, E.M. de Jong, and A.W. Evers, Biopsychosocial mechanisms of chronic itch in patients with skin diseases: a review. Acta Derm Venereol, 2008. 88(3): p. 211-8.
Vincent et al., "Identification and characterization of novel TRPV4 modulators," Biochem Biophys Res Commun, 2009. 389(3): p. 490-4.
Vincent, F., and Duncton, M.A. (2011). TRPV4 agonists and antagonists. Current topics in medicinal chemistry 11, 2216-2226.
Von Banchet et al., "Neuronal IL-17 receptor upregulates TRPV4 but not TRPV1 receptors in DRG neurons and mediates mechanical but not thermal hyperalgesia," Mol Cell Neurosci, 2013. 52: p. 152-60.
Walker SL & Young AR (1997) Sunscreens offer the same UVB protection factors for inflammation and immunosuppression in the mouse. J Invest Dermatol 108(2): 133-138.
Wolf G, Livshits D, Beilin B, Yirmiya R, & Shavit Y (2008) Interleukin-1 signaling is required for induction and maintenance of postoperative incisional pain: genetic and pharmacological studies in mice. Brain, behavior, and immunity 22(7):1072-1077.
Woo SH, Stumpfova M, Jensen UB, Lumpkin EA, & Owens DM (2010) Identification of epidermal progenitors for the Merkel cell lineage. Development 137(23):3965-3971.
Yamaguchi, Y., "Periostin in skin tissue and skin-related diseases," Allergol Int, 2014. 63(2): p. 161-70.
Yang et al., "Histamine contributes to tissue remodeling via periostin expression," J Invest Dermatol, 2014. 134(8): p. 2105-13.

(56) References Cited

OTHER PUBLICATIONS

Yang et al., "Transient receptor potential ankyrin-1 participates in visceral hyperalgesia following experimental colitis," Neurosci Lett, 2008. 440(3): p. 237-41.
Ye, L., S. Kleiner, J. Wu, R. Sah, R.K. Gupta, A.S. Banks, P. Cohen, M.J. Khandekar, P. Bostrom, R.J. Mepani, D. Laznik, T.M. Kamenecka, X. Song, W. Liedtke, V.K. Mootha, P. Puigserver, P.R. Griffin, D.E. Clapham, and B.M. Spiegelman, TRPV4 is a regulator of adipose oxidative metabolism, inflammation, and energy homeostasis. Cell, 2012. 151(1): p. 96-110.
Yeo M, Berglund K, Augustine G, & Liedtke W (2009) Novel repression of Kcc2 transcription by REST-RE-1 controls developmental switch in neuronal chloride. J Neurosci 29(46):14652-14662.
Ying et al., "The transient receptor potential vanilloid 4 channel modulates uterine tone during pregnancy," Sci Transl Med, 2015. 7(319): p. 319ra204.
Yohn JJ, et al. (1993) Cultured human keratinocytes synthesize and secrete endothelin-1. J Invest Dermatol 100(1):23-26.
Yuspa, S.H., Kilkenny, A.E., Steinert, P.M., and Roop, D.R. (1989). Expression of murine epidermal differentiation markers is tightly regulated by restricted extracellular calcium concentrations in vitro. J Cell Biol 109, 1207-1217.
Zarpelon, A.C., T.M. Cunha, J.C. Alves-Filho, L.G. Pinto, S.H. Ferreira, I.B. McInnes, D. Xu, F.Y. Liew, F.Q. Cunha, and W.A. Verri, Jr., IL-33/ST2 signalling contributes to carrageenin-induced innate inflammation and inflammatory pain: role of cytokines, endothelin-1 and prostaglandin E2. Br J Pharmacol, 2013. 169(1): p. 90-101.
Zeichen et al., "Immunohistochemical localization of collagen VI in arthrofibrosis," Arch Orthop Trauma Surg, 1999. 119(5-6): p. 315-8.
Zhang et al., "Alcohol and high fat induced chronic pancreatitis: TRPV4 antagonist reduces hypersensitivity," Neuroscience, 2015. 311: p. 166-79.
Zhang et al., "Next-Gen Sequencing-Based Mapping and Identification of Ethyl Methanesulfonate-Induced Mutations in *Arabidopsis thaliana*," Current Protocols in Molecular Biology, 2014, 108:7. 18:7.18.1-7.18.16.
Zhang et al., "Overview of Peptide and protein analysis by mass spectrometry," Curr Protoc Mol Biol, 2014. 108: p. 10 21 1-10 21 30.
Zhang et al., "Prolonged high fat/alcohol exposure increases TRPV4 and its functional responses in pancreatic stellate cells," Am J Physiol Regul Integr Comp Physiol, 2013. 304(9): p. R702-11.
Zhang, Y., Wang, Y.H., Ge, H.Y., Arendt-Nielsen, L., Wang, R., and Yue, S.W. (2008). A transient receptor potential vanilloid 4 contributes to mechanical allodynia following chronic compression of dorsal root ganglion in rats. Neuroscience letters 432, 222-227.
Zhao et al., "Cathepsin S causes inflammatory pain via biased agonism of PAR2 and TRPV4," J Biol Chem, 2014. 289(39): p. 27215-34.
Zhao et al., "Neutrophil elastase activates PAR2 and TRPV4 to cause inflammation and pain," J Biol Chem, 2015, vol. 290, No. 22, p. 13875-13887.
Zhou et al., "Spatiotemporal expression of periostin during skin development and incisional wound healing: lessons for human fibrotic scar formation," J Cell Commun Signal, 2010. 4(2): p. 99-107.
United States Patent Office Notice of Allowance for U.S. Appl. No. 14/413,172 dated Nov. 9, 2015 (9 pages).
European Patent Office Search Report for Application No. 13813477.0 dated Apr. 18, 2016 (8 pages).
United States Patent Office Action for U.S. Appl. No. 15/018,595 dated Aug. 18, 2016 (15 pages).
Heagerty et al., "Time-dependent ROC curves for censored survival data and a diagnostic marker," Biometrics, 2000, 56, 337-44.
Su et al., "TRPA1 and TRPV1 contribute to iodine antiseptics-associated pain and allergy," EMBO Reports, 2016, vol. 17, p. 1422-1430.
International Search Report and Written Opinion for Application No. PCT/US2017/026714 dated Jul. 21, 2017 (10 pages).
United States Patent Office Action for U.S. Appl. No. 15/505,898 dated Oct. 16, 2017 (13 pages).
United States Patent Office Notice of Allowance for U.S. Appl. No. 15/018,595 dated Mar. 7, 2017 (6 pages).
Norris et al. Journal of Cellular Biochemistry 2007, 101, 695-711.
Yang et al. Annals of the Rheumatic Diseases 2013, 71, 133-134.
Okada et al. Laboratory Investigation 2014, 94, 1030-1041.
United States Patent Office Action for U.S. Appl. No. 15/624,508 dated Jan. 16, 2018 (15 pages).
Yamaguchi, Periostin in Skin Tissue and Skin-Related Diseases, Allergology International, vol. 63, No. 2, 2014.
United States Patent Office Action for U.S. Appl. No. 15/505,898 dated Jun. 12, 2018 (6 pages).
United States Patent Office Action for U.S. Appl. No. 15/624,508 dated Aug. 24, 2018 (7 pages).
United States Patent Office Notice of Allowance for U.S. Appl. No. 15/505,898 dated Jan. 22, 2019 (7 pages).
Trojanowska et al., "Pathogenesis of fibrosis: type 1 collagen and the skin," Journal of Molecular Medicine, 1998, 76(3-4):266-274.
Gilchrist et al., "TRPV4-mediated calcium signaling in mesenchymal stem cells regulates aligned collagen matrix formation and vinculin tension," PNAS 2019, 116, 1992-1997.
Naitoh et al., "Upregulation of HSP47 and collagen type III in the dermal fibrotic disease, keloid," Biochem Biophys Res Commun, 2001, 280(5):1316-22.
European Patent Office Action for Application No. 13813477.0 dated Aug. 29, 2018 (5 pages).
United States Patent Office Action for U.S. Appl. No. 16/217,948 dated Jun. 3, 2019 (16 pages).
United States Patent Office Action for U.S. Appl. No. 16/391,047 dated Sep. 9, 2019 (11 pages).
United States Patent Office Action for U.S. Appl. No. 16/217,948 dated Dec. 31, 2019 (7 pages).
European Patent Office Partial Supplementary Search Report for Application No. 17779954.1 dated Oct. 31, 2019 (14 pages).
United States Patent Office Action for U.S. Appl. No. 16/391,047 dated Feb. 3, 2020 (7 pages).
European Patent Office Extended Search Report for Application No. 17779954.1 dated Feb. 10, 2020 (12 pages).
United States Patent Office Action for U.S. Appl. No. 16/091,960 dated May 20, 2020 (11 pages).
United States Patent Office Action for U.S. Appl. No. 16/217,948 dated Jul. 27, 2020 (6 pages).
United States Patent Office Notice of Allowance for U.S. Appl. No. 16/391,047 dated Jul. 29, 2020 (7 pages).
Zhao, "Discovery and Mechanism Study of the Irritating Effects of Iodine and Lead Ions and Targets," CMFD of Kunming University of Science and Technology, Jan. 2016, 85 pages.
Chinese Patent Office Action for Application No. 201780029193.5 dated Jul. 28, 2020 (18 pages, English translation included).
Nilius et al., "The transient receptor potential family of ion channels," Genome Biology, 2011, 12:218.
Ning et al., "Functional interaction of TRPV4 channel protein with annexin A2 in DRG," Neurol Res, 2012. 34(7): p. 685-93.
Ning et al., "Role of colchicine-induced microtubule depolymerization in hyperalgesia via TRPV4 in rats with chronic compression of the dorsal root ganglion," Neurol Res, 2014. 36(1): p. 70-8.
O'Conor et al., "TRPV4-mediated mechanotransduction regulates the metabolic response of chondrocytes to dynamic loading," Proc Natl Acad Sci U S A, 2014. 111(4): p. 1316-21.
O'Neil et al., "The mechanosensitive nature of TRPV channels," Pflugers Arch, 2005. 451(1): p. 193-203.
Ovaere, P., Lippens, S., Vandenabeele, P., and Declercq, W. (2009). The emerging roles of serine protease cascades in the epidermis. Trends in biochemical sciences 34, 453-463.
Pande et al. Acta Pharmaceutica Jugoslavica 1984, 34(2), 61-8.
Patapoutian, A. (2005). TRP Channels and Thermosensation. Chem Senses 30 Suppl 1, i193-i194.
Patel KN, Liu Q, Meeker S, Undem BJ, & Dong X (2011) Pirt, a TRPV1 modulator, is required for histamine-dependent and -independent itch. PLoS ONE 6(5):e20559.

(56) References Cited

OTHER PUBLICATIONS

Paus, R., Theoharides, T.C., and Arck, P.C. (2006). Neuroimmunoendocrine circuitry of the 'brain-skin connection'. Trends in immunology 27, 32-39.
Wang, X., Zinkel, S., Polonsky, K., and Fuchs, E. (1997). Transgenic studies with a keratin promoter-driven growth hormone transgene: prospects for gene therapy. Proc Natl Acad Sci U S A 94, 219-226.
Wegierski, T., Lewandrowski, U., Muller, B., Sickmann, A., and Walz, G. (2009). Tyrosine phosphorylation modulates the activity of TRPV4 in response to defined stimuli. The Journal of biological chemistry 284, 2923-2933.
Wei et al., "Activation of TRPV4 on dural afferents produces headache-related behavior in a preclinical rat model," Cephalalgia, 2011. 31(16): p. 1595-600.
Wenzel RR, Zbinden S, Noll G, Meier B, Lüscher TF. Endothelin-1 induces vasodilation in human skin by nociceptor fibres and release of nitric oxide. Br J Clin Pharmacol. May 1998;45(5):441-6.
Willis WD, Jr. (2009) The role of TRPV1 receptors in pain evoked by noxious thermal and chemical stimuli. Exp Brain Res 196(1):5-11.
Wilson et al., "The ion channel TRPA1 is required for chronic itch," J Neurosci, 2013. 33(22): p. 9283-94.
Wilson, S.R., A.M. Nelson, L. Batia, T. Morita, D. Estandian, D.M. Owens, E.A. Lumpkin, and D.M. Bautista, The ion channel TRPA1 is required for chronic itch. J Neurosci, 2013. 33(22): p. 9283-94.
Wilson, S.R., L. The, L.M. Batia, K. Beattie, G.E. Katibah, S.P. McClain, M. Pellegrino, D.M. Estandian, and D.M. Bautista, The epithelial cell-derived atopic dermatitis cytokine TSLP activates neurons to induce itch. Cell, 2013. 155(2): p. 285-95.
Wolf G, Gabay E, Tai M, Yirmiya R, & Shavit Y (2006) Genetic impairment of interleukin-1 signaling attenuates neuropathic pain, autotomy, and spontaneous ectopic neuronal activity, following nerve injury in mice. Pain 120(3):315-324.

* cited by examiner

A

Trpv4 wildtype insertion loxP, frt-neo, PacI excision frt-neo using FLPe (ES cells)

excision exon13 by CRE in KC in-vivo

TRPA1 AND TRPV4 INHIBITORS AND METHODS OF USING THE SAME FOR ORGAN-SPECIFIC INFLAMMATION AND ITCH

CROSS-REFERENCE TO RELATED APPLICATIONS

This application claims priority to U.S. Provisional Patent Application No. 62/101,883, filed Jan. 9, 2015, which is incorporated herein by reference in its entirety.

SEQUENCE LISTING

The sequence listing is filed with the application in electronic format only and is incorporated by reference herein. The sequence listing text file "028193-9128-US05_As_Filed_Sequence_List.txt" was created on Mar. 22, 2016, and is 698 bytes in size.

STATEMENT REGARDING FEDERALLY SPONSORED RESEARCH

This invention was made with government support under grant numbers DE018549 and DE018529S1 awarded by the National Institutes of Health/National Institute of Dental and Craniofacial Research (NIH/NIDCR), and grant numbers AR059402, AR31737, and AR050452 awarded by the National Institutes of Health/National Institute of Arthritis and Musculoskeletal and Skin Diseases (NIH/NIAMS). The government has certain rights in the invention.

FIELD

This disclosure relates to methods and compositions for treating inflammation, pain, itch, cancer, autoimmune diseases, fibrotic diseases, skin pigmentation, and/or other dermatological disorders.

INTRODUCTION

The skin is the largest organ in many vertebrates, including humans. It provides barrier protection against the potentially harmful external environment. The skin also represents the site of first interaction of the ambient environment to immunologically competent and sentient structures of the organism. Cells endowed with sensory transduction capacity for warmth, cold, mechanical cues, pain, and itch are sensory neurons in the dorsal root and trigeminal ganglia with their peripheral axons directly interfacing with skin. However, successfully targeting the skin for treatment of inflammation, pain, itch, cancer, autoimmune diseases, fibrotic diseases, skin pigmentation, and other dermatological disorders has remained elusive.

Biochemical pathways in to the skin include those relating to the transient receptor potential (TRP) superfamily of ion channels. One ion channel in this family is TRPV4. TRPV4 is a multimodally-activated non-selective cation channel permeable to calcium (i.e., Ca++). In epidermal keratinocytes of mammalian skin, the TRPV4 ion channel is expressed robustly. However, TRPV4 is also expressed in skin-innervating sensory neurons. In Trpv4−/− mice, an epidermal phenotype of impaired barrier function between epidermis and dermis has been shown. In regards to pain signaling, TRPV4 has been found critical for physiological withdrawal responses to noxious osmotic and mechanical, but not thermal cues, and has also been found relevant for inflammation or nerve-damage-induced sensitization of nociception. While it is understood that TRPV4 is expressed in epidermal keratinocytes and skin-innervating sensory neurons, an in vivo role of TRPV4 in pathological pain evoked by UVB exposure has not been demonstrated. Moreover, a direct role of TRPV4 in itch transmission has not been demonstrated as of yet. TRPA1 is another TRP ion channel located on the plasma membrane. TRPA1 acts as sensor for environmental irritants, pain, cold, and stretch. Although TRPV4 and TRPA1 function in the skin, it is not known whether targeting TRPV4 and/or TRPA1 would be useful in the treatment of inflammation, pain, itch, cancer, autoimmune diseases, fibrotic diseases, skin pigmentation, and other dermatological disorders. Furthermore, specific TRPV4 and TRPA1 inhibitors are not presently known. New and successful treatments for dermatological disorders are needed.

SUMMARY

In an aspect, the disclosure relates to methods of treating and/or preventing a fibrotic disease in a subject in need thereof. The methods may include administering to the subject an effective amount of a TRPV4 and/or TRPA1 inhibitor. The fibrotic disease may be selected from pathologic skin fibrotic response, synovial fibrosis, and lung fibrosis. The pathologic skin fibrotic response may be selected from skin fibrosis, keloid formation, chemical or actinic injury, a pathologic response to skin irradiation ("radio-derm"), psoriasis, chronic atopic dermatitis, chronic UV-dermatitis, scleroderma, and conditions characterized by a chronic maladaptive injury response to an ongoing noxious insult to the skin or inappropriate scar formation. The TRPV4 and/or TRPA1 inhibitor may be a compound according to Formula I:

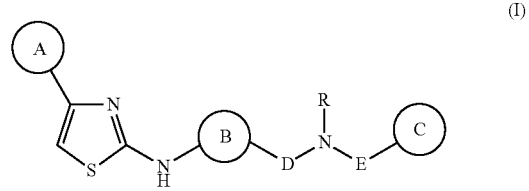

(I)

wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring. The TRPV4 and/or TRPA1 inhibitor may be at least one compound selected from the following:

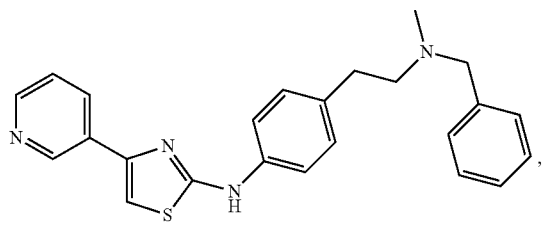

GSK205

16-18

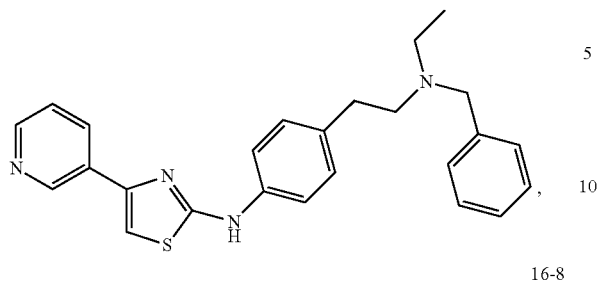

16-8

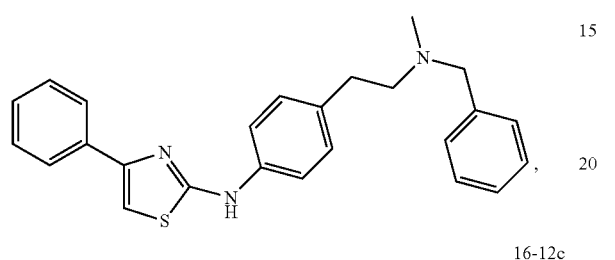

16-12c

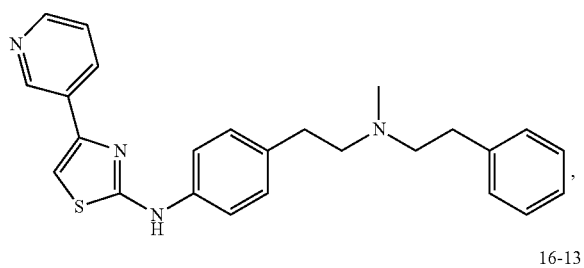

16-13

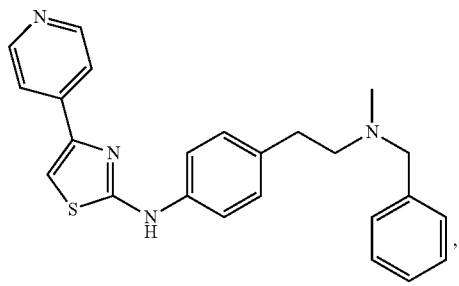

16-14

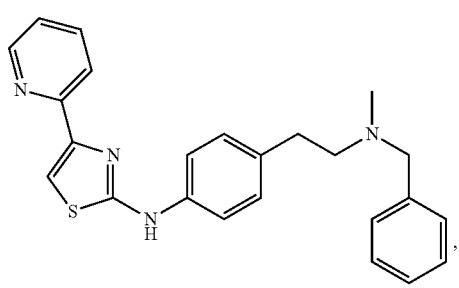

16-16

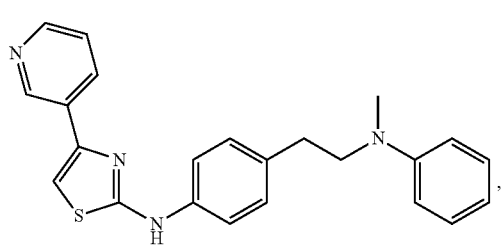

16-8/18hy

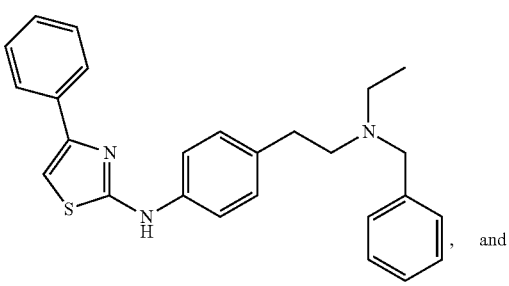

and 15-43

In a further aspect, the disclosure relates to methods of treating and/or preventing a dermatological disorder in a subject in need thereof. The methods may include administering to the subject an effective amount of a TRPV4 and/or TRPA1 inhibitor. The dermatological disorder may be selected from inflammation, pain, itch, cancer, autoimmune diseases, fibrotic diseases, skin pigmentation, and/or other dermatological disorders. The TRPV4 and/or TRPA1 inhibitor may be a compound according to Formula I:

(I)

wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring. The TRPV4 and/or TRPA1 inhibitor may be at least one compound selected from the following:

GSK205

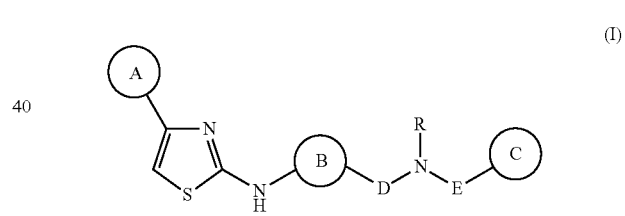

16-18

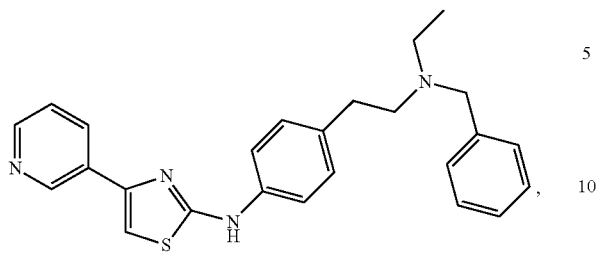

16-8

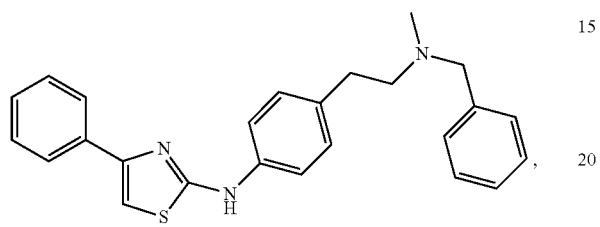

16-12c

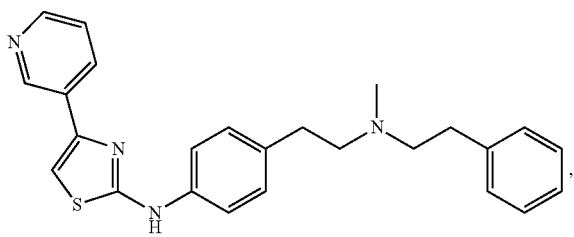

16-13

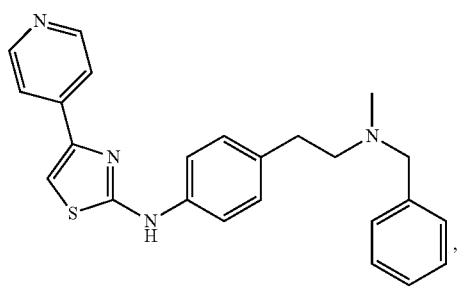

16-14

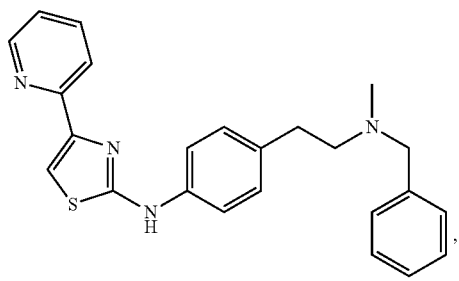

16-16

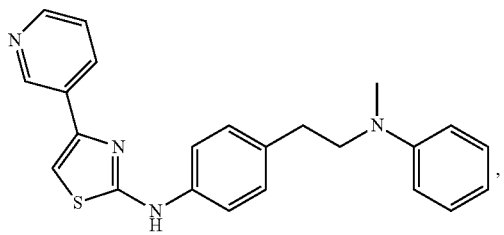

16-8/18hy

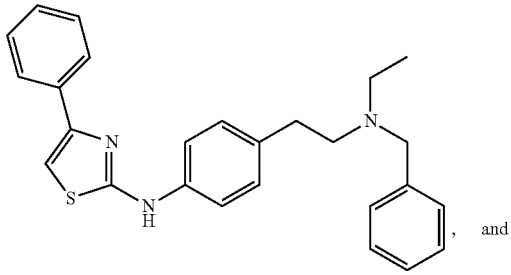

, and 15-43

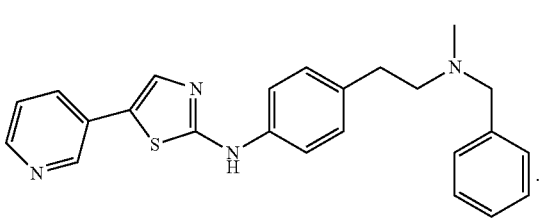

.

In an aspect, the disclosure relates to methods of reducing skin inflammation in a subject in need thereof. The methods may include administering to the subject an effective amount of a TRPV4 and/or TRPA1 inhibitor. The skin inflammation may be related to UVB exposure. The skin inflammation may be associated with a dermatological disorder selected from sunburn, rosacea, Xeroderma pigmentosum, non-melanoma skin cancer, and photoaging, or with a disorder selected from non-UV skin burn, disturbed wound healing, and pain of bone fractures. The method may further include reducing pain in the subject. The TRPV4 and/or TRPA1 inhibitor may be a compound according to Formula I:

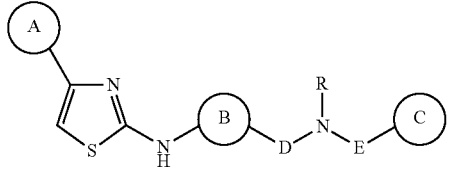

(I)

wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring. The TRPV4 and/or TRPA1 inhibitor may be at least one compound selected from the following:

GSK205

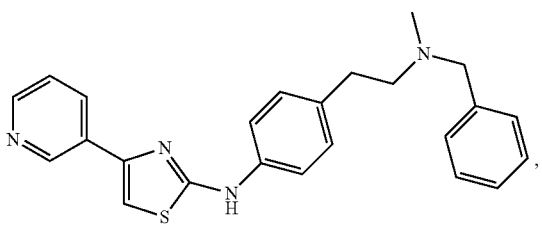

, 16-18

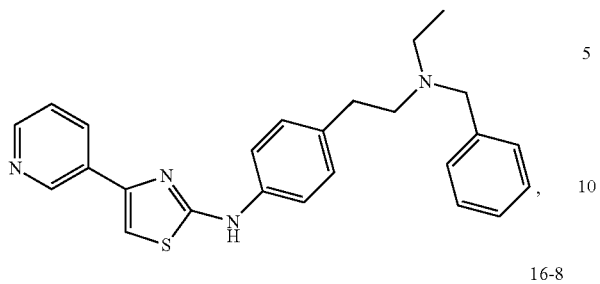

16-8/18hy

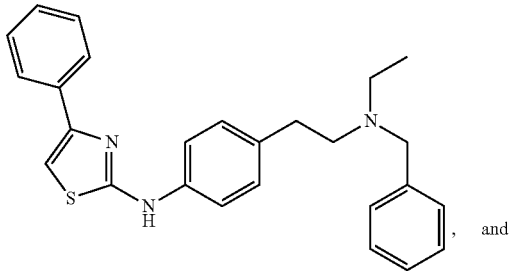
, and 16-8

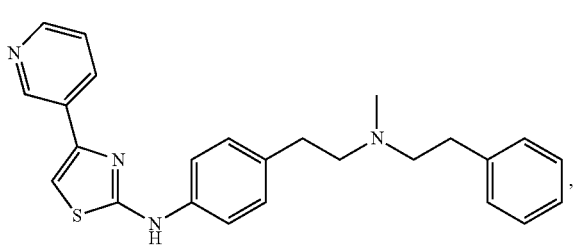
, 15-43

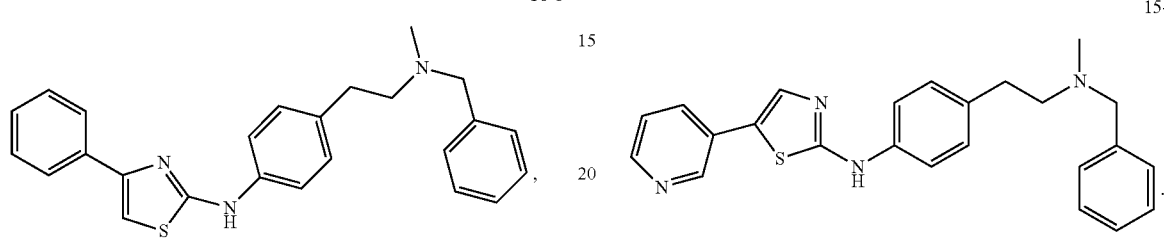
.

16-12c

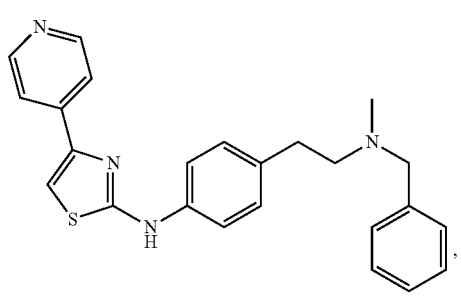
,

In a further aspect, the disclosure relates to methods of pain management. The methods may include administering to at least a portion of the skin of a subject in need thereof an effective amount of a TRPV4 and/or TRPA1 inhibitor. The pain may be associated with a dermatological disorder selected from sunburn, rosacea, Xeroderma pigmentosum, non-melanoma skin cancer, and photoaging, or with a disorder selected from non-UV skin burn, disturbed wound healing, and pain of bone fractures. The method may further include reducing pain in the subject. The TRPV4 and/or TRPA1 inhibitor may be a compound according to Formula I:

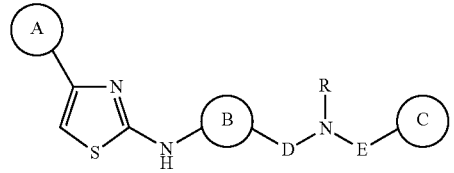

(I)

16-13

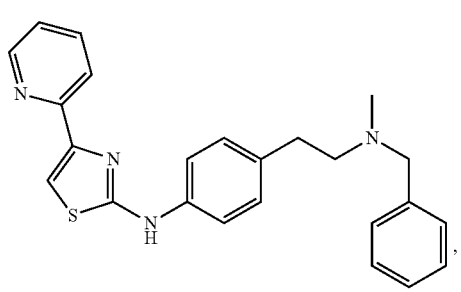
, wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring. The TRPV4 and/or TRPA1 inhibitor may be at least one compound selected from the following:

16-14

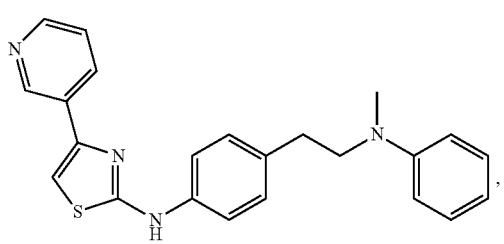
, 16-16

GSK205

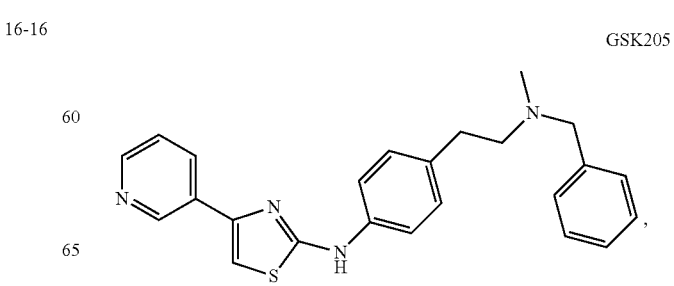
, 16-18

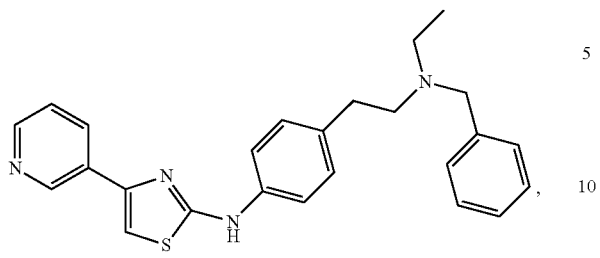

16-8/18hy

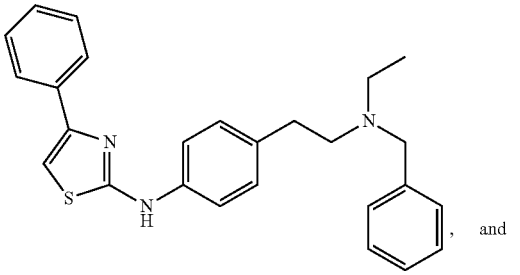
, and 16-8

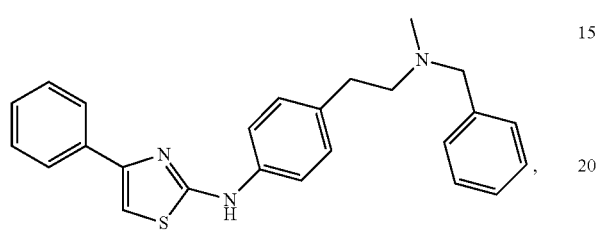
, 15-43

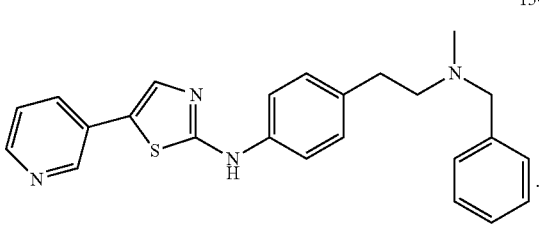
.

16-12c

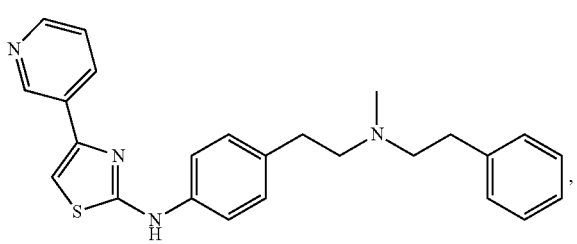
,

Another aspect of the disclosure provides methods of reducing itch in a subject in need thereof. The methods may include administering to the subject an effective amount of a TRPV4 and/or TRPA1 inhibitor.

In a further aspect, the disclosure relates to compositions including a TRPV4 and/or TRPA1 inhibitor compound in combination with a carrier, vehicle, or diluent that is suitable for topical application.

In a further aspect, the disclosure relates to topical formulations including a TRPV4 and/or TRPA1 inhibitor, wherein the TRPV4 and/or TRPA1 inhibitor may be a compound according to Formula I:

16-13

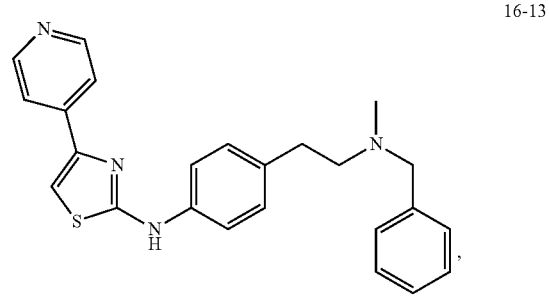
, (I)

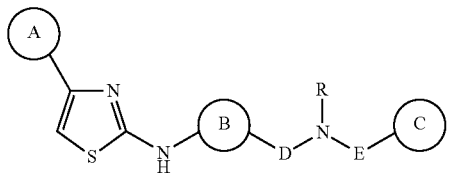

wherein A, B, and C are independently selected from the group consisting of aromatic, heteroaromatic, cycloalkenyl, and heterocycloalkenyl groups; D is $C_1$-$C_3$ alkylene; E is a bond, or $C_1$-$C_2$ alkylene; and R is selected from the group consisting of hydrogen, hydroxyl, amino, alkyl, alkenyl, heteroalkyl, aromatic ring, or heteroaromatic ring. The TRPV4 and/or TRPA1 inhibitor may be at least one compound selected from the following:

16-14

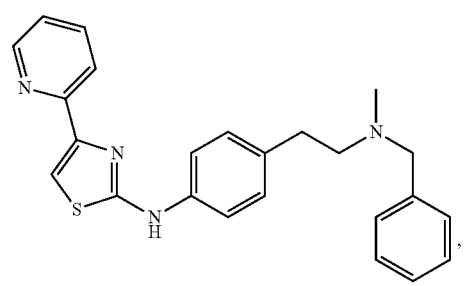
, 16-16

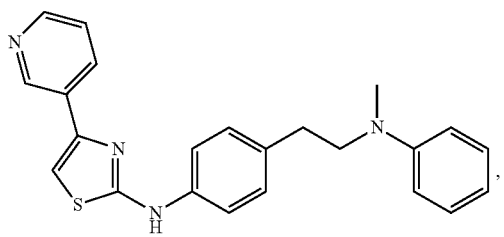
,

GSK205

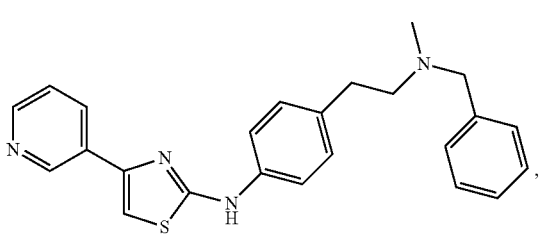
, 16-18
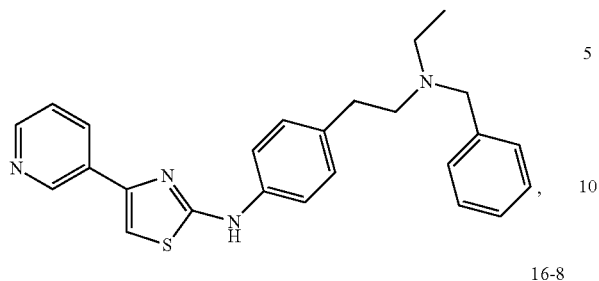
16-8
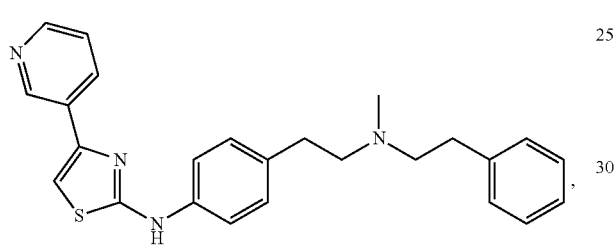
16-12c
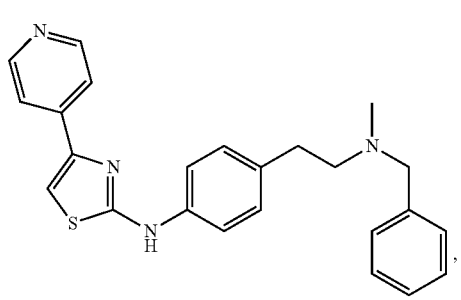
16-13
16-14
16-16
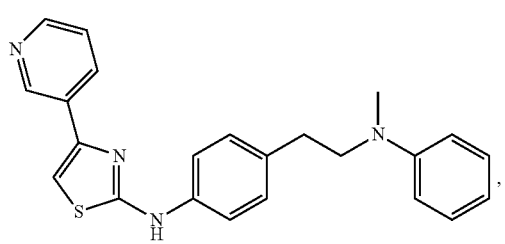
16-8/18hy
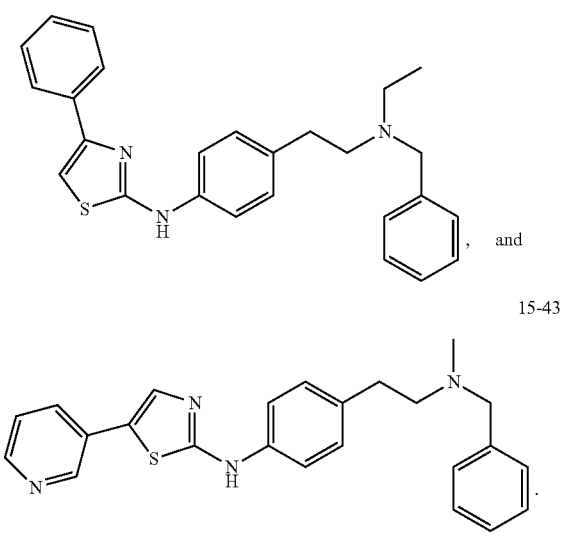
and
15-43
In a further aspect, the disclosure relates to novel TRPV4 and/or TRPA1 inhibitors. The TRPV4 and/or TRPA1 inhibitor may be at least one compound selected from the following:
16-18
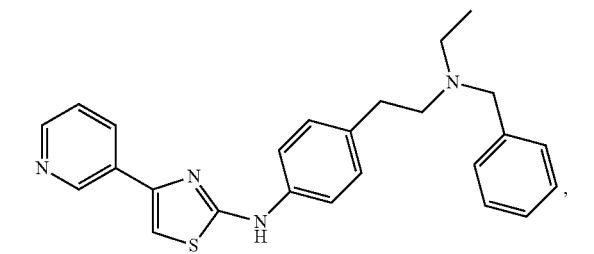
16-8
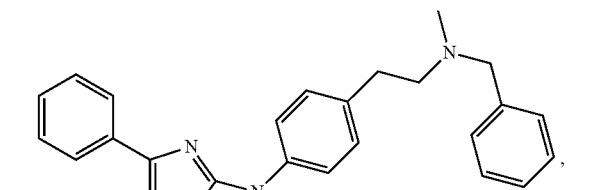
16-12c
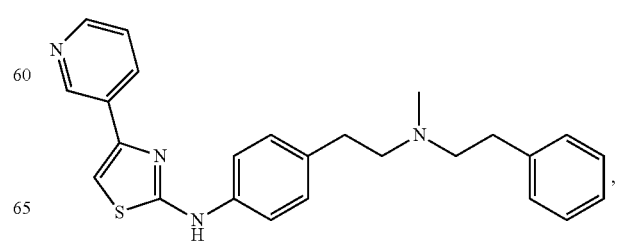

-continued 16-13
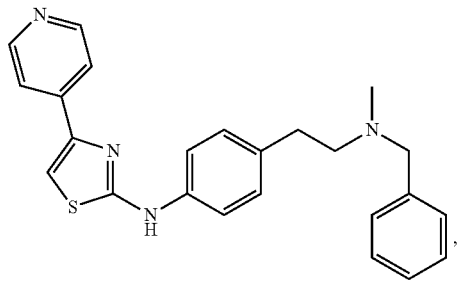, 16-14
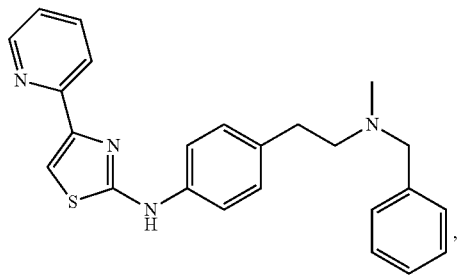, 16-16
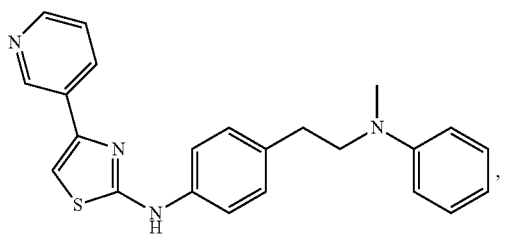, 16-8/18hy

[structure], and 15-43

[structure].

The inhibitors may inhibit TRPV4. The inhibitors may inhibit TRPA1. The inhibitors may inhibit TRPV4 and TRPA1. The TRPA1 inhibitors may not inhibit TRPV1, TRPV2, or TRPV3. The inhibitor may be specific for TRPV4. The inhibitor may be specific for TRPA1. The inhibitor may be specific for TRPV4 and TRPA1.

The disclosure provides for other aspects and embodiments that will be apparent in light of the following detailed description and accompanying Figures.

DETAILED DESCRIPTION

Figure 1:
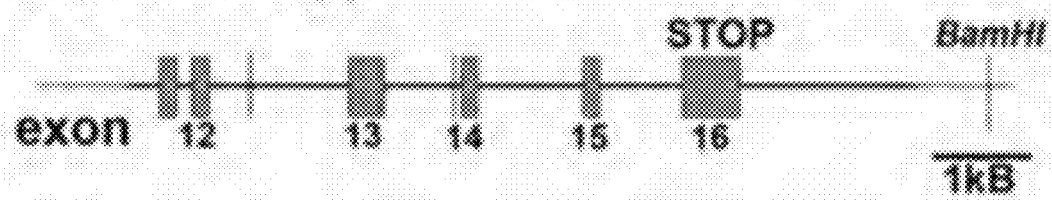
FIG. 1: Keratinocyte-specific and inducible Trpv4 null mouse and its UVB response. (A) Gene-targeting of Trpv4 and genetic manipulation underlying generation of keratinocyte-specific and inducible Trpv4 knockout mice. Shown are sequential steps of mouse Trpv4 targeting, starting with flanking Trvp4 exon13 with loxP elements and insertion of a selection cassette, flanked by frt sites, in mouse embryonic stem cells. After generation of chimeric mice and stable transmission of the engineered mutation, the selection cassette was removed by breeding to FLPe mice. Resulting mice were homozygosed and crossed with K14-CRE-ER$^{tam}$ mice, which then permitted keratinocyte-specific and inducible Trpv4 knockout/knockdown. (B) DNA genotyping. Shown are PCR products of WT, heterozygote and homozygous Trpv4$^{lox/lox}$ mice. Note that the PCR products needed to be digested with PacI, and that all mice were pre-screened to be CRE+ by another genotyping PCR. (C) Co-labeling of mouse skin for keratin-1 and keratin-14 indicate the established pattern for vehicle-induced control mice (upper panel), and a similar pattern for specific TRPV4 knockdown in keratinocytes (lower panel). However, in these animals note a slightly increased expression of K14 in the stratum spinosum, reflecting attenuated TRPV4 expression and thus reduced Ca$^{++}$ influx. K14 is normally down-regulated at the basal-to-suprabasal transition, concomitant with the rise in Ca$^{++}$-signaling and induction of terminal differentiation. (D) TRPV4 protein expression in L5 DRG neurons not different between genotypes. Densitometry of TRPV4 immunohistochemistry in L5 (=foot-pad innervating) DRG neurons (upper panel micrographs), the bar-diagram illustrates the lack of a difference in terms of TRPV4 protein abundance in oil- vs. tam-treated mice, for both base-line and 48 hours after UV exposure, confirming the specificity of TRPV4 knockdown in skin when using K14 as CRE driver. Note the characteristic morphology of decorated cells identifying them as DRG sensory neurons. Note also the different levels of TRPV4 expression in these neurons, as noted previously; n=3 mice/group, ≥50 neurons/mouse. (E) Lack of TRPV4 expression in Merkel cells in foot-pad epidermis. A confocal triple-fluorescent micrograph panel is shown, depicting representative images of immuno-labeled paw-pads from iKO control vs. tamoxifen-induced mice. Note complete knockdown of TRPV4 in this example (red channel). For Merkel cells (green channel), an anti-cytokeratin 8 antibody was used. Note lack of TRPV4 co-labeling in Merkel cells. Blue channel=DAPI. (F) Lack of effect of tamoxifen application in K14-CRE-ER$^{tam}$ mice on UVB behavioral sensitization. Note very similar withdrawal thresholds in (K14-CRE-ER$^{tam}$ X Trpv4$^{lox/+}$) mice (=Trpv4 heterozygotes in keratinocytes when induced with tamoxifen) for noxious mechanical (upper diagram) and thermal (lower diagram) stimulation; n=7 mice per group. Also note the time-course with peak sensitivity at time-point 48 hours. (G) Size distribution of pERK-expressing L5 DRG neurons in oil-treated iKO mice, exposed to UVB. The bar diagram illustrates size prevalence of small and medium-size sensory neurons that express pERK 48 hours after UVB exposure, note absence of larger neurons (>1200 μm$^2$), n=22 neurons.
Figure 1:
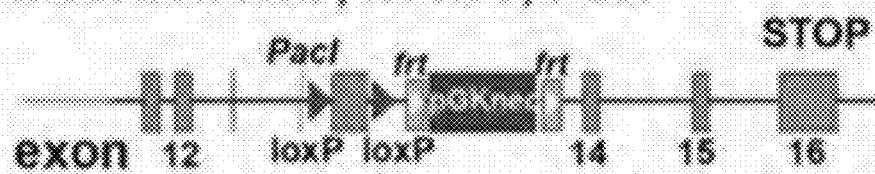
Figure 1:
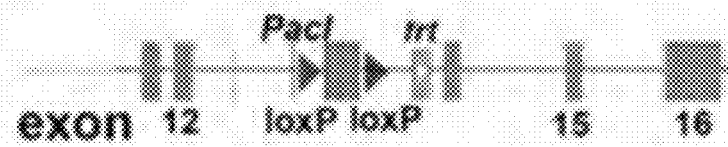
Figure 1:
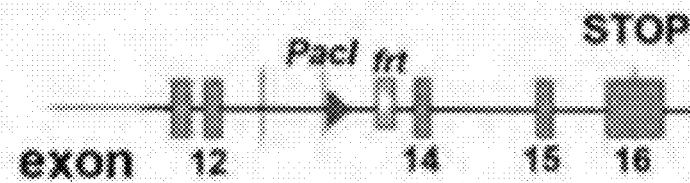
Figure 1:
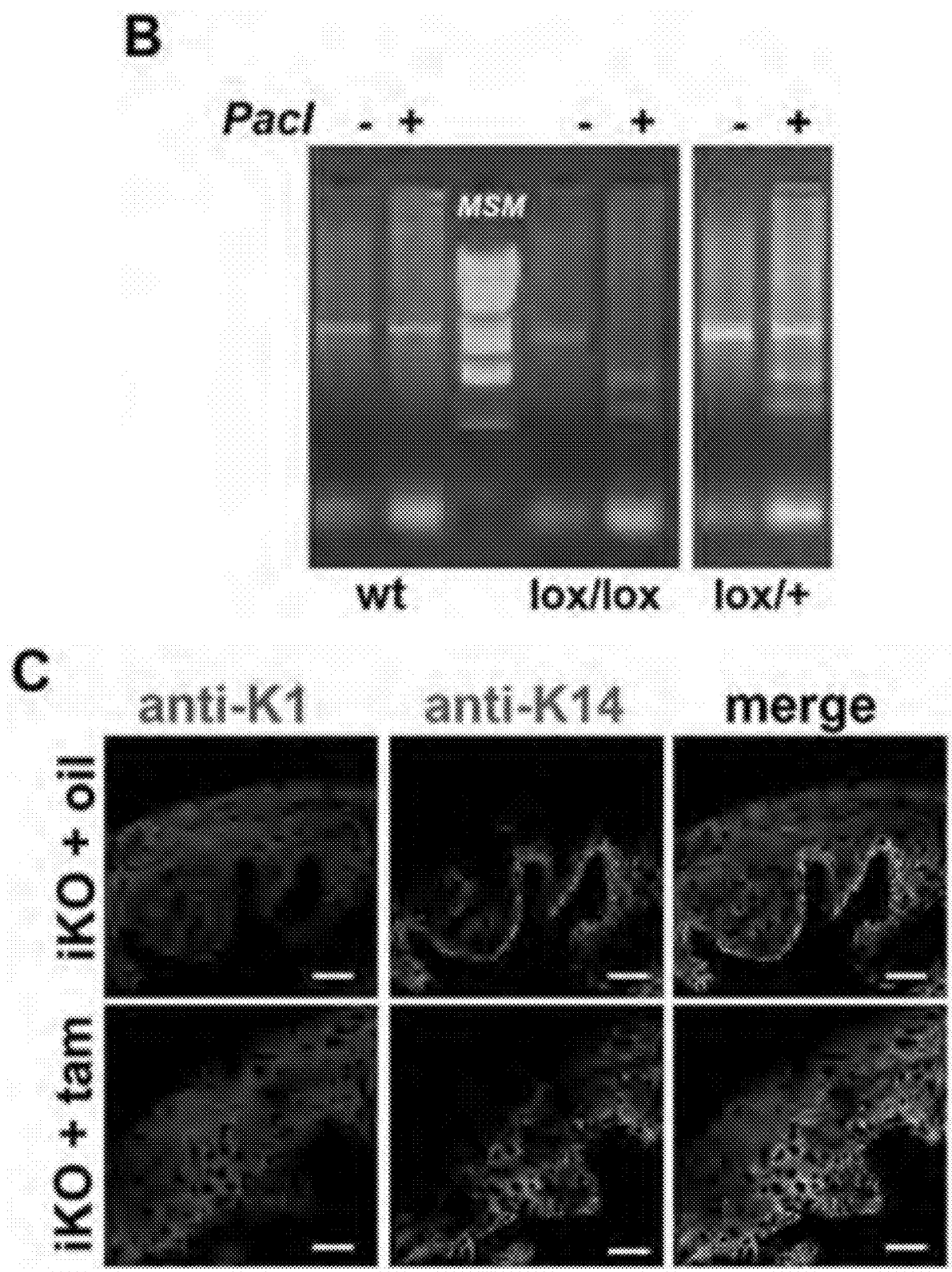
Figure 1:
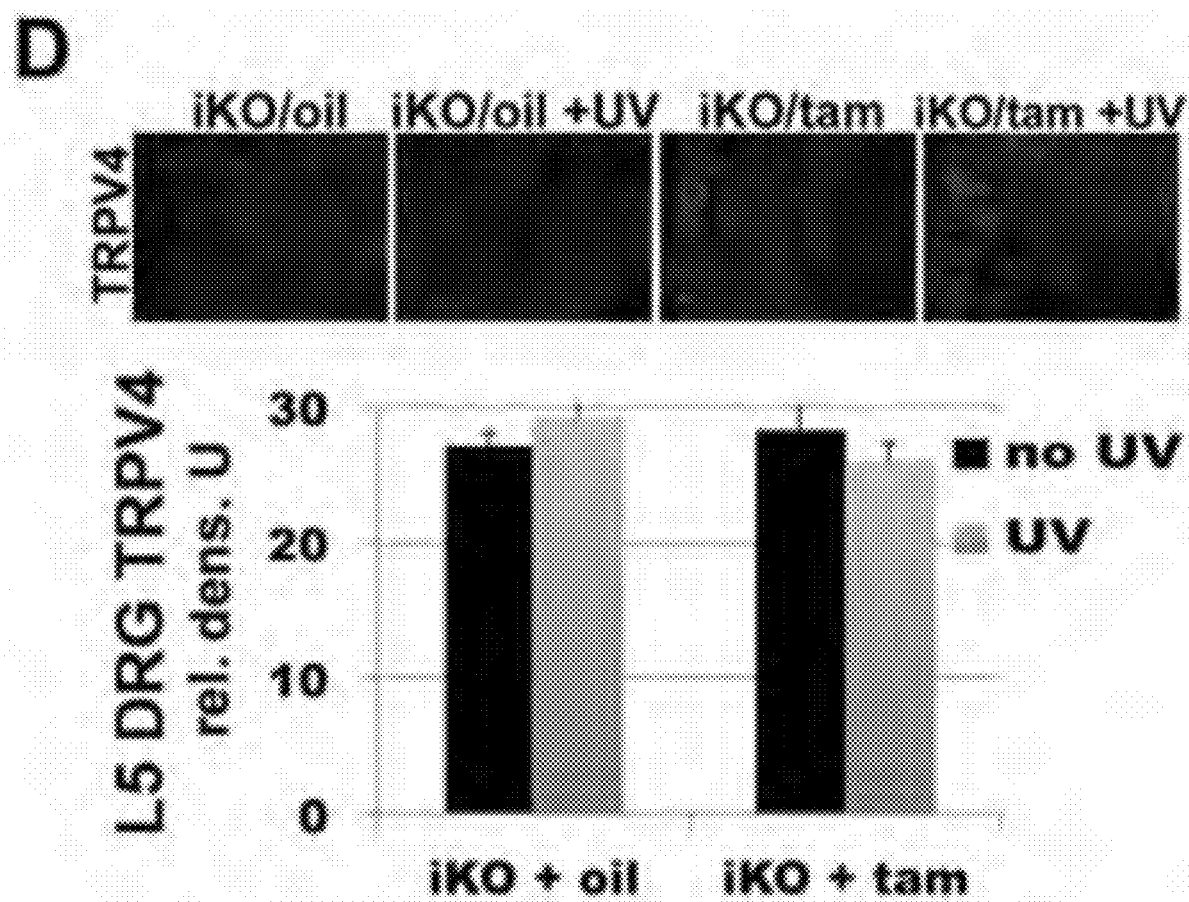
Figure 1:
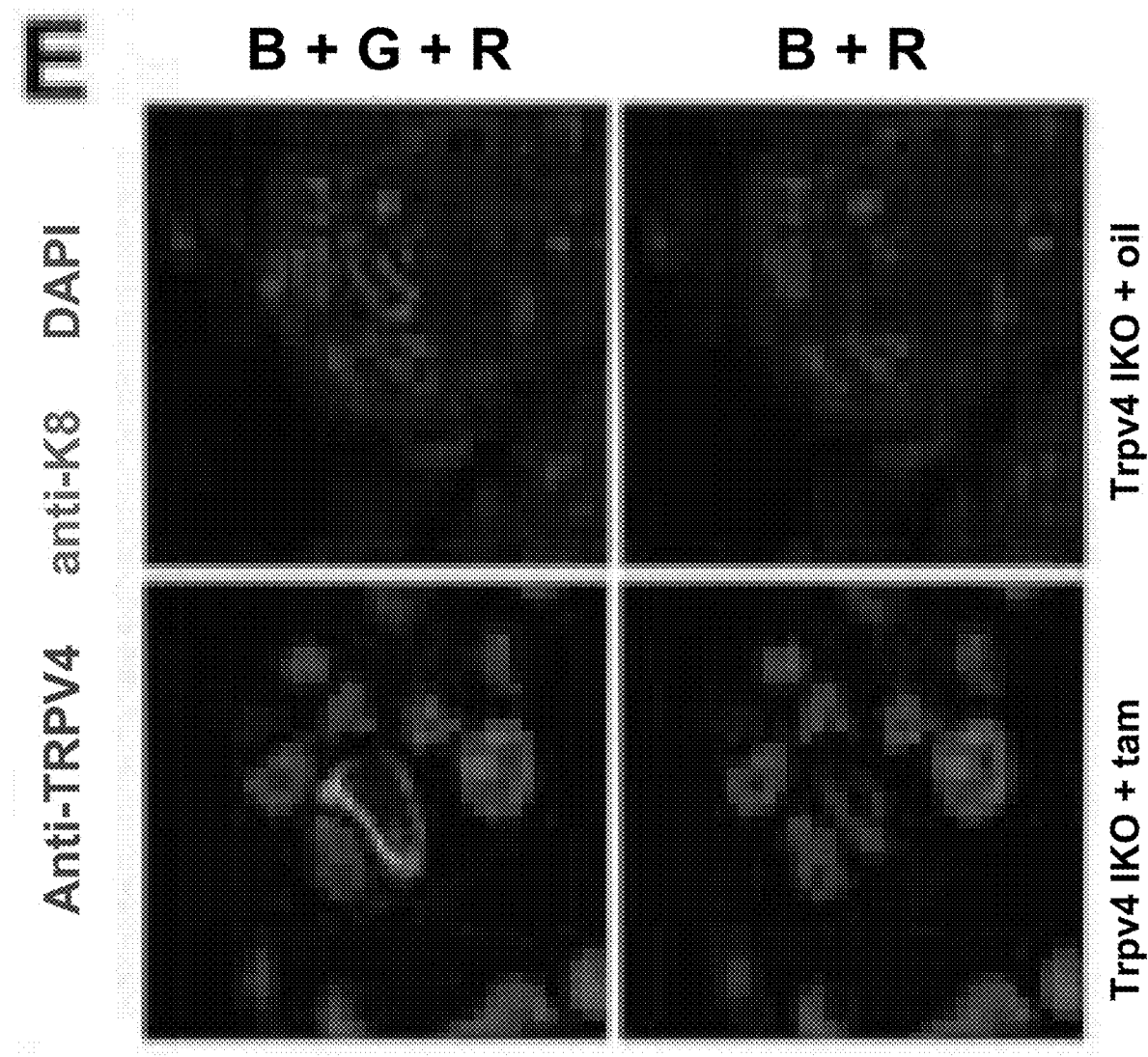
Figure 1:
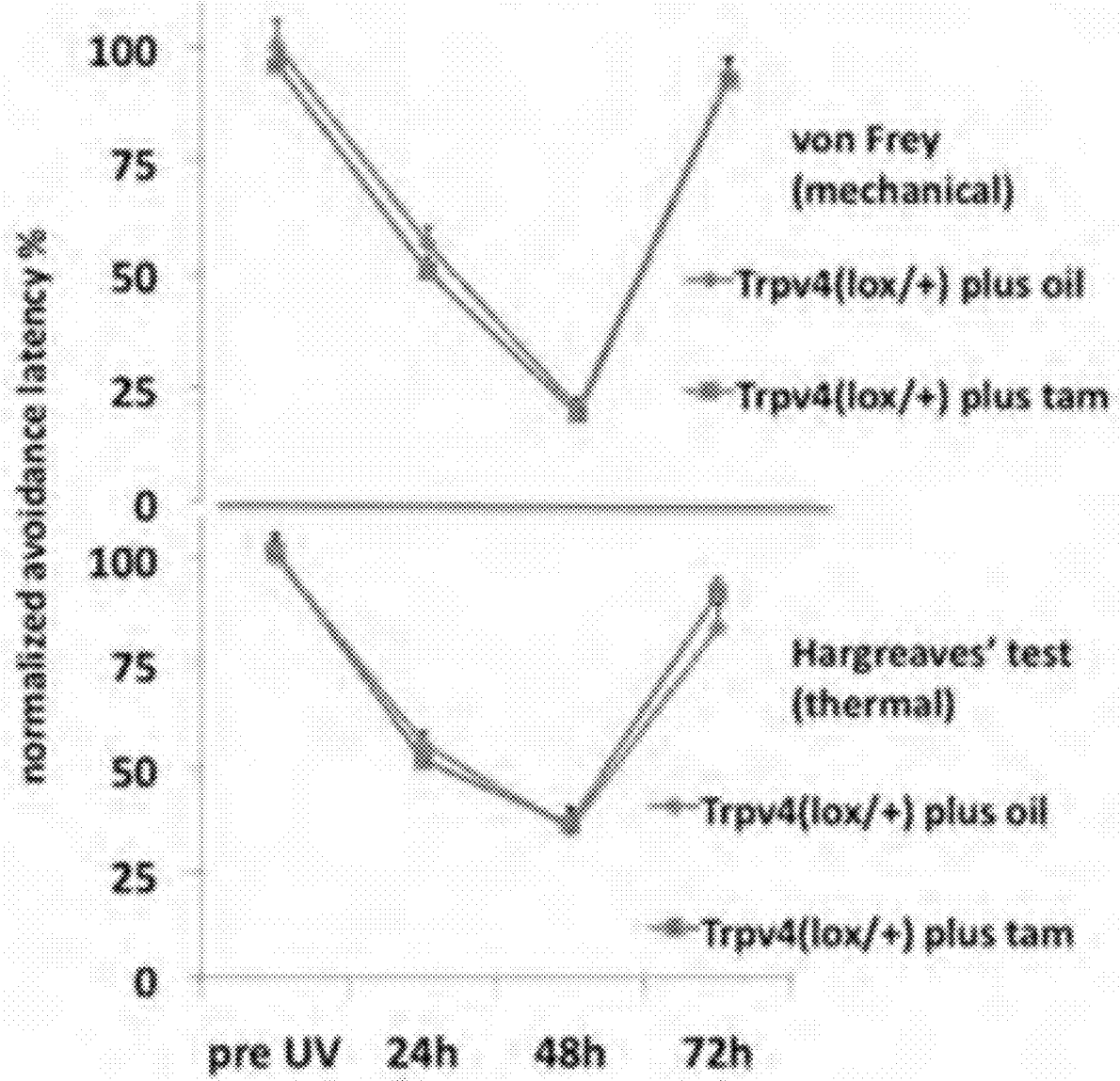
Figure 1:
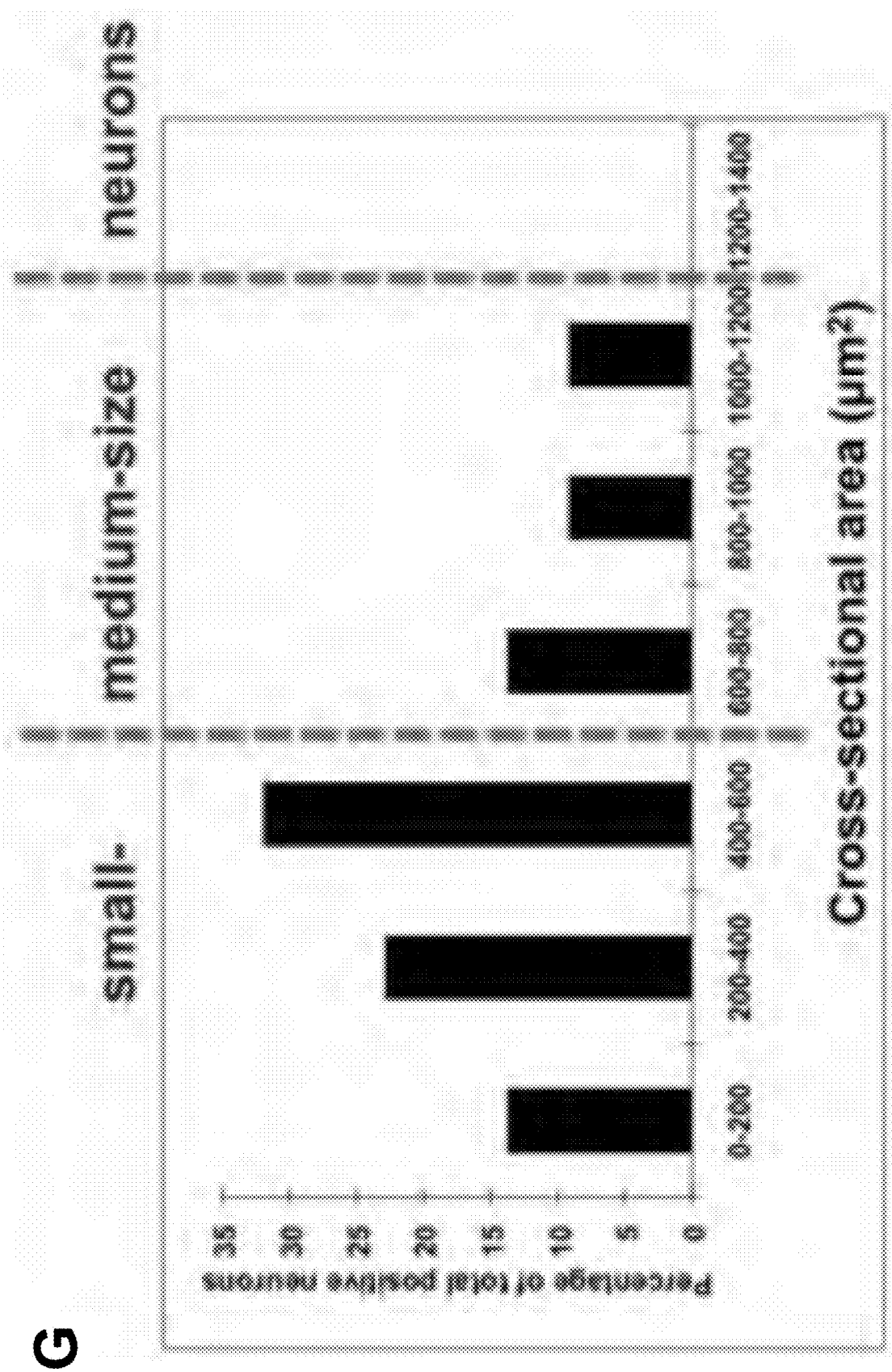

In a broad sense, the disclosure relates to compositions and methods for treating and/or preventing a dermatological disorder. The skin functions as an essential barrier between the external environment and the vertebrate organism. Keratinocytes in the skin absorb UV-light, leading to skin inflammation, pain, and itch after over-exposure, subsequently to skin pigmentation. The inventors have identified that the skin, in particular its epidermal epithelia, is more substantially involved in sensory transduction. For this, the inventors used a mouse model of sunburn in order to induce a state of lowered sensory thresholds evoked by a limited, self-resolving inflammation in response to UV spectrum of light. UV-evoked lowering of sensory thresholds shares major hallmarks of pathological pain, which is another valuable feature of this model.

The compositions and methods disclosed herein relate to the identification and characterization that epidermal keratinocytes function prominently to orchestrate UVB-mediated inflammation and sensitization of peripheral nerve endings in the skin, and in that respect, epidermal keratinocytes have a role similar to a co-sensory cell. Keratinocytes abundantly express the cation channel protein TRPV4, and the inventors have determined that TRPV4, expressed in epidermal keratinocytes, plays a role in UV-induced inflammation and pain and other inflammatory and/or dermatological disorders. The channel exerts its role as a master regulator of UVB-evoked skin inflammation and nociception through Ca++ influx into keratinocytes. This UVB-evoked, TRPV4-mediated Ca++ influx re-programs the keratinocyte to function in a pro-inflammatory and pro-algesic (pro-pain) manner, via TRPV4-dependent secretion of endothelin-1, which may lead to sensation of itch and skin pigmentation. TRPV4 is activated contemporaneously with UVB exposure, which leads to activation of pro-algesic pathways via secreted factors previously demonstrated to have relevance in human pain. As disclosed in further detail herein, mice with inducible Trpv4 deletions targeted to keratinocytes were induced for TRPV4 deletion, subsequently UVB-exposed, and found to be less sensitive to noxious thermal and mechanical stimulation than control mice. Epidermal TRPV4 was identified as a protein involved in the orchestration of UVB-mediated skin inflammation. In mouse skin, UVB-evoked inflammasome activation and increased expression of pro-algesic/algogenic mediators, such as IL1-β, CXCL5, ET-1, and IL-6, were TRPV4-dependent. ET-1 has been shown in humans to not only elicit painful sensations, but to also elicit itch, when injected into the skin. Also, ET-1 has been identified as a melanogen, that is, to increase skin pigmentation by signaling to melanocytes. In primary murine keratinocytes, UVB caused a direct, TRPV4-dependent $Ca^{++}$-response. Moreover, in mice, topical application of a TRPV4-selective inhibitor reduced UVB-evoked epidermal inflammation and pain behavior. Additionally, it was found that epidermal expression of TRPV4, ET1, and IL1β were increased in acute human UV-photodermatitis. The term photodermatitis is used in this application referring to skin inflammation in response to UV radiation/light. This tissue response can include pain, irritation, itch, influx of inflammatory and pain-enhancing cells and tissue injury. The compounds as detailed herein may inhibit TRPA1. The compounds as detailed herein may inhibit TRPV4 and TRPA1. The compounds as disclosed herein may not inhibit TRPV1, TRPV2, or TRPV3. The inhibitor may specific for TRPV4 and TRPA1.

The dermatological disorder may be associated with the TRPA1 or TRPV4 pathway. Dermatological disorders include, but are not limited to, photo-induced inflammation, pain in diseases involving skin pain, itch, cancer, autoimmune diseases, fibrotic diseases, other acneiform or inflammatory skin diseases, and pigmentation disorders. For example, dermatological disorders may include, but are not limited to, sunburn; photoallergic reaction; phototoxic reaction; phytophotodermatitis (Berloque dermatitis); acute and chronic actinic dermatitis; atopic dermatitis exacerbation; all subtypes of rosacea including trigeminal-pain associated rosacea; all lupus erythematosus subtypes (systemic, discoid, subacute); atopic dermatitis; actinic prurigo; prurigo nodularis; prurigo subacuta; prurigo pigmentosa; Lichen simplex (also called neurodermatitis); diabetic pruritus; uremic pruritus; pruritus induced by metabolic (liver) diseases; pruritus induced by malignancies like lymphoma; pruritus induced by polycythemia vera; pruritus induced by scabies; pruritus induced by bullous pemphigoid; pruritus induced by urticaria (especially but not exclusively actinic urticaria); pruritus induced by insect/arachnoid vector bite; pruritus induced by parasitosis; melanoma; non-melanoma skin cancer (BCC, SCC); actinic keratosis and other premalignant skin cancers; mycosis fungoides; Sézary syndrome; Xeroderma pigmentosum; Cockayne syndrome; all lupus erythematosus subtypes (systemic, discoid, subacute); dermatomyositis; erythema multiforme; lichen planus; fibrotic diseases induced by UV-exposure (Rhinophyma, chronic actinic dermatitis, actinic reticuloid, photoaging, hyalinosis cutis et mucosae; polymorph light eruption; Acne aestivalis; all porphyria subforms with implications on photo-induced skin changes (erythropoetic porphyria, erythropoetic protoporphyria, Porphyria variegate); photo-induced Herpes simplex infection (Herpes labialis); morbus Darier; disseminated superficial actinic porokeratosis; pityriasis rubra pilaris; Bloom syndrome; Rothmund-Thomson syndrome; Hartnup syndrome photoaging; wrinkles; photo-induced inflammation; pathologic skin fibrotic response; synovial fibrosis; lung fibrosis; keloid formation; chemical or actinic injury; a pathologic response to skin irradiation ("radio-derm"); psoriasis; chronic atopic dermatitis; chronic UV-dermatitis; scleroderma; conditions characterized by a chronic maladaptive injury response to an ongoing noxious insult to the skin; inappropriate scar formation, pigmentation; and pigmentation disorders.

Methods

In an aspect, the disclosure provides methods of reducing skin inflammation in a subject in need thereof. The methods may comprise administering to the subject an effective amount of a TRPA1 and/or TRPV4 inhibitor. The skin inflammation may be related to UVB exposure.

Skin inflammation may be associated with conditions including, but not limited to, sunburn (acute photodermatitis), photoallergic reaction, phototoxic reaction, phytophotodermatitis (Berloque dermatitis), acute and chronic actinic dermatitis, atopic dermatitis exacerbation, and rosacea.

In other aspects, the disclosure provides methods of pain management. The methods may comprise administering to at least a portion of the skin of a subject in need thereof an effective amount of a TRPA1 and/or TRPV4 inhibitor. The pain may be related to UVB exposure.

Pain may be chronic or acute. Pain may be associated with or result from conditions including, but not limited to, all subtypes of rosacea including trigeminal-pain associated rosacea, reflex sympathetic dystrophy (RSD), and all lupus erythematosus subtypes (systemic, discoid, subacute).

In other aspects, the disclosure provides methods of reducing itch in a subject in need thereof. ET-1 has been shown to elicit itch, and as shown in the Examples, increased expression of ET-1 was TRPV4-dependent. The methods may comprise administering to the subject an effective amount of a TRPA1 and/or TRPV4 inhibitor.

Itch may be chronic or acute. Itch may be associated with or result from conditions including, but not limited to, rosacea, atopic dermatitis, actinic prurigo, prurigo nodularis, prurigo subacuta, prurigo pigmentosa, Lichen simplex (also called neurodermatitis), diabetic pruritus, and uremic pruritus. Itch or pruritus may be associated with or result from conditions including metabolic (liver) diseases, malignancies like lymphoma, polycythemia vera, scabies, bullous pemphigoid, urticaria (especially but not exclusively actinic urticaria), insect/arachnoid vector bite, and parasitosis.

In other aspects, the disclosure provides methods of treating cancer in a subject in need thereof. The methods may comprise administering to the subject an effective amount of a TRPA1 and/or TRPV4 inhibitor.

The cancer and related conditions may include, but are not limited to, melanoma, non-melanoma skin cancer (BCC, SCC), actinic keratosis and other premalignant skin cancers, mycosis fungoides, Sézary syndrome, and Xeroderma pigmentosum.

In other aspects, the disclosure provides methods of treating an autoimmune disease in a subject in need thereof. The methods may comprise administering to the subject an effective amount of a TRPA1 and/or TRPV4 inhibitor.

Autoimmune diseases may include, but are not limited to, all lupus erythematosus subtypes (systemic, discoid, subacute), dermatomyositis, erythema multiforme, and lichen planus.

In other aspects, the disclosure provides methods of treating a fibrotic disease in a subject in need thereof. The methods may comprise administering to the subject an effective amount of a TRPA1 and/or TRPV4 inhibitor.

Fibrotic diseases may include conditions induced by UV-exposure, such as, for example, Rhinophyma, chronic actinic dermatitis, actinic reticuloid, photoaging, and hyalinosis cutis et mucosae. Fibrotic disease may include at least one disorder or condition selected from pathologic skin fibrotic response, synovial fibrosis, and lung fibrosis. Pathologic skin fibrotic response may include at least one disorder or condition selected from skin fibrosis, keloid formation, chemical or actinic injury, a pathologic response to skin irradiation ("radio-derm"), psoriasis, chronic atopic dermatitis, chronic UV-dermatitis, scleroderma, and conditions characterized by a chronic maladaptive injury response to an ongoing noxious insult to the skin or inappropriate scar formation.

As detailed in the Examples, secretion of periostin (93 kDa protein) by keratinocytes in response to histamine exposure is dependent on TRPV4. Periostin was detected in the histamine-stimulated cells, but the protein was not detectable in vehicle-stimulated cultures, and GSK205 completely eliminated secretion of periostin. Periostin has a role in chronic allergic skin inflammation and also pathologic-fibrotic remodeling of the skin. Histamine activates TRPV4 channels via specific activation of histamine H1R-receptors in keratinocytes. This TRPV4-dependent calcium influx regulates release of periostin from keratinocytes. In terms of fibrotic tissue remodeling of organs, TRPV4 channels expressed by fibroblasts may have a role in lung fibrosis evoked by bleomycin, which may relate to fibroblasts elsewhere, including skin fibroblasts and synovial fibroblasts. Inhibitors as detailed herein may potently block TRPV4 activation in keratinocytes and also skin fibroblasts. Based on the above signaling mechanisms, this will attenuate and prevent fibrotic responses in the skin, also chronic skin-remodeling tissue responses mediated by endogenous pathogenetic mediator molecules such as periostin. As for synovia of the joint, one response to joint trauma is development of synovial fibrosis and contracture. Synoviocytes, synovial fibroblasts and infiltrating inflammatory cells may have roles in this maladaptive response, as all of these cells are known to express TRPV4.

In other aspects, the disclosure provides methods of treating other acneiform or inflammatory skin disease in a subject in need thereof. The methods may comprise administering to the subject an effective amount of a TRPA1 and/or TRPV4 inhibitor.

Acneiform or inflammatory skin diseases may include, but are not limited to, polymorph light eruption, Acne aestivalis, photo-induced Herpes simplex infection (Herpes labialis), morbus Darier, disseminated superficial actinic porokeratosis, Pityriasis rubra pilaris, and all porphyria subforms with implications on photo-induced skin changes such as, for example, erythropoetic porphyria, erythropoetic protoporphyria, and Porphyria variegate.

In other aspects, the disclosure provides methods of reducing skin pigmentation in a subject in need thereof. ET-1 has been shown to signal to skin melanocytes and function as a major melanogen (=enhancing skin pigmentation), and as shown in the Examples, increased expression of ET-1 was TRPV4-dependent. The methods may comprise administering to the subject an effective amount of a TRPA1 and/or TRPV4 inhibitor.

Skin inflammation, pain, itch, and/or pigmentation may also be associated with disorders including, but not limited to, Cockayne syndrome, non-UV skin burn less than $3^{rd}$ degree, disturbed wound healing, exposure and pathological response to poison ivy, and pain of bone fractures directly adjacent to the skin such as fractures of the tibia, digits, or skull. For example, one or more of these disorders may be symptomatic of reflex sympathetic dystrophy (RSD).

In other aspects, the disclosure provides methods of preventing dermatological diseases or disorders such as irritation, pain, itch, pruritus, autoimmune diseases, skin cancer (including melanoma, for example, with topical treatment of TRPA1 and/or TRPV4 inhibitor-based UV protection), autoimmune diseases, fibrotic disorders, pigmentation disorders, and others as described above. In some embodiments, the disclosure provides methods of preventing the development and/or exacerbation of Xeroderma pigmentosum, Cockayne syndrome, Bloom syndrome, Rothmund-Thomson syndrome, and Hartnup syndrome.

In other aspects, the disclosure provides methods of treating or preventing cosmetic conditions. For example, the disclosure provides methods of treating or preventing photoaging, wrinkles, photo-induced inflammation, pigmentation, and pigmentation disorders.

TRPA1 and/or TRPV4 Inhibitor

As TRPV4 is a $Ca^{2+}$-permeable, nonselective cation channel, some embodiments provide for a TRPA1 and/or TRPV4 inhibitor that can inhibit the biological function of TRPA1 and/or TRPV4 (e.g., inhibit cation channel activity, inhibit Ca++ transport and/or availability). Other embodiments provide for a TRPA1 and/or TRPV4 inhibitor that may inhibit the expression of mRNA encoding TRPA1 or TRPV4. Some embodiments provide a TRPA1 and/or TRPV4 inhibitor that may inhibit the translation of mRNA encoding TRPA1 or TRPV4 to protein. Thus, a TRPA1 and/or TRPV4 inhibitor may indirectly or directly bind and inhibit the activity of TRPA1 and/or TRPV4 (e.g., binding activity or enzymatic activity), reduce the expression of TRPA1 and/or TRPV4, prevent expression of TRPA1 and/or TRPV4, or inhibit the production of TRPA1 and/or TRPV4 in a cell. Inhibit or inhibiting relates to any measurable reduction or attenuation of amounts or activity, e.g., amounts or activity of TRPA1 and/or TRPV4, such as those disclosed herein.

In some embodiments, a TRPA1 and/or TRPV4 inhibitor can increase the amount of, or the biological activity of a protein that can reduce the activity of TRPA1 and/or TRPV4. Agents capable of increasing the level of such a protein may include any agent capable of increasing protein or mRNA levels or increasing the expression of the protein. In one embodiment, a TRPA1 and/or TRPV4 inhibitor may comprise the protein itself. For example, a TRPA1 and/or TRPV4 inhibitor may include exogenously expressed and isolated protein capable of being delivered to the cells. The protein may be delivered to cells by a variety of methods, including fusion to Tat or VP16 or via a delivery vehicle, such as a liposome, all of which allow delivery of protein-based agents across the cellular membrane. Those of skill in the art will appreciate that other delivery mechanisms for proteins may be used. Alternatively, mRNA expression may be enhanced relative to control cells by contact with a TRPA1 and/or TRPV4 inhibitor. For example, the agent capable of increasing the level of natively expressed protein may include a gene expression activator or de-repressor. As another example, a TRPA1 and/or TRPV4 inhibitor capable of decreasing the level of natively expressed protein may include a gene expression repressor. An agent capable of increasing the level of protein may also include agents that bind to directly or indirectly and increase the effective level of protein, for example, by enhancing the binding or other activity of the protein. The agent capable of decreasing the level of protein may also include agents that bind to directly or indirectly and decrease the effective level of protein, for example, by inhibiting or reducing the binding or other activity of the protein.

The amount or level of expression of a biomolecule (e.g., mRNA or protein) in a cell may be evaluated by any variety of techniques that are known in the art. Thus, inhibit or inhibiting, such as, for example, the level of protein expression (e.g., TRPA1 and/or TRPV4), may be evaluated at either the protein or mRNA level using techniques including, but not limited to, Western blot, ELISA, Northern blot, real time PCR, immunofluorescence, or FACS analysis. For example, the expression level of a protein may be evaluated by immunofluorescence by visualizing cells stained with a fluorescently-labeled protein-specific antibody, Western blot analysis of protein expression, and RT-PCR of protein transcripts. The expression level of TRPA1 and/or TRPV4 may be compared to a control. A control may include comparison to the level of expression in a control cell, such as a non-disease cell or other normal cell. Alternatively a control may include an average range of the level of expression from a population of normal cells. Alternatively, a standard value developed by analyzing the results of a population of cells with known responses to therapies or agents may be used. Those skilled in the art will appreciate that a variety of controls may be used.

A TRPA1 and/or TRPV4 inhibitor may comprise a variety of compounds and compositions and agents. For example, a TRPA1 and/or TRPV4 inhibitor may comprise a compound. A TRPA1 and/or TRPV4 inhibitor may comprise a biological molecule, including nucleic acid molecules, such as a polynucleotide having RNAi activity against TRPA1 and/or TRPV4 or a substrate thereof. In embodiments, the nucleic acid molecules can include decoy RNAs, dsRNAs, miRNAs, siRNAs, nucleic acid aptamers, antisense nucleic acid molecules, and enzymatic nucleic acid molecules that comprise a sequence that is sufficient allow for binding to an encoding nucleic acid sequence and inhibit activity thereof (i.e., are complementary to such encoding nucleic acid sequences). Suitably, an RNAi molecule comprises a sequence that is complementary to at least a portion of a target sequence such that the RNAi can hybridize to the target sequence under physiological or artificially defined (e.g., reaction) conditions. In some embodiments an RNAi molecule comprises a sequence that is complementary such that the molecule can hybridize to a target sequence under moderate or high stringency conditions, which are well known and can be determined by one of skill in the art. In some embodiments an RNAi molecule has complete (100%) complementarity over its entire length to a target sequence. A variety of RNAi molecules are known in the art, and can include chemical modifications, such as modifications to the sugar-phosphate backbone or nucleobase that are known in the art. The modifications may be selected by one of skill in the art to alter activity, binding, immune response, or other properties. In some embodiments, the RNAi can comprise an siRNA having a length from about 18 to about 24 nucleotides.

In some embodiments, the inhibitory nucleic acid molecule can bind to a target nucleic acid sequence under stringent binding conditions. The terms "stringent conditions" or "stringent hybridization conditions" includes reference to conditions under which a polynucleotide will hybridize to its target sequence, to a detectably greater degree than other sequences (e.g., at least 2-fold over background). An example of stringent conditions include those in which hybridization in 50% formamide, 1 M NaCl, 1% SDS at 37° C., and a wash in 0.1×SSC at 60 to 65° C. is performed. Amino acid and polynucleotide identity, homology and/or similarity can be determined using the ClustalW algorithm, MEGALIGN™ (Lasergene, WI). Given a target polynucleotide sequence, for example of TRPA1 and/or TRPV4 or biological substrate thereof, an inhibitory nucleic acid molecule can be designed using motifs and targeted to a region that is anticipated to be effective for inhibitory activity, such as is known in the art.

In other embodiments, a TRPA1 and/or TRPV4 inhibitor comprises an antibody that can specifically bind to a protein such as TRPA1 and/or TRPV4 or a fragment thereof. Embodiments also provide for an antibody that inhibits TRPA1 and/or TRPV4 through specific binding to a TRPA1 and/or TRPV4 substrate molecule. The antibodies can be produced by any method known in the art, such as by immunization with a full-length protein such as TRPA1 and/or TRPV4, or fragments thereof. The antibodies can be polyclonal or monoclonal, and/or may be recombinant antibodies. In embodiments, antibodies that are human antibodies can be prepared, for example, by immunization of transgenic animals capable of producing a human antibody (see, for example, International Patent Application Publication No. WO 93/12227). Monoclonal antibodies (mAbs) can be produced by a variety of techniques, including conventional monoclonal antibody methodology, e.g., the standard somatic cell hybridization technique of Kohler and Milstein, and other techniques, e.g., viral or oncogenic transformation of B-lymphocytes. Animal systems for preparing hybridomas include mouse. Hybridoma production in the mouse is very well established, and immunization protocols and techniques for isolation of immunized splenocytes for fusion are well known in the art. Fusion partners (e.g., murine myeloma cells) and fusion procedures are also known.

Any suitable methods can be used to evaluate a candidate active agent for inhibitory activity toward TRPA1 and/or TRPV4. Such methods can include, for example, in vitro assays, in vitro cell-based assays, ex vivo assays, and in vivo methods. The methods can evaluate binding activity, or an activity downstream of the enzyme of interest. Ex vivo assays may involve treatment of cells with an agent of the invention, followed by detection of changes in transcription levels of certain genes, such as TRPA1 and/or TRPV4 through collection of cellular RNA, conversion to cDNA, and quantification by quantitative real time polymerase chain reaction (RT-QPCR). Additionally, the cell viability or inflammation may be determined after treatment with an agent.

In certain embodiments, the TRPA1 and/or TRPV4 inhibitor is according to Formula I:

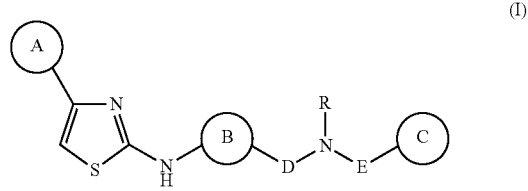

wherein A, B, and C are independently selected from the group consisting of aromatic, heteroaromatic, cycloalkenyl, and heterocycloalkenyl groups;

D is $C_1$-$C_3$ alkylene;

E is a bond, or $C_1$-$C_2$ alkylene; and

R is selected from the group consisting of hydrogen, hydroxyl, amino, alkyl, alkenyl, heteroalkyl, aromatic ring, or heteroaromatic ring. In some embodiments, B and C are independently a phenyl group. In some embodiments, A is phenyl or heteroaryl. In some embodiments, A is pyridnyl. In some embodiments, R is C1-C4 alkyl. In some embodiments, A is heteroaryl, B and C are phenyl, D is ethylene, E is methylene, and R is methyl. In some embodiments, R is ethyl.

In certain embodiments, the TRPA1 and/or TRPV4 inhibitor is the following compound:

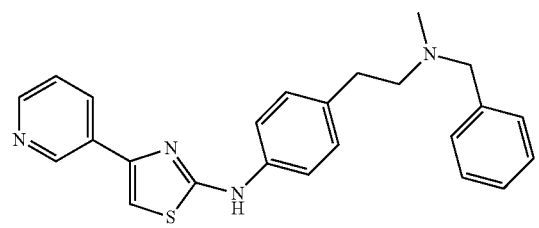

In certain embodiments, the TRPA1 and/or TRPV4 inhibitor excludes the following compound:

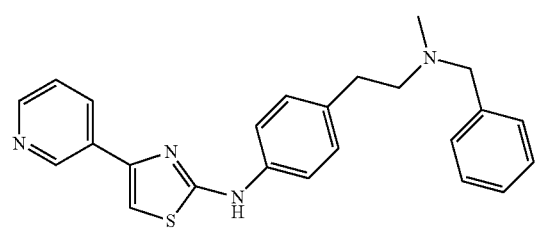

In certain embodiments, the TRPA1 and/or TRPV4 inhibitor is the following compound:

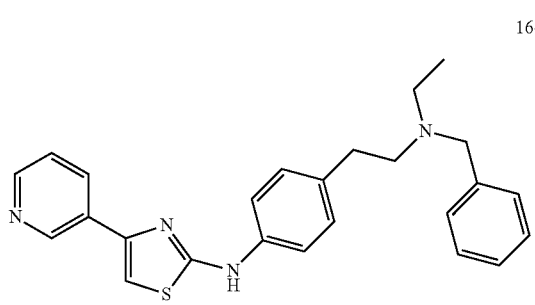

16-18

In certain embodiments, the TRPA1 and/or TRPV4 inhibitor is the following compound:

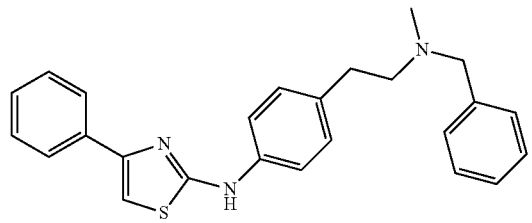

16-18

In certain embodiments, the TRPA1 and/or TRPV4 inhibitor is the following compound:

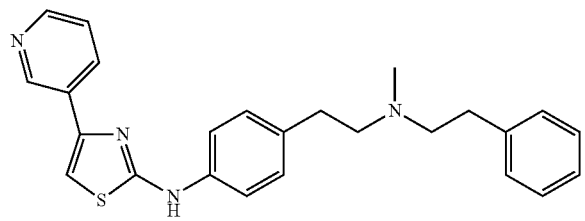

16-12c

In certain embodiments, the TRPA1 and/or TRPV4 inhibitor is the following compound:

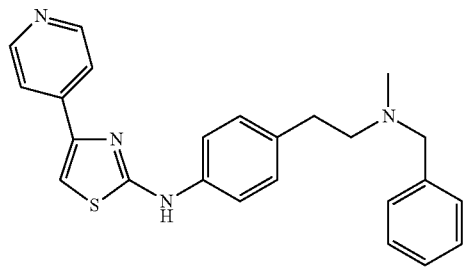

16-13

In certain embodiments, the TRPA1 and/or TRPV4 inhibitor is the following compound:

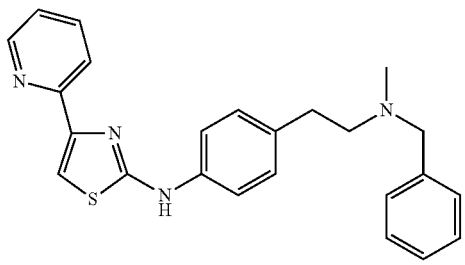

16-14

In certain embodiments, the TRPA1 and/or TRPV4 inhibitor is the following compound:

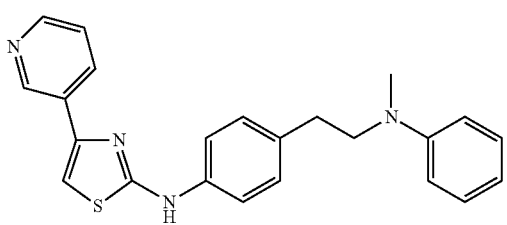

16-16

In certain embodiments, the TRPA1 and/or TRPV4 inhibitor is the following compound:

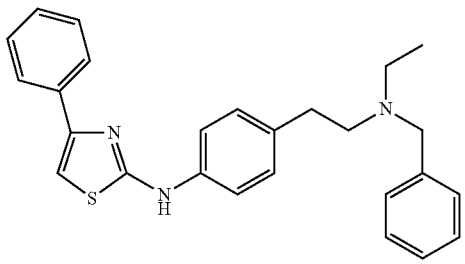

16-8/18hy

In certain embodiments, the TRPA1 and/or TRPV4 inhibitor is the following compound:

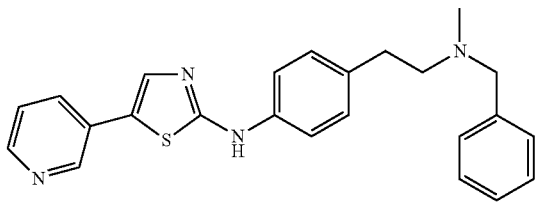

15-43

In some embodiments, the disclosure provides a method of treating a subject wherein the method comprises administering an inhibitor of TRPA1 and/or TRPV4 in a pharmaceutically acceptable composition.

In other aspects, the disclosure provides compositions comprising a TRPA1 and/or TRPV4 inhibitor.

"Administration" or "administering" refers to delivery of a compound or composition by any appropriate route to achieve the desired effect. Administration may include any convenient route of administration, whether systemically/peripherally or at the site of desired action, including but not limited to, oral (e.g. by ingestion); topical (including e.g. transdermal, intranasal, ocular, buccal, and sublingual); pulmonary; respiratory (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. In certain embodiments, administration may be topical. "Co-administered" refers to simultaneous or sequential administration. A compound or composition may be administered before, concurrently with, or after administration of another compound or composition. TRPV4 and/or TRPA1 inhibitors can be applied topically to joints, either with penetration-enhancing delivery vehicles (knee and ankle, finger joints, elbow, temporomandibular joint), or by targeted injection (hip, shoulder, spinal). Topical application may be used for the cornea of the eye to prevent scarring and fibrotic response in this sensitive spot. For prevention of lung fibrosis, e.g. upon treatment with bleomycin, topical application by inhalation of the TRPV4 and/or TRPA1 inhibitors may be used for effective treatment of lung fibrosis.

One skilled in the art can select an appropriate dosage and route of administration depending on the patient, the particular disease, disorder, or condition being treated, the duration of the treatment, concurrent therapies, etc. In certain embodiments, a dosage is selected that balances the effectiveness with the potential side effects, considering the severity of the disease, disorder, or condition (e.g., skin inflammation, pain, or itch).

"Pharmaceutically acceptable" means suitable for use in a human or other mammal. The terms "pharmaceutically acceptable carriers" and "pharmaceutically acceptable excipients" are used interchangeably and refer to substances that are useful for the preparation of a pharmaceutically acceptable composition. In certain embodiments, pharmaceutically acceptable carriers are generally compatible with the other ingredients of the composition, not deleterious to the recipient, and/or neither biologically nor otherwise undesirable.

The composition may comprise the TRPA1 and/or TRPV4 inhibitor in combination with a carrier, vehicle, or diluent. Embodiments provide for pharmaceutically acceptable carriers including, but not limited to, substances useful for topical, intrathecal, ocular, parenteral, intravenous, intraperitoneal intramuscular, sublingual, nasal, and oral administration. Administration may be systemic. "Pharmaceutically acceptable carrier" also includes agents for preparation of aqueous dispersions and sterile powders for injection or dispersions. Examples of pharmaceutically acceptable carriers and excipients are discussed, e.g., in *Remington Pharmaceutical Science,* 16th Ed. Certain exemplary techniques and compositions for making dosage forms are described in the following references: *Modern Pharmaceutics,* Chapters 9 and 10, Banker & Rhodes, eds. (1979); Lieberman et al., *Pharmaceutical Dosage Forms: Tablets* (1981); and Ansel, *Introduction to Pharmaceutical Dosage Forms,* 2nd Ed., (1976). The carrier, vehicle, or diluent may be suitable for topical application.

In certain embodiments, compositions are formulated for topical administration. For compositions suitable for topical administration, the composition may be combined with one or more carriers and used in the form of cosmetic formulations. Formulations may include a foam, cream, gel, lotion, ointment, or solution. For example, a TRPA1 and/or TRPV4 inhibitor may be suitably dissolved in the alcohol of skin disinfectant gel or in lotions, creams, or other formulations. In certain embodiments, a TRPA1 and/or TRPV4 inhibitor may be included in or added to a cosmetic formulation. In certain embodiments, a TRPA1 and/or TRPV4 inhibitor may be included in or added to sun protection topical formulations.

For oral therapeutic administration, the composition may be combined with one or more carriers and used in the form of ingestible tablets, buccal tablets, troches, capsules, elixirs, suspensions, syrups, wafers, chewing gums, foods, and the like. The percentage of the compositions and preparations may, of course, be varied and may conveniently be between about 0.1 to about 100% of the weight of a given unit dosage form. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like.

"Effective amount" refers to a dosage of a compound or composition effective for eliciting a desired effect, commensurate with a reasonable benefit/risk ratio. This term as used herein may also refer to an amount effective at bringing about a desired in vivo effect in an animal, preferably, a human, such as reduction in skin inflammation, reduction in pain, or reduction in itch.

The amount of a TRPA1 and/or TRPV4 inhibitor in such therapeutically useful compositions is such that an effective dosage level will be obtained. The selected dosage level will depend upon a variety of factors including the activity of the particular compound employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

In general, the daily dose contains from about 0.1 mg to about 2000 mg of the active ingredient, or about 0.5 to about 60 mg of the active ingredient. This dosage form permits the full daily dosage to be administered in one or two oral doses. More than once daily or twice daily administrations, e.g., 3, 4, 5, or 6 administrations per day, are also contemplated herein.

In some embodiments, as noted above, administering relates to providing an amount effective at bringing about a desired in vivo effect such as inhibition of TRPA1 and/or TRPV4 in an animal, such as a human. As used herein, a "subject in need of treatment" refers to a subject having been diagnosed with a dermatological disease or disorder associated with skin inflammation, pain, itch, or a combination thereof. A subject may be a mammalian subject. In embodiments a subject can include human and non-human animals. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.). Accordingly, embodiments of the methods described herein relate to treatment of a cell or tissue, a cell or tissue from a subject, or a subject that may be a eukaryote, an animal, a vertebrate animal, a mammal, a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), an ape (e.g., gorilla, chimpanzee, orangutan, gibbon), or a human.

In other aspects, the disclosure provides a transgenic mouse whose genome comprises deletions of the Trpv4 gene in keratinocytes of the epidermis. The transgenic mouse may be a knockout for the Trpv4 gene in keratinocytes of the epidermis following keratinocyte-specific activation and expression of a site-specific recombination enzyme. Knockout of the Trpv4 gene may be carried out by any suitable means known in the art. For example, the transgenic mouse may be generated by Keratin-14 promoter expression of a site-specific recombination enzyme. Site-specific recombination enzymes may include CRE recombinase. The site-specific recombination enzyme may be fused to a mutated estrogen receptor. An anti-estrogen may have increased affinity to the mutated estrogen receptor relative to wild-type estrogen. The anti-estrogen may comprise tamoxifen. In some embodiments, addition of the anti-estrogen to the transgenic mouse drives the site-specific recombination enzyme to the nucleus and results in knockdown of expression of the Trpv4 gene. As such, the keratinocyte-specific deletion of the Trpv4 gene may be induced by applying an anti-estrogen. In some embodiments, deletion of the Trpv4 gene can be specifically and conditionally induced in keratinocytes of the epidermis. In some embodiments, deletion of the Trpv4 gene may be achieved by expression of a constitutively active or inducible recombination enzyme in keratinocytes of the epidermis. In some embodiments, the transgenic mouse may exhibit reduced expression relative to a control of at least one of IL6, ET1, caspase1, IL1β, and CXCL5, or a combination thereof, in response to UVB exposure.

In a further aspect, the disclosure provides methods for identifying a selective inhibitor of TRPA1 and/or TRPV4. The methods may include (a) contacting a mouse with a test compound; (b) determining a biological activity of TRPA1 and/or TRPV4 after contacting with the test compound; and (c) determining a control level of biological activity of TRPA1 and/or TRPV4 in the absence of the test compound; (d) comparing the biological activity of TRPA1 and/or TRPV4 from step (b) with the biological activity of TRPA1 and/or TRPV4 from a model of TRPV4 deletion, wherein the model of TRPV4 deletion includes the transgenic mouse as disclosed herein or a pan-null Trpv4−/− mouse; and (e) identifying the test compound as a selective inhibitor of TRPA1 and/or TRPV4 when at least one of (i) the TRPA1 and/or TRPV4 biological activity is lower in the presence of the test compound than the TRPA1 and/or TRPV4 biological activity in the absence of the test compound; (ii) the TRPA1 and/or TRPV4 biological activity in the presence of the test compound is about the same as, or lower than, the TRPA1 and/or TRPV4 biological activity in the model of TRPV4 deletion; or (iii) any combination of (i) and (ii).

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including but not limited to") unless otherwise noted. All methods described herein can be performed in any suitable order unless otherwise indicated herein or otherwise clearly contradicted by context. The use of any and all examples, or exemplary language (e.g., "such as") provided herein, is intended merely to illustrate aspects and embodiments of the disclosure and does not limit the scope of the claims.

EXAMPLES

Example 1

Materials and Methods

Animals.

The Trpv4 genomic locus was engineered so that loxP sites surrounded exon13 which encodes TM5-6. This mutation was propagated in mice which were crossed to K14-CRE-ERtam mice, so that ((Trpv4lox/lox)X(K14-CRE-ERtam))-mice could be induced by tamoxifen administration via oral gavage for 5 consecutive days at 6 mg/day in 0.3 mL cornoil, at age 2-4 months of age, plus a one-time booster two weeks after the last application. Male and female mice were induced equally. Efficiency of knockdown was verified by qRT-PCR for Trpv4 using primers sense 5'-CCTGCTGGTCACCTACATCA (SEQ ID NO: 1) and antisense 5'-CTCAGGAACACAGGGAAGGA (SEQ ID NO: 2), with the former primer located in exon 13. All animal experimentation described here was conducted in full compliance with NIH and Duke University internal guidelines, and under a valid IACUC protocol.

Using the same genomic clone that was used for generating the Trpv4−/− pan-null mouse, the Trpv4 targeting construct was electroporated into mouse ES cells (C57BL6 background), and orthotopic integration was verified by PCR and Southern blot. The engineered mutation was introduced into the germline by mating of chimeric mice with C57BL6 WT mice. The selection marker was deleted by FLPemediated excision of the frt-pGK-neo-frt cassette in FLPe deleter mice. Genotyping was accomplished by PCR and subsequent PacI digest (FIG. 1B).

Behavioral Assessment of Withdrawal Thresholds.

Behavioral tests were performed to evaluate the decrease in withdrawal thresholds in response to mechanical von Frey hair or thermal stimuli applied to hind paws. Tests were conducted. These withdrawal thresholds were ascertained before and after UV exposure. Mice were exposed using a Bio Rad Gel Doc 2000 UV transilluminator (302 nm) for 5 minutes with an exposure of 600 mJ/cm$^2$, 3-5 days after the last application of tamoxifen/oil.

Paw Interstitial Fluid Analysis.

48 hours after UV exposure, each animal received an intraplantar injection of 10 μL PBS directly posteuthanasia.

The interstitial fluid was immediately collected and analyzed by ELISA (Biorad) for presence of IL-1β.

In-Vivo Topical Interventions.

ET1 injections: After determining base-line withdrawal thresholds, each animal received an intraplantar injection of 10 µL 100 nM ET-1 plus contralateral vehicle. Thresholds were again evaluated 1 hour after injection.

GSK205 Topical Treatment:

A viscous solution of 68% EtOH/5% glycerol plus 1 mM or 5 mM GSK205 (none for control) was applied to hindpaws by rubbing in 20 µL, applied at time-points 1 hour and again 10 min before UV exposure.

Formalin-Induced Nocifensive Behavior:

4% formalin was injected into the right hindpaw. Mice were then videotaped for 50 mins and behavior analyzed by blinded observers.

Mouse Tissue Processing for 1 µm Semithin Sections and EM.

Samples were processed and subjected to EM.

Mouse and Human Tissue Processing for Immunohistochemistry.

Routine procedures were followed, and human tissue was processed under institutional review-board approval (UCSF).

Primary Mouse Keratinocyte Cell Culture.

Primary mouse keratinocytes were derived from back skin of newborn mice.

Analysis of IL-1β Secreted by Cultured Keratinocytes after UV Exposure.

Before UV irradiation, culture media was replaced with PBS. The cells were then irradiated at a dose of 50 $mJ/cm^2$ with UVB. 24 hours later, supernatants were assayed using IL-1β ELISA (R&D Systems, Minneapolis, Minn.).

Ca++ Imaging of Cultured Keratinocytes.

Ca++ imaging of 1° MK was conducted following routine procedures. For UVB stimulation, a customized device was built. The system comprised a printed circuit board for electrical interconnects and mechanical support and an ultraviolet light-emitting diode (UV LED). Customized provisions at the cellular end included a quartz coverslip as the bottom of the cell culture dish plus a thermal equilibration stage (HW-101 Dagan Corporation), fitted to an Olympus BX61 upright microscope. The UV LED was a III-nitride-based type (UVTOP-295 BL; Sensor Electronic Technology).

Figure 2:
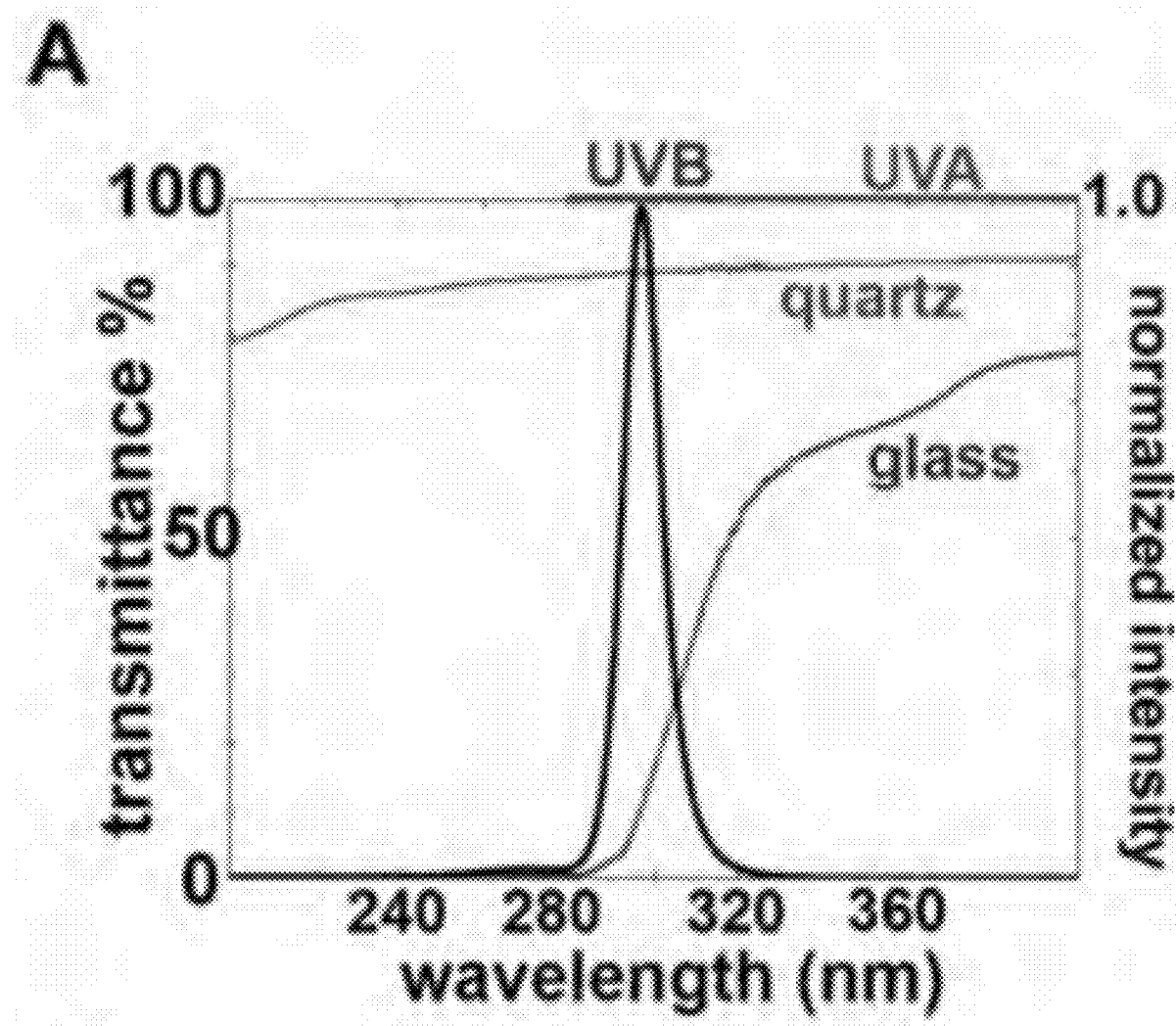
FIG. 2: UVB stimulation device and UVB keratinocyte control experiments. (A) UV spectrum emitted by the LEDs, overlapped with the spectrum of quartz (red trace), which is almost fully permeable to UVB, and glass (blue trace), which has a very low UVB permeability. (B) Focusing properties of the ball lens. (C) Focal geometry of the combination of UV-LED and ball lens. (D) Absence of thermal effects of the UV-LEDs; measurement of temperature in the focal point over time. (E) TRPV3 activation experiment. Induction of a Ca++ transient by camphor, which can be blocked effectively by 10 µM IPP, suggesting TRPV3-mediated signaling. (F) TRPV4 selective activator GSK101-related findings. Ca++ transient in 1° MK in response to 5 nM GSK101, which can be completely blocked by 20 µM GSK205, suggesting it is specifically mediated by TRPV4. The GSK101-response can also be eliminated by absence of external Ca++, in keeping with TRPV4 signaling. (G) TRPV4 is sufficient for the UVB-Ca++ response—HEK293T cell heterologous transfection. Directed expression of TRPV4 in HEK293T cells leads to a Ca++-transient in response to UVB radiation, which is greatly reduced in control-transfected cells. Preexposure to 20 µM GSK205 virtually eliminates the Ca++-signal in TRPV4-transfected cells, and eliminates the moderate signal of control-transfected cells.
Figure 2:
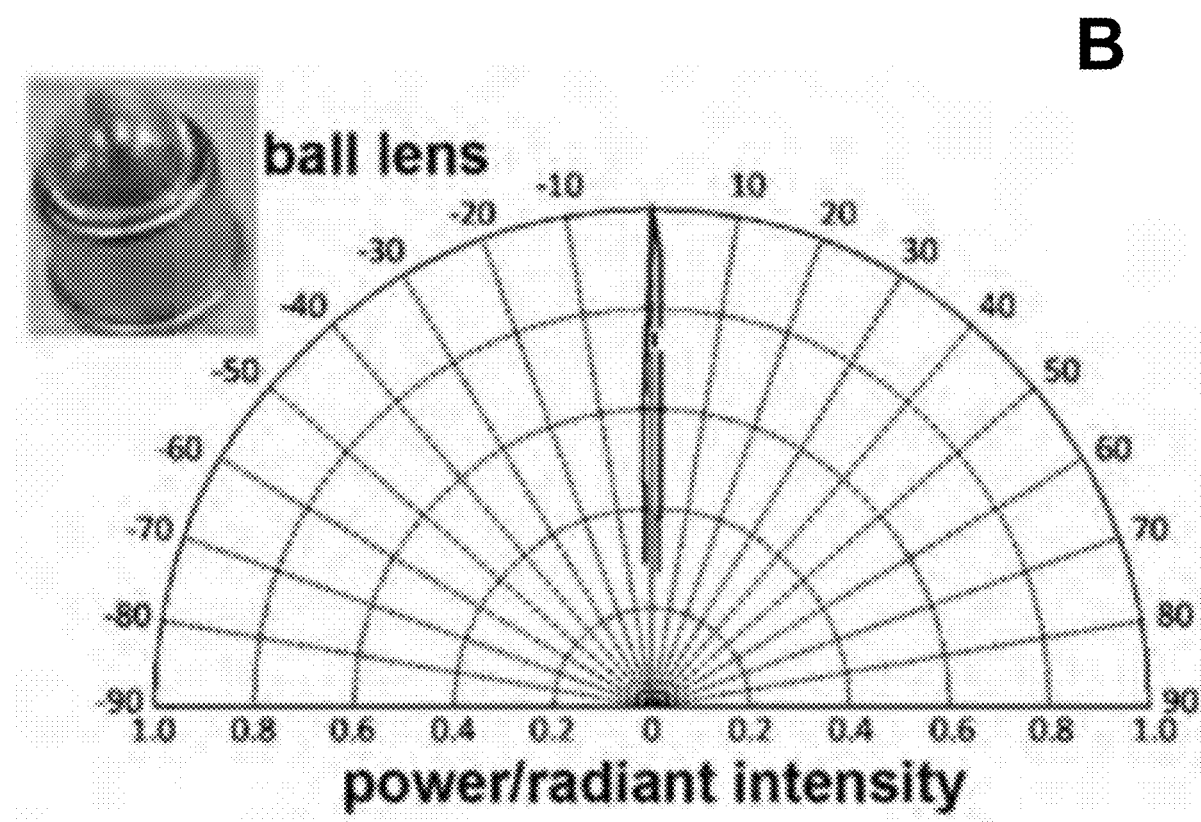
Figure 2:
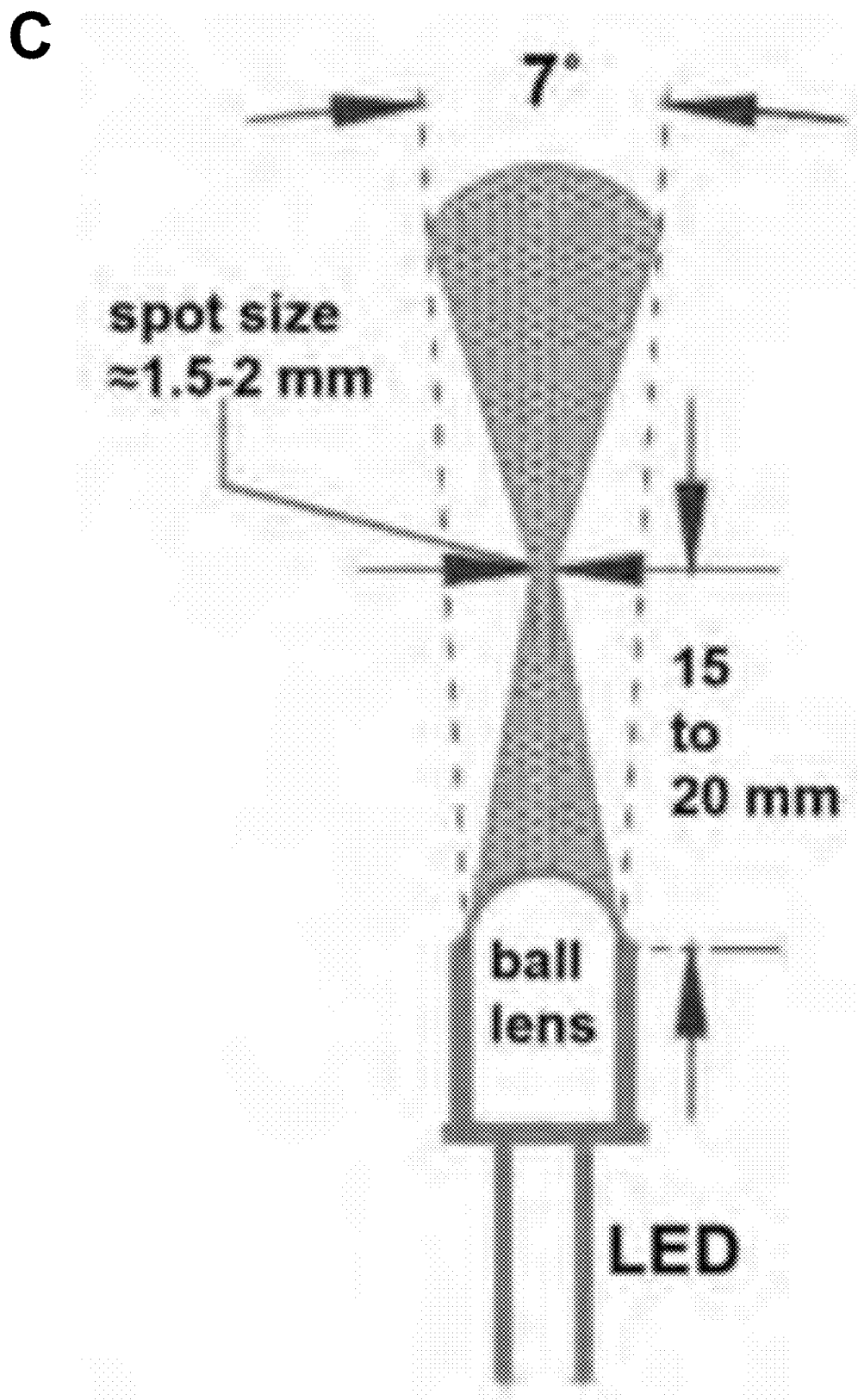
Figure 2:
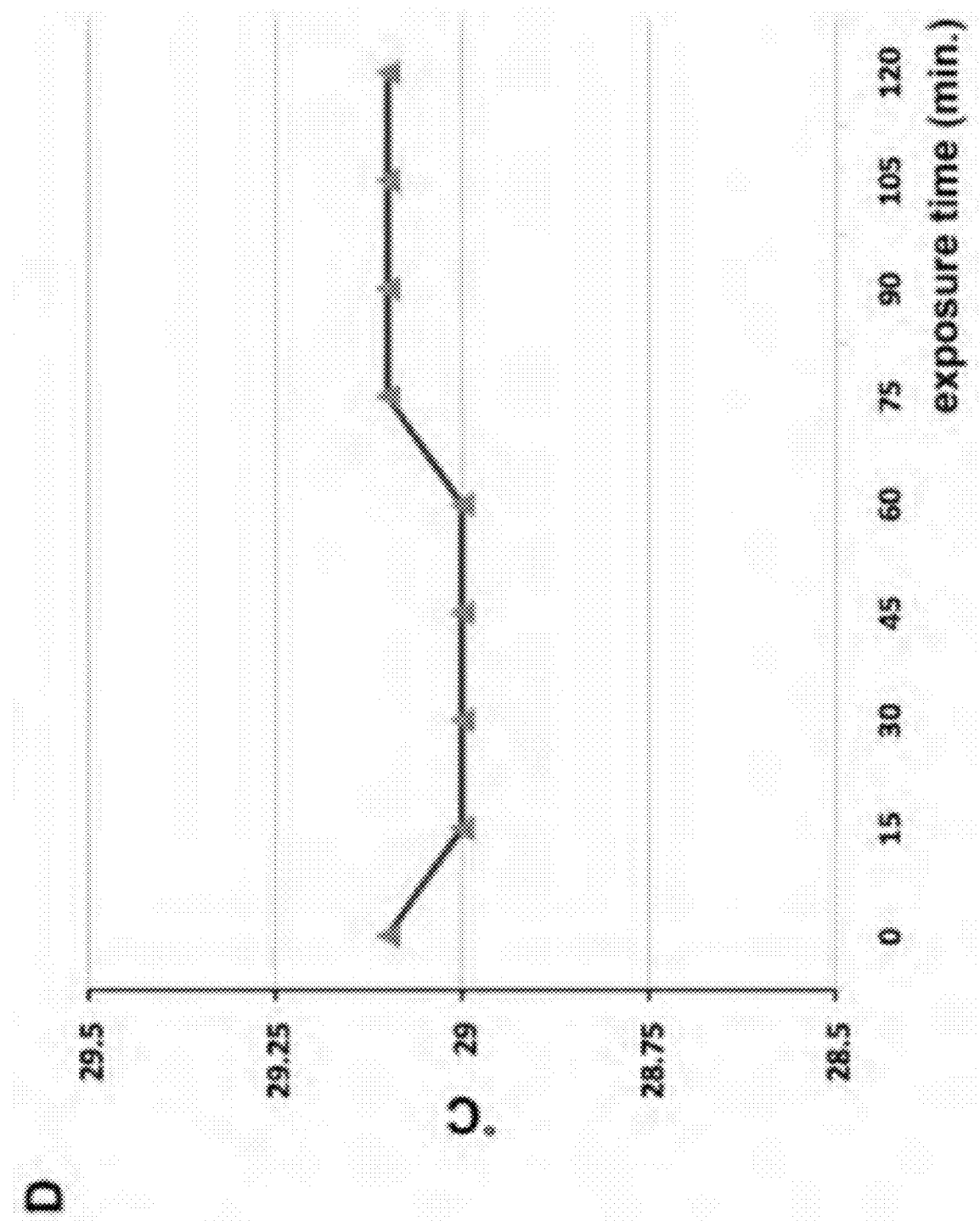
Figure 2:
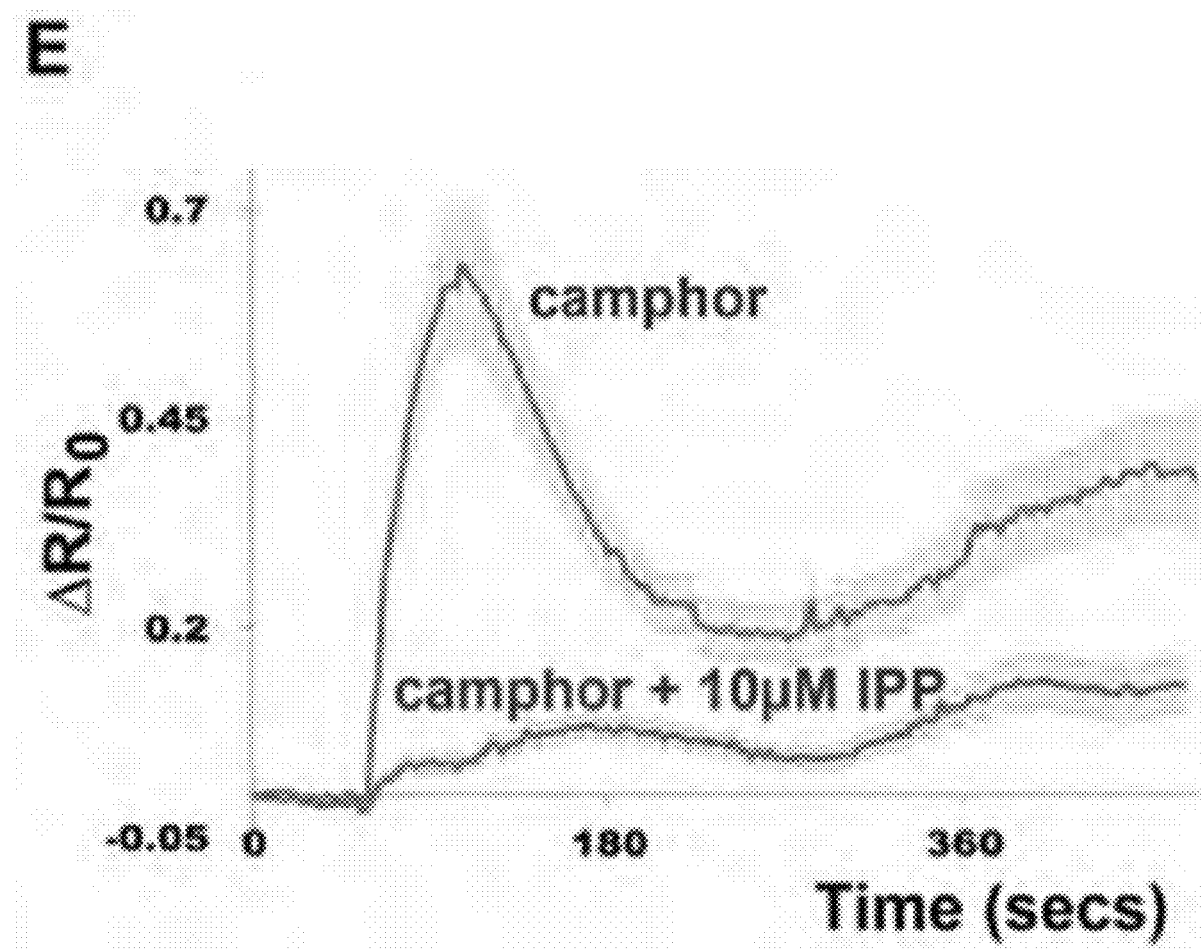
Figure 2:
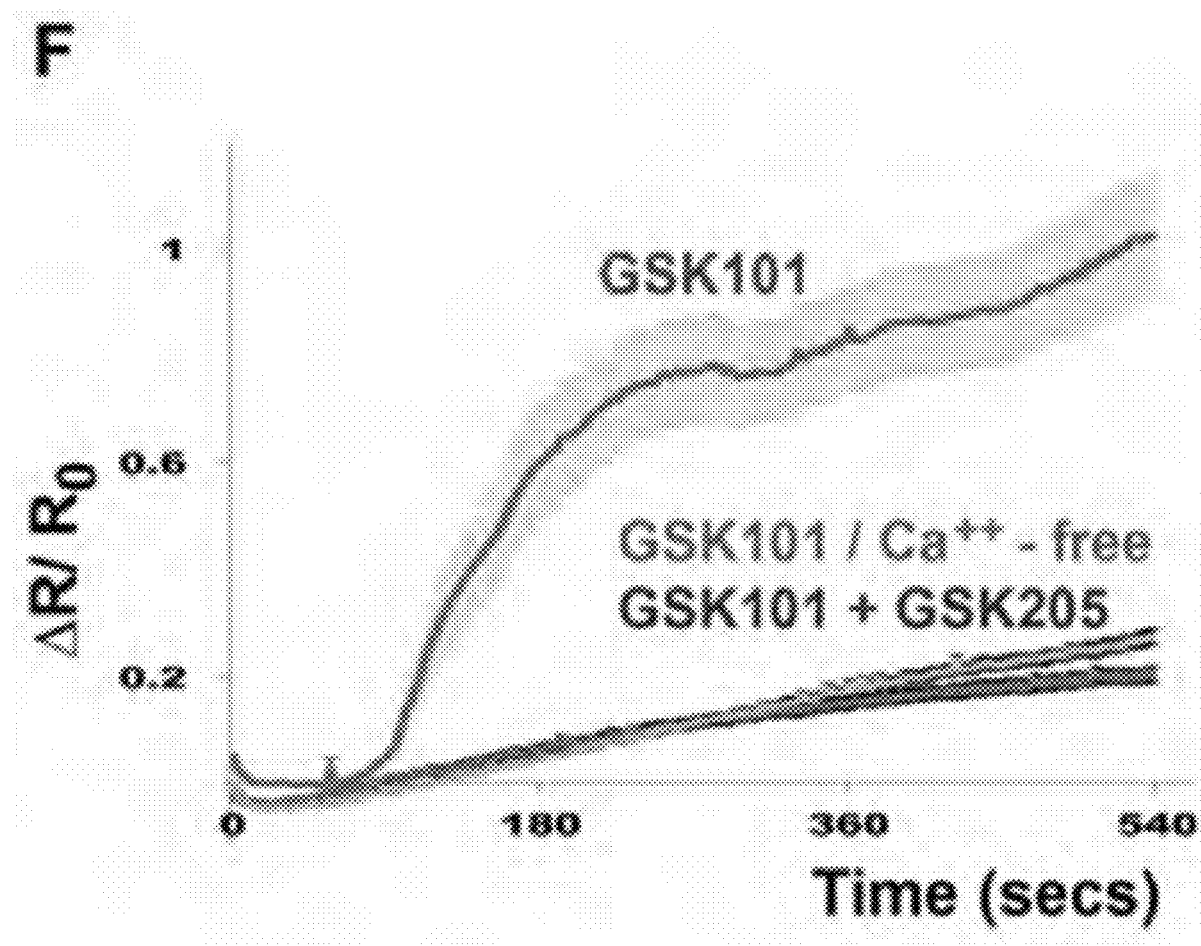
Figure 2:
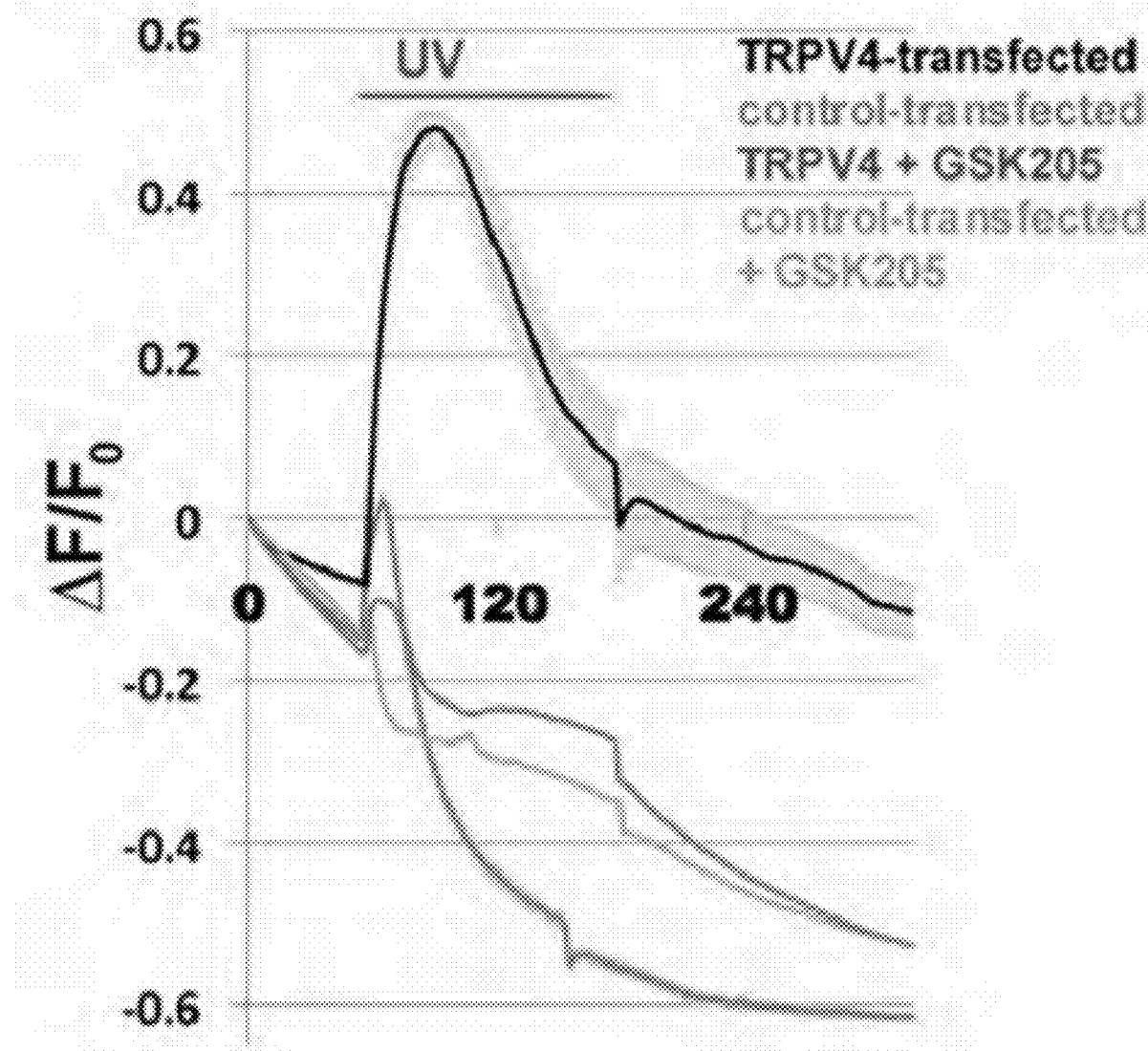

The operating wavelength was 295 nm (FIG. 2A), with a full-width half-max of 12 nm. The optical power was 500 mW. The focal point was aimed at the plane of the upper surface of the quartz coverslip, which was used to minimize UV absorption along the optical path towards the cells (FIG. 2A-C). The optical intensity at the focal point was estimated to be 150 $mW/mm^2$.

Keratinocyte UV Irradiation Using 295 nm LED and Immunocytochemistry.

1° MK were exposed to UVB using the UV optical system (295 nm LED). 24 hours later the cells were fixed and fluorescently immunolabeled for ET1. Digital images were captured and subjected to morphometry.

Statistical Analysis.

Numeric signals or values were averaged for their respective groups and the statistical mean+/− standard error of the mean were compared between groups by using a fixed-effect one-way ANOVA and post-hoc Scheffe test or Student's t-test, at a significance level of p<0.05.

Chemicals/Biological.

The following biologicals and compounds were used: Endothelin1; BQ123 and BQ788 (ET(R)) blockers for ET(R)-A and ET(R)-B; Sigma, St. Louis, Mo.), U73122 (PLC inhibitor; Tocris, Ellisville, Mo.), 4α-phorbol 12,13 didecanoate (4α-PDD; TRPV4 activator; Tocris), GSK205 (TRPV4 inhibitor (Li et al., 2011; Phan et al., 2009; Vincent and Duncton, 2011)), RN-1734 (TRPV4 inhibitor; Tocris), CGS35066 (endothelin-converting enzyme inhibitor, Tocris), isopentenyl pyrophosphate, IPP (TRPV3 inhibitor; Sigma); and Camphor (TRPV3 activator; Whole Foods).

Behavioral Assessment of Withdrawal Thresholds and Nocifensive Behavior.

Behavioral tests were performed to evaluate the decrease in withdrawal thresholds in response to mechanical or thermal stimuli applied to hind paws. These withdrawal thresholds were ascertained before and after UVB exposure. Mice were confined by plexi-glass enclosures on top of 25×26 cm Bio Rad Gel Doc 2000 UV transilluminator (302 nm), and otherwise allowed to openly explore this environment. UV-exposure lasted for 5 minutes with an exposure of 600 $mJ/cm^2$. Careful observations upon initiation of this method demonstrated that hindpaws were exposed to UV throughout this period.

Automated Von Frey Hair Testing.

Hindpaw mechanical withdrawal thresholds were determined by the automated von Frey hair method, using a 0.5 mm diameter stainless steel filament, part of an automated plantar touch stimulator (Ugo Basile, Modena, Italy). Relevant detail included pre-test acclimatization in a quiet room for 30 min, conducting the test at the same time of day and blinded observers. The stimulus was delivered to the hindpaw, automatically discontinued upon withdrawal, and its intensity recorded automatically. 6-8 trials per animal were conducted, with equal exposure of both hindpaws, leading to an average withdrawal threshold. Results are reported as Δ-threshold, which was calculated by subtracting post-treatment from pre-treatment measurements, expressed as % or relative to 1.0.

Hargreaves' Test.

Hindpaw thermal (hot) withdrawal thresholds were determined by the well-established Hargreaves' method, using an infra-red thermal stimulation device that delivers the stimulus from underneath the hindpaw combined with automatic shut-off upon withdrawal (Ugo Basile). Stimulation and measurements were conducted as described for von Frey hair testing. A cutoff of 20 sec was set to prevent tissue damage.

Formalin-Induced Nocifensive Behavior.

Videos were read by blinded observers for the total amount of time each mouse spent flinching or licking the injected hindpaw.

Mouse Tissue Processing for 1 µm Semithin Sections and Electron Microscopy.

Samples were fixed in 2% glutaraldehyde, 4% PFA, and 2 mM $CaCl_2$ in 0.05 M sodium cacodylate buffer, pH 7.2, at room temperature for >1 h, dehydrated, postfixed in 1% osmium tetroxide, and processed for Epon embedding. Semi-thin sections (1 µm) were stained with toluidine blue and photographed with an Axioplan 2 microscope (Zeiss). For EM analysis, ultrathin sections (60-70 nm) were counterstained with uranyl acetate and lead citrate. EM images were taken with a transmission electron microscope (Tecnai G2-12; FEI) equipped with a digital camera (model XR60; Advanced Microscopy Techniques, Corp.).

Mouse Tissue Processing for Immunohistochemistry.

Routine procedures were followed as described previously (Chen et al., 2009). Mice were perfused transcardially with 30 mL PBS, followed by 30 mL 4% paraformaldehyde. Tissues, including the L5 DRGs (bilateral), and footpad preparations, were dissected and post-fixed in 4% paraformaldehyde. Tissue blocks were further cryoprotected in 30% sucrose in PBS for 24-48 hours. For mouse TRPV4, keratin-specific antibodies, phospho-ERK, IL-6, IL-1β, CXCL5 and caspase-1, tissue was prepared as frozen blocks and subsequently sectioned on a cryostat. For CD68, CD15 (neutrophil elastase) and CD3, mouse skin was prepared by 2% PFA perfusion. Footpad and DRG sections (both at 6-10 μm) were thaw-mounted, blocked with 5% normal goat serum (NGS; Jackson), then incubated overnight at 4° C. with the following primary antibodies: rabbit anti-TRPV4 (1:300; Abcam), mouse anti-keratin 14 (1:300; Abcam against C-terminal peptide beyond residue 850); rabbit anti-keratin 14 (1:1000; Fuchs-Lab), rabbit anti-phosph-ERK1/2 (1:500; Cell signaling technologies), goat anti-IL-1β (1:800; Abcam), goat anti-IL-6 (1:200; Santa Cruz Biotechnology Inc); rabbit anti-caspase-1 (1:200; Biovision Research Products, CA); goat anti-mouse LIX/CXCL5 (1:200; R&D Systems Inc), anti-CD68, anti-CD25, and anti-CD3 (AbDSerotec). Immunodetection was accomplished with appropriate fluorescently-labeled secondary antibodies (AlexaFluor595, AlexaFluor488-conjugated antibodies at 1:600; Invitrogen; for CD15 biotinylated secondary antibody from donkey, 1:400 followed by rhodamine-streptavidine 1:250), or with peroxidase-linked detection reagents (for CD68) for 2 hours at room-temperature. Sections were rinsed, mounted, and cover-slipped with fluoromount (Sigma). Digital micrographs were obtained using a BX61 Olympus upright microscope, also with a Zeiss LSM510 confocal, both equipped with high-res CCD camera, and acquired with constant exposure settings, using ISEE or Zeiss Zen software. Morphometric analysis was conducted using ImageJ freeware (v1.45) with tailored regions-of-interest that spared the nuclear compartment. ImageJ was also used for determination of DRG surface area.

Human Tissue Specimens Immunolabeling.

Human tissue was deparaffinized with xylene and ethanol series, then washed in PBS, and incubated at 80° C. for 20 min in Antigen Retrieval buffer (Biogenex). Subsequently, specimens were washed in PBS. Endogenous peroxidase was blocked with 0.3% $H_2O_2$+0.01% sodium azide in PBS for 10 min at room temperature, followed by washing steps in PBS. Blocking was performed in 5% normal horse serum+0.3% Triton-X-100 in PBS for 1 hour at room temperature. Primary antibodies (anti-TRPV4, Abcam, same as for mouse, 1:8,000; anti-ET1; anti-IL-1b as for mouse tissue) were incubated overnight at 4° C. in Ventana Antibody dilution buffer (Fisher). After washing in PBS, specimens were incubated with biotinylated donkey-anti-rabbit secondary (Vector, BA-1000), in diluted blocking buffer for 30 min. After washing with PBS, Avidin Biotin block was applied (Vector, PK4000) for 30 min at room temperature, and the positive immunoreactivity was visualized with DAB (Fisher, NC 9567138). After washing in water, hematoxylin was used to counterstain nuclei. Tissues were washed, dehydrated, and then mounted in Permount (Fisher). For morphometric quantification of TRPV4, IL-1β, and ET1, five sections from each patient and healthy volunteers (n=3/group) were examined at a magnification of ×20 and photographed. The entire section was digitalized using Leica software, and analyzed using ImageJ. For quantification, DAB and HE staining in 3 randomly selected epidermal regions (3.5×1.25 inches) of each image were separated using the IsoData thresholding method in the Color Threshold Plugin. Relative signal intensities were calculated from background-corrected measurements. Values are expressed as mean of averages determined from five sections per patient. Quantification of human skin tissue for TRPV4, ET1, and IL-1β was performed from acute photodermatitis as compared to healthy skin (n=3 per group). Quantification of various subforms of chronic photodermatitis as compared to acute photodermatitis and healthy skin is currently under active study. More final results await availability and proper staining of at least 3 cases per subgroup of human chronic photodermatitis.

Primary Mouse Keratinocyte Cell Culture.

The epidermis was separated from the dermis by a 1-hour dispase (BD Biosciences) treatment. Then the keratinocytes were dissociated from the epidermis using trypsin. Keratinocytes were plated on collagen coated dishes or glass or quartz coverslips and grown in keratinocyte serum free media (Gibco) supplemented with bovine pituitary extract and epidermal growth factor (EGF) (R&D Systems), 100 pmol cholera toxin (Calbiochem, San Diego, Calif., USA) and 1× antibiotics/antimycotics (Gibco), in an incubator at 5% $CO_2$ and 37° C.

UVB-Stimulation of Cultured Keratinocytes; Calcium Imaging.

Ca++ imaging of mouse 1° MK in response to chemical activation of TRPV4 was conducted after loading with 2 μM fura2-AM, following a ratiometric Ca2+ imaging protocol with 340/380 nm blue light for dual excitation. Ratios of emissions were acquired at 0.5 Hz. ΔR/R0 was determined as the fraction of the increase of a given ratio over baseline ratio, divided by baseline ratio. For stimulation of cells with UVB, where fura-2 was not suitable because of the proximity of stimulation with 340/380 nm and 295 nm, 2 μM fluo4-AM was used instead. Ca++ imaging was carried out at 488 nm excitation, acquisition of emissions at 0.5 Hz, expressed as ΔF/F0. In the custom-built UV optical system, UV LEDs were capped with a ball lens, a transparent optical window in the shape of a hemispherical lens (FIG. 2B). The LED output optical beam focused at 15-20 mm from the lens, with a spot diameter of approximately 1.5~2.0 mm (FIG. 2C). The electrical power supply for the UV LEDs was a surface mount component on the printed circuit board, which had a steady state 20 mA current output that was controlled by an external switch. The thermal equilibration stage was set for physiological temperature. We confirmed the non-thermal nature of UVB stimulation using the customized 295 nm LED device in a dedicated experiment (FIG. 2D), thus confirming the specific modality of stimulation as UVB.

Keratinocyte UV Irradiation Using 295 nm LED and Immunocytochemistry.

Mouse keratinocytes were cultured on collagen coated quartz coverslips and then stimulated from the bottom using the previously mentioned UV optical system using the 295 nm LED. 24 hours later the cells were fixed in 4% formaldehyde in PBS for 20 minutes, permeabilized with 0.1% Triton X-100 in PBS for 10 minutes, washed, then blocked in 10% normal goat serum in PBS for 45 minutes. Coverslips were incubated overnight with primary antibody mouse anti-ET1 (1:200; Abcam), washed three times in PBS and incubated with secondary antibody for 2 hours at 25° C. Coverslips were washed three times in PBS, once with double-distilled $H_2O$. Digital images were captured using a 40× immersion lens on the BX61 Olympus upright microscope. Morphometric analysis was conducted using ImageJ freeware with tailored regions-of-interest.

Determining UVB Permeation of the Skin.

Figure 16:
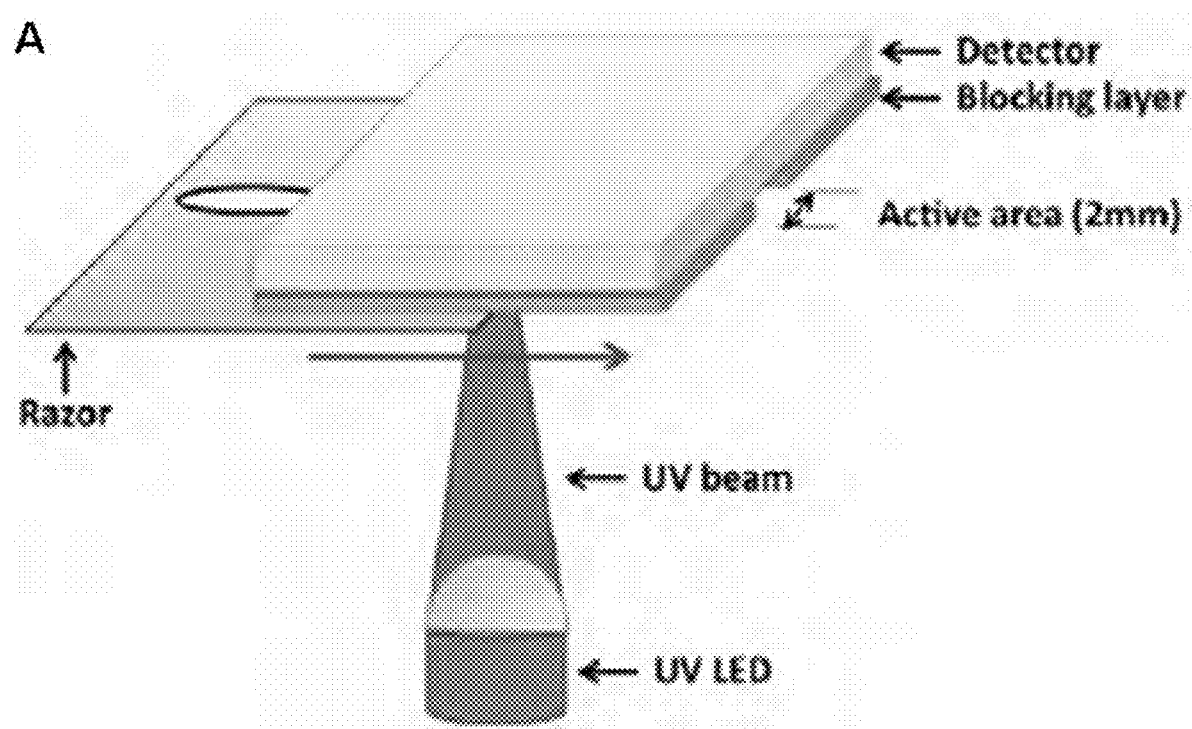
FIG. 16: Skin UVB permeability testing. (A) Experimental set-up for testing of skin permeability to UVB. (B) Results from A. Note that intensity is 70% within 500 μm radius to the center of the UV beam.
Figure 16:
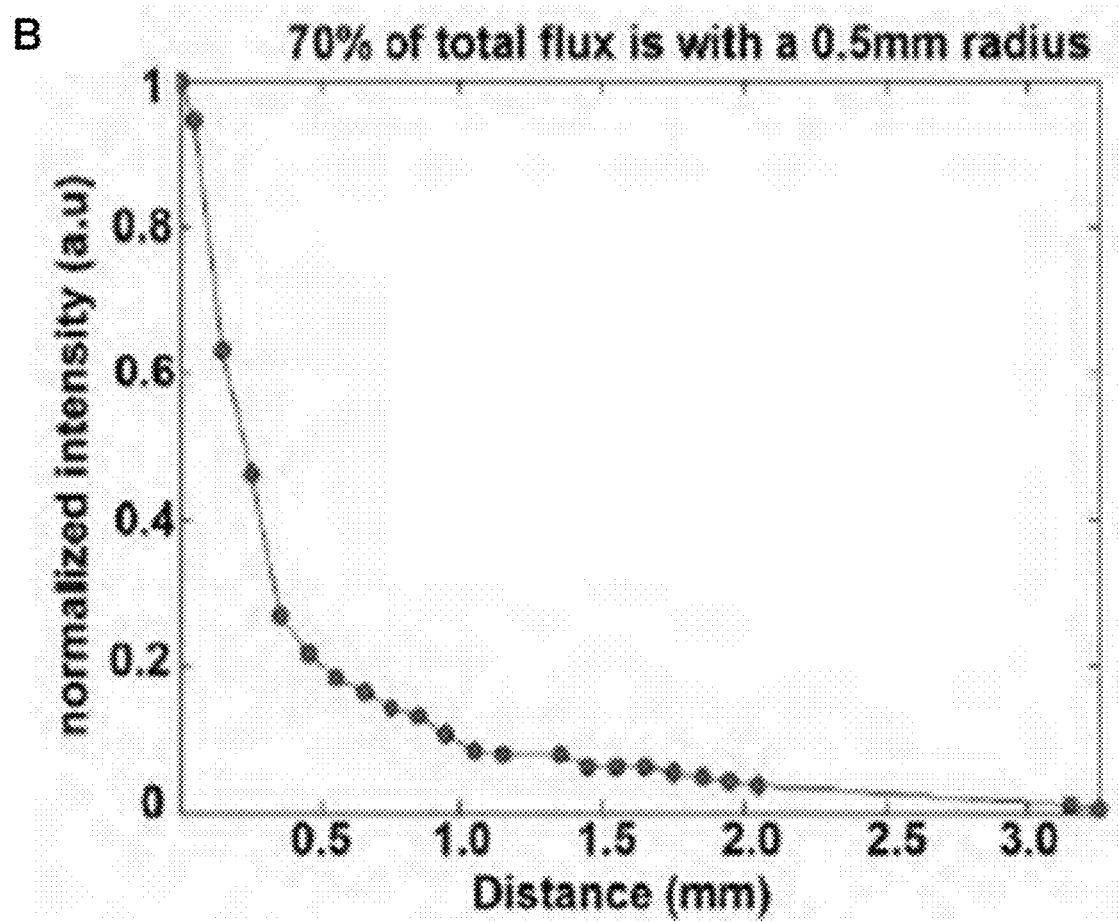

First, the spot size of the UV input optical beam from a LED (UVTOP-295 UV) was estimated, as shown in FIG. 16A, using the razor-edge optical spot occlusion method (results shown in FIG. 16B). The UV LED was powered with 20 mA of current, resulting in 500 µW of optical power in a circular focal spot 1.5 mm in diameter, with 70% of the total flux in a 0.5 mm beam radius. The UV optical power transmitted through the sample was detected by a Hamamatsu S127-66BR UV detector, and the output of the photodetector was measured using a Keithley 236 source measure unit. Next, the foot-pad epidermis of a mouse was measured for UV transmission by placing it on a quartz coverslip and exposure to the UV beam. The GSK205 was administered to the foot-pad skin in an alcohol and glycerol solution as for the experiments shown in FIG. 12A. The vehicle-control group was treated with the alcohol and glycerol solution only. Another control group consisted of a commercially-available SPF100 preparation sunscreen in form of a cream, which was applied similar to the vehicle-control. The data for the GSK205 and sunscreen was normalized to this control data.

Western Blotting.

Samples were separated by SDS-PAGE, and transferred to PVDF membranes (Bio-Rad). Membranes were blocked with dry milk, then probed with primary antibodies (rabbit anti-TRPV4 (immunogen=final C-terminal epitope of TRPV4 as for immunolabeling), Alomone; anti-caspase-1, Biovision; mouse anti-β-actin, (clone AC-5) Abcam; mouse anti-β-tubulin, Iowa Hybridoma bank), followed by horseradishperoxidase-conjugated secondary antibodies (Jackson Immunoresearch). Secondary antibodies were detected using Supersignal West Dura Extended Duration substrate (Amersham).

Example 2

Generation of an Epidermal-Specific, Tamoxifen-Inducible Trpv4 Null Mouse

To circumvent developmental issues that can arise in gene-targeted mice with ubiquitous deletions, we developed an inducible conditional system to assess the roles of TRPV4 in UVBmediated skin irritation, inflammation, and sensory sensitization. Using mouse ES cells, we first built Trpv4lox/lox mice so that the sizable exon coding for transmembrane domains 5, 6, and the interjacent pore loop was flanked by loxP elements. After crossing to FLPe mice to remove the selection marker, flanked by frt elements, these animals were mated with tamoxifen (tam)-inducible, Keratin-14 (K14)-$CRE^{ER}$ transgenic mice. The constructs and genotyping are summarized in FIG. 1A-B.

Figure 3:
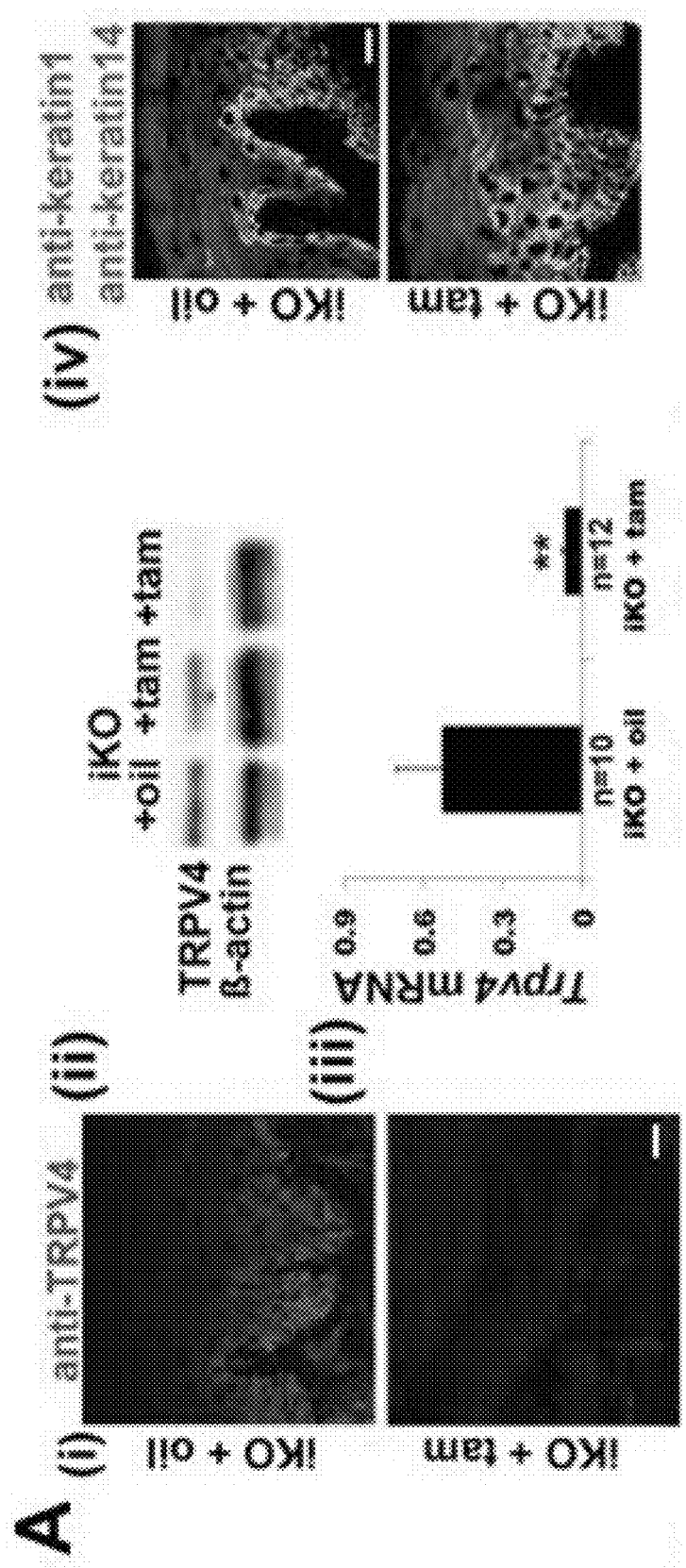
FIG. 3: Keratinocyte-specific ablation of Trpv4 leads to alterations in nocifensive behavior in response to UVB. (A) Epidermal TRPV4 expression and its loss upon keratinocyte-specific ablation of Trpv4 in tam-induced iKO mice. (i) TRPV4 immunofluorescence. Note TRPV4 in epidermis of vehicle (oil) treated control, but not tam-induced iKO mice. Bar=10 µm. (ii) Western blot of epidermal lysates from paw-pad skin. Note knockdown and more complete loss of TRPV4 following induced Trpv4-ablation (β-actin used for normalization). (iii) qRT-PCR for Trpv4 mRNA from paw-pad skin is shown, indicating significant Trpv4 knockdown in response to tam-treatment vs. carrier (oil). P<0.0001, t-test. (iv) Immunofluorescence for epidermal lineage markers. In WT skin, basal epidermal marker keratin-14 is downregulated and suprabasal marker keratin-1 is induced upon commitment to terminal differentiation. Upon knockdown of TRPV4, this balance appears perturbed, with some spinous layer cells showing co-labeling. Bar=10 µm. (B) Nocifensive behavior in response to UVB exposure. Time-course (in hours) for nocifensive behavior elicited by either a noxious mechanical stimulus (automatic von Frey hair assay, left) or thermally-evoked nocifensive behavior (Hargreaves' assay, right). Note significantly less sensitization in Trpv4$^{-/-}$ and in tam-treated iKO mice, relative to oil-treated (vehicle) iKO and WT mice. n≥10 animals per group;  p<0.01 ANOVA. (C) Correlation between nocifensive behavior and level of Trpv4 knockdown. n=12 animals are shown for which both parameters were available and Trpv4 mRNA levels <0.45. Note the four vehicle-induced animals (green symbols) vs. their tamoxifen-induced counterparts (red symbols). (D) Loss of epidermal TRPV4 shows no significant effect on nocifensive behaviors caused by formalin injection. Bars depict average cumulative nocifensive behavior within the first 10 minutes (phase I), and 10-45 minutes (phase II) post-injection. n=4 per group. (E) Phosphorylated ERK in L5 DRG neurons. pERK immunofluorescence of L5 DRG sections are shown for oil- and tam-treated iKO animals±exposure to UVB. Note that only UVB-exposed control mice show pERK expression in the paw-pad-innervating L5 DRG. Quantifications are shown at right. n=3 animals per group, 6 sections per DRG per animal,  p<0.01 ANOVA.
Figure 3:
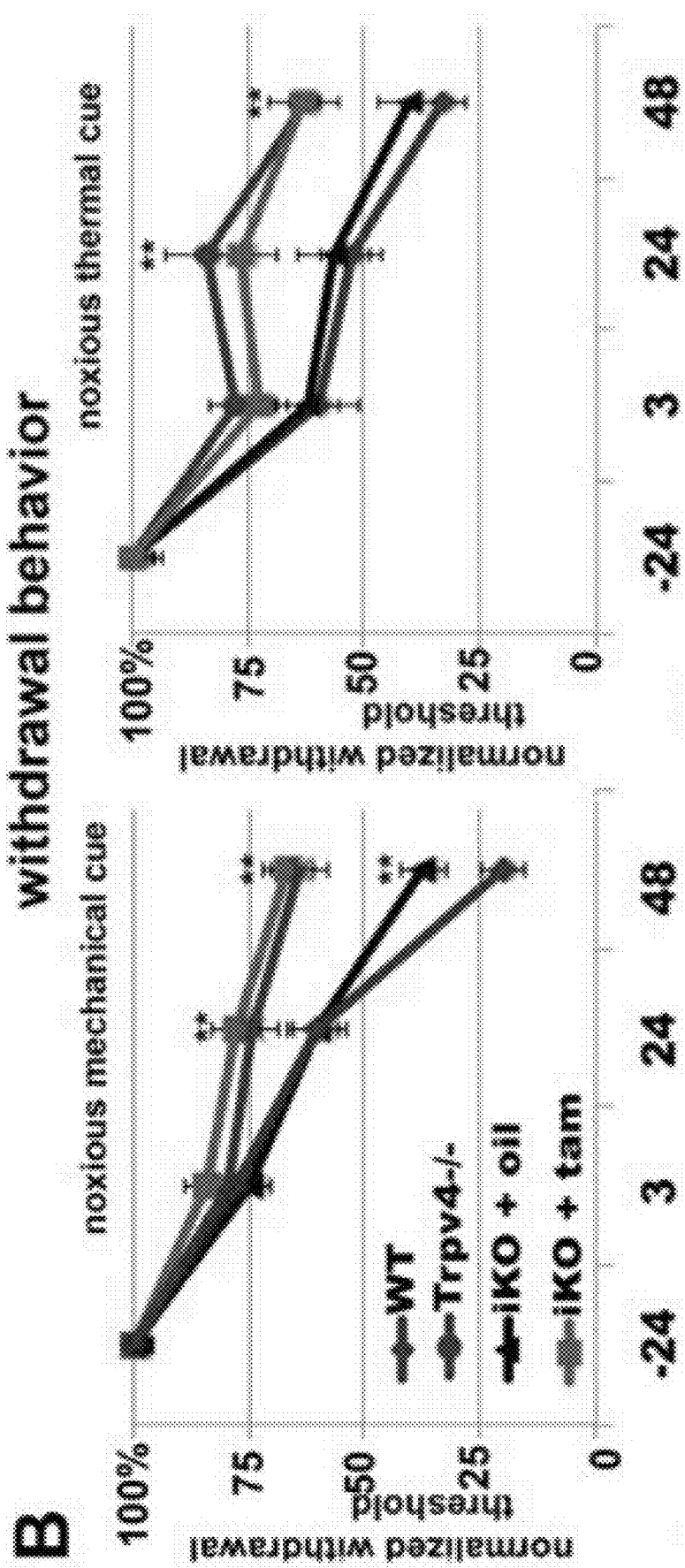
Figure 3:
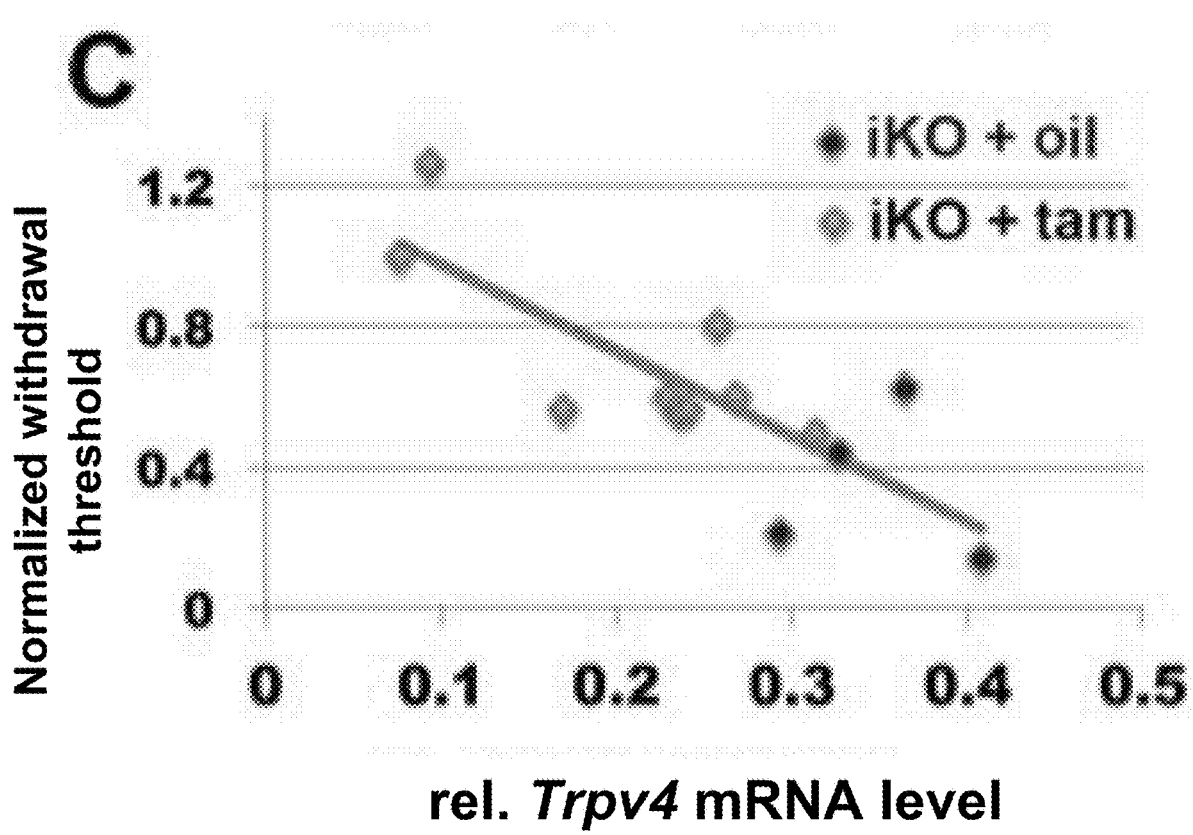
Figure 3:
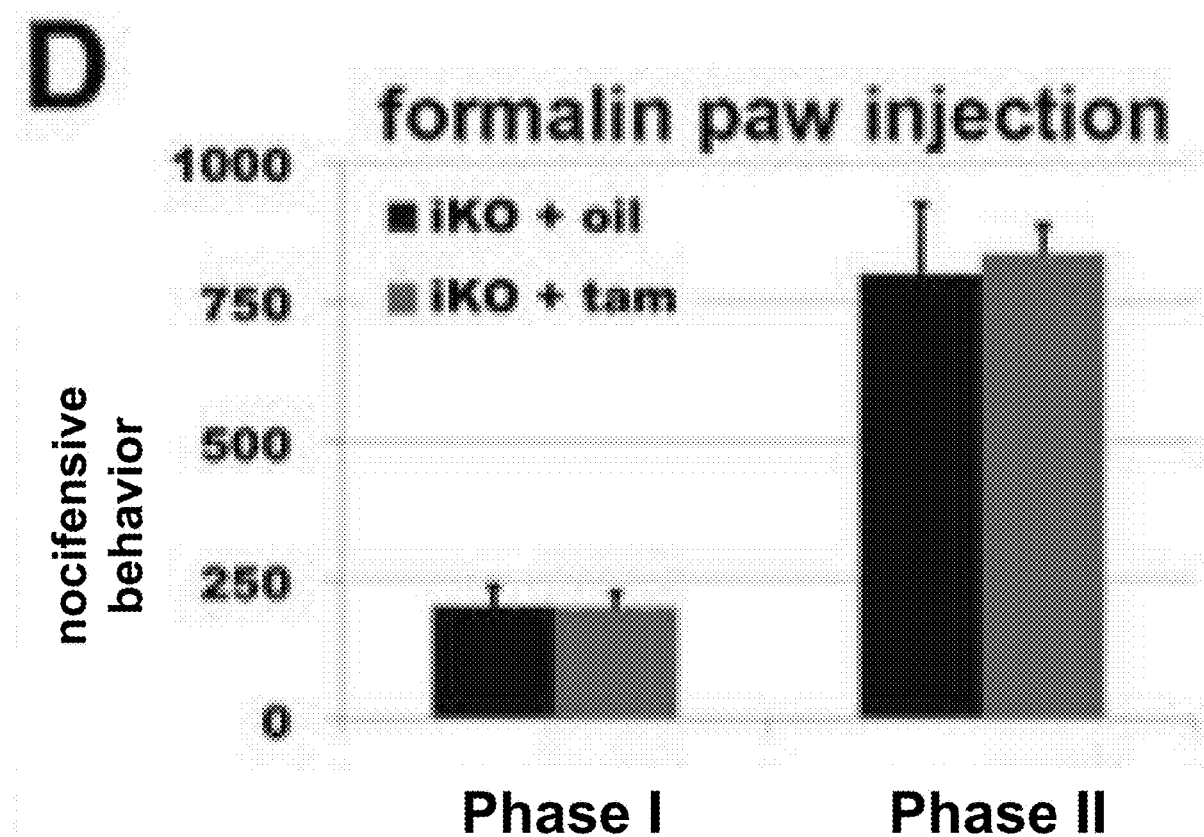
Figure 3:
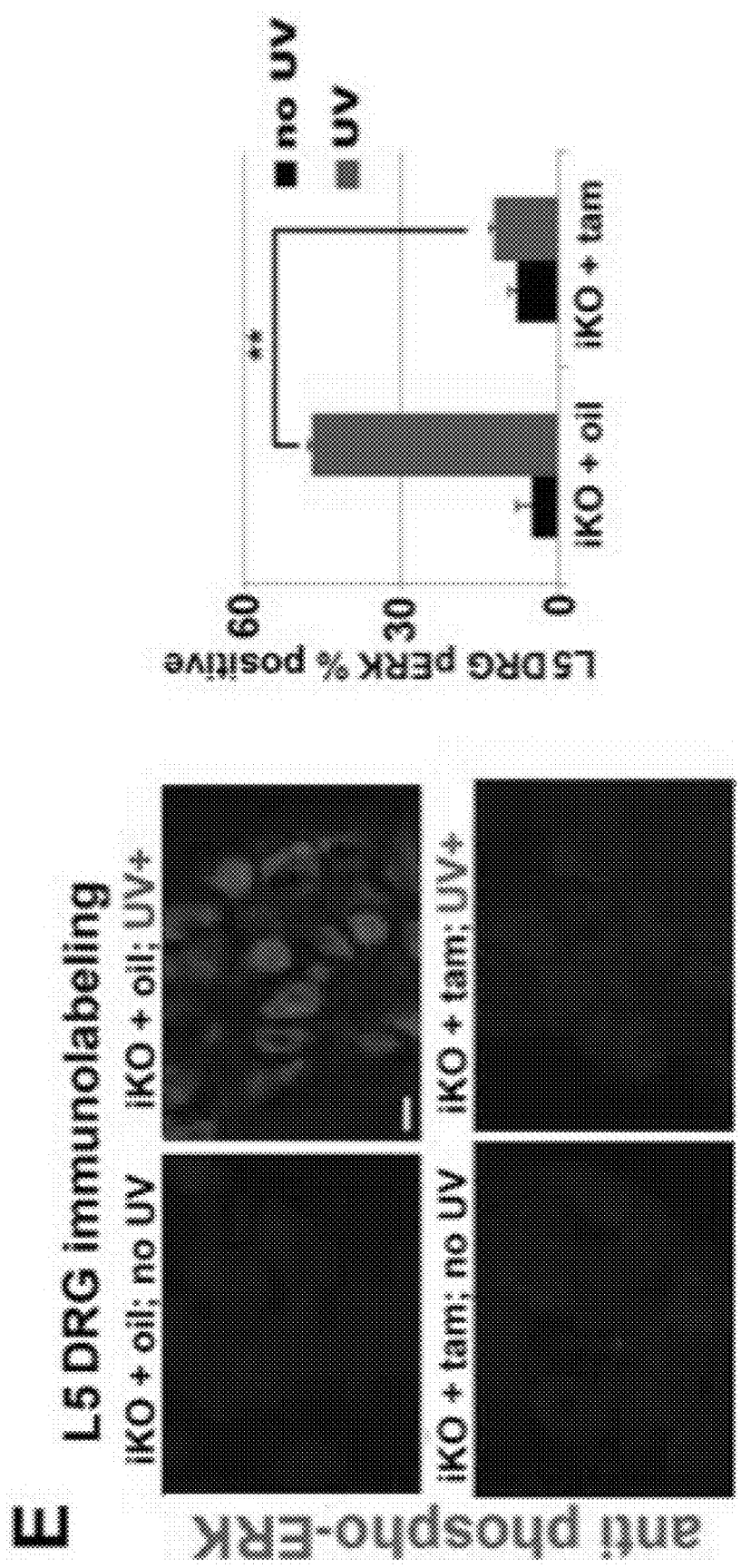

We focused on adult (2 month) glandular mouse paw-pad skin for our analyses, as it more closely resembles human skin. Tamoxifen-induction resulted in efficient knockdown of Trpv4 expression in skin epidermis, as judged by anti-TRPV4 immunolabeling, qRT-PCR and Western blotting (FIG. 3A). However, the gross and microscopic appearance of the skin/epidermis in tam-treated inducible Trpv4 knockout (iKO) mice was normal. Given the established dependence of skin renewal on keratinocyte Ca++ signaling, we noted that, interestingly, Trpv4-knockdown resulted in no gross alterations in the skin/epidermis nor in the induction of the terminal differentiation-specific marker keratin-1 (K1), which is known to be governed by elevated Ca++ influx suprabasally (FIG. 3A and FIG. 1C). Closer analysis of Trpv4-deficient skin revealed that expression of K14 was sustained suprabasally. This keratin is normally down-regulated at the basal-to-suprabasal transition, concomitant with the rise in Ca++ signaling and induction of terminal differentiation.

Taken together, despite these more moderate abnormalities, inducing Trpv4 knockdown in keratinocytes at age 8 weeks does not lead to gross interference with cyto- and layer architecture of the epidermis.

Example 3

Nocifensive Behavior Elicited by UVB Exposure is Dependent on Epidermally-Expressed TRPV4

Underscoring the specificity of Trpv4 gene targeting, peripheral sensory neurons innervating the footpad still showed robust expression of TRPV4 (FIG. 1D). This enabled us to evaluate whether epidermal Trpv4-deficiency critically affects UVB-mediated nocifensive behaviors. For this purpose, we assayed two relevant submodalities— thermal and mechanical stimulation—and compared our iKO mice to pan-null Trpv4−/− and their wild-type (WT) controls (FIG. 3B). 48 hours after UV-exposure, both tamtreated iKO and Trpv4−/− mice displayed much lower sensitivity to noxious radiant heat (Hargreaves' test), also towards noxious mechanical stimulation (using automated von Frey hair testing), than their respective controls. We concluded that epidermal-specific TRPV4 deficiency is equivalent to global Trpv4 ablation in reducing UVB-induced behavioral sensitization to radiant heat and mechanical stimuli, that is, in attenuating thermal and mechanical allodynia.

Further underscoring the importance of epidermal TRPV4 in regulating nocifensive behavior, a good correlation existed between UV-sensitivity to thermal stimuli and the level of Trpv4 gene knockdown, particularly at <0.45 the WT levels of Trpv4 mRNA (FIG. 3C). This indicated presence of a threshold for Trpv4 knockdown to influence nocifensive behavior. Although the dose-responsiveness was less obvious in our mechanical assay (not shown), we attributed this to the involvement of forced hind limb (foot) movement in the assay, which will confound the stimulus. By contrast, the Hargreaves' assay applies a purely thermal cue which becomes noxious without involving confounding stimuli.

In order to assess the specificity of the injurious stimulus, we induced irritation with foot-pad injections of formalin, eliciting the well-established bi-phasic response. In this assay, conditional epidermal knockdown of TRPV4 had no effect on direct peripheral chemical irritation (phase I) or the early maladaptive neural response (phase II) (FIG. 3D). Taken together, these results suggested that the level of epidermal Trpv4 knockdown is the determining factor for the degree of attenuation of nocifensive behavior caused by UVB-irradiation. This is specific because chemical irritant-induced nocifensive behavior is not affected by epidermal Trpv4 knockdown.

In additional control experiments, Trpv4lox/+ heterozygous mice had virtually identical behavioral sensitization (similar to WT) in response to UVB, irrespective of CRE-induction with tamoxifen or vehicle (FIG. 1E). These findings exclude a functional role for $CRE^{ER}$ on its own and reiterate the specificity of our approach in targeting Trpv4 ablation to keratinocytes. Also, Trpv4−/− skin was equally permeable to UVB as its WT counterpart.

Example 4

Activation Markers of Skin-innervating Peripheral Neurons Support Behavioral Findings In WT mice, the footpad is innervated by sensory neurons of the L5 DRG, which we examined by immunolabeling.

TRPV4 expression was unchanged with foot-pad exposure to UVB, an irritant cue known to sensitize innervating neurons (FIG. 1D). Interestingly, while sensitization could be verified in control mice, it appeared to be absent in tam-treated iKO mice, as documented by labeling for phosphorylated ERK (pERK), a known marker of sensory neuron activation in response to inflammation and irritation (FIG. 3E). Furthermore, size-measurements of pERK-expressing L5 DRG neurons revealed them to be small-to-medium size, suggesting their possible involvement in relay of noxious stimuli (FIG. 1F). These results are in good agreement with the nocifensive behavior defects seen in our mice, and further underscore a role for epithelial-expressed TRPV4 in governing UVB-induced activation in skin-innervating DRG sensory neurons.

Example 5

UVB-Induced Skin Inflammation Depends Upon Epidermal Expression of TRPV4

To understand how loss of TRPV4 affects UVB-induced skin, we performed light microscopy and ultrastructural analyses (FIG. 4A and FIG. 5A-C). In response to UVB, robust signs of inflammation appeared within control skin, as evidenced by intra-epidermal infiltrates of granulocytes. With the epidermis, focal blistering occurred, accompanied by extensive vacuolization. In skin of tam-treated iKO mice with incomplete targeting, inflammatory changes were still observed and were perhaps moderately less severe. In striking contrast, however, in skin areas where conditional epidermal ablation of Trpv4 was complete, no signs of inflammation or blistering were seen. These data demonstrated convincingly that epidermal TRPV4 is necessary for skin to mount a pro-inflammatory response to UVB exposure. Moreover, since the inflammation involved immune cells and the conditional knockout was specific to epidermis, the data further highlight the importance of epidermal-inflammatory cell crosstalk in the response. Specifically, these data imply that in normal skin, the epidermal keratinocyte triggers inflammatory cell recruitment as part of a UVB response, and that this circuitry is interrupted when epidermal TRPV4 is knocked down.

Figure 4:
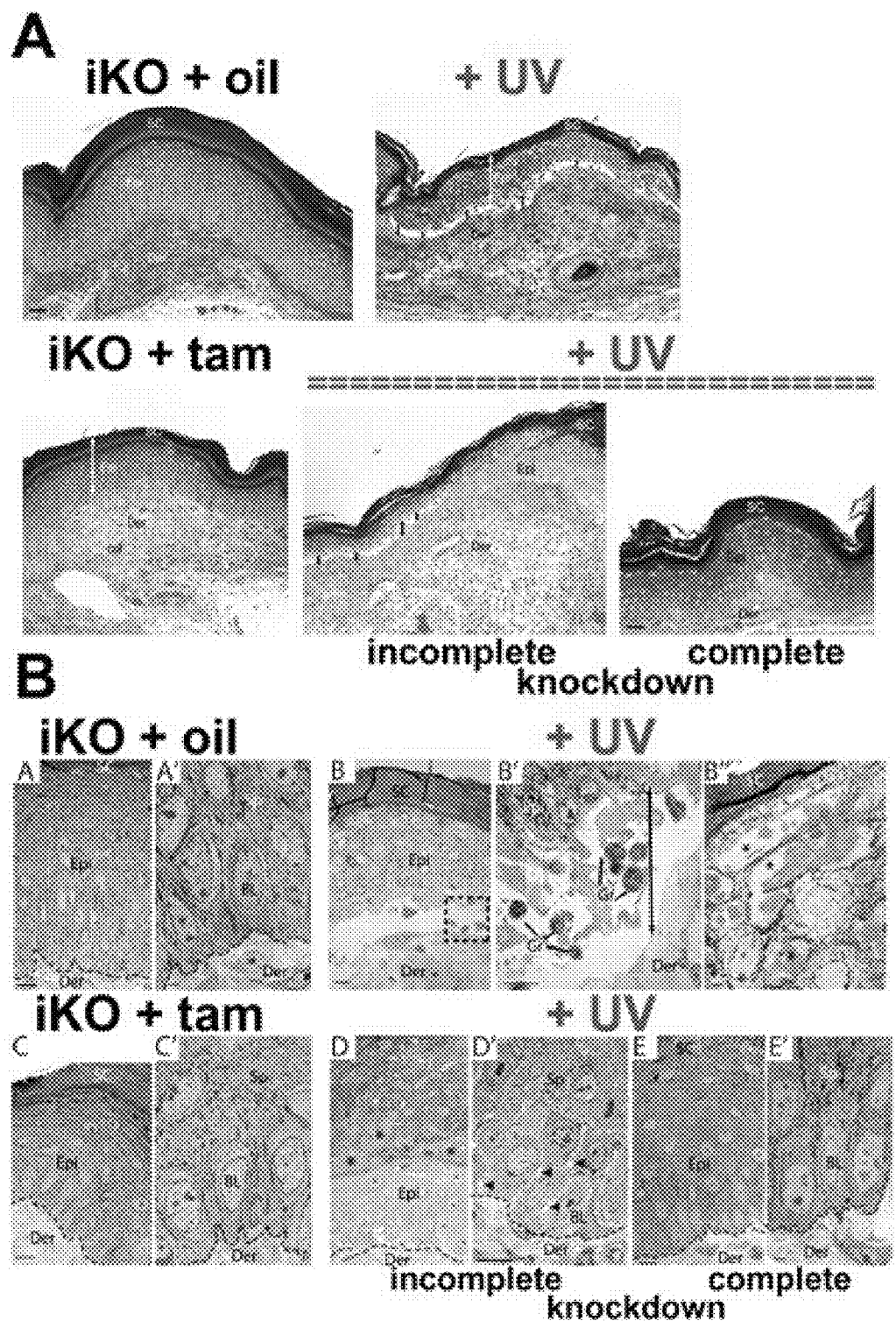
FIG. 4: Structural and ultrastructural analyses showing that UVB-mediated skin tissue injury depends upon keratinocyte TRPV4, and Immuno-histochemical analysis demonstrates that UVB-mediated activation of keratinocytes and recruitment of macrophages and neutrophils depends upon keratinocyte TRPV4. (A) 1 µm toluidine-blue semi-thin sections. Micrographs show representative findings of skin in response to UVB, sampled 48 hours after UVB exposure. Note that upon UVB stimulation, oil- (TRPV+) but not tam-treated (TRPV–) iKO mice exhibit separations at the epidermal-dermal boundary and robust signs of tissue injury; note granulocytes (Gr, neutrophil). Note also that just beneath the stratum corneum (SC), the upper epidermis shows extensive structural damage which could also be seen in skin of tam-treated iKO mice where Trpv4 knockdown was incomplete, but not in those animals where it was more complete (see FIG. S2A). Bars=20 µm. Der=dermis; Epi=epidermis. (B) Ultrastructural findings by EM. Selected areas from 1 µm semithin sections of paw skin were examined by transmission electron microscopy. (A-A') and (C-C') show normal epidermal (Epi) structure for both, oil- and tam-treated iKO mice, in the absence of UVB stimulation. (A) and (C) show and intact epidermis. Basal (BL) and spinous (Sp) layers are magnified A' and C' displaying a normal organization with no evidence of epidermal damage. (B,B'B''), (D-D') and (E-E') show representative findings of skin in response to UVB, sampled 48 h after UVB exposure. (B) Disrupted epidermis in oil treated iKO mice. An area equivalent to the boxed area is magnified in (B'), where granulocyte infiltration of epidermis is evident (Gr) and blistering with detachment of the epidermis from the dermis (double arrows). (B'') Upper part of epidermis in contact with stratum corneum (SC), showing extensive vacuolization and deposits of fibrin inside the vacuoles (asterisks). (D) Tamoxifen treated iKO mice with incomplete knockdown of trvp4 show similar skin phenotype to oil treated iKO mice, with robust signs of tissue damage to basal and spinous layer, fibrin deposits (asterisks) and intercellular spaces (arrowheads in D'). (E) Intact epidermis in iKO with complete knockdown of trvp4, with normal basal and spinous layers in (E'). Der, dermis. Dotted lines indicate the dermo-epidermal boundary. Bars=20 µm for A, B, C and D; 10 µm for B' and E' and 2 µm for the other micrographs. (C) IL-6 upregulation in keratinocytes as marker of epidermal activation. IL-6 immunofluorescence reveals a reduced ability of TRPV4-deficient mice to elevate keratinocyte IL-6 expression in response to UVB exposure. Quantifications for protein is shown next to micrograph. Densitometries are for n≥3 mice per group, showing significant upregulation for oil-treated iKO mice, lack thereof for tam-treated. Right-hand bar diagram shows 11-6 mRNA quantification and time-course. Il-6 mRNA was determined by qPCR after isolation of total RNA from paw-pad epidermis. Note the early and robust increase, albeit with variation, at the 2 hour time-point, in WT control epidermis, in contrast the very moderate increase in Trpv4$^{-/-}$ epidermis. Note also the sustained robust upregulation at 24 hours, again moderately upregulated in Trpv4$^{-/-}$ epidermis. Quantifications are for n=8-12 mice/group. * denotes statistically significant (p=0.011, t-test); scale-bar=20 µm. (D) Recruitment of macrophages in UVB-exposed skin. Note that the numbers of dermal CD68+ macrophages induced by UVB-exposure in control mice is significantly reduced when Trpv4 is ablated in the epidermis. Quantifications are shown at right (n=3 mice/group; * p<0.05 t-test); scale-bar=20 µm. (E) Recruitment of elastase-expressing neutrophils to UVB-exposed skin. Shown are representative immunofluorescence micrographs and respective quantifications. Note a strong increase in abundance of elastase-expressing neutrophils in control mice, and a lack thereof in tam-treated iKO mice. (n=4 mice/group, * p<0.05 t-test); scale-bar=40 µm.
Figure 4:
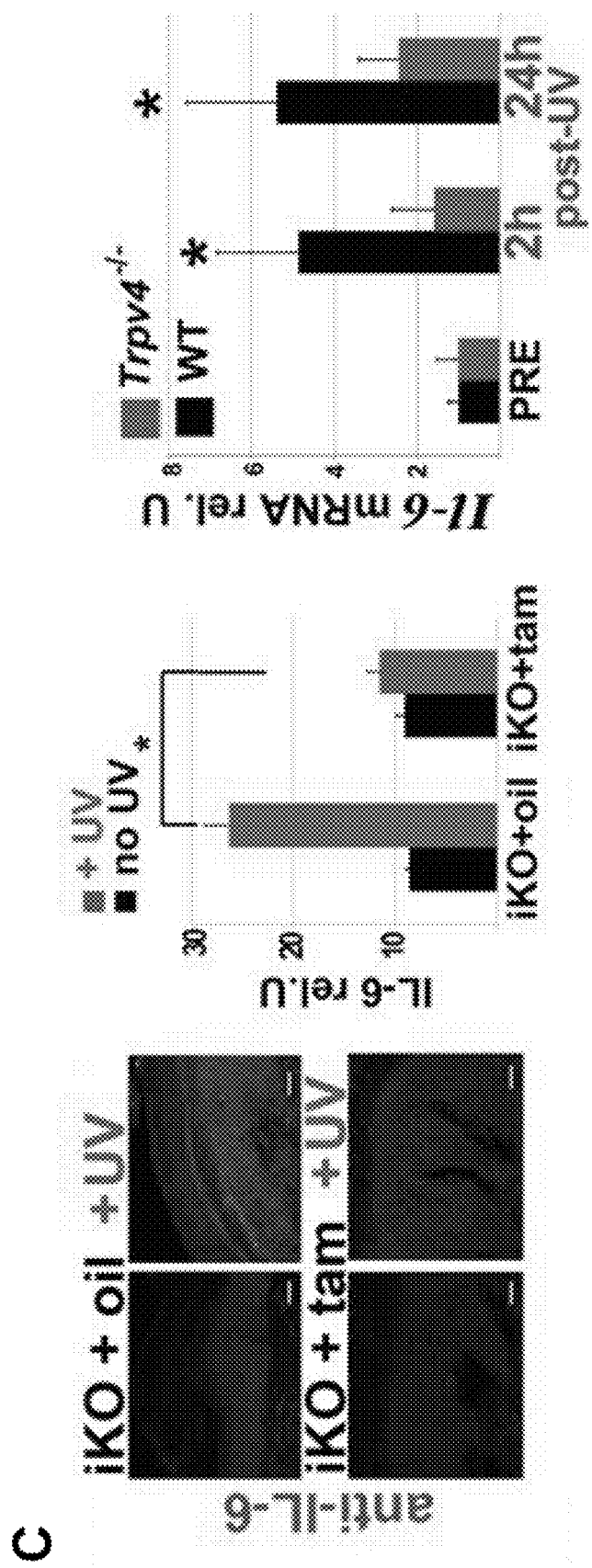
Figure 4:
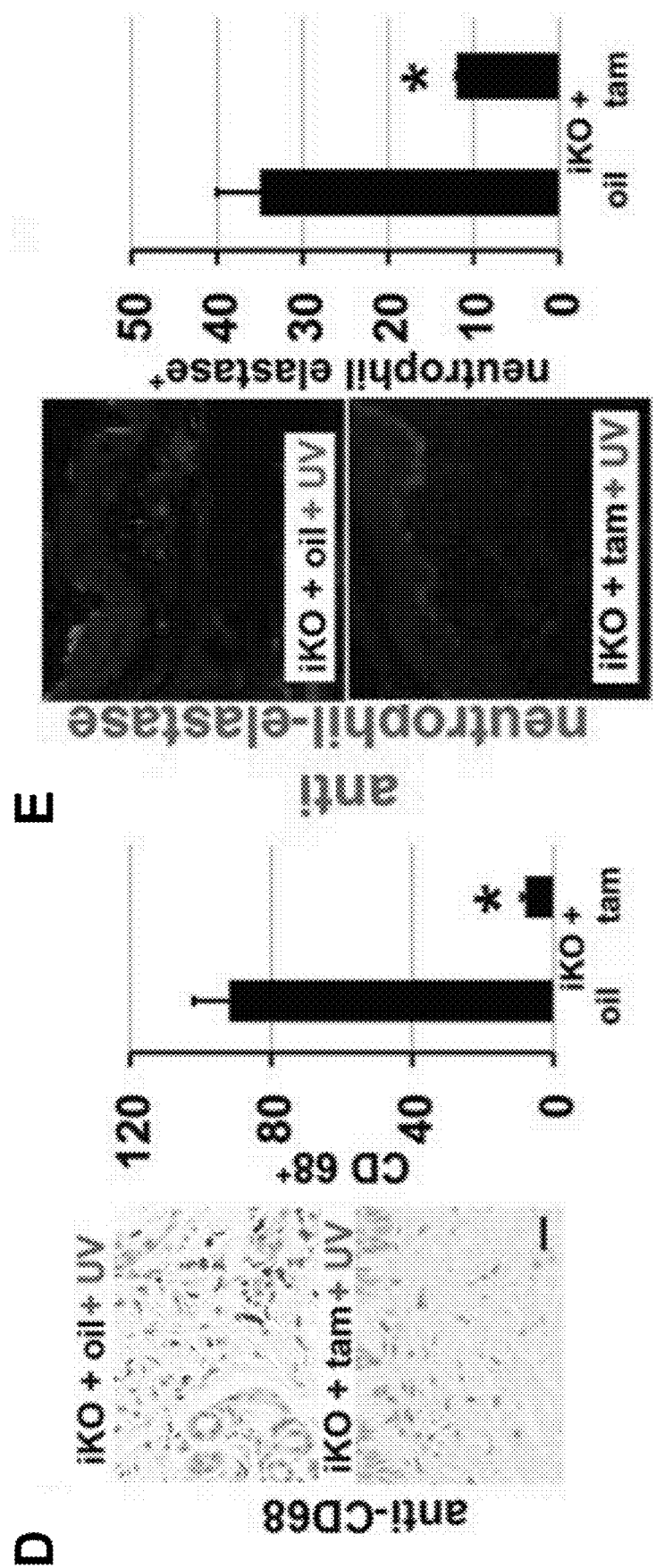
Figure 5:
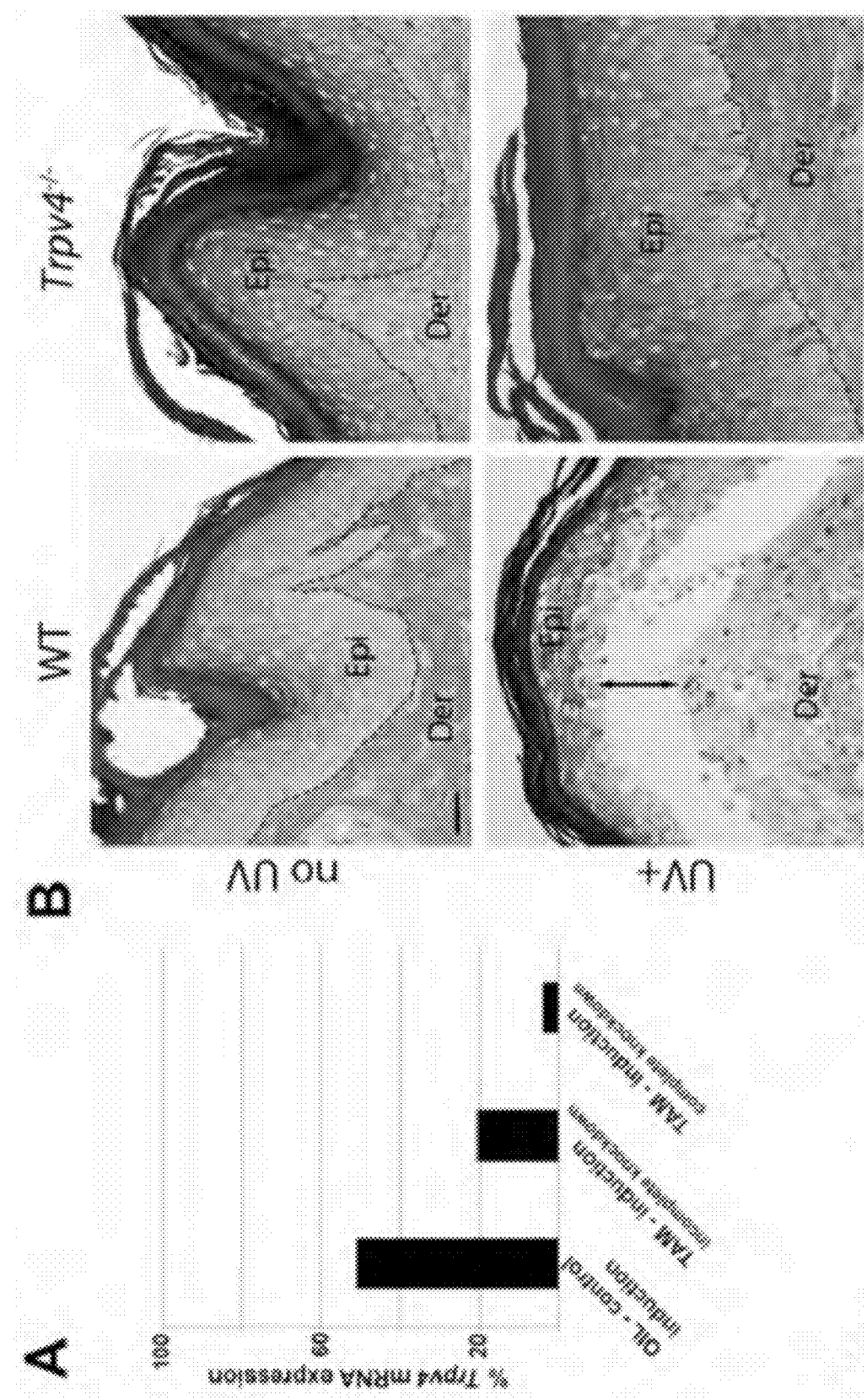
FIG. 5: Histopathology in Trpv4–/– and control mice in response to UVB. (A) Trpv4 knockdown level of samples shown in FIG. 4A-E. This bar diagram shows relative level of knockdown of Trpv4 in comparison with WT, of UVB-exposed skin samples shown in FIG. 4. An adjacent sample of hindpaw skin was RNA-extracted at 48 h post-exposure and subjected to Trpv4 qRT-PCR; pooled WT mRNA values from 10 mice were set as 100%. (B) Light microscopic analyses of 1 μm semithin sections findings from Trpv4−/− and WT control mice. Normal skin is shown in the upper row for both genotypes in the unstimulated state, presence of epidermal and dermal inflammation in WT control vs. absence thereof in Trpv4−/− when exposing the skin to UVB, sampling conducted at 48 hours. Note inflammatory changes similar to those of oil-treated iKO mice, as shown in FIG. 4. (C) Ultrastructural analyses of Trpv4−/− and WT control mice. (A-A') and (B-B') WT and Trpv4−/− mice show normal skin morphology with intact epidermis (Epi) in the absence of UVB stimulation. A' and B' show higher magnification of basal layer (BL) cells. (C-C') Damaged epidermis with vacuolization (inset in C) and granulocyte (neutrophil) (granulocyte—Gr) infiltrate (C'). (D-D') Normal epidermal and dermal ultrastructure in Trpv4−/− mice exposed to UVB. Der—dermis; NT, nerve terminals. Dotted lines indicate the dermo-epidermal boundary. Bars=10 μm for A, B, C, C' and D and 2 μm for the other micrographs. (D) IL-6 upregulation in epidermal keratinocytes in response to UVB depends on Trpv4; findings from Trpv4−/− and WT control mice. Fluorescent micrographs from Trpv4−/− and WT control skin, unexposed and exposed to UVB are shown. Note strong IL-6 signal in WT, exposed to UVB, and low signal in Trpv4−/− for both non-exposed and UVB-exposed states. Also note IL-6-expressing innervating peripheral nerve endings in the dermis. (E) No difference in mast cell abundance in UVB-photodermatitis in iKO mice. Left-hand micrograph shows mast-cells within sub-epidermal inflammatory tissue, stained with toluidine-blue, in an iKO mouse induced with tamoxifen, right micrograph its counterpart in an oil-treated iKO mouse. Mast-cells are indicated by white arrow-heads. Bar=20 μm. Right-hand bar diagram indicates quantification of mast-cell count per 63× visual field (5 fields per mouse, 3 mice per group).
Figure 5:
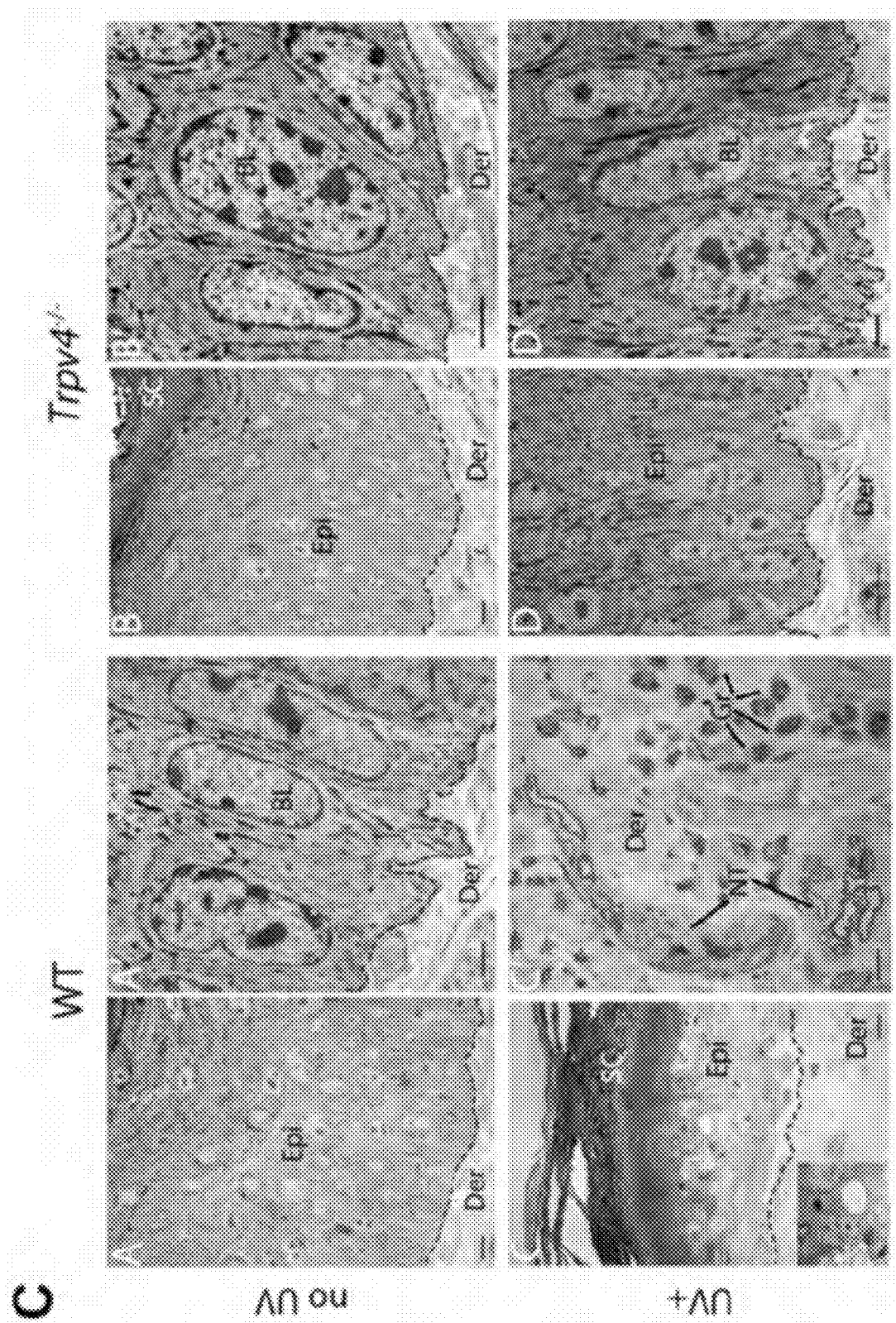
Figure 5:
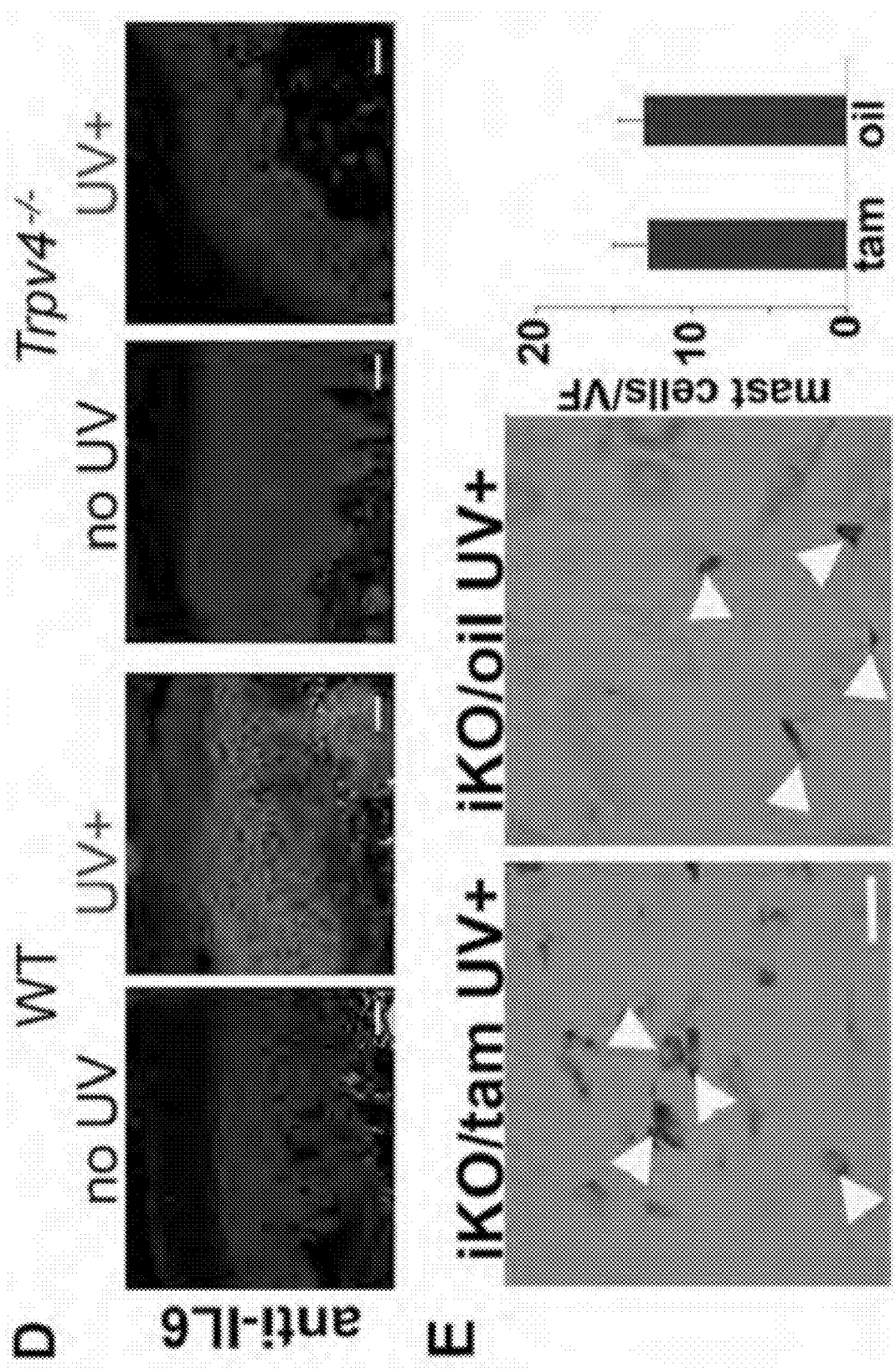

We next sought to identify the specific TRPV4-dependent epidermal signals that occur in WT mice exposed to UVB, and the immune cell populations that respond. IL-6 was a suitable candidate for the epidermal signal since it is an established marker of skin epidermal activation during UV dermatitis, and in addition, IL-6 is robustly algogenic. Indeed not only was IL-6 immunoreactivity observed in the UVB-exposed epidermis of control mice, but in addition, this robust IL-6 upregulation was virtually eliminated in conditionally targeted as well as pan-null Trpv4 knockout skin (FIG. 4B and FIG. 5D).

Both macrophages and neutrophils are known to contribute to the reduction of pain thresholds via their expression of a host of proalgesic/algogenic mediators such as TNFα, IL-6, IL-8, proteases, and chemokines. As judged by immunostaining for CD68 (macrophages) and a cell type-specific elastase (indicative of activated neutrophils, also known to enhance nociception), UVB-induced infiltration of both of these cell populations was markedly reduced in the skin of Trvp4-conditional knockout mice (FIG. 4C-D). By contrast, the mast cell infiltrate was unaffected (FIG. 5E), underscoring the specificity of macrophage and activated neutrophil findings; T-cell count was not changed between genotypes either. Taken together, these findings showed that TRPV4 expression by keratinocytes is critical for their ability to generate IL-6 and attract macrophages and activated neutrophils in response to UVB radiation.

Example 6

The UVB-Induced Ca++ Response in Primary Mouse Keratinocytes to UVB is Critically Dependent on Extracellular Ca++ Influx Through TRPV4

Figure 6:
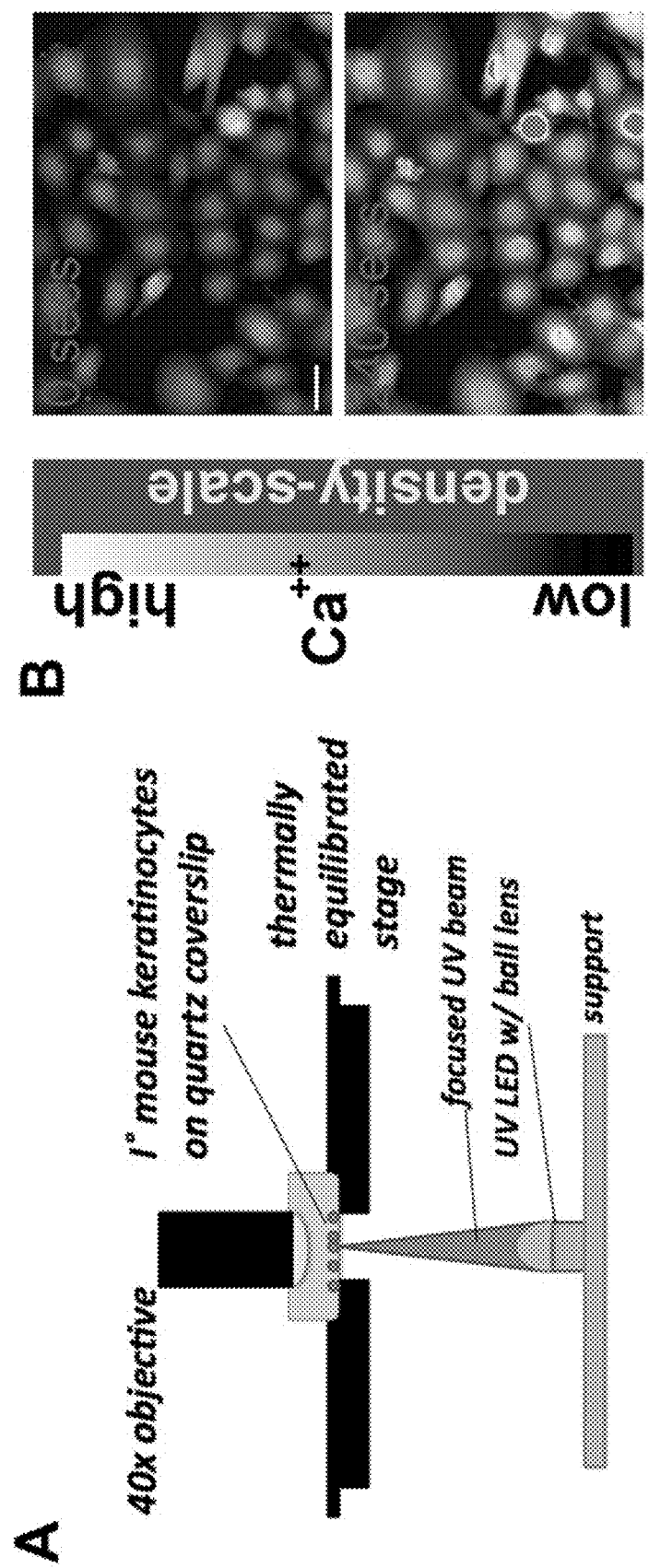
FIG. 6: Ca++ influx into keratinocytes in response to UVB depends on TRPV4. (A) Custom-built UVB cell illumination apparatus. See also FIG. 2. (B) Fluo-4 Ca++ imaging in 1° MKs. Fluorescent micrographs of 1° MKs after loading with Ca++-sensitive dye, fluo-4, before (upper) and at the end of UVB exposure (lower). Bar=10 μm. C-H UVB-evoked Ca++ signaling profiles. Fluo-4 imaging was used to detect Ca++ transients in 1° MKs following UVB exposure. y-axis indicates the increase in fluorescence, ΔF, normalized for prestimulation signal, F0 (ΔF/F0). The signal shown is that averaged from ≥50 cells. (C) Ca++ signaling is dependent upon UVB, and is strikingly reduced when quartz coverslips are replaced by glass ones, which prevent UVB permeation (see FIG. 2A). Note that this particular Ca++ signal in WT 1° MKs persisted after UVB, as is sometimes observed. (D) UVB-evoked Ca++ signaling is dependent on external [Ca++]. (E) UVB-evoked Ca++ signaling is not seen in Trpv4−/− 1° MKs, revealing the importance of the TRPV4 ion channel. (F) UVB-evoked Ca++ signaling is strongly down-regulated in the presence of TRPV4-selective inhibitor, GSK205 (20 μM). (G) The UVB-evoked Ca++ signal is not inhibited by the TRPV3-selective inhibitor, IPP. For validation of IPP's activity, see FIG. 2E. (H) The UVB-evoked Ca++ signal can be strongly reduced with specific PLC inhibitor, U73122.
Figure 6:
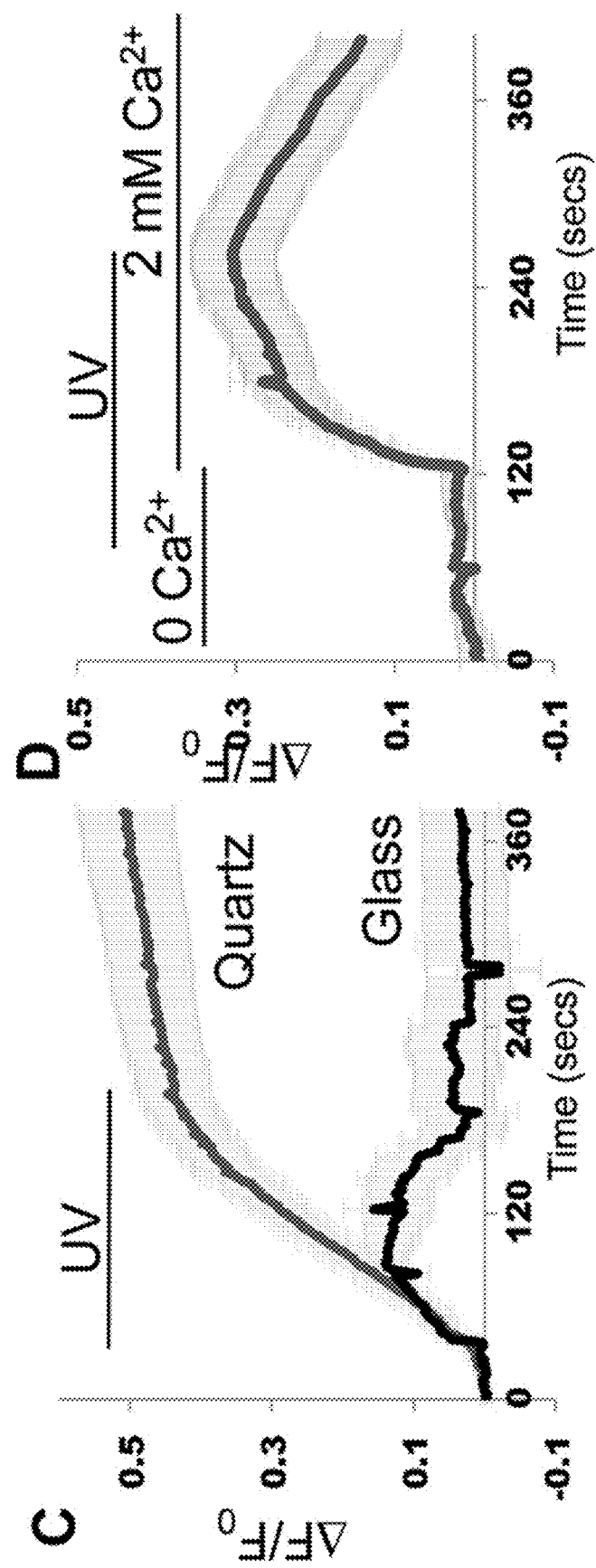
Figure 6:
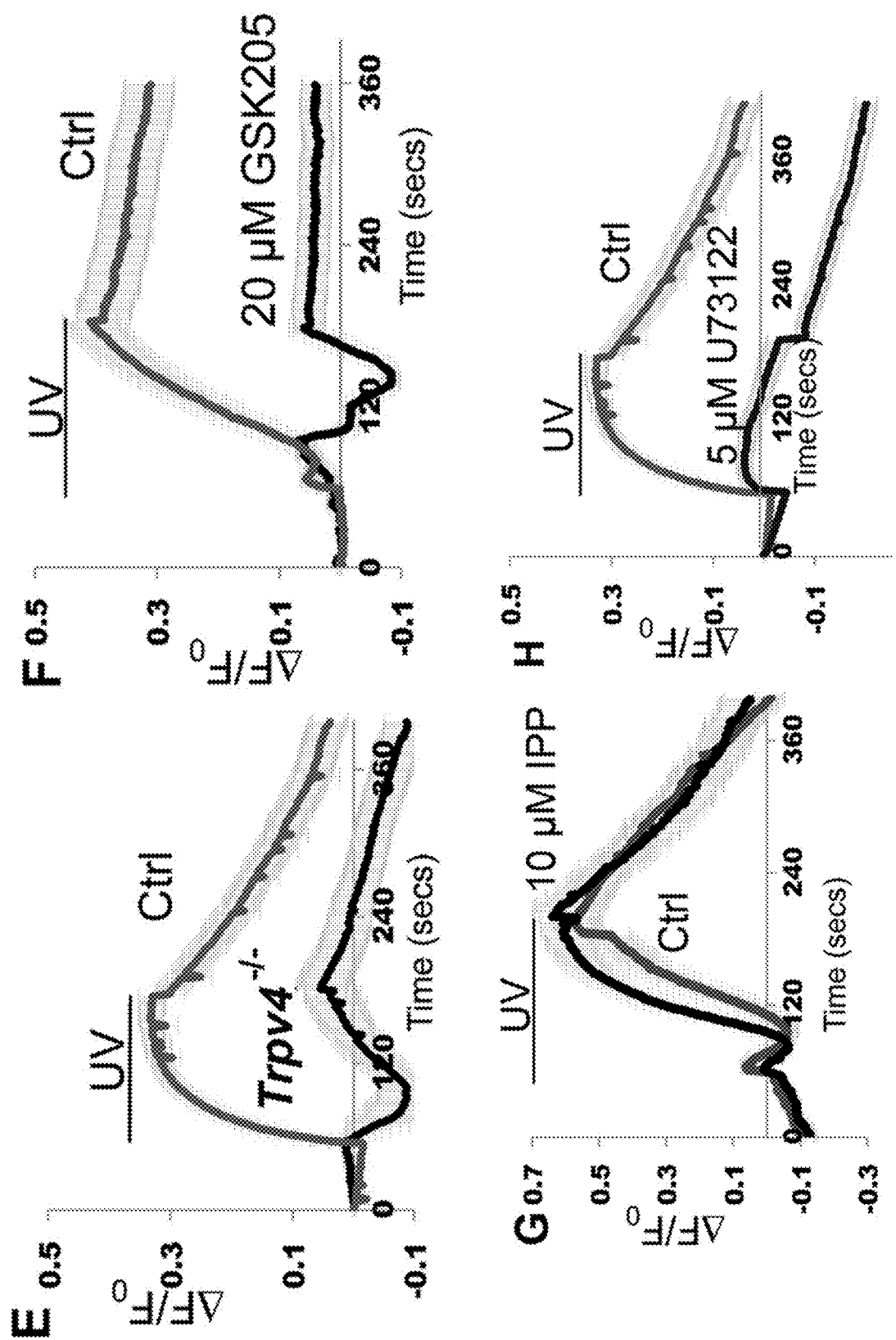

To further dissect the underlying mechanisms involved, we built a customized device for specific and narrow-band UVB stimulation of primary mouse epidermal keratinocytes (1° MK) cultured in vitro (FIG. 6A-B and FIG. 2A-D). This allowed use of the Ca++ sensitive dye, fluo-4, and assessment of 1° MK's Ca++ dynamics following UVB exposure (FIG. 6B). The elicited Ca++ signal was obliterated by a UV-refracting glass coverslip, underscoring the strict dependence of the calcium response on UVB (FIG. 6C and FIG. 2A).

Next, we asked whether the UVB-mediated Ca++ response is dependent on extracellular Ca++, and recorded affirmative findings by sequential exposure to first UVB, then Ca++(FIG. 6D). This finding prompted us to directly query the role of TRPV4 in the UVB-mediated Ca++ response. Indeed, 1° MK from Trpv4−/− mice exhibited a greatly diminished response relative to their WT counterparts (FIG. 6E). Moreover, when a selective small molecule-compound, GSK205 (Vincent and Duncton. Current Topics in Medicinal Chemistry 2011, 11, 2216-2226), was used to block TRPV4 channel function, WT 1° MK showed a very similar response to that of Trpv4−/− 1° MK (FIG. 6F).

In view of the known robust expression of TRPV3 in keratinocytes (Moqrich et al., 2005; Peier et al., 2002), we also addressed TRPV3's role in UVB-mediated Ca++ increase, but observed no effect with the TRPV3-selective inhibitor, IPP (FIG. 6G). The same dose of IPP was effective in inhibiting camphor-evoked Ca++ transients (FIG. 2E), validating the negative result.

Together, our experiments indicated that UVB exposure to the epidermis elicits the influx of extracellular Ca++ through TRPV4 and not TRPV3 channels. Since both channels were present, the data further suggested that TRPV4 channels are selectively activated by UVB light. We obtained corroborating findings by chemically activating TRPV4 with GSK101, which can directly stimulate TRPV4 in WT 1° MK. The GSK101-mediated response was dependent upon external Ca++ and was eliminated by the TRPV4 inhibitor GSK205 (FIG. 2F). These findings showed that direct chemical channel activation of TRPV4 shares critical properties of UVB-evoked Ca++ dynamics.

To assess whether TRPV4 is sufficient for the UVB-evoked Ca++ influx, we introduced high levels of TRPV4 into HEK293 epithelial cells. TRPV4 expression endowed these cells with the ability to generate robust Ca++ signaling in response to UVB (FIG. 2G). Moreover, if they were pre-exposed to GSK205, the response was blocked. Thus, heterologous TRPV4 expression is sufficient for UVB radiation to cause a cellular Ca++ transient.

Example 7

Elevated Endothelin-1 is a Critical Epidermal Effector of the UVB-TRPV4-Ca++ Response The UVB-TRPV4-Ca++ response depended on upon phospholipase-C (PLC), as it was virtually eliminated by the specific PLC inhibitor, U73122 (FIG. 6H). The reliance of TRPV4 activation upon PLC signaling suggested that PLC's respective lipid products, such as IP3, might be involved. It also hinted at possible involvement of G protein-coupled receptor signaling.

Using a candidate approach, we focused on endothelin receptors [ET(R)], which are known to be expressed in skin keratinocytes. ET(R)s were particularly good candidates since they function pro-algesic-/algogenically, and their cognate peptide ligand, endothelin-1 (ET1), is elevated when keratinocytes are exposed to UVB. When our 1° MK were exposed to ET1, they exhibited a significant increase in their UVB-induced Ca++ signaling (FIG. 7A(i)). This response was dependent upon TRPV4, as it was greatly diminished by GSK205. Consistent with this result, ET1 augmented GSK101-evoked Ca++ signaling (FIG. 8A).

We next blocked ET1 secretion by applying the proendothelin convertase-inhibitor, CGS35066. This inhibitor significantly diminished UVB-induced Ca++ signaling in 1° MK (FIG. 7A(i)). Since ET1's enhancing effect on Ca++ signaling was dependent upon TRPV4, and the UVB-Ca++ response was significantly sustained by ET1 secretion in vitro, we posited that autocrine/paracrine signaling involving ET1 may function to activate its cognate receptors, ET-R(A) and ET-R(B). In good agreement with this notion, ET-R inhibitors markedly attenuated the Ca++ signal in response to UVB and ET1 co-exposure. Interestingly, antagonism of ET-R(A) eliminated later phases of the Ca++ response, while leaving the initial rise unaffected; by contrast, antagonism of ET-R(B) converted the UVB-Ca++ response into a more protracted one (FIG. 7A(ii)). Co-application of both inhibitors completely eliminated the UVB-induced Ca++ response by 1° MKs (FIG. 7A(iii)).

Figure 7:
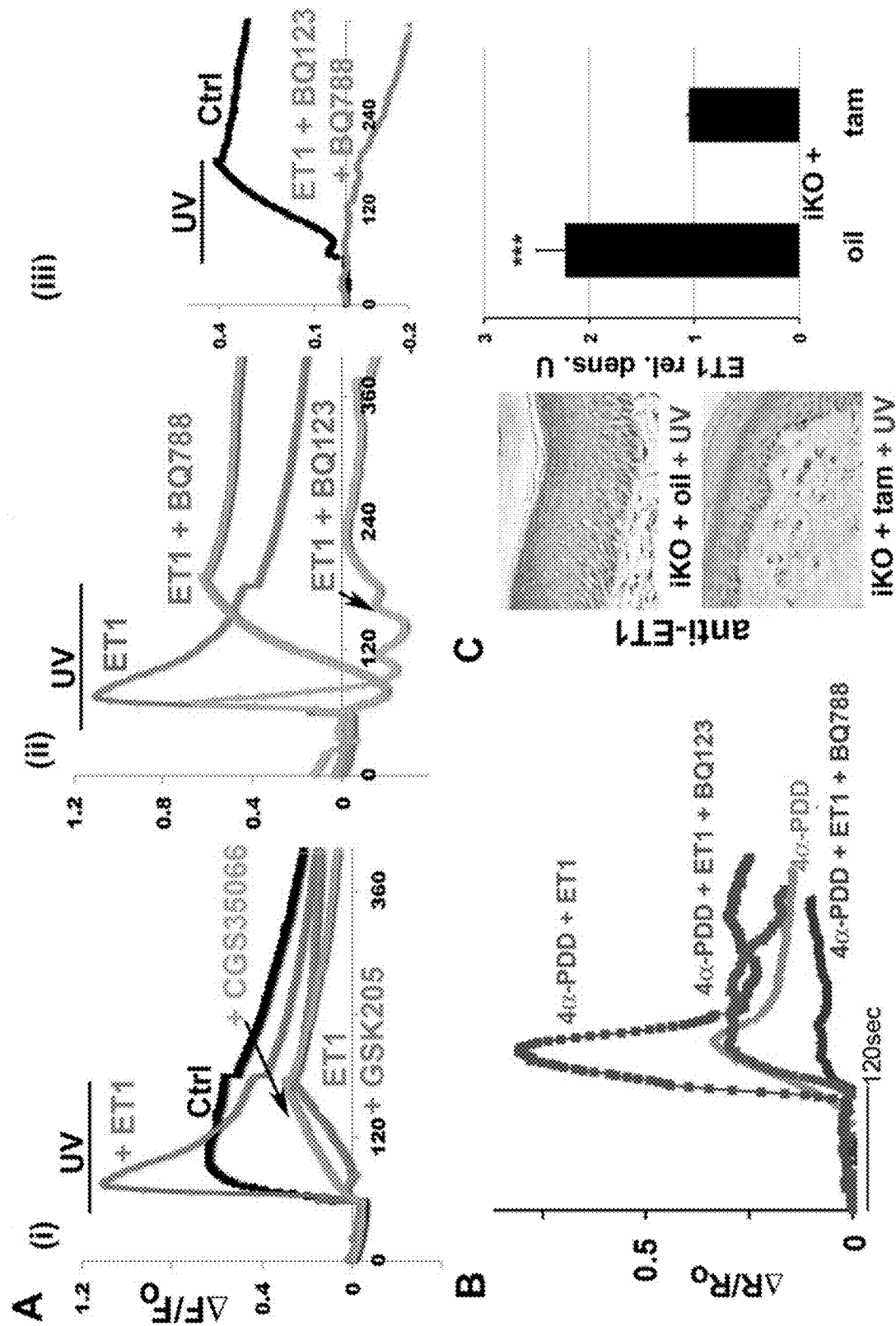
FIG. 7: Central role for keratinocyte TRPV4 in UVB-evoked Ca++ signaling and nocifensive behavior—effects of ET1. (A) Effects of ET1 on UVB-evoked Ca++ signaling in 1° MKs. Panel (i) shows averaged Ca++ transients in 1° MK in response to UVB, their augmentation by co-exposure to ET1 peptide, and their significant attenuation by either GSK205, which inhibits TRPV4, or ET-convertase inhibitor CGS35066, which blocks ET1 proteolytic processing. Panel (ii) shows ET-augmented, UVB-induced Ca++ transients as in (i), but in this case, where they are attenuated by selective antagonism of ET(R)-A (BQ123) and ET(R)-B (BQ788). Panel (iii) illustrates the complete elimination of the ET1-augmented Ca++ transients when both subtypes of ET(R) are blocked. (B) 4α-PDD-evoked Ca++ signaling in 1° MKs—ET1-related findings. Left-hand panel shows Ca++ transients (as per fura-2 ratiometric imaging) in response to the selective TRPV4 activator 4α-PDD. A significant increase in the response can be observed by co-application of ET1, and this is partially dependent on ET(R)-A and completely dependent on ET(R)-B. (C) Upregulation of ET1 in mouse paw in response to UVB. Immunohistochemistry reveals a significantly stronger ET1 signal in UVB-exposed skin of oil-vehicle-treated (TRPV4+) rather than tamtreated iKO mice. Quantifications are for n=3 mice/group. * denotes statistically significant ($p<0.001$, t-test). (D) Nocifensive behavior in response to ET1 footpad injection depends on epidermal TRPV4. Bar diagram summarizes behavioral findings for Trpv4−/− vs. WT and for oil-treated vs. tam-treated iKO mice. Note that in WT and oil-treated iKO mice, footpad injection of ET1 leads to significant levels of mechanical allodynia. Trpv4−/− and tam-treated iKO mice fail to respond; n≥7 mice/group,  $p<0.01$, ANOVA.
Figure 7:
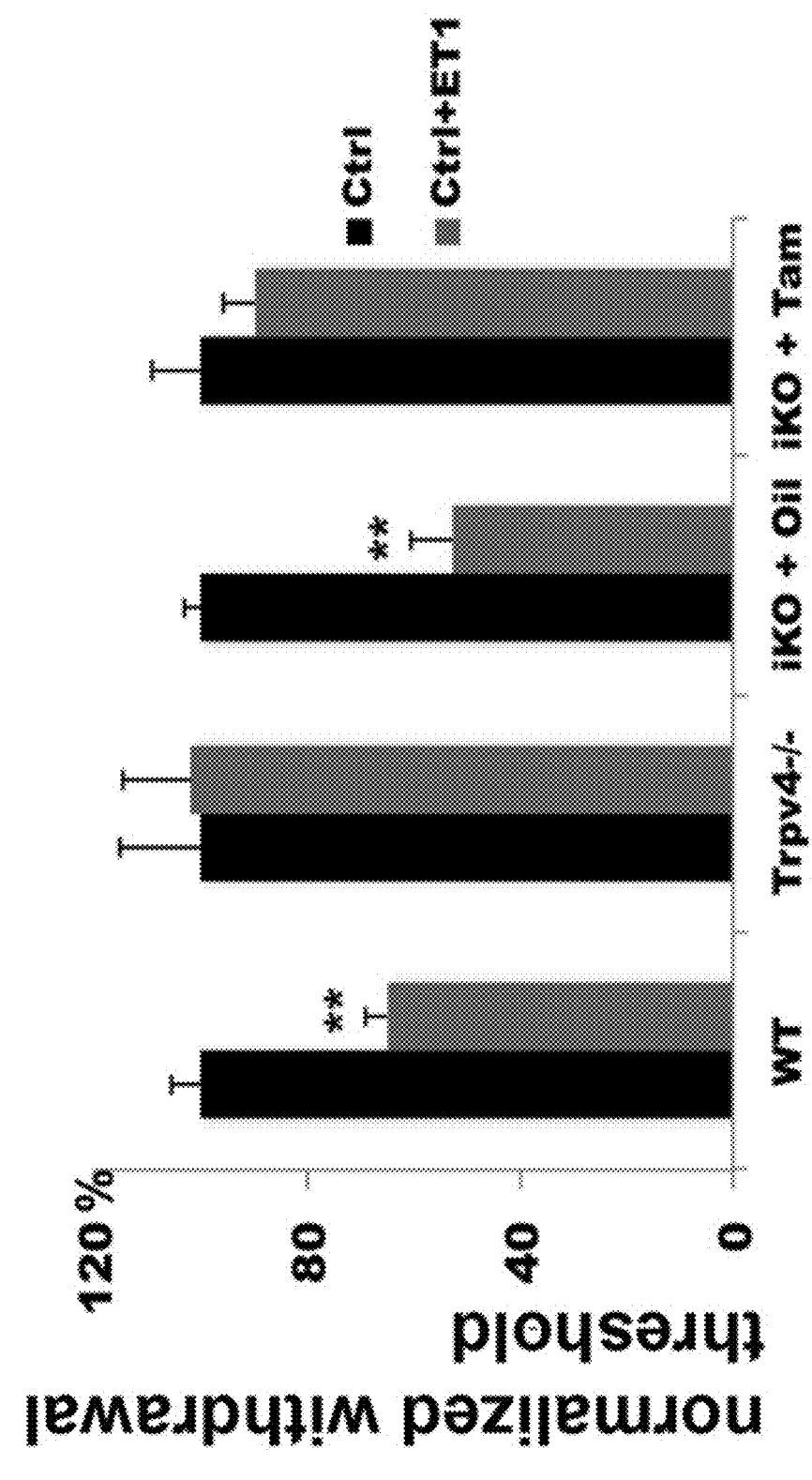

Taken together, these findings indicate that UVB-mediated ET1 secretion is a significant contributor to the UVB-TRPV4-Ca++ response. The data further suggest that independently from UVB's other effects, ET1-ET(R) co-signaling can amplify a TRPV4-dependent Ca++ response. In support of this notion, the UVB-Ca++ response could be recapitulated by omitting UVB-exposure and instead co-treating 1° MKs with ET1 and the selective TRPV4 activator 4α-PDD. Moreover, this response was significantly attenuated by ET(R)-A inhibition, and greatly diminished by ET(R)-B inhibition (FIG. 7B). Selective antagonism of ET(R)s led to attenuation for both compounds, yet showed a slight difference to the pattern observed with UVB, namely co-dependency for both ET(R)s for UVB, and recruitment of ET(R)-B more than -A for 4α-PDD. Given the pleiotropic effects of UVB, these minor differences were not surprising, and overall, the results provided compelling support for the interdependence of TRPV4 and ET(R) signaling in the response.

Figure 8:
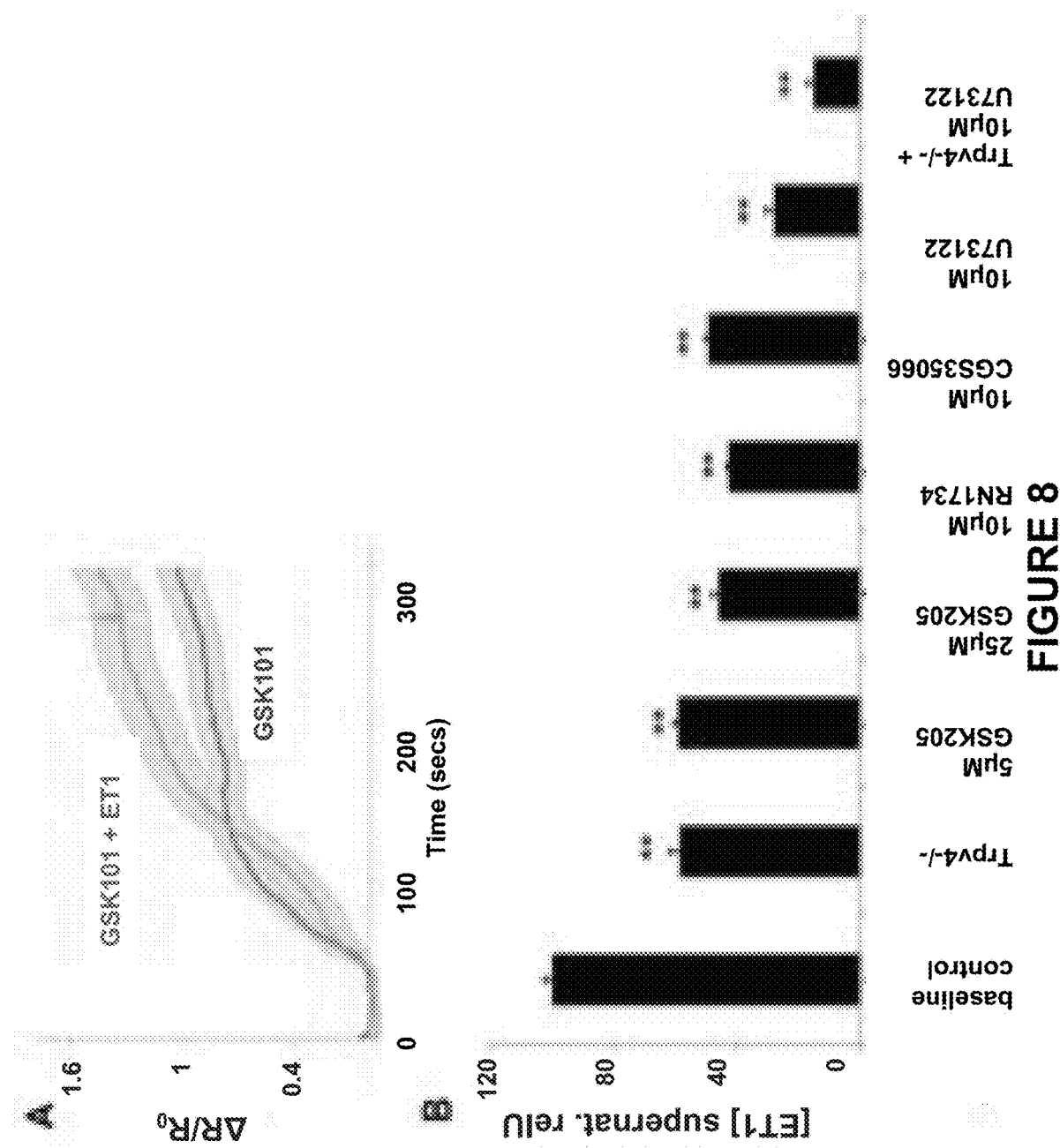
FIG. 8: Central role for KC TRPV4 in UVB-evoked $Ca^{++}$ signaling and nocifensive behavior—ET1-related supplementary findings. (A) Augmentation of GSK101-evoked $Ca^{++}$ signaling by ET1. Shown are averaged $Ca^{++}$ measurements (fura-2) in response to 5 nM GSK101. Note the increase in signal in response to co-exposure to ET1. (B) ET1 secretion by non-stimulated 1° MK depends on TRPV4 and PLC. Shown are relative ET1 concentrations (determined by ELISA, pg/mL; vehicle-treated and WT control normalized to 100) in supernatant of non-stimulated 1° MK. Note the clear dependence on TRPV4, as indicated by a 50% reduction in Trpv4$^{-/-}$ 1° MK. Moreover, there is a significant down-regulation by specific inhibition of TRPV4, which is dose-dependent (two doses of GSK205) and can be mediated by two different compounds (GSK205, RN1734). There is also down-regulation of ET1 secretion by a specific inhibitor of PLC (U73122), and by an ET-convertase inhibitor, CGS35066, which served as a control compound. In addition, PLC-inhibitor robustly affects ET1 secretion in WT and Trpv4$^{-/-}$ 1° MK. (C) ET1 expression by UVB-exposed 1° MK depends on TRPV4 and PLC—immunocytochemistry. Shown is specific ET1 immunolabeling in 1° MK, exposed to UVB using the UVB-LEDs, as for $Ca^{++}$ imaging. Use of the UVB-LED device precluded application of a ET1 ELISA, only irradiated cells could be examined. Note the significant down-regulation of ET1 immunoreactivity by specific inhibition of TRPV4 (two different compounds, GSK205, RN1734), by PLC inhibition (U73122), also by inhibition of ET-convertase (CGS35066). (D) ET1 expression by UVB-exposed 1° MK depends on TRPV4 and PLC—quantification of immunocytochemistry. Densitometric measurements of n≥25 cells per condition, background subtracted, are shown, indicating a significant upregulation of ET1 in response to UVB (* $p<0.05$ ANOVA), and significant down-regulation vs. control-treated and UVB-exposed cells for treatments with selective TRPV4 antagonists (GSK205, RN1734), PLC-inhibitor U73122 and ET-convertase inhibitor CGS35066; * p<0.05, t-test; # p<0.05 ANOVA.
Figure 8:
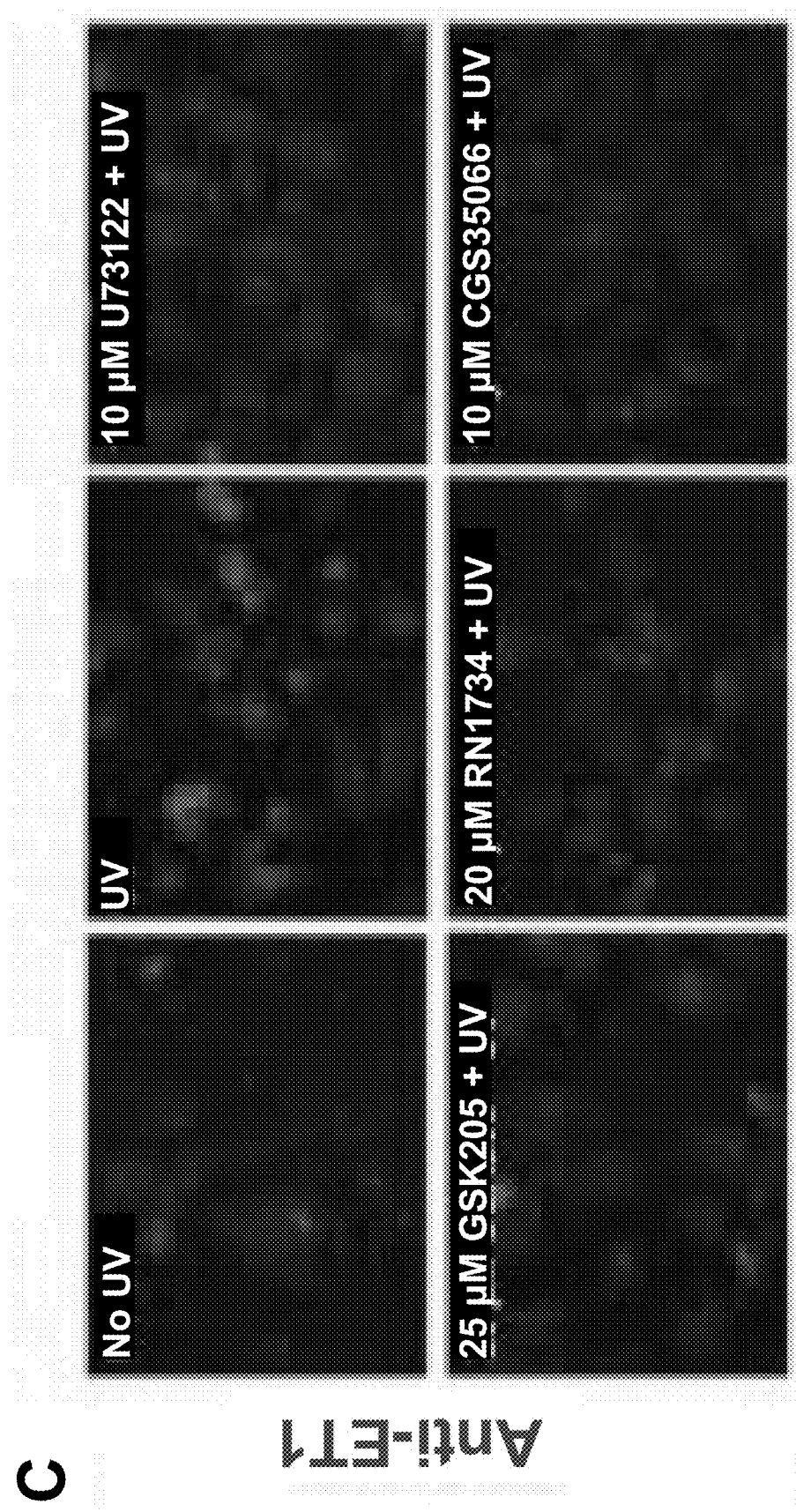
Figure 8:
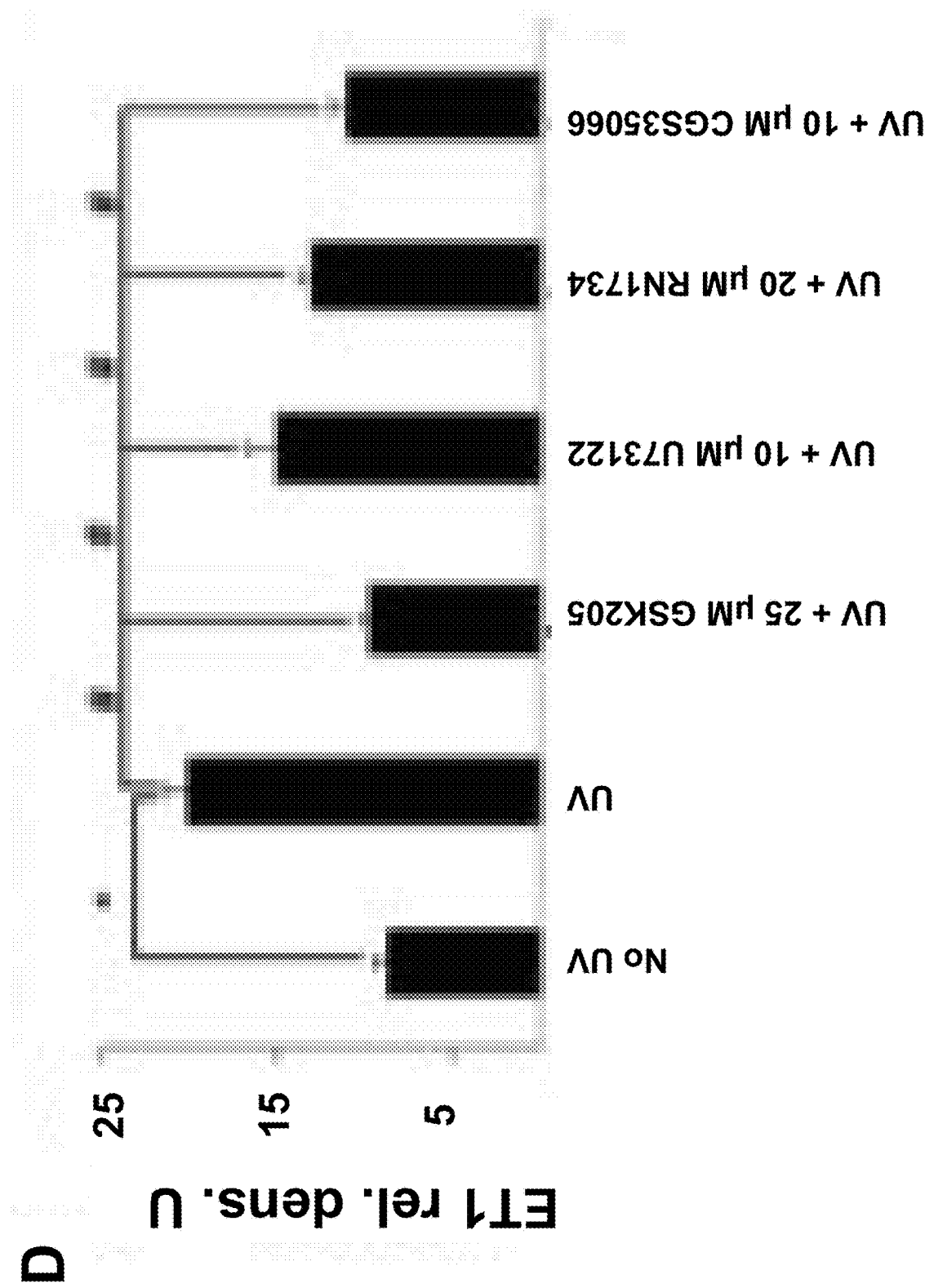

Interestingly, un-stimulated 1° MKs produced appreciable levels of ET1, secretory behavior which was dependent upon TRPV4 and PLC (FIG. 8B). We tested whether UVB causes ET1 upregulation in a TRPV4-dependent manner. Given the exquisite wave-length dependence of ET1 expression in 1° MKs, we resorted to the UVB-LED device as for Ca++ imaging (FIG. 6A and FIG. 2A-D). UVB-exposed 1° MKs showed increased ET1 immunolabeling, which was diminished when cells were preincubated with TRPV4-inhibitors, GSK205 and RN1734 (FIG. 8C-D). Consistent with its effects on UVB-evoked Ca++ transients, PLC-inhibitor U73122 also dampened ET1 expression. Together, these findings suggested a limited feed-forward mechanism that involves TRPV4-dependent increase of ET1 expression in response to UVB, and autocrine/paracrine signaling via ET(R)s. This leads to TRPV4-dependent Ca++ signaling, which in turn amplifies ET1 signaling in a paracrine/autocrine fashion.

To assess the physiological relevance of our findings in vivo, we exposed paw-pads to UVB. An interesting time course of Edn1 mRNA expression was apparent in paw-pad skin of WT mice where it peaked after 120 min and relented at 24 hours, but remained significantly elevated. In contrast, there was no regulated expression of Edn1 in paw-pad skin of Trpv4−/− mice. These findings suggest a more direct regulation of Edn1 gene-expression by TRPV4 in response to UVB. ET1 was readily detected in control epidermis but reduced in TRPV4-deficient epidermis (FIG. 7C). TRPV4 was also critical for the facilitatory effect of ET1 on nocifensive behavior, as judged by the finding that the withdrawal thresholds in response to von Frey hair stimulation were significantly lowered in control but not Trpv4−/− mice, both pan- and conditional null, in response to subepidermal ET1 injections (FIG. 7D). This result suggested that ET1's pro-algesic/algogenic effect is fully dependent on TRPV4 in keratinocytes. Although previous studies had shown that ET1 is sufficient to elicit nocifensive behavior, the elimination of ET1's pro-algesic/algogenic effect in our Trpv4-conditional null mice was unexpected given that both ET(R)s and TRPV4 are expressed by sensory afferents, which were unaffected in our tam-treated iKO mice.

Example 8

UVB-Induced Activation of Inflammasomes by Keratinocytes Depends Upon TRPV4

Figure 9:
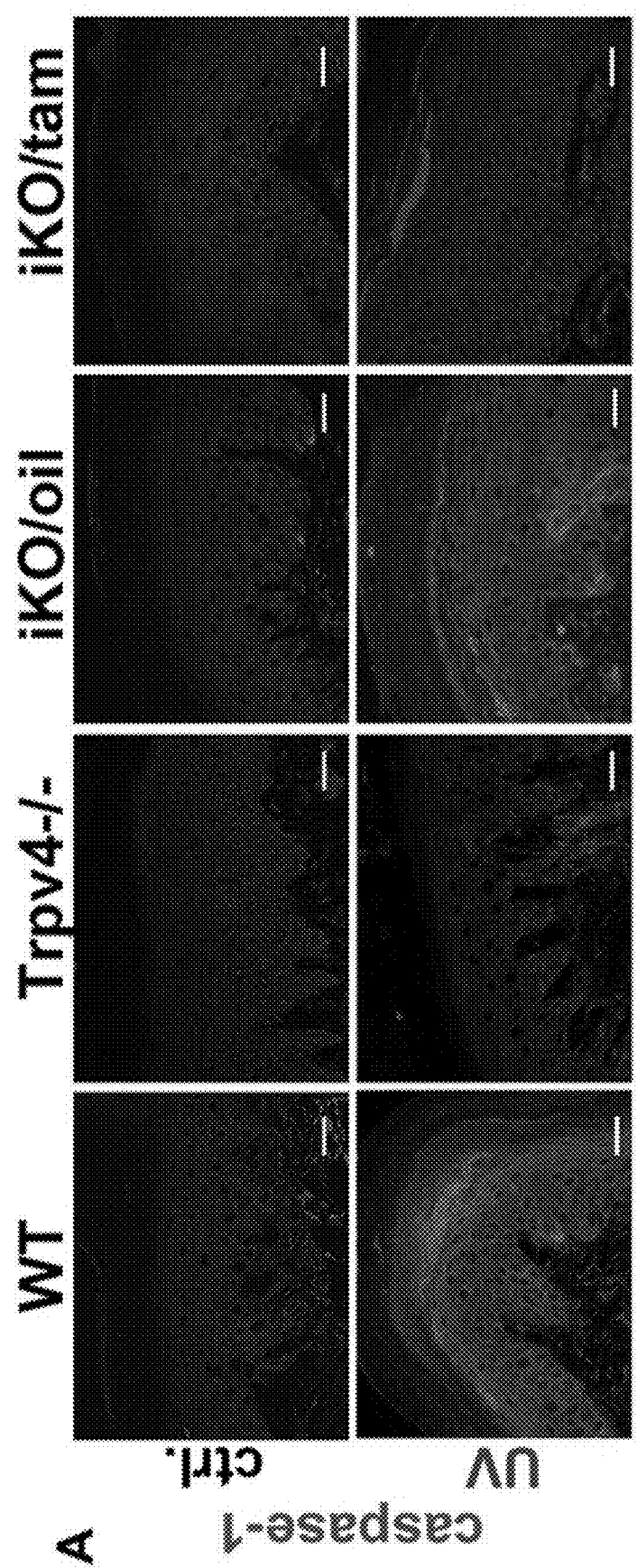
FIG. 9: UVB-evoked inflammasome activation in keratinocytes depends on TRPV4. (A) Caspase-1 immunolabeling in footpad skin in response to UVB. Representative images are from sections of skins before stimulation (control) or 48 hours post-UVB exposure. Bars=20 µm. (B) Quantifications of caspase-1 immunolabeling. Bar diagrams show densitometry, n≥3 animals/group. Comparisons: UVB exposed WT vs. Trpv4−/− and iKO+oil vs. iKO+tam. p<0.01 ANOVA. (C) Western blotting for caspase-1 from 1° MK±UVB-exposure. Note that caspase-1 levels, in particular cleaved caspase-1 (lower band), are elevated in UVB-exposed WT cells, but there is a complete absence of both procaspase-1 and cleaved caspase-1 in 1° MK from Trpv4−/− mice. (D) IL-1β is induced upon UVB-exposure and is dependent on TRPV4. Anti-IL-1β immunofluorescence, otherwise as in panel A. (E) Quantifications of IL-1β immunolabeling, n≥3 animals/group. Comparisons: UVB exposed WT vs. Trpv4−/− and iKO+oil vs. iKO+tam,  p<0.01 ANOVA. (F) IL-1β concentrations in interstitial fluid of UVB-exposed footpad. IL-1β levels (ELISA) are shown in lavaged interstitial fluid. Note strong up-regulation in WT and oil-treated iKO mice after UVB, in contrast significant attenuation in Trpv4−/− and tam-treated iKO mice. n≥5 mice/group,  p<0.01 ANOVA. (G) CXCL5 is induced upon UVB-exposure and is dependent upon TRPV4. Anti-CXCL5 immunolabeling, otherwise as in panel A. (H) Quantifications of CXCL5 immunolabeling, n≥3 animals/group. Comparisons: UVB exposed WT vs. Trpv4−/− and iKO+oil vs. iKO+tam,  p<0.01 ANOVA.
Figure 9:
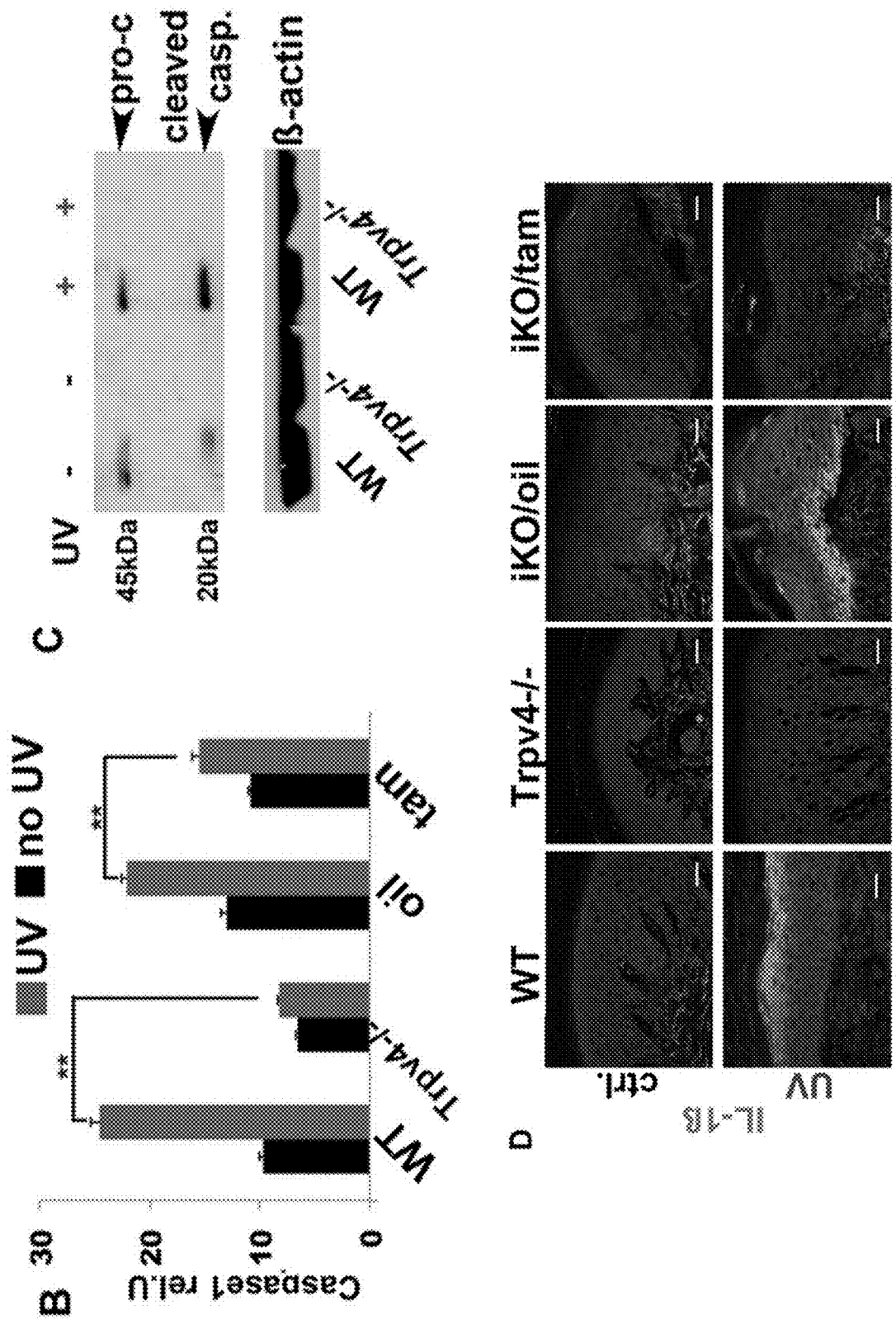
Figure 9:
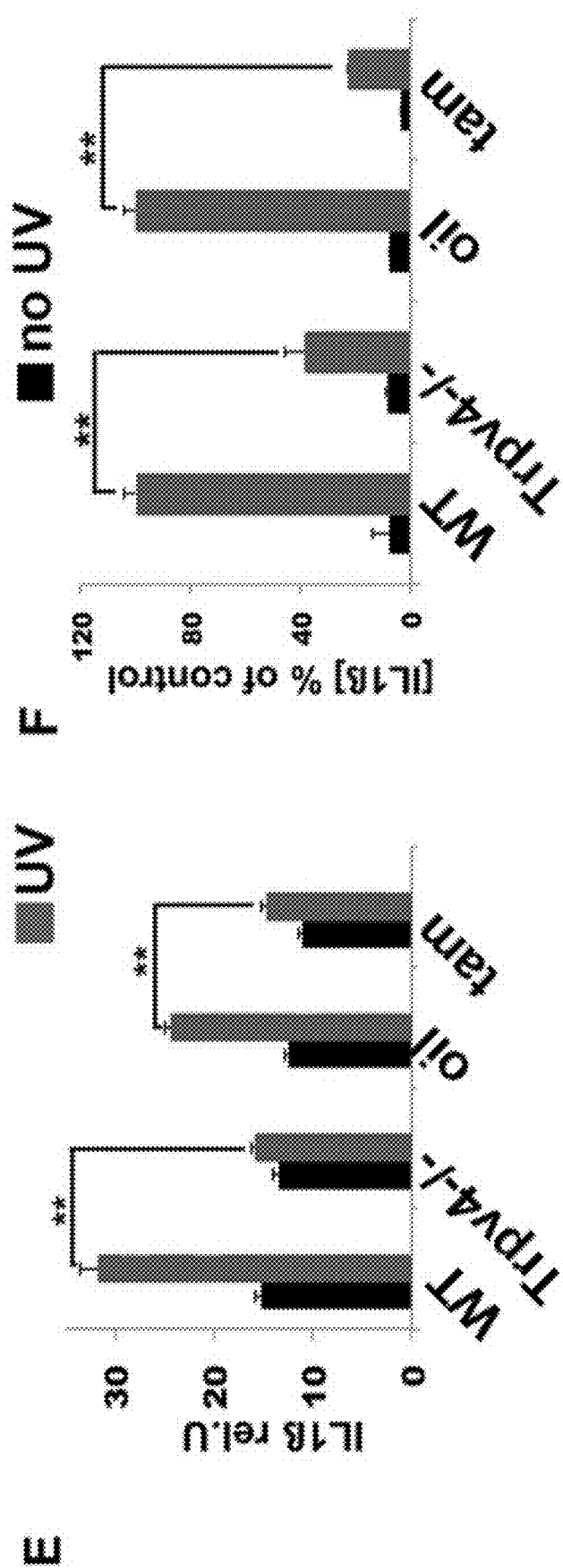
Figure 9:
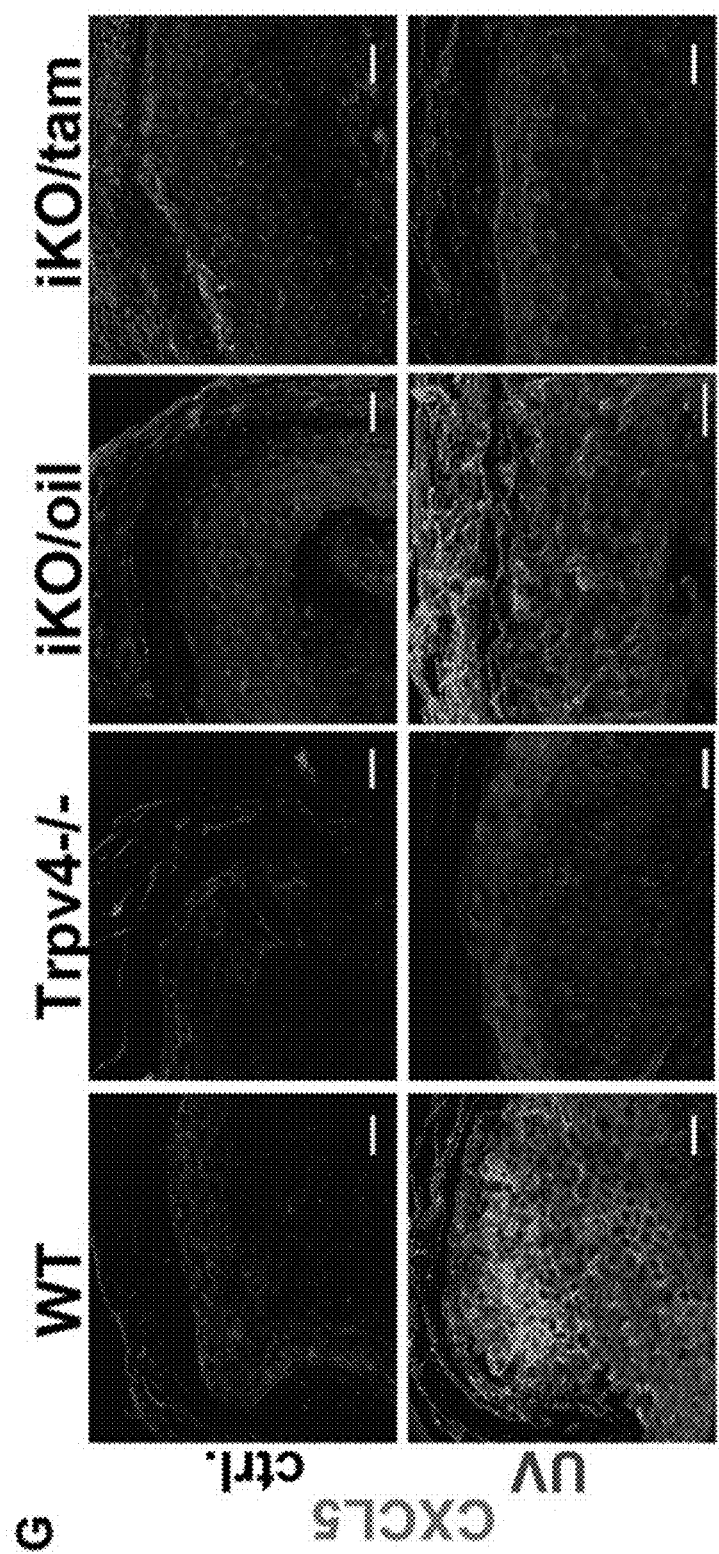
Figure 9:
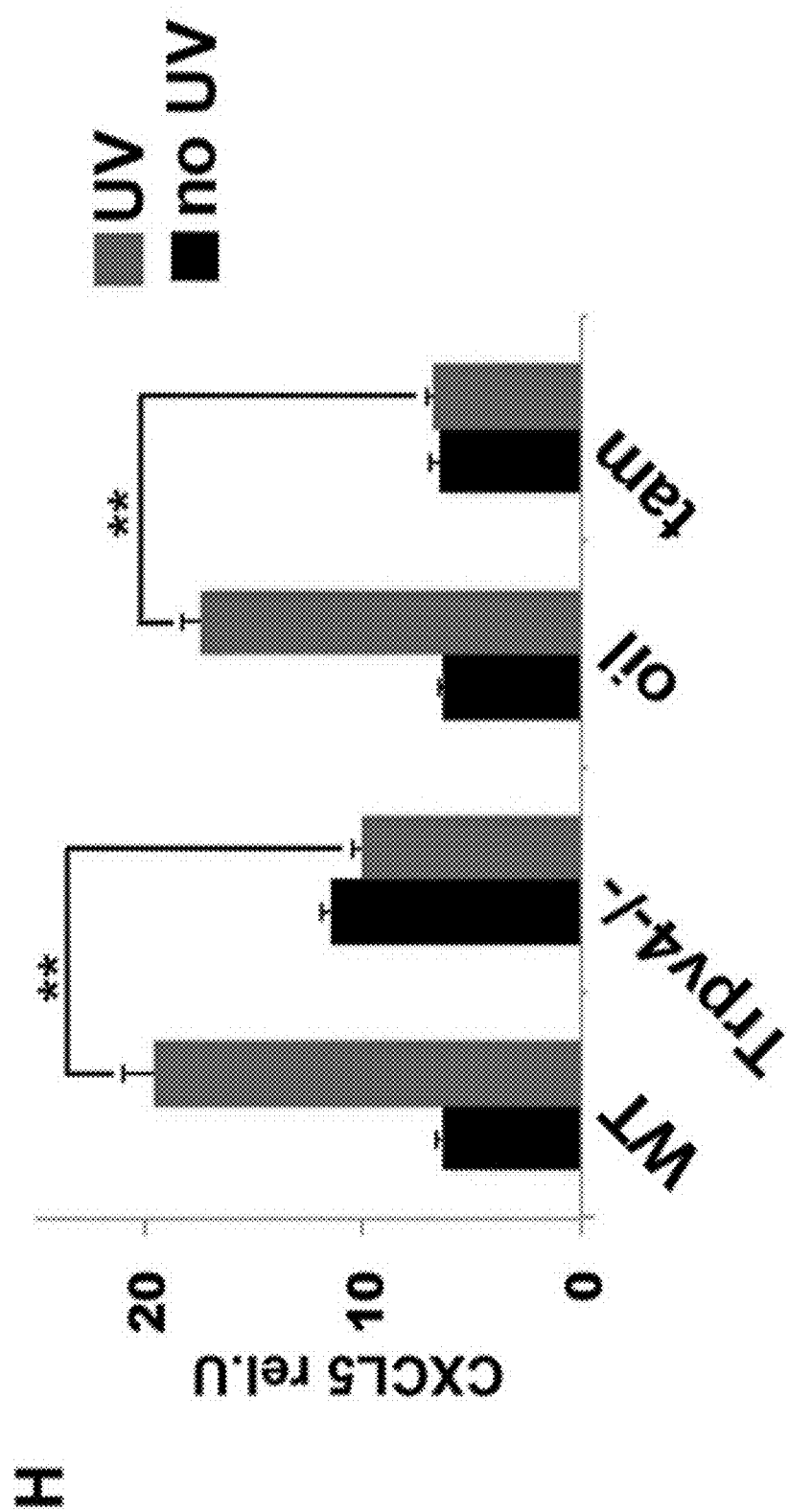

Another signaling mechanism linking UVB exposure to inflammation and nociception in keratinocytes is the inflammasome, a large multiprotein complex that assembles in response to infection and other cellular injury, and triggers an inflammatory cascade culminating in caspase-activation and production of cytokines IL-1 and IL-18. Previously, its formation was shown to depend upon Ca++ signaling, prompting us to query the dependence of inflammasome activation on TRPV4. Indeed, although caspase-1 was upregulated in UVB-treated control skin, this was largely eliminated in Trpv4−/− and greatly attenuated in tam-treated iKO skin (FIG. 9A-B). Moreover, even though caspase-1 cleavage (activation) was readily detected by Western blotting of lysates from WT 1° MK exposed to UVB, caspase-1 expression was lacking in Trpv4-null counterparts, even without UVB (FIG. 9C).

Similarly, upregulation of the pro-algesic inflammasome product IL-1β was readily detected in response to UVB treatment of control skin epidermis but not TRPV4-deficient epidermis. This was demonstrated not only by immunolabeling but also by measuring IL-1β levels in paw-pad edema interstitial fluid (FIG. 9D-F). Together, these results establish a fundamental importance of TRPV4 in keratinocyte-mediated activation of inflammasomes, which enhance caspase-1-mediated proteolytic cleavage of pro-IL-1β to form active IL-1β.

Related to IL-1β secretion by skin in response to UVB, we queried dependence of CXCL5 on Trpv4. CXCL5, whose expression is dependent upon IL1β/IL1R1 signaling, has recently been reported to function in a proalgesic/algogenic manner in keratinocytes in response to UVB in rodents and humans. Consistent with the reliance of inflammasome function and IL-1β expression on TRPV4, we found that similarly, UVB-induced proalgesic/algogenic CXCL5 upregulation is also dependent upon keratinocyte-derived TRPV4 (FIG. 9G-H).

Example 9

Figure 10:
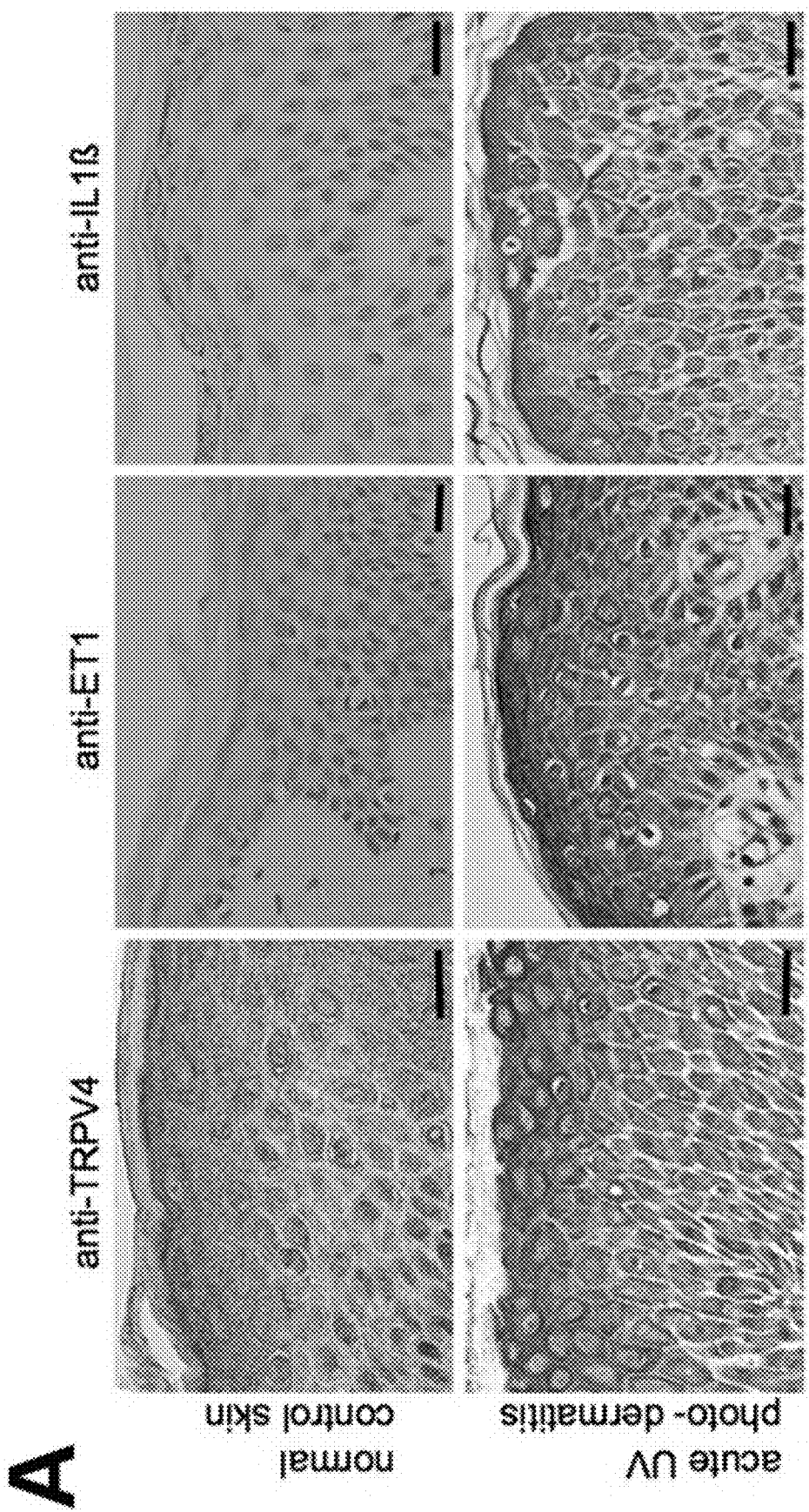
FIG. 10: Epidermal TRPV4, ET1 and IL-1β are elevated in photodermatitis as compared to healthy human skin. (A) Representative micrographs of TRPV4, ET1 and IL-1β distribution in the epidermis of acute photodermatitis, as compared to healthy human skin. Immunostaining for each antigen is increased in acute photodermatitis vs. healthy skin. Scale-bars=50 µm (left), 100 µm (middle), 50 µm (right). (B) Morphometric analysis for immunoreactive TRPV4, ET1 and IL-1β. Findings reveal significantly increased immunolabeling for all three proteins in acute photodermatitis as compared to healthy human skin (n=3 subjects for normal, healthy skin, and 3 patients for acute UV photodermatitis).
Figure 10:
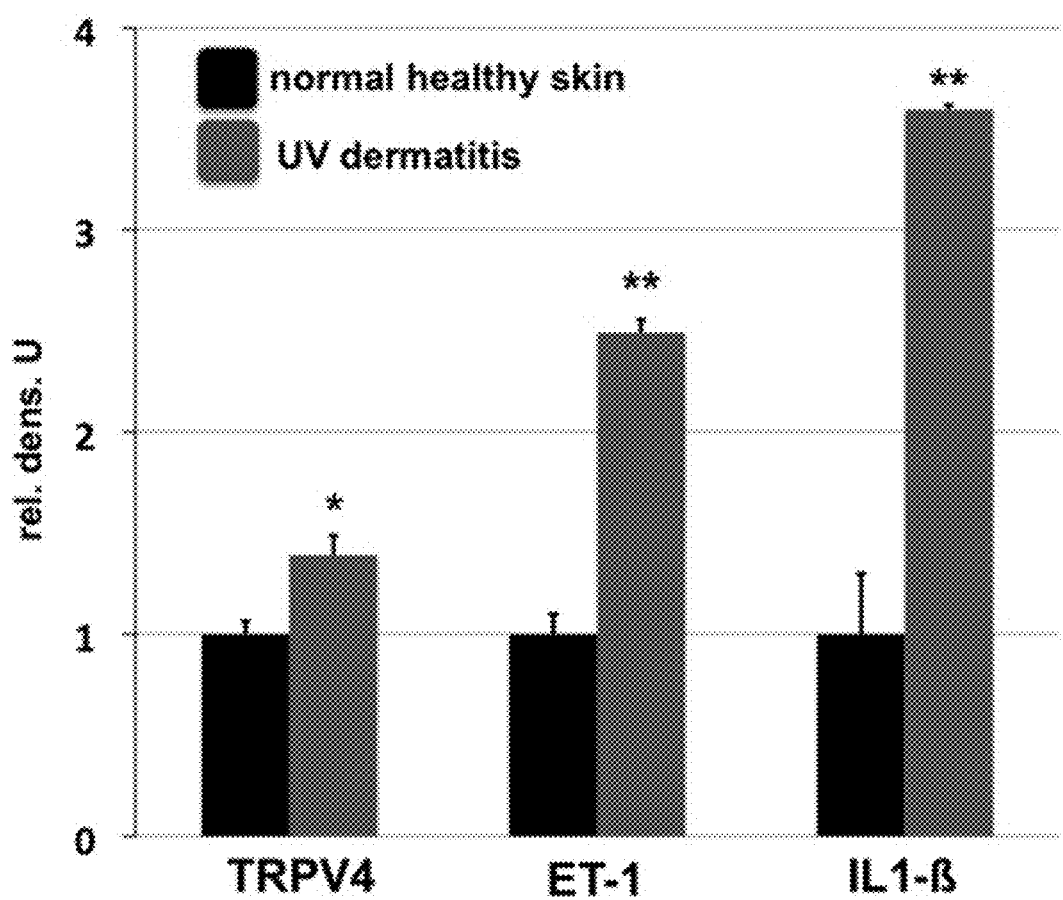
Figure 11:
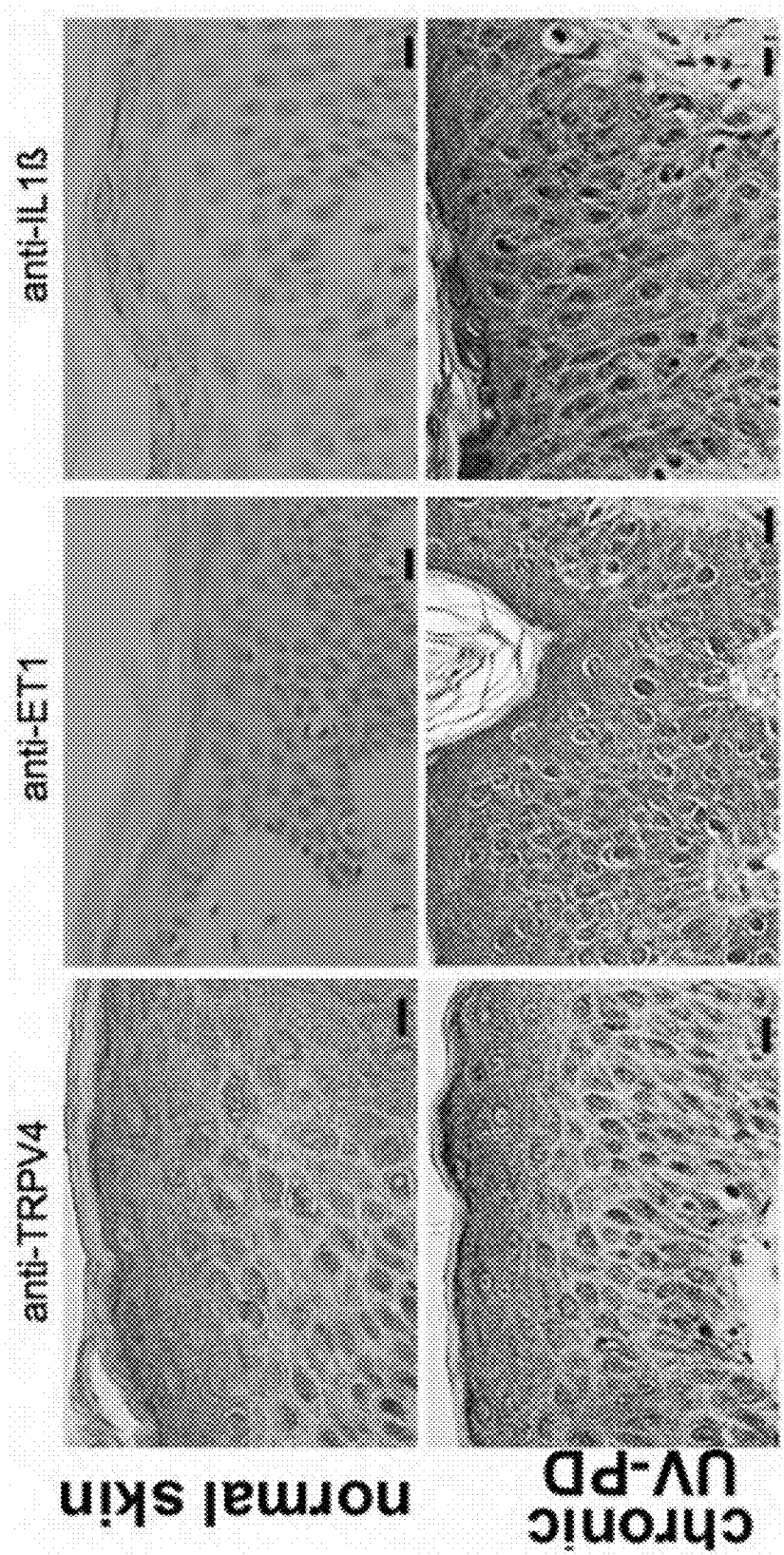
FIG. 11: Exemplars of human chronic photodermatitis. Upper panel shows normal healthy human skin, as displayed in FIG. 10A, for comparison. Lower panel shows examples of chronic photodermatitis with elevated expression of TRPV4, in spinous and basal layers, ET1 (throughout) and IL-1β (throughout). In comparison to acute photodermatitis, note reduced interstitial intraepidermal edema. Bar=50 µm.

Clinical Relevance of Epidermally-Derived TRPV4 in Transmitting Nociceptive Responses to UVB Exposure Interestingly, TRPV4 was significantly increased in the epidermis of human patients with UV photodermatitis (FIG. 10A and FIG. 11). As compared to healthy skin controls, a robust increase was also seen for ET1 and IL-1β immunostaining in acute photodermatitis (FIG. 10A-B). These findings suggest that TRPV4 is also likely to be involved in UVB-induced photodermatitis, one of the various responses of human skin to damaging UV radiation.

Figure 12:
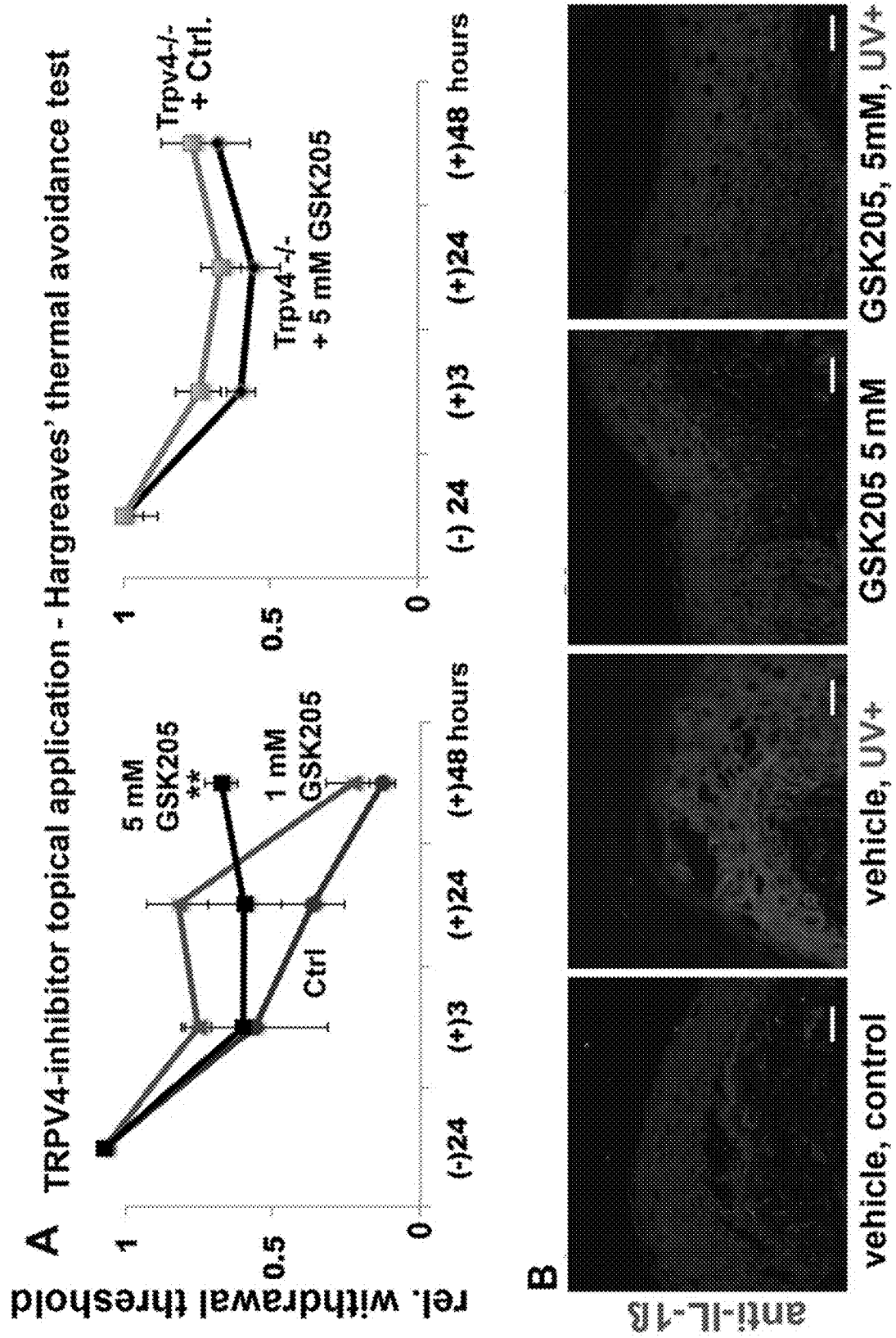
FIG. 12: External-topical application of a selective TRPV4 inhibitor attenuates UVB-evoked nocifensive behavior and inflammation. (A) UVB-induced nocifensive behavior. Pain behavior is attenuated by topical application of GSK205. The left-hand diagram shows withdrawal thresholds after UVB-exposure in response to noxious thermal cues (Hargreaves' test), and their modulation by two doses of topically applied GSK205 (1 mM and 5 mM; applied 60' and 10' pre-exposure). The higher dose led to a significant attenuation of thermal allodynia at 48 hours post-UVB; n=6 mice/group;  p<0.01 ANOVA. The right-hand diagram shows development of moderate thermal allodynia in Trpv4−/− mice, and similar sensitization for vehicle-treated vs. 5 mM GSK205-treated mice, indicating lack of off-target effects of the compound at 5 mM; n=5 mice/group. (B) GSK205-treatment attenuates keratinocyte expression of IL-1β in UVB-exposed footpad—representative micrographs. Bars=20 µm. (C) GSK205-treatment attenuates keratinocyte expression of IL-1β in UVB-exposed footpad quantifications. Bar diagrams show densitometry results from n=3 mice/group,  p<0.01 ANOVA. (D) GSK205-treatment attenuates secretion of IL-1β by UVB-exposed 1° MK. IL-1β concentrations in supernatant (ELISA), are shown in response to UVB. Cells were cultured +/−5 µM GSK205. Note prevention of increase in IL-1β secretion in response to UVB upon treatment with GSK205. ** P<0.01 ANOVA.
Figure 12:
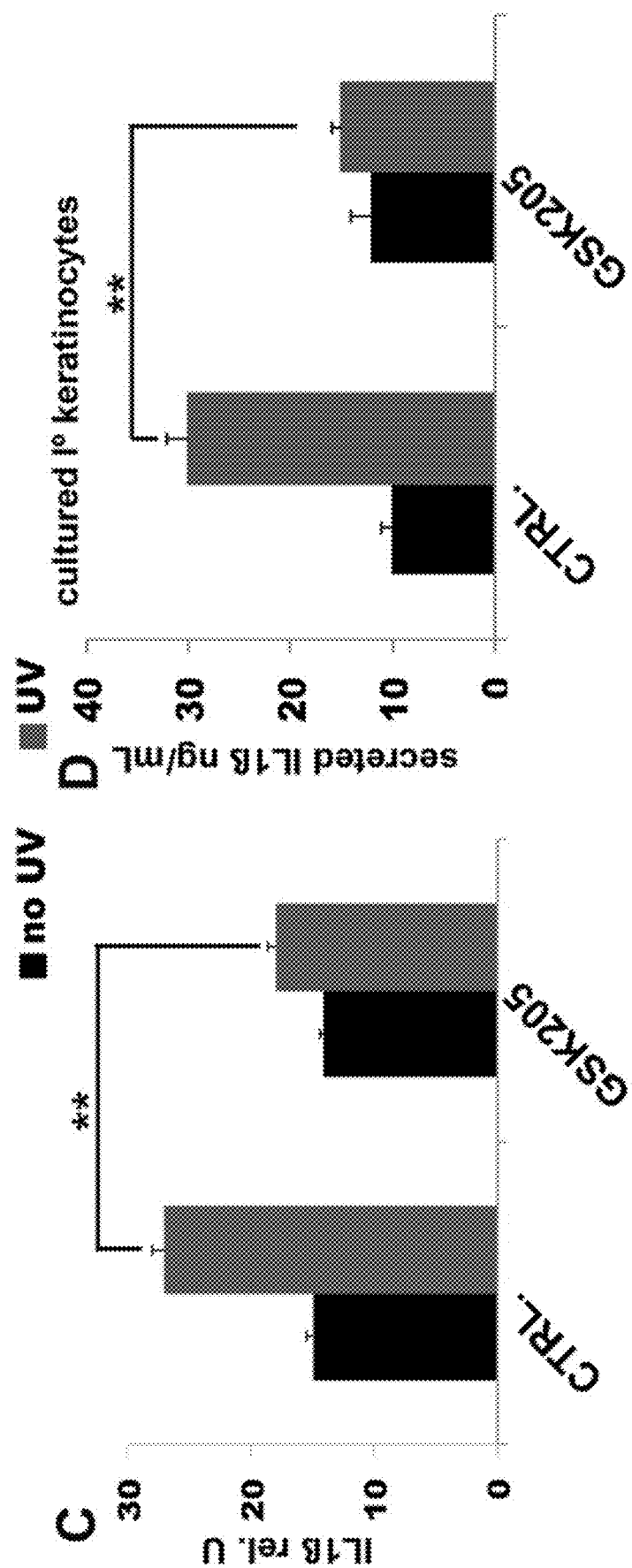

In view of the observed impact of epidermal-specific TRPV4-deficiency on mouse nociception in response to UVB, and because of the unambiguous effects of selective TRPV4 blockers on 1° MK in vitro, we tested the possible clinical relevance of our findings. For this purpose, we topically applied TRPV4 inhibitor GSK205 to WT mouse skin and subsequently exposed animals to UVB (FIG. 12A). While solvent-treated control mice displayed a normal thermal hypersensitivity response, mice treated with 1 mM GSK205 showed a ~24 hour delay in sensitivity, and increasing the dose to 5 mM GSK205 resulted in a sustained attenuation of thermally-evoked nocifensive behavior. Of note, this treatment also resulted in a significantly reduced sensitivity of mice to von Frey hair mechanical stimulation.

To assess specificity of the external-topical treatment, we applied 5 mM GSK205 to Trpv4–/– mice vs. vehicle control (FIG. 12A). Nocifensive behavior did not show any inter-group differences, yet was significantly different from pre-stimulation thresholds. Based upon these results, topical treatment with 5 mM GSK205 in vivo did not elicit off-target effects on other channels or signaling pathways that might measurably influence withdrawal behavior. Although GSK205-mediated antagonism of macrophage and neural TRPV4 cannot be excluded, the epidermis is the initial target of topically applied drugs, and the effects we measured with 5 mM GSK205 were consistent with those we observed in Trpv4 tam-induced iKO skin.

Figure 14:
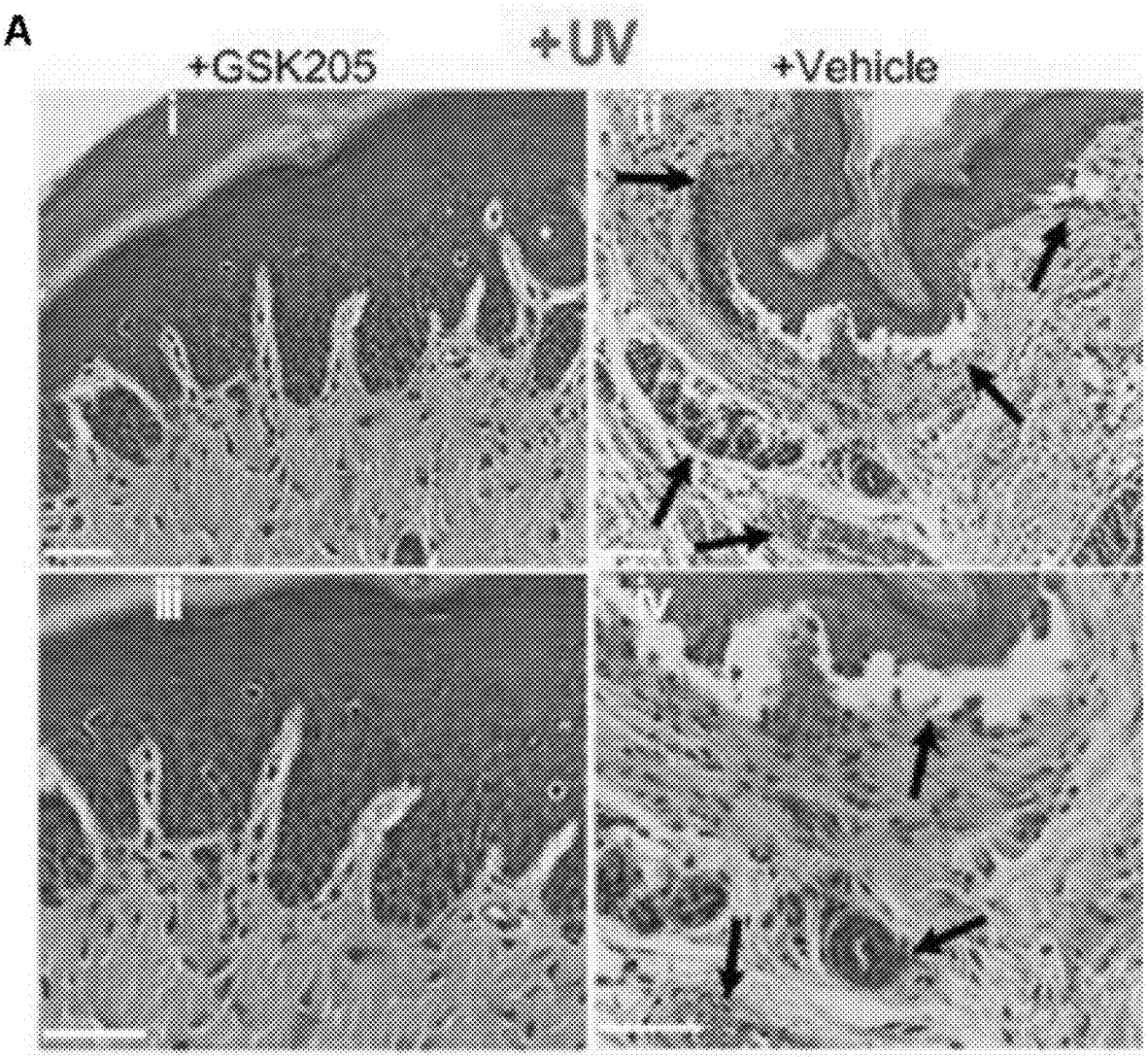
FIG. 14: External-topical application of a selective TRPV4 inhibitor attenuates UVB-evoked nocifensive behavior and inflammation. (A) UVB-photodermatitis is attenuated in mice treated with GSK205. Representative H&E micrographs of paw-pad skin are shown, bars=20 µm. Treatment of UVB-exposed skin with GSK205 improved the skin architecture in mice as compared to vehicle-treated mice after 24 hours. (i) and (iii) Representative skin sections of UVB-induced photodermatitis after GSK205 treatment showed markedly reduced inflammatory infiltrate, less spongiosis and dermal-epidermal blisters with remaining epidermal thickening. (ii) and (iv) Vehicle-treated mice after UVB-induced photodermatitis were characterized by signs of severe acute photodermatitis such as spongiosis, epidermal hyperkeratosis, disrupted dermal-epidermal border (blister), and a marked inflammatory infiltrate with dilated blood vessels and dermal edema (arrows). Also note the erythrocyte accumulation in blood vessels indicative of dermatitis. (B) Topical treatment with a TRPV4-specific inhibitor attenuates upregulation of algogenic ET1/Edn1. Edn1 mRNA was determined by qPCR after extraction of total RNA from paw-pad epidermis. In vehicle treated skin, note increase of Edn1 expression with early up-regulation at the 2 hour time-point, and sustained elevation up to the 24 hour time-point. This time-course resembles that seen in WT control mice, when comparing to Trpv4−/−(FIG. 15). Importantly, topical treatment with 5 mM GSK205 results in complete lack of this regulation; n=4 mice/group, *p<0.05 ANOVA. (C) GSK205 does not function as sunscreen. Schematic illustrates the experimental set-up. (D) GSK205 does not function as sunscreen. The bar diagram shows results from n=7-8 mice/group, note absence of a change in UVB permeation with 5 mM GSK205, topically applied as for (B), vs. vehicle control, yet significantly reduced with sunscreen SPF100.
Figure 14:
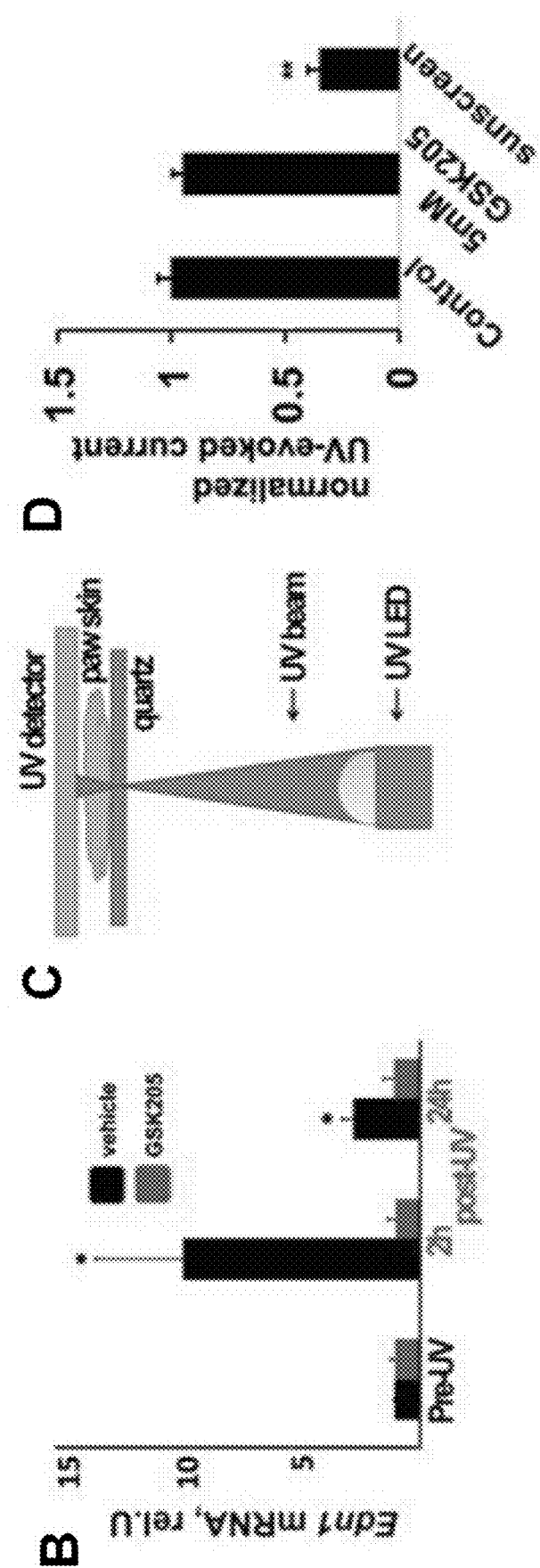
Figure 15:
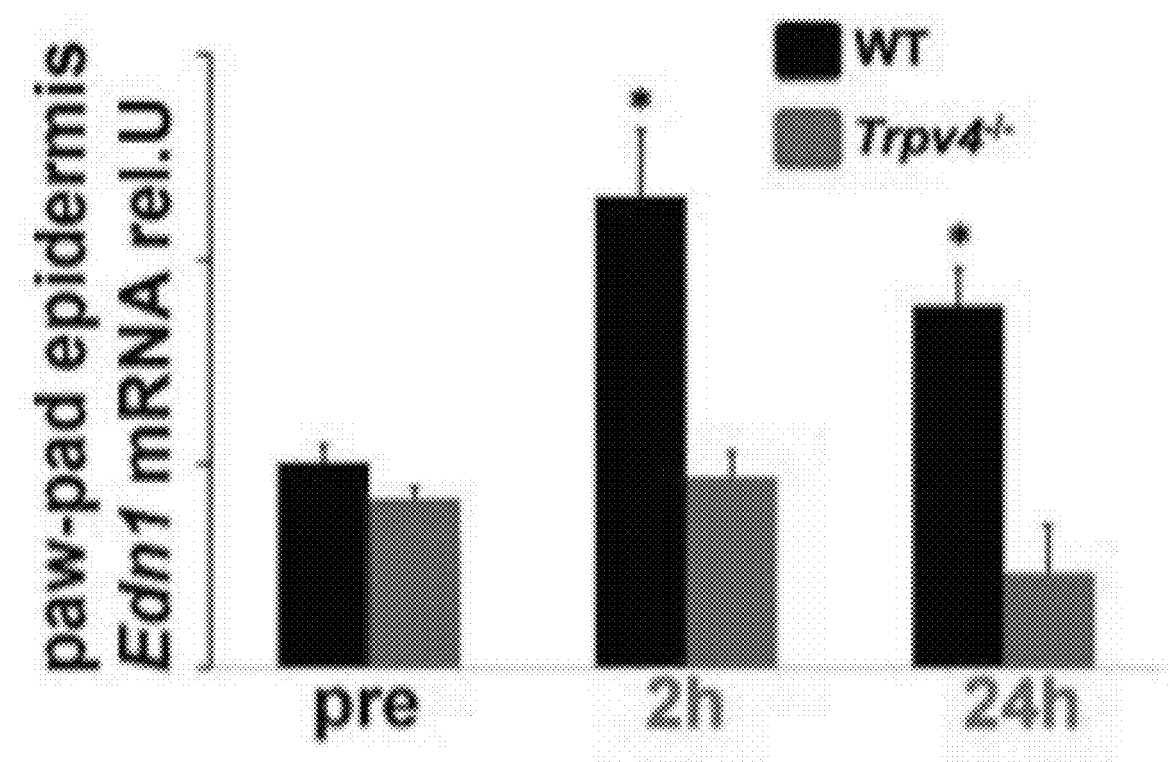
FIG. 15: Upregulation of ET1/End1 in mouse paw in response to UVB. Edn1 mRNA was determined by qPCR after isolation of total RNA from paw-pad epidermis. Note the early increase, at the 2 hour time-point, in WT control epidermis, and its complete lack in Trpv4−/−, and sustained upregulation at 24 hours, slightly reduced vs. 2 hour time-point, again complete lack of upregulation in Trpv4−/−. Quantifications are for n=4 mice/group. ** denotes statistically significant (p<0.01, t-test).

Histopathology of GSK205-topically-treated skin showed hallmarks of UVB-photodermatitis in vehicle-treated paws, strikingly contrasting to GSK205-treated animals (5 mM), whose paws showed virtual elimination of inflammation (FIG. 14A). In view of TRPV4-dependence of ET/Edn1 expression in skin, we measured Edn1 mRNA abundance in GSK205 vs. vehicle treated paw-pad skin. We detected an early upregulation in vehicle-treated mice at the 2 hour time-point which was still significantly elevated over pre-exposure animals at 24 hours, resembling Edn1 regulation and time-course in untreated WT mice (FIG. 14B, compare to FIG. 15). In striking contrast, and in keeping with histopathology, Edn1 mRNA-expression in GSK205 topically-treated skin was found unchanged.

To validate these finding, we tested UVB absorption in GSK205-treated paw-pad skin, and whether GSK205 thus functions as sunscreen. Results were negative, as demonstrated by equal UVB permeation of GSK205- vs. vehicle-treated paw-pad skin, yet valid, as demonstrated by significant decrease of UVB permeation with SPF100 sunscreen (FIG. 14CD and FIG. 16AB). These results corroborate that effects of topically applied GSK205 are caused by TRPV4 antagonism, likely by affecting TRPV4 in epidermal keratinocytes.

Figure 13:
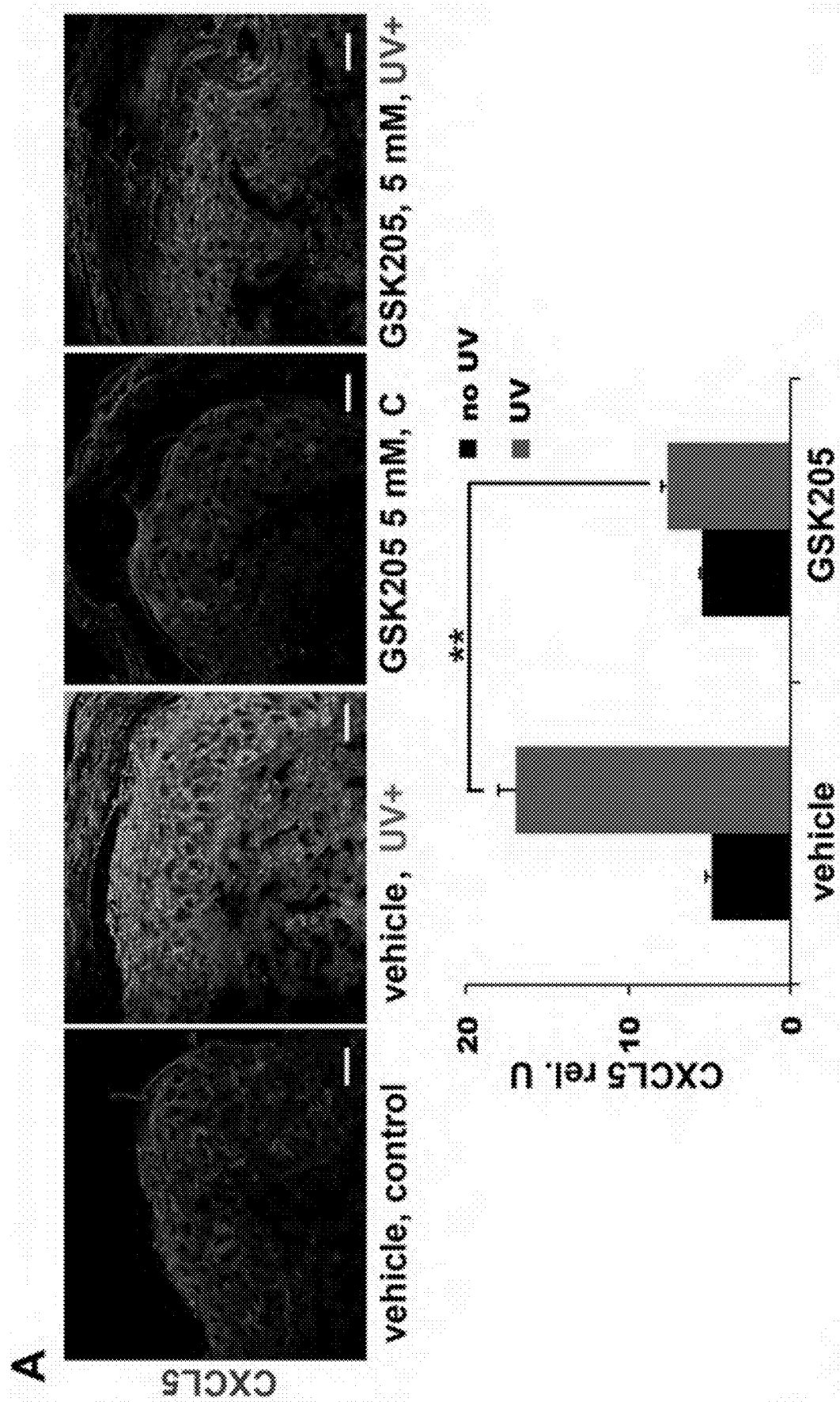
FIG. 13: Topical application of a selective TRPV4 inhibitor attenuates UVB-evoked nocifensive behavior by suppressing upregulation of pro-algesic/algogenic mediators in murine keratinocytes—Findings for CXCL5 and IL6. (A) GSK205-treatment attenuates keratinocyte expression of CXCL5 in UVB-exposed footpad—micrographs and quantitation. As in FIG. 12B, specific immunolabeling for CXCL5, which is selectively upregulated in footpad keratinocytes in response to UVB, note attenuation with GSK205 treatment. Bar diagrams show densitometry of CXCL5 immunolabeling, n=3 animals per group, ≥3 sections analyzed per animal. Note significant differences for vehicle-treated mice between UVB-exposed and non-exposed, no such difference for mice treated topically with 5 mM GSK205. Comparison UVBexposed between vehicle and GSK205-treated,  p<0.01 ANOVA. Bar=20 µm. (B) GSK205-treatment attenuates keratinocyte expression of IL-6 in UVB-exposed footpad—micrographs and quantification. As in FIG. 12B and FIG. 13A, specific immunolabeling for IL-6, demonstrates similar regulation of IL-6 as for CXCL5 and IL-1β. Comparison UVB-exposed between vehicle and GSK205-treated,  p<0.01 ANOVA. Bar=20 µm.
Figure 13:
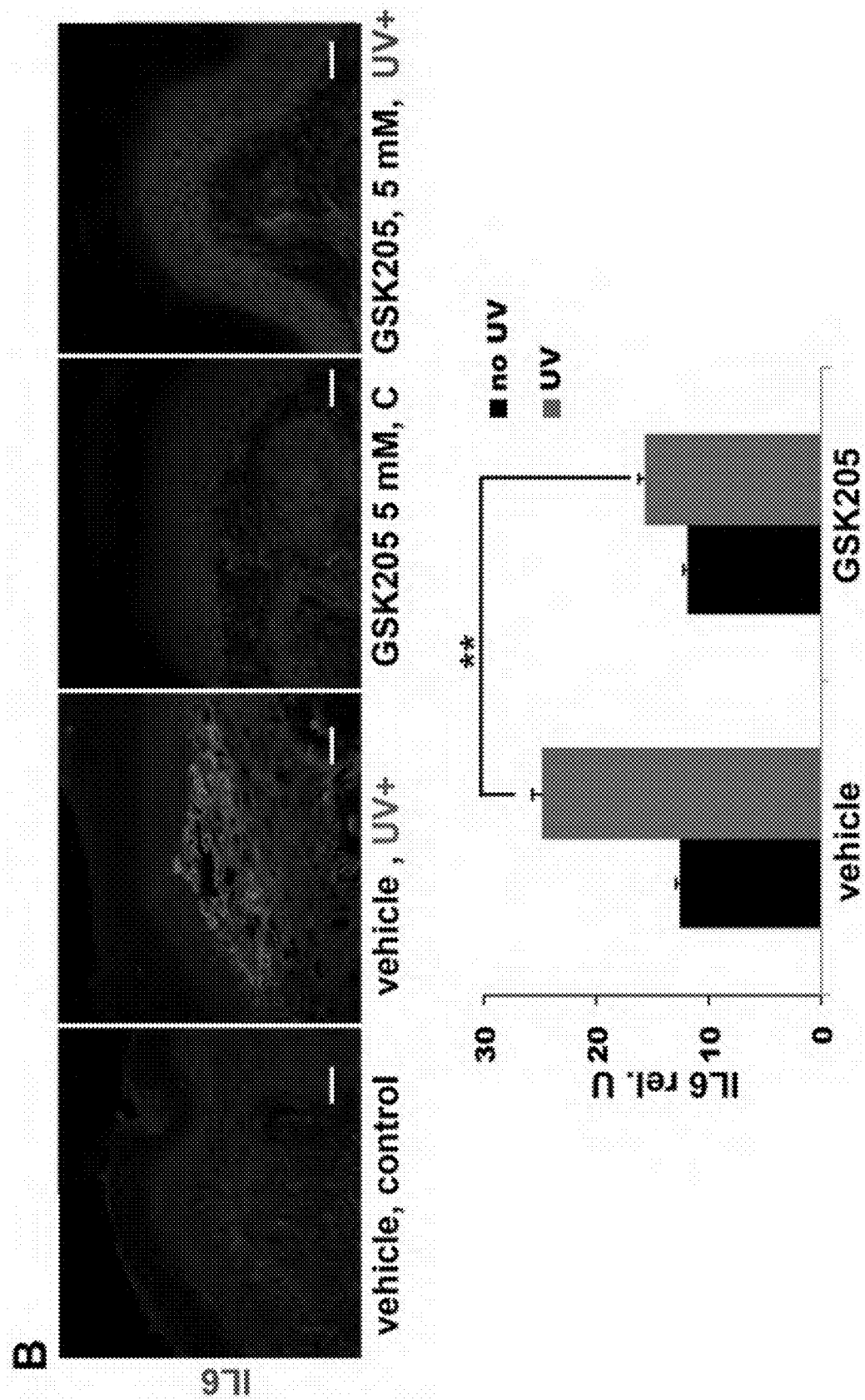

We also tested the response of down-stream UVB effector mechanisms to GSK205 treatment in vivo. In mouse skin, IL-1β was upregulated in response to UVB with vehicle treatment, yet failed to upregulate with 5 mM GSK205 (FIG. 12B-C). This in vivo finding was recapitulated in 1° MK whose UVB-induced increase in IL-1β secretion was completely eliminated in the presence of 5 μM GSK205 (FIG. 12D). Comparably significant blocks were observed on CXCL5 and IL-6 upregulation (FIG. 13A-B).

Thus, the UVB-evoked signaling in the epidermis was reduced both when TRPV4 was antagonized by topical application of specific small molecule inhibitors, and when Trpv4 was targeted genetically in our keratinocyte-specific and inducible Trpv4 conditional null mice. This suggests ion channel function of TRPV4 to be the critical factor common to both experimental approaches. Taken together, these findings render selective TRPV4 blockers, such as GSK205, excellent candidates for therapeutic approaches to reduce damaging inflammatory responses caused by UVB exposure in humans.

Example 10

Importance of TRPV4 for the Itch-Response

Figure 17:
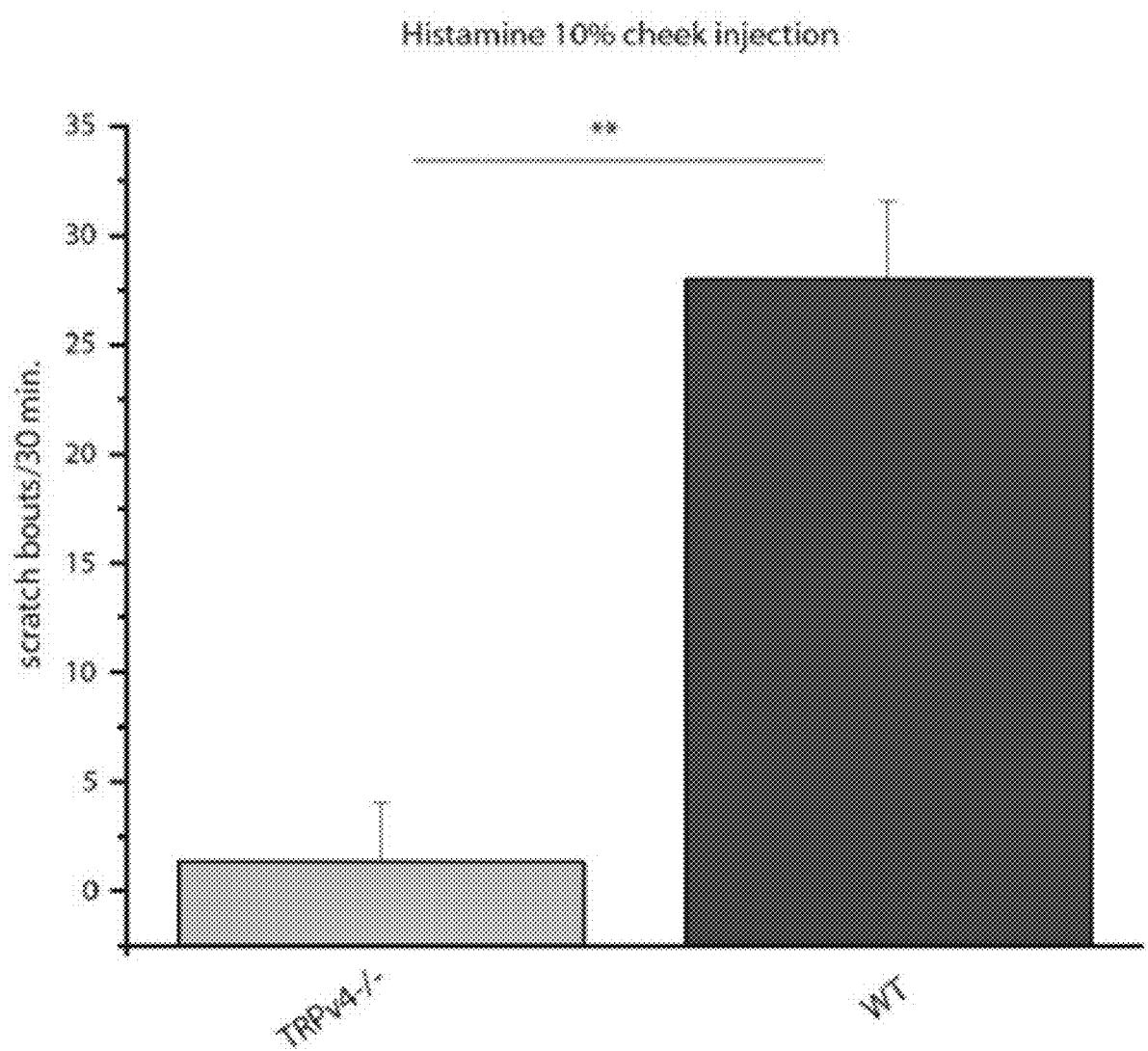
FIG. 17: Role of TRPV4 in itch transmission in mice in vivo. Histamine (10%) was injected intracutaneously into the cheek of C57b/6 control (WT) or TRPV4 knockout mice (Trpv4 pan-knockout; n=6 per group). Over 30 min, TRPV4 null mice showed a significant reduction ((p<0.01) t-test)) of itch-behavior as compared to WT mice.

Behavioral studies show reduced scratching behavior in Trpv4 null mice compared to WT mice. Histamine (10%) was injected intracutaneously into the cheek of C57b/6 control (WT) or Trpv4 null mice (n=6 per group). Over 30 min, Trpv4 null mice showed a significant reduction ((p<0.01) t-test) as compared to WT mice (FIG. 17). The results demonstrated that similar to TRPV1 and TRPA1, TRPV4 is involved in itch, and that blockers of TRPV4 activation may be beneficial for the treatment of itch.

Example 11

Evidence for the Role of TRPV4 in Itch

It was further examined whether TRPV4 has a role in itch using mice with a selective TRPV4 deletion and Compound 48/80. Compound 48/80 (available from Sigma-Aldrich, St. Louis, Mo.) is a well-established pruritogen and elicits histamine-dependent itch by degranulating mast-cells. Mice were used in which TRPV4 channels had been selectively deleted in skin keratinoctyes by gene targeting, and the targeted allele was induced by feeding of tamoxifen, as detailed in Example 2. Wild-type mice were used as a control.

Figure 18:
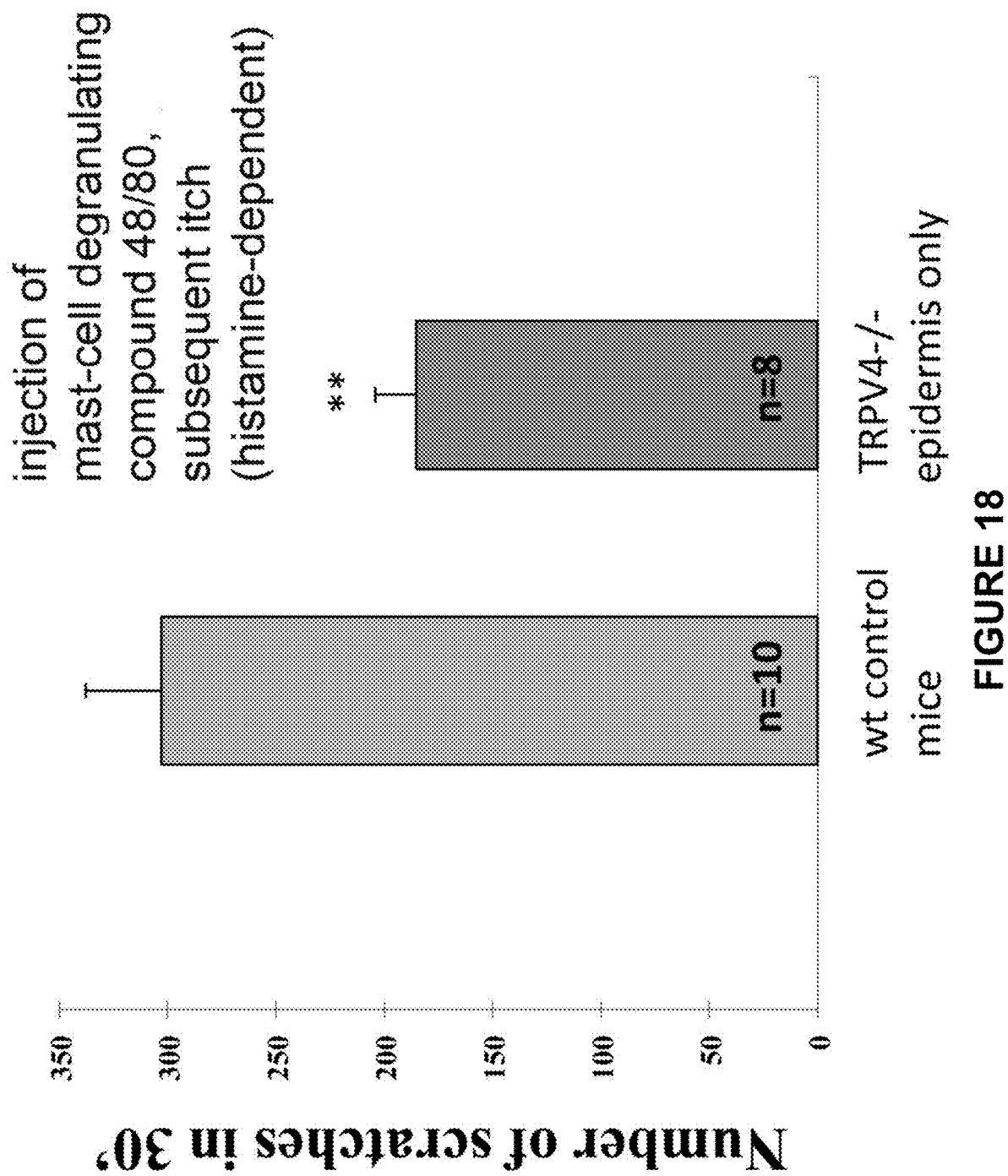
FIG. 18: The role of TRPV4 in itch. Shown is a graph of scratching behavior after administration of a pruritogen in mice with TRPV4 deletion in keratinocytes after induction of the TRPV4 knockout, as compared to mice without induction. Without induction, the mice function as wild-type control mice (Moore et al. *Proc. Natl. Acad. Sci. U.S.A.* 2013, 110, E3225-E3234). Compared to control mice, scratch behavior was significantly reduced for mice in which TRPV4 channels had been selectively deleted in skin keratinocytes.

Compound 48/80 (100 micrograms in 50 μL) was injected retro-auricularly into the mice, and mouse scratch behavior in response thereto was monitored. Results are shown in FIG. 18. Compared to control mice, scratch behavior over 30 min was significantly reduced for mice in which TRPV4 channels had been selectively deleted in skin keratinoctyes.

The results provided additional evidence for the role of TRPV4 in itch, and in particular, dependence of itch on the TRPV4 ion channel expressed in keratinocytes of the skin. The results clearly indicated that TRPV4 in skin epithelial cells (keratinocytes), and not sensory neurons or immune-related or allergy-related cells, is the critical site of TRPV4 expression and function in histamine-dependent itch. These findings also suggested that topical targeting of TRPV4 channels may be successful in combating itch.

Example 12

Overall Preparation of Compounds

The general scheme for preparation of compounds 16-8, 16-12c, 16-13, 16-14, 16-16, 16-18, and 16-8/18hy is below, with the following reagents and conditions for each step: (i) $K_2CO_3$, $CH_3CN$; (ii) Zn, MeOH, 12 M HCl; (iii) 1,1'-Thiocarbonyldiimidazole (iv) 7 M $NH_3$ in MeOH; (v) EtOH, reflux:

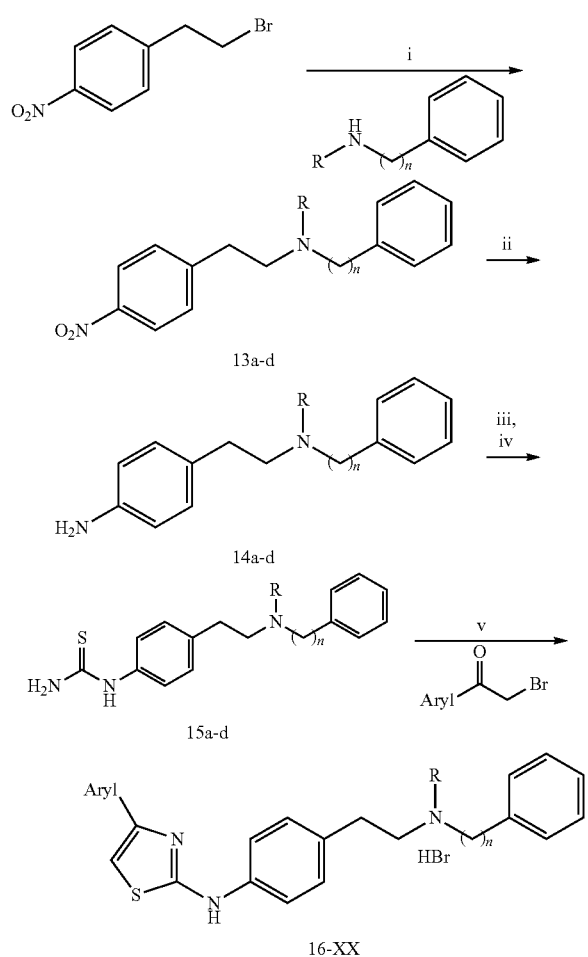

Step (i) General Procedure for the SN2 Displacement of 4-Nitrophenethyl Bromide.

Powdered, oven-dried $K_2CO_3$ (1.5 eq.) and the amine (1.5 eq.) were added sequentially to a room temperature solution of the bromide (0.33 M) in anhydrous $CH_3CN$. The reaction mixture was heated to 80° C. (oil bath temp) until analysis of the reaction mixture by LCMS indicated complete consumption of the bromide (~6-18 hours). The mixture was cooled to room temperature and diluted with brine (two volume equivalents). The resulting emulsion was extracted with EtOAc (2× one volume equivalent). The combined extracts were added to silica gel (mass of silica gel=2× mass of starting bromide) and the mixture was concentrated to dryness under reduced pressure. Flash column chromatography (RediSepRf $SiO_2$, 100% $CH_2Cl_2 \rightarrow 5\%$ MeOH in $CH_2Cl_2$) gave the product as a brown to amber oil. The yield of the intermediates 13a-d (the tertiary amines formed in step (i)) are presented in Table 1.

TABLE 1

Yield of tertiary amines 13a-d formed in step (i)

| Intermediate No. | R | n | yield |
|---|---|---|---|
| 13a | Me | 0 | 17% |
| 13b | Me | 1 | 49% |
| 13c | Me | 2 | 42% |
| 13d | Et | 1 | 15% |

Step (ii) General Procedure for the Nitro to Aniline Reduction.

A solution of the nitro compound (0.5 M in MeOH) was cooled in an ice-NaCl bath. Zinc dust (4.5 eq.) was added in one portion followed by drop wise addition of 12 M HCl (4.5 eq.) over 2-3 minutes. After 1 hour, the cooling bath was removed, and the reaction mixture was allowed to stir over night at room temperature. The following morning, the mixture was cooled in an ice-NaCl bath once again and 30% aqueous NaOH was added drop wise until pH 14 (universal indicating pH paper) was reached. The mixture was diluted with $CH_2Cl_2$ (five volume equivalents) and stirred for 5 minutes. After this time, insolubles were removed at the vacuum, and the filter cake was washed with $CH_2Cl_2$ (2×25 mL). The organic phase of the filtrate was separated, washed with brine (100 mL), and dried ($MgSO_4$). The drying agent was removed by filtration. Silica gel (~5 g) was added, and the filtrate was concentrated to dryness under reduced pressure. Flash column chromatography (RediSepRf $SiO_2$, 100% $CH_2Cl_2 \rightarrow 5\%$ MeOH in $CH_2Cl_2$) gave the product as a clear, amber oil. The yield of the intermediates 14a-d (the anilines formed in step (ii)) are presented in Table 2.

TABLE 2

Yield of anilines 14a-d formed in step (ii)

| Intermediate No. | R | n | yield |
|---|---|---|---|
| 14a | Me | 0 | 75% |
| 14b | Me | 1 | 84% |
| 14c | Me | 2 | 97% |
| 14d | Et | 1 | 85% |

Steps (iii) and (iv) General Procedure for Thiourea Formation.

A solution of the aniline (0.22 M) in anhydrous $CH_2Cl_2$ was added drop wise over 2-5 minutes to an ice-NaCl bath cooled solution of 1,1'-thiocarbonyldiimidazole (2 eq., 0.15 M) in anhydrous $CH_2Cl_2$. After 15 minutes, the cooling bath was removed and the reaction mixture was stirred at room temperature until analysis by TLC (5% MeOH in $CH_2Cl_2$) indicated complete consumption of the starting aniline. The mixture was cooled once again in an ice bath and 7 M $NH_3$ in MeOH (10.5 eq.) was added drop wise over 2-5 minutes. The bath was removed and the mixture was stirred over night at room temperature. Silica gel (mass of silica gel=2× mass of starting aniline) was added and the mixture was concentrated to dryness under reduce pressure. Flash column chromatography (RediSepRf $SiO_2$, 100% $CH_2Cl_2 \rightarrow 10\%$ MeOH in $CH_2Cl_2$) gave the pure thiourea. The yield of the intermediates 15a-d (the thioureas formed in steps (iii)-(iv)) are presented in Table 3.

TABLE 3

Yield of thioureas 15a-d formed in steps (iii)-(iv)

| Intermediate No. | R | n | yield |
|---|---|---|---|
| 15a | Me | 0 | 99% |
| 15b | Me | 1 | 96% |
| 15c | Me | 2 | 88% |
| 15d | Et | 1 | 67% |

Step (v) General Procedure for Thiazole Formation.

A mixture of the thiourea (0.1 M) in EtOH and the α-bromoacetophenone derivative (1.1 eq.) was heated to 75° C. (oil bath temperature) until analysis by TLC (5% MeOH in CH$_2$Cl$_2$) indicated complete consumption of the thiourea. Silica gel (mass of silica gel=2× mass of starting thiourea) was added, and the mixture was concentrated to dryness under reduced pressure. Flash column chromatography (RediSepRf SiO$_2$, 100% CH$_2$Cl$_2$→10% MeOH in CH$_2$Cl$_2$) gave the pure thiazole hydrobromide. The yield of the final products 16-8 to 16-8/18hy (the thiazole hydrobromides formed in step (v)) are presented in Table 4.

TABLE 4

Yield of thiazole hydrobromides 16-8 to 16-8/18hy formed in step (v)

| Compound No. | R | n | aryl | yield |
|---|---|---|---|---|
| 16-8 | Me | 1 | phenyl | 56% |
| 16-12c | Me | 2 | 3-pyridyl | 82% |
| 16-13 | Me | 1 | 4-pyridyl | 83% |
| 16-14 | Me | 1 | 2-pyridyl | 94% |
| 16-16 | Me | 0 | 3-pyridyl | 98% |
| 16-18 | Et | 1 | 3-pyridyl | 31% |
| 16-8/18hy | Et | 1 | phenyl | 93% |

Example 13

Preparation of Compounds 16-8 and 16-8/18hy

Compound 16-8.

Compound 16-8 was prepared as detailed in Example 11. Briefly, a suspension of the bromide (5.01 g, 21.8 mmol), N-benzyl methylamine (4.2 mL, 33 mmol, 1.5 eq.) and K$_2$CO$_3$ (4.6 g, 33 mmol, 1.5 eq.) in anhydrous CH$_3$CN (65 mL) was heated to 80° C. (oil bath temp) for 18 hours, after which time the starting material was nearly complete. The mixture was cooled to room temperature and diluted with brine (120 mL). The resulting emulsion was extracted with EtOAc (2×60 mL). The combined extracts were added to silica gel (~10 g) and the mixture was concentrated to dryness under reduced pressure. Flash column chromatography (RediSepRf SiO$_2$ (120 g), 100% CH$_2$Cl$_2$→5% MeOH in CH$_2$Cl$_2$) gave the product as a clear, dark orange oil (2.91 g, 49%). $^1$H NMR (CDCl$_3$, 400 MHz): 8.13 (d, J=8.4 Hz, 2H), 7.32 (d, J=8.4 Hz, 2H), 7.30-7.22 (m, 5H), 3.55 (s, 2H), 2.91 (t, J=6.8 Hz, 2H), 2.68 (t, J=6.8 Hz, 2H), 2.29 (s, 3H). ESIMS: m/z 271 [(M+H)+].

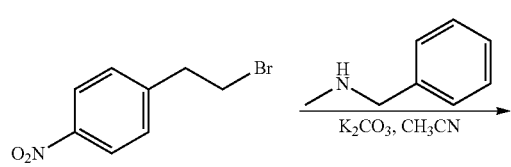

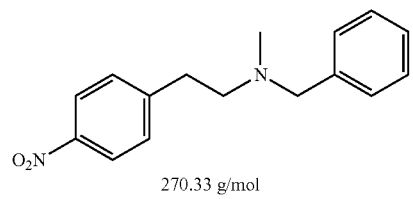

270.33 g/mol

A solution of the nitro compound (2.8 g, 10.4 mmol) in MeOH (20 mL) was cooled in an ice-NaCl bath. Zinc dust (325 mesh, 3 g, 4.5 eq.) was added followed by drop wise addition of 12 M HCl (3.8 mL, 4.5 eq.) over 2-3 minutes. After 1 hour, the cooling bath was removed and the reaction mixture was allowed to stir over night at room temperature. The following morning, the mixture was cooled in an ice-NaCl bath once again and 30% aqueous NaOH was added drop wise until pH 14 (universal indicating pH paper) was reached. The mixture was diluted with CH$_2$Cl$_2$ (100 mL) and stirred for 5 minutes. After this time, insolubles were removed at the vacuum and the filter cake was washed with CH$_2$Cl$_2$ (2×25 mL). The organic phase of the filtrate was separated, washed with brine (100 mL) and dried (MgSO$_4$). The drying agent was removed by filtration. Silica gel (~5 g) was added and the filtrate was concentrated to dryness under reduced pressure. Flash column chromatography (RediSepRf SiO$_2$ (120 g), 100% CH$_2$Cl$_2$→5% MeOH in CH$_2$Cl$_2$) gave the product as a clear, amber oil (2.1 g, 84%). ESIMS: m/z 241 [(M+H)+]. This material was used in the next step without further analysis or purification.

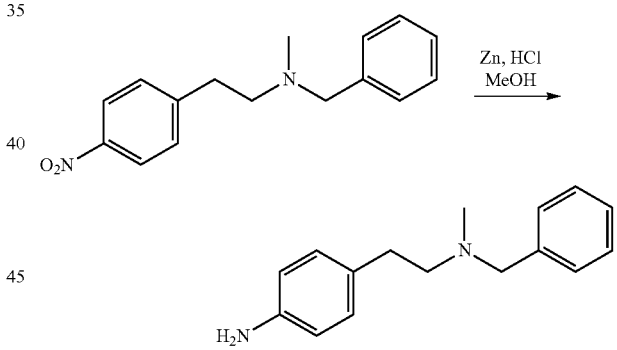

A solution of the amine (2.1 g, 8.7 mmol) in anhydrous CH$_2$Cl$_2$ (40 mL) was added dropwise over 2-5 minutes to an ice-NaCl bath cooled solution of 1,1'-thiocarbonyldiimidazole (95%, 3.1 g, 17.4 mmol, 2 eq.) in anhydrous CH$_2$Cl$_2$ (120 mL). After 15 minutes, the cooling bath was removed and the reaction mixture was stirred at room temperature for 1.5 hours after which time analysis by TLC (5% MeOH in CH$_2$Cl$_2$) indicated complete consumption of the starting aniline. The mixture was cooled once again in an ice bath and 7 M NH$_3$ in MeOH (13 mL, 91 mmol, 10.5 eq.) was added dropwise over 2-5 minutes. The bath was removed and the mixture was stirred over night at room temperature. Silica gel (~5 g) was added and the mixture was concentrated to dryness under reduce pressure. Flash column chromatography (RediSepRf SiO$_2$ (120 g), 100% CH$_2$Cl$_2$→10% MeOH in CH$_2$Cl$_2$) gave the thiourea as an amber oil that solidified to a tacky residue upon standing (2.5 g, 96%).

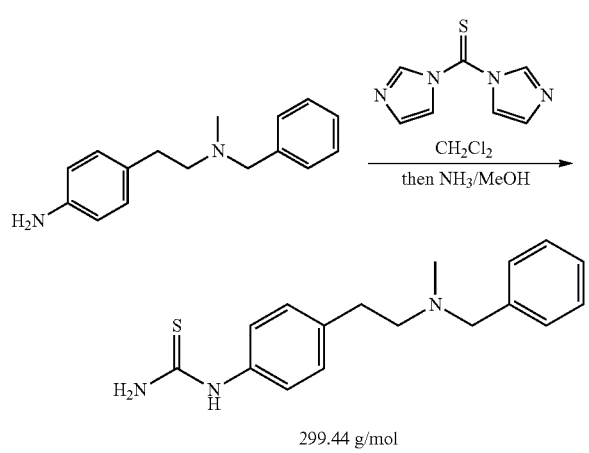

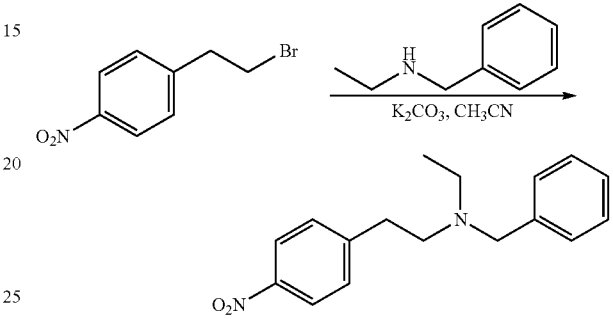

A mixture of the thiourea (2.5 g, 8.3 mmol) and 2-bromoacetophenone (1.8 g, 9.1 mmol, 1.1 eq.) in EtOH (80 mL) was heated to 75° C. (oil bath temperature) for 20 minutes after which time analysis by TLC (5% MeOH in $CH_2Cl_2$) indicated complete consumption of the thiourea. Silica gel (~5 g) was added and the mixture was concentrated to dryness under reduce pressure. Flash column chromatography (RediSepRf $SiO_2$ (120 g), 100% $CH_2Cl_2 \rightarrow 10\%$ MeOH in $CH_2Cl_2$) gave the thiazole hydrobromide as a straw colored glass (3.73 g, 93%).

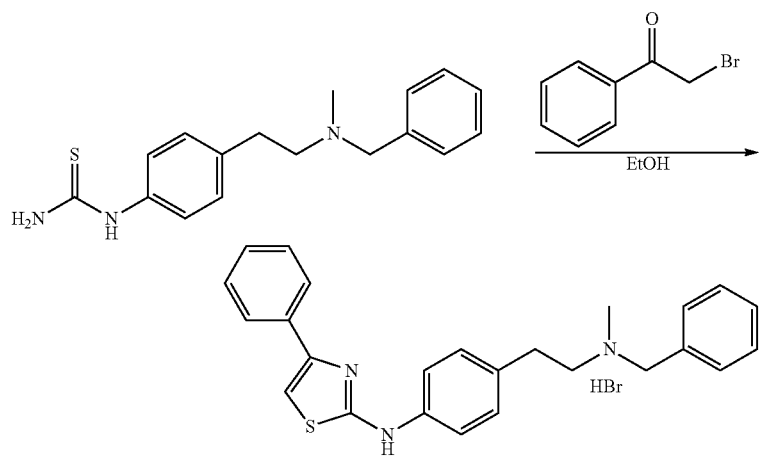

Compound 16-8

Compound 16-8/18hy.

Figure 19:
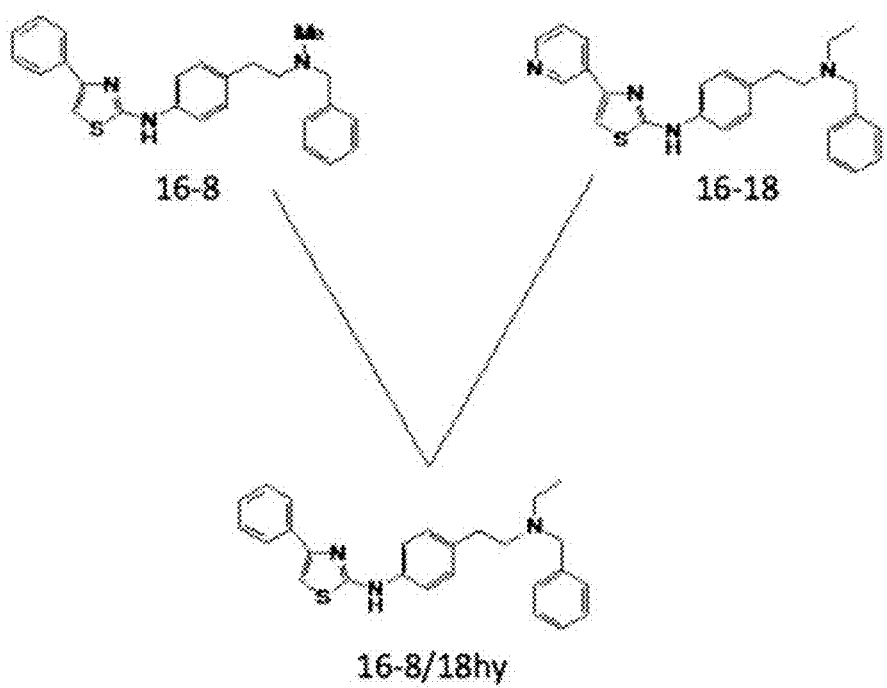
FIG. 19: Compound 16-8/18hy. Compound 16-8/18h was designed as a hybrid of compounds 16-8 and 16-18.

Upon examination of the activity of GSK205 relative to compounds 16-8 and 16-18, it seemed that removal of a nitrogen from the pyridyl group increased the potency of the TRPV4 antagonist, and addition of an extra carbon to the nitrogen carbon side chain increased the potency of the TRPV4 antagonist. Compound 16-8/18hy was formed and based on the structures of 16-8 and 16-18. See FIG. 19.

Compound 16-8/18hy was prepared as detailed in Example 11. Briefly, a suspension of the bromide (5.01 g, 21.8 mmol), N-benzyl ethylamine (4.9 mL, 33 mmol, 1.5 eq.) and $K_2CO_3$ (4.6 g, 33 mmol, 1.5 eq.) in anhydrous $CH_3CN$ (65 mL) was heated to 80° C. (oil bath temp) for 18 hours, after which time the starting material was nearly complete. The mixture was cooled to room temperature and diluted with brine (120 mL). The resulting emulsion was extracted with EtOAc (2×60 mL). The combined extracts were added to silica gel (~10 g) and the mixture was concentrated to dryness under reduced pressure. Flash column chromatography (RediSepRf $SiO_2$ (120 g), 100% $CH_2Cl_2 \rightarrow 5\%$ MeOH in $CH_2Cl_2$) gave the product as an orange oil that solidified upon standing at room temperature (3.3 g, 53%). $^1$H NMR ($CDCl_3$, 400 MHz): 8.13 (d, J=8.4 Hz, 2H), 7.32 (d, J=8.4 Hz, 2H), 7.30-7.22 (m, 5H), 3.55 (s, 2H), 2.91 (t, J=6.8 Hz, 2H), 2.68 (t, J=6.8 Hz, 2H), 2.87 (q, J=6.8 Hz, 2H), 1.20 (t, J=6.8 Hz, 3H). ESIMS: m/z 285 [(M+H)+].

A solution of the nitro compound (3.0 g, 10.4 mmol) in MeOH (20 mL) was cooled in an ice-NaCl bath. Zinc dust (325 mesh, 3 g, 4.5 eq.) was added followed by drop wise addition of 12 M HCl (3.8 mL, 4.5 eq.) over 2-3 minutes. After 1 hour, the cooling bath was removed and the reaction mixture was allowed to stir over night at room temperature. The following morning, the mixture was cooled in an ice-NaCl bath once again and 30% aqueous NaOH was added drop wise until pH 14 (universal indicating pH paper) was reached. The mixture was diluted with $CH_2Cl_2$ (100 mL) and stirred for 5 minutes. After this time, insolubles were removed at the vacuum and the filter cake was washed with $CH_2Cl_2$ (2×25 mL). The organic phase of the filtrate was separated, washed with brine (100 mL) and dried ($MgSO_4$). The drying agent was removed by filtration. Silica gel (~5 g) was added and the filtrate was concentrated to dryness under reduced pressure. Flash column chromatography (RediSepRf SiO₂ (120 g), 100% CH₂Cl₂→5% MeOH in CH₂Cl₂) gave the product as a clear, amber oil (2.3 g, 87%). ESIMS: m/z 255 [(M+H)+]. This material was used in the next step without further analysis or purification.

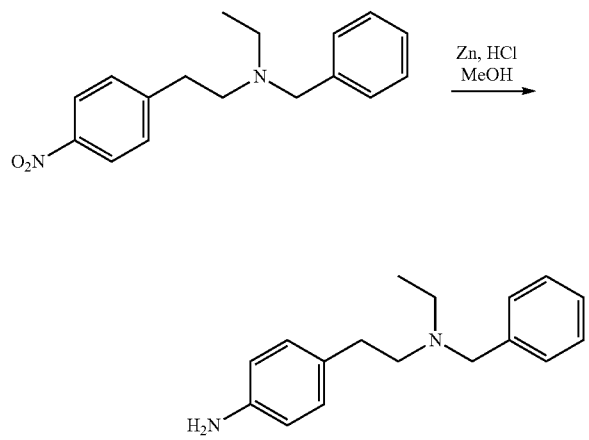

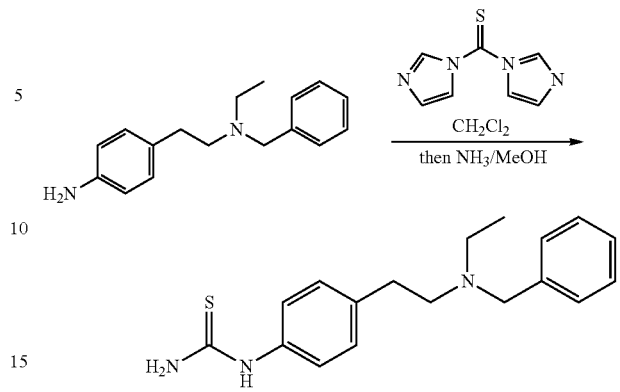

A solution of the amine (0.110 g, 0.43 mmol) in anhydrous CH₂Cl₂ (2 mL) was added dropwise over 2-5 minutes to an ice-salt bath cooled solution of 1,1'-thiocarbonyldiimidazole (95%, 0.162 g, 0.87 mmol, 2 eq.) in anhydrous CH₂Cl₂ (6 mL). After 15 minutes, the cooling bath was removed and the reaction mixture was stirred at room temperature for 1.5 hours after which time analysis by TLC (10% MeOH in CH₂Cl₂) indicated complete consumption of the starting aniline. The mixture was cooled once again in an ice bath and 7 M NH₃ in MeOH (620 µL, 4.3 mmol, 10 eq.) was added dropwise over 2-5 minutes. The bath was removed and the mixture was stirred over night at room temperature. Silica gel (~1 g) was added and the mixture was concentrated to dryness under reduce pressure. Flash column chromatography (RediSepRf SiO₂ (40 g), 100% CH₂Cl₂→10% MeOH in CH₂Cl₂) gave the thiourea as an amber oil that solidified upon standing (0.130 g, 97%).

A mixture of the thiourea (159 mg, 0.51 mmol) and 2-bromoacetophenone (0.113 g, 0.56 mmol, 1.1 eq.) in EtOH (5 mL) was heated to 75° C. (oil bath temperature) for 1 hour, after which time analysis by TLC (10% MeOH in CH₂Cl₂) indicated complete consumption of the thiourea. Silica gel (~1 g) was added and the mixture was concentrated to dryness under reduce pressure. Flash column chromatography (RediSepRf SiO₂ (40 g), 100% CH₂Cl₂→10% MeOH in CH₂Cl₂) gave the thiazole hydrobromide as a straw colored glass (0.165 g, 78%).

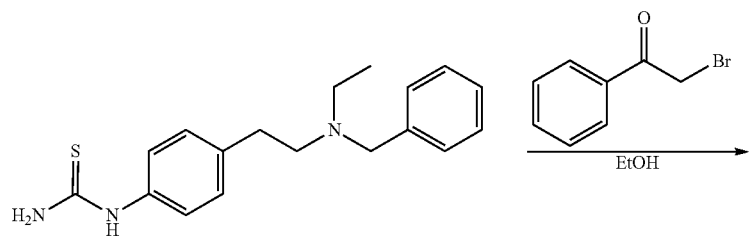

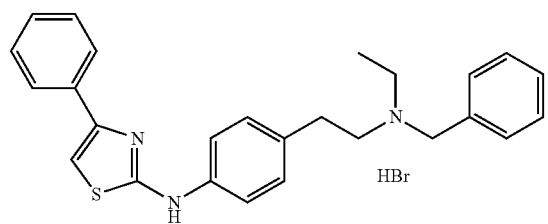

Compound 16-8/18hy

Example 14

Effect on TRPV4-Mediated Calcium Transport

Compounds (GSK205, 16-12, 16-13, 16-14, 16-18, 16-8, and 16-8/18hy) were tested for their effect on TRPV4-mediated calcium influx in N2a cultured cells with targeted expression of human TRPV4. Ca2+ imaging was performed according to Li et al. (*Environ. Health Perspect.* 2011, 119, 784-93) and Moore et al. (*Proc. Natl. Acad. Sci. U.S.A.* 2013, 110, E3225-E3234). Briefly, Ca2+ imaging of primary mouse epidermal keratinocytes (1° MK) in response to chemical activation of TRPV4 was conducted after loading with 2 μM fura2-AM, following a ratiometric Ca2+-imaging protocol with 340/380 nm blue light for dual excitation. Ratios of emissions were acquired at 0.5 Hz. ΔR/R0 was determined as the fraction of the increase of a given ratio over baseline ratio, divided by baseline ratio. For stimulation of cells with UVB, where fura-2 was not suitable because of the proximity of stimulation with 340/380 nm vs. 295 nm, 2 μM fluo4-AM was used instead. Ca2+ imaging was carried out at 488 nm excitation, acquisition of emissions at 0.5 Hz, expressed as ΔF/F0. TRPV4 was activated with 10 nM GSK101, a specific activator, which had no effect on RFP-transfected cells. Each of the six compounds were added to a concentration of 2.5 μM, and its effect was observed.

Figure 20:
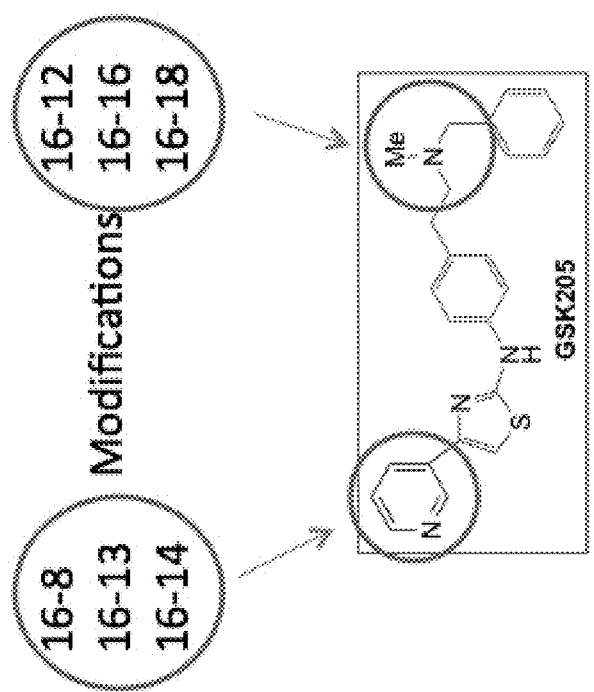
FIG. 20: Inhibition of calcium ion flux through TRPV4. Compounds of the present invention demonstrated inhibitory activity against TRPV4 and were stronger antagonists that GSK205.
Figure 20:
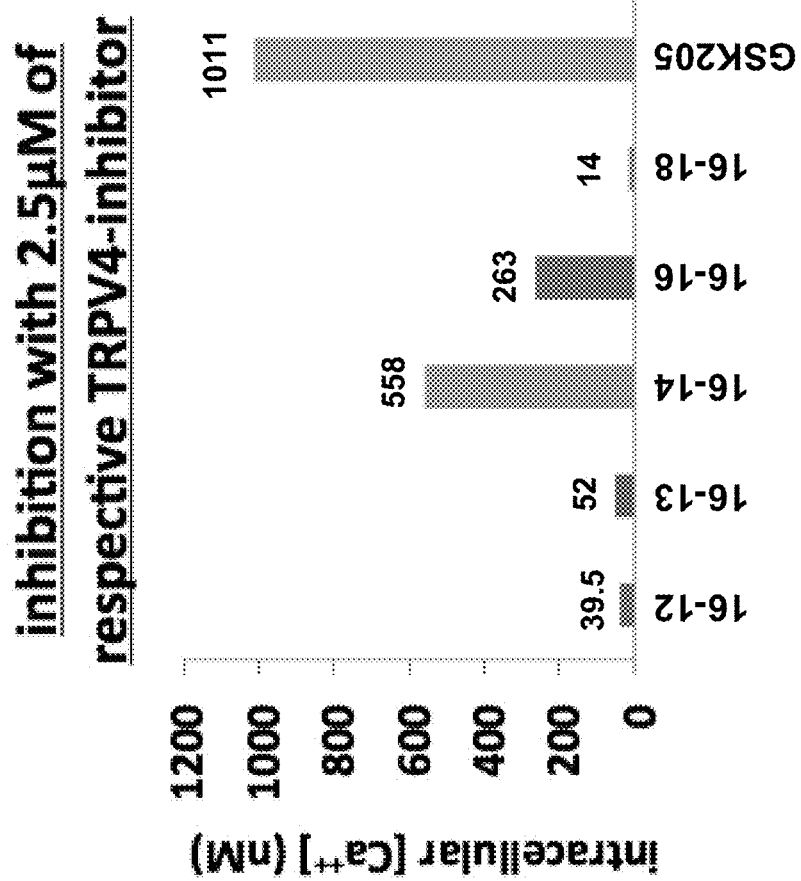

Results are shown in FIG. 20. The bar diagram to the left shows the effects of 2.5 μM of the respective inhibitor (pre-incubation for 10 min). The ordinate is the peak calcium concentration in the cells (average n>75 cells) in nM. All six compounds were effective in inhibiting TRPV4-mediated calcium influx, with 16-18 and 16-8 being the most potent. 16-8/18hy did not show enhanced inhibition over 16-8 (data not shown). It was noted that GSK205 had a very low potency at this concentration in cultured cells with targeted over-expression.

Example 15

In Vivo Pain Model in Mice

Compounds were tested for their effect in reducing pain using an in vivo pain model in mice. For mouse formalin-evoked irritant behavior measurements, mice were well-fed, well-rested, and tested at the same time of day, at the same time-point of their circadian rhythm. They were allowed to acclimate to a plexiglas chamber for at least 30 min before testing, and received 10 μL subcutaneous injection of 4% of formalin (diluted from an aqueous solution of commercial 37% formaldehyde with normal saline (NS)) through a 30-gauge needle into the right whiskerpad, as further detailed in Luccarini et al. (*J. Pain,* 2006, 7, 908-914). Normal saline was used as control injection. After injection, mice were immediately placed back into the chamber and the rubbing behavior was recorded by a private consumer-type video-camera for a 45 min observation period. The recording time was divided into 9 blocks of 5 min, and a nociceptive score was determined per block by measuring the time that the animals spent rubbing the injected area predominantly with the ipsilateral fore-paw and rarely with hind-paw. This rubbing behavior with fore-paw is evoked by pain, which is distinct from itch behavior. Behavioral analysis was conducted by observers blinded to treatment.

To investigate the effects of the specific compounds GSK205, 16-8, and 16-8/18hy on formalin-induced nociceptive behavior, mice received a single subcutaneous injection of the compounds into the whiskerpad (10 μL, dissolved in 4% DMSO) 15 min before formalin injection. Control animals received the same volume of NS, 4% DMSO.

Figure 21:
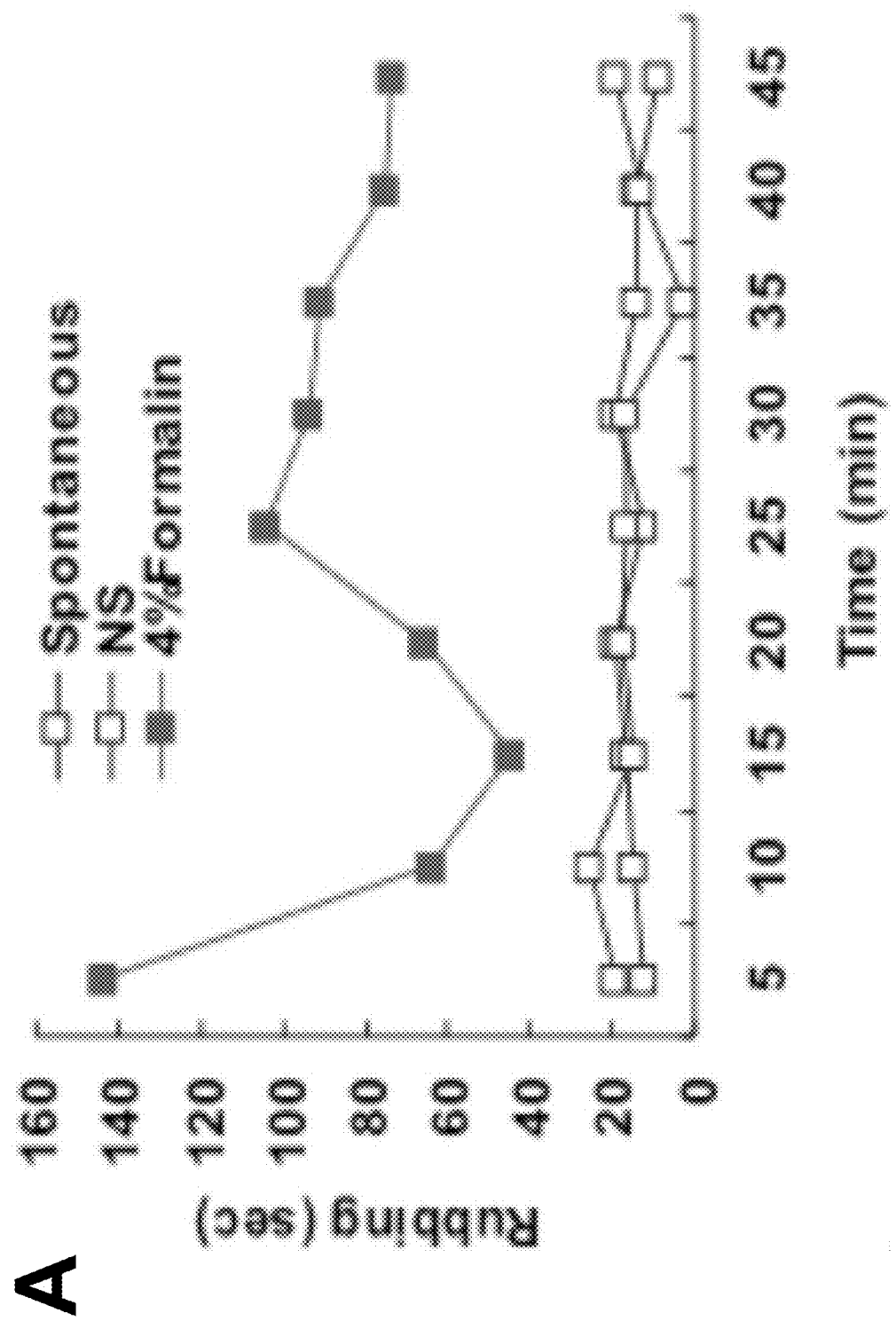
FIG. 21: Treatment of pain. Compounds as disclosed herein attenuated nocifensive behavior in mice.
Figure 21:
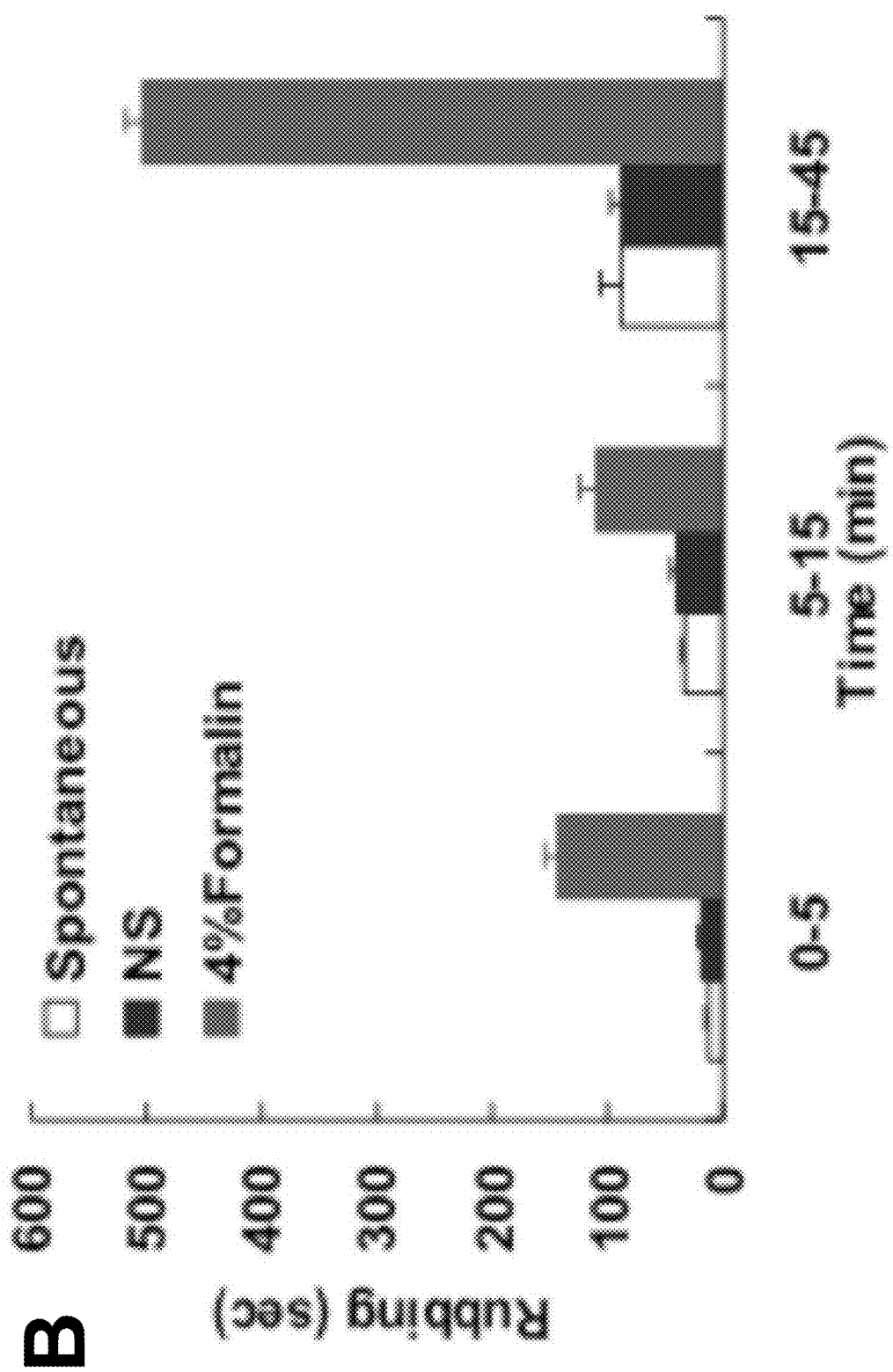
Figure 21:
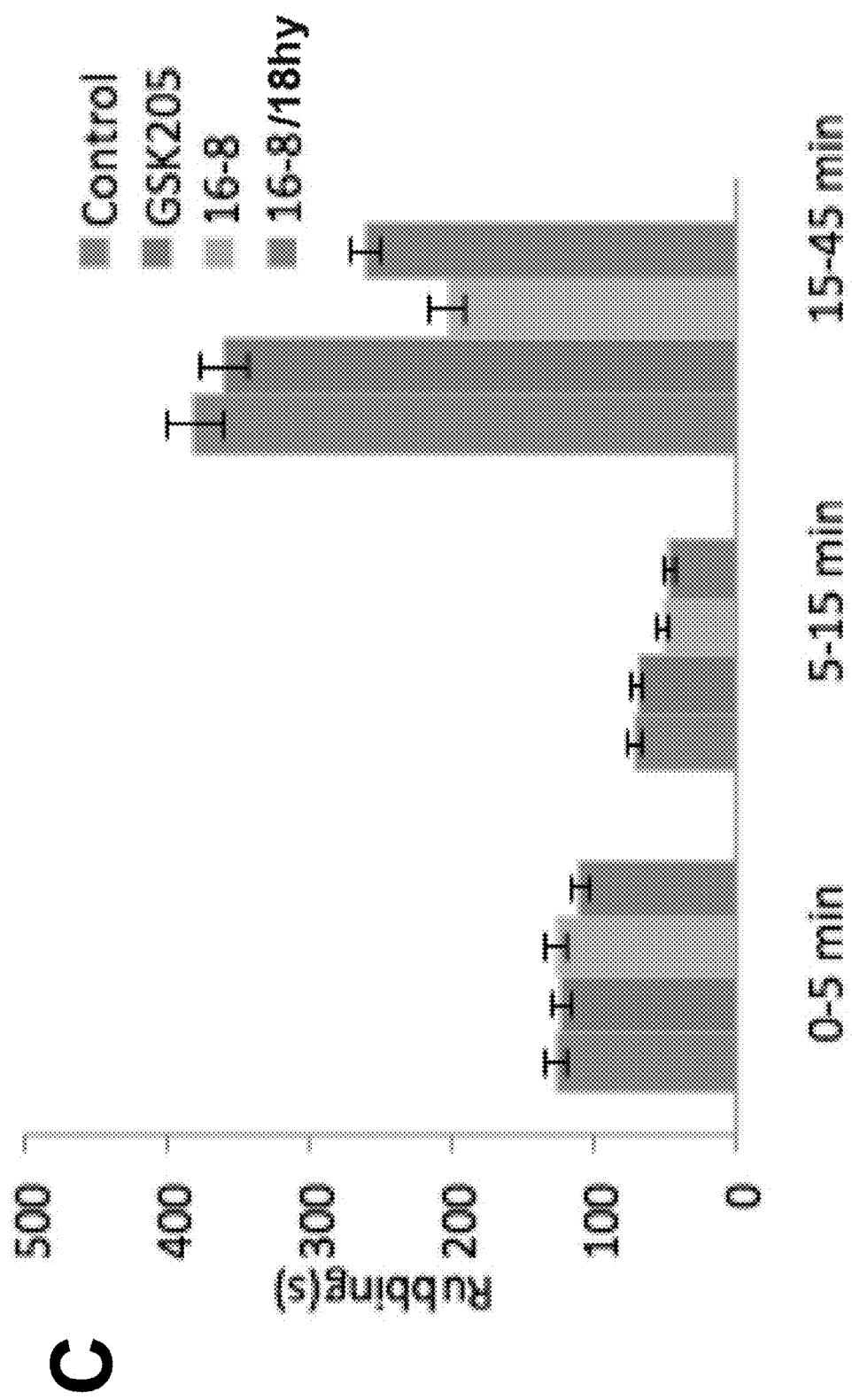
Figure 21:
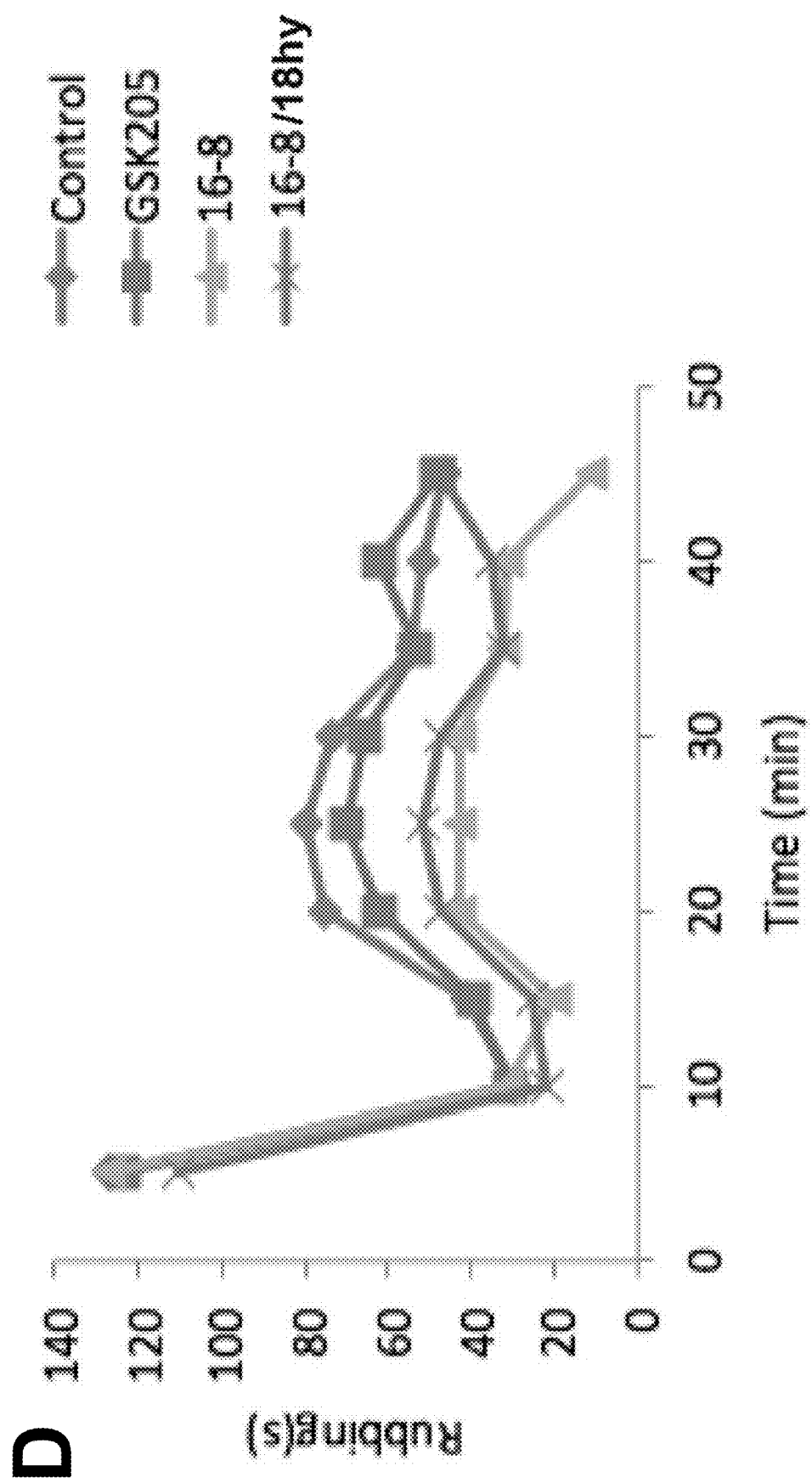

Results are shown in FIG. 21. FIG. 21A shows the time-course of nocifensive behavior in response to whisker-pad injection of formalin to BL6 mice. Note the biphasic response and "clean" controls. FIG. 21B shows quantitation of FIG. 21A, with n=10 animals per group. Note the significant increase in response to formalin injection. FIG. 21C shows similar quantitation when compounds where pre-injected topically at 0.5 mM/10 μL. This concentration had no effect on residual nocifensive behavior in Trpv4−/− mice. Note the lack of effect of GSK205 at this concentration, yet a significant attenuation of nocifensive behavior, in particular of the centrally caused second phase, in response to 16-8 and 16-8/18hy. FIG. 21D shows the time course for the three compounds. GSK205, at this concentration, was not different from control, whereas 16-8/18hy and 16-8 significantly attenuated nocifensive behavior. Note the reduction to control levels with the less lipophilic 16-8 at the 45-min time-point, and the reversal to control levels with the more lipophilic 16-8/18hy at this time-point. Also note that none of the compounds influenced the first phase, which was caused by the direct irritation that formalin causes on peripheral whisker-pad nerve endings.

Example 16

UVB-Exposure Evoked Nocifensive Behavior

Compounds were tested for their effect on nocifensive behavior (response to pain) following UVB overexposure. Behavioral tests were performed to evaluate the decrease in withdrawal thresholds in response to mechanical von Frey hair or thermal stimuli applied to hind paws. The Von-Frey apparatus (Ugo Basile) applied a mechanical stimulus with a flexible steel wire from underneath the hind paw. The force leading to withdrawal was determined. For the thermal stimuli test, paws were stimulated with heat from underneath applied by an infrared beam (Hargreave's test apparatus; Ugo Basile), and withdrawal latencies were recorded. The withdrawal thresholds were ascertained before and after UV exposure. Mice were exposed to UVB 3-5 days after the last application of tam/oil, using a Bio-Rad Gel Doc 2000 UV transilluminator (302 nm) for 5 min with an exposure of 600 mJ/cm$^2$. This represents 5-10 times the minimal erythema-inducing dose, in keeping with the rationale of inducing sunburn and studying sunburn-evoked pain.

Figure 22:
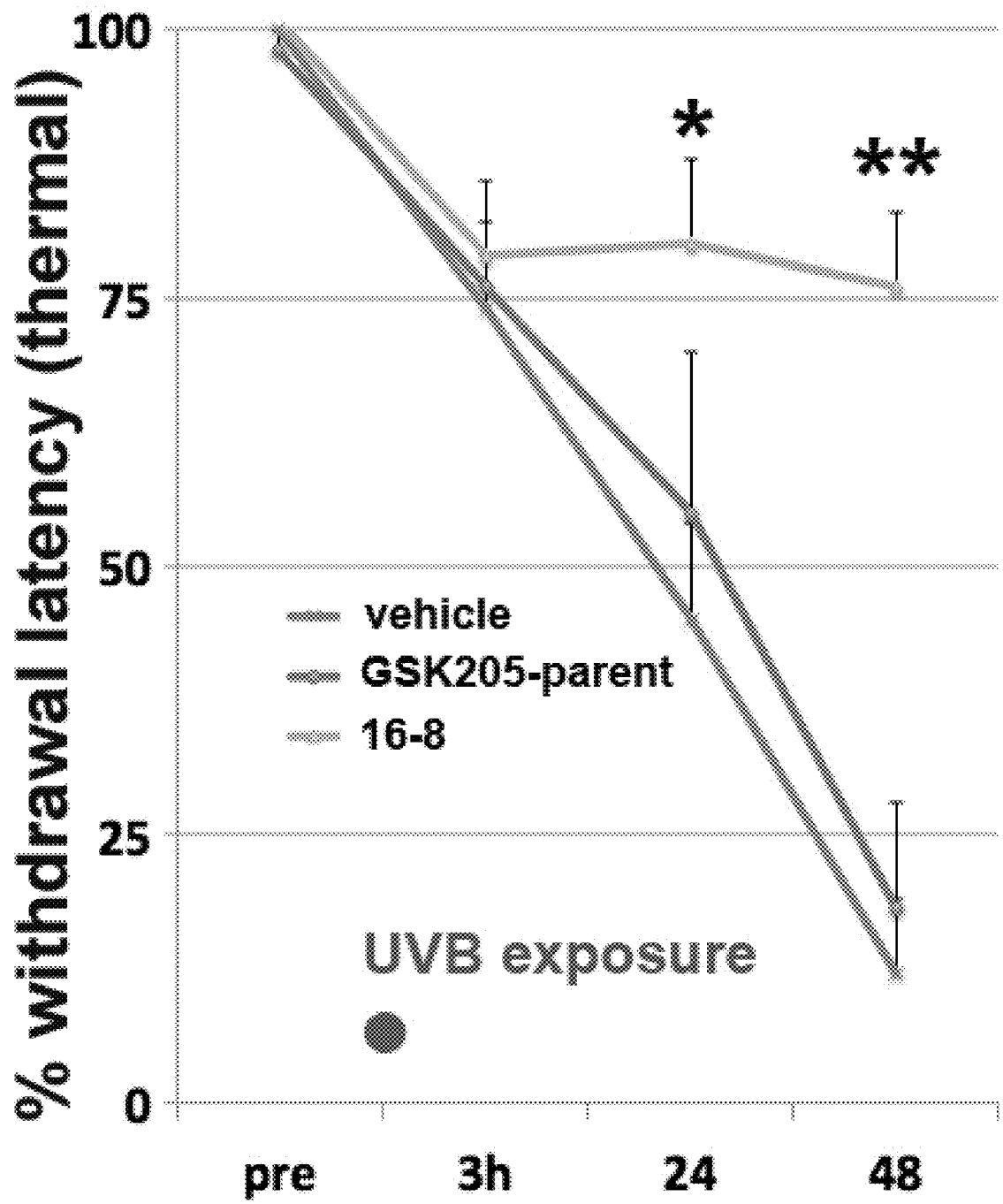
FIG. 22: Treatment of pain after UVB exposure. Compounds as disclosed herein attenuated nocifensive behavior in a mouse model for sunburn.

Results are shown in FIG. 22, demonstrating the effective topical treatment of UVB-overexposure evoked nocifensive behavior by compound 16-8. Topically applied 16-8 was especially effective in reducing the response to pain following UVB exposure, whereas GSK205 at this concentration (0.5 mM in 40 μL), was as effective as vehicle (n=4/group).

Example 17

Effect on TRPA1

Compounds were tested for their effect on TRPA1. N2a permanent cells were transfected with human TRPA1 cDNA, using a pcDNA3.1 expression plasmid. They were co-transfected with eGFP-expressing plasmid, or, for control, with eGFP plasmid only.

Vehicle-treated TRPA1-expressing cells showed a robust Ca2+ transience in response to 60 μM AITC and also to 1 mM mustard oil, which are both known electrophilic TRPA1-activators. However, eGFP-expressing control-transfected cells (no TRPA1) did not respond to the TRPA1-activator AITC. Cells were then pre-exposed to 5 μM of compounds 16-8 and 16-8/18hy for 10 min.

Figure 23:
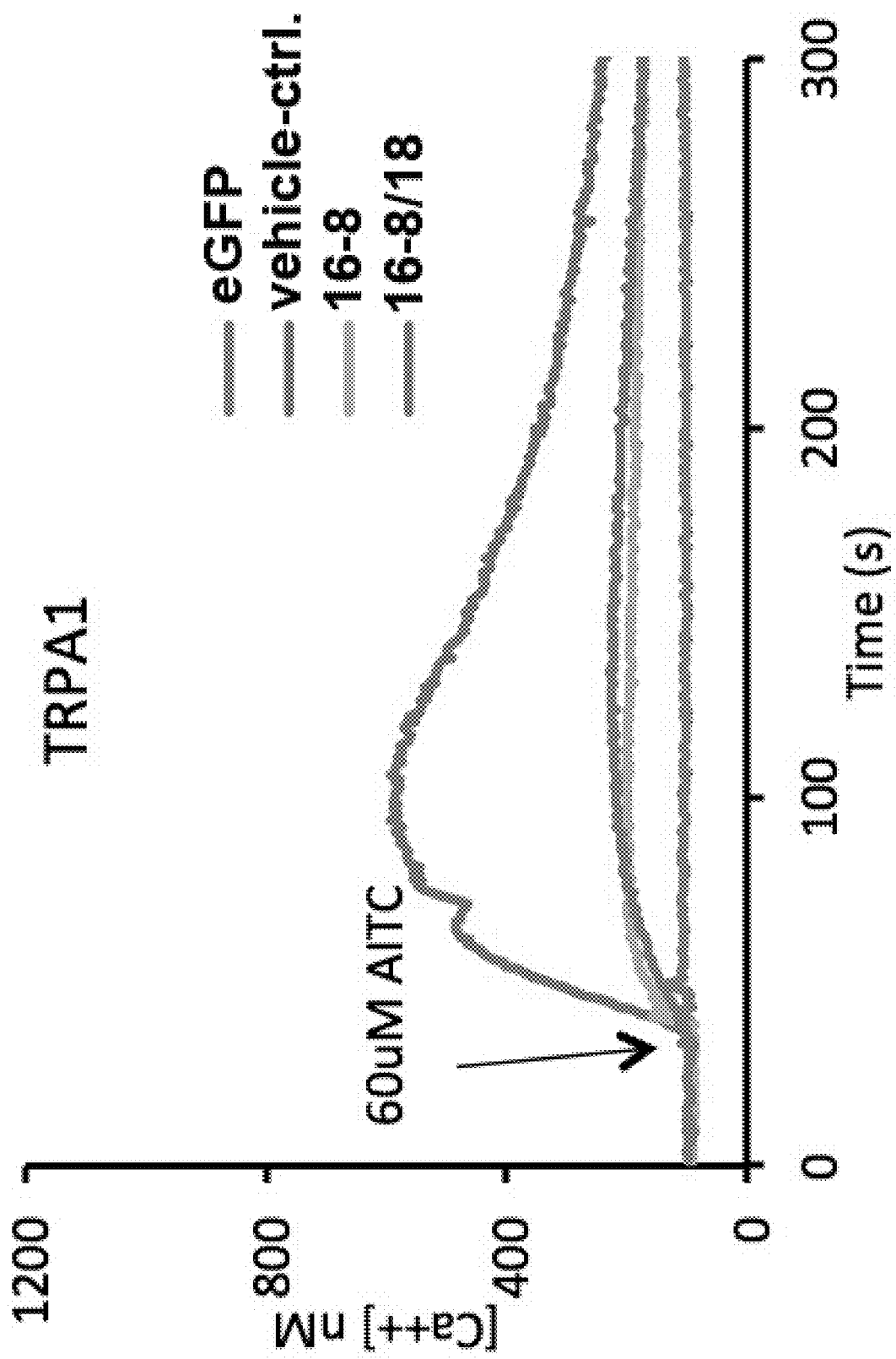
FIG. 23: Effect on TRPA1. Compounds as disclosed herein inhibited TRPA1, as indicated by measuring calcium transience.

Results are shown in FIG. 23. Averaged Ca2+ signal is shown from >75 cells. The resulting Ca2+ transient evoked by 60 μM AITC was reduced by >80% upon administration of compound 16-8 or 16-8/18hy at 5 μM, indicating appreciable TRPA1-inhibitory effects of both compounds. Therefore, compounds 16-8 and 16/8-18hy showed inhibitory activity against human TRPA1. For doses below or equaling 25 μM, GSK205 did not inhibit TRPA1 activity.

Example 18

Effect on TRPV1, TRPV2, and TRPV3

Compounds were tested for their effect on TRPV1, TRPV2, and TRPV3. Methods were similar to those described in Example 15. Briefly, N2a cells were transfected with human TRPV1, TRPV2, or TRPV3. eGFP-transfection was used as control. For specific stimulation of TRPV1, 5 µM capsaicin was used. For stimulation of TRPV2, hypotonicity (260 mosmol/L) was used, based on previous reports of TRPV2 being osmotically responsive. N2a cells were not responsive to hypotonicity, and neither were control-transfected cells. For TRPV3-expressing cells, camphor (20% of a commercially available stock solution) was used. Camphor by itself did not stimulate eGFP-expressing control N2a cells or native N2a cells. Stimulation and control protocols were applied as for TRPA1-expressing N2a cells as detailed above in Example 15.

Figure 24:
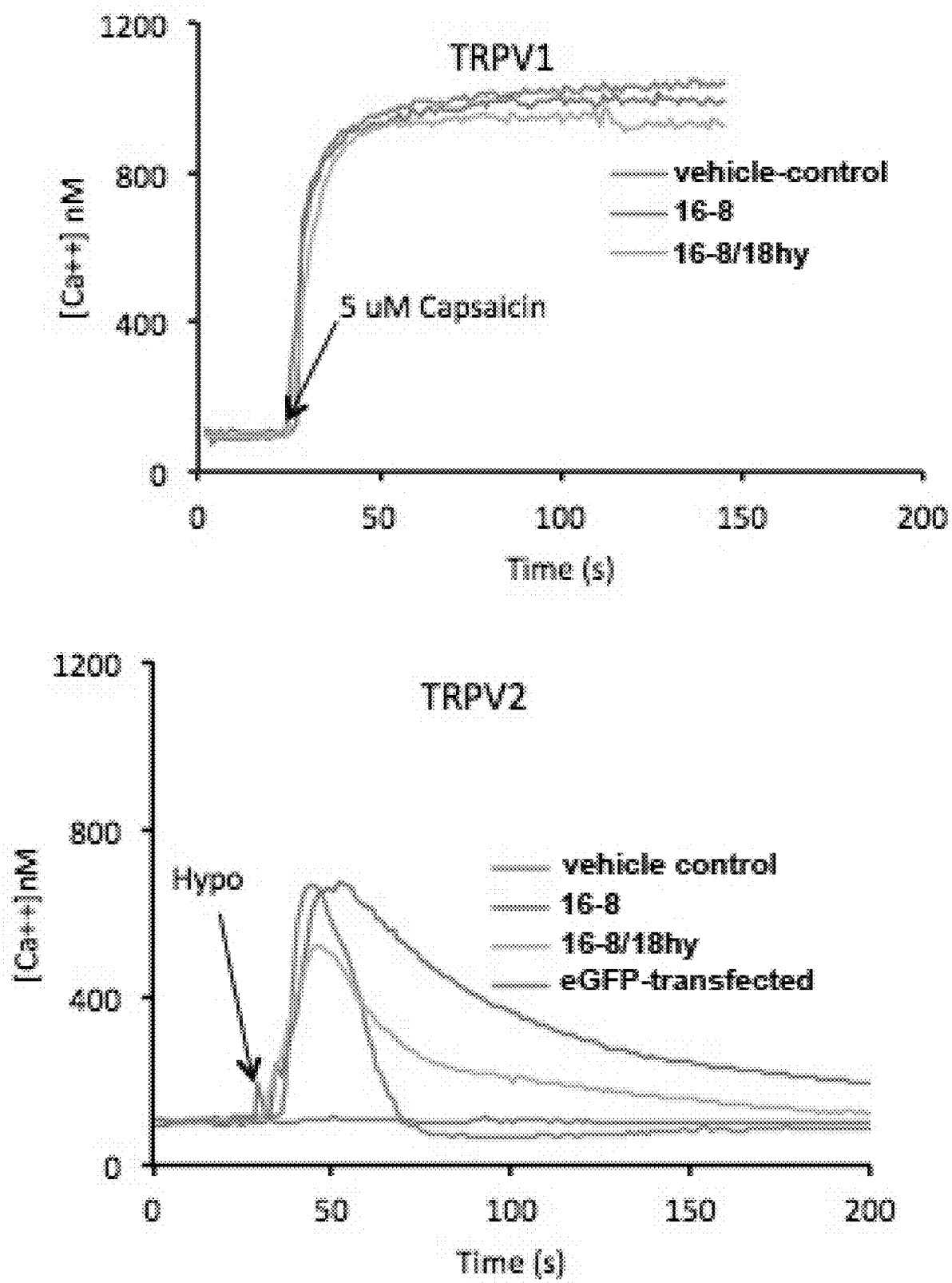
FIG. 24: Effect on TRPV1, TRPV2, and TRPV3. Compounds as disclosed herein did not inhibit TRPV1, TRPV2, or TRPV3, as indicated by measuring calcium transience.
Figure 24:
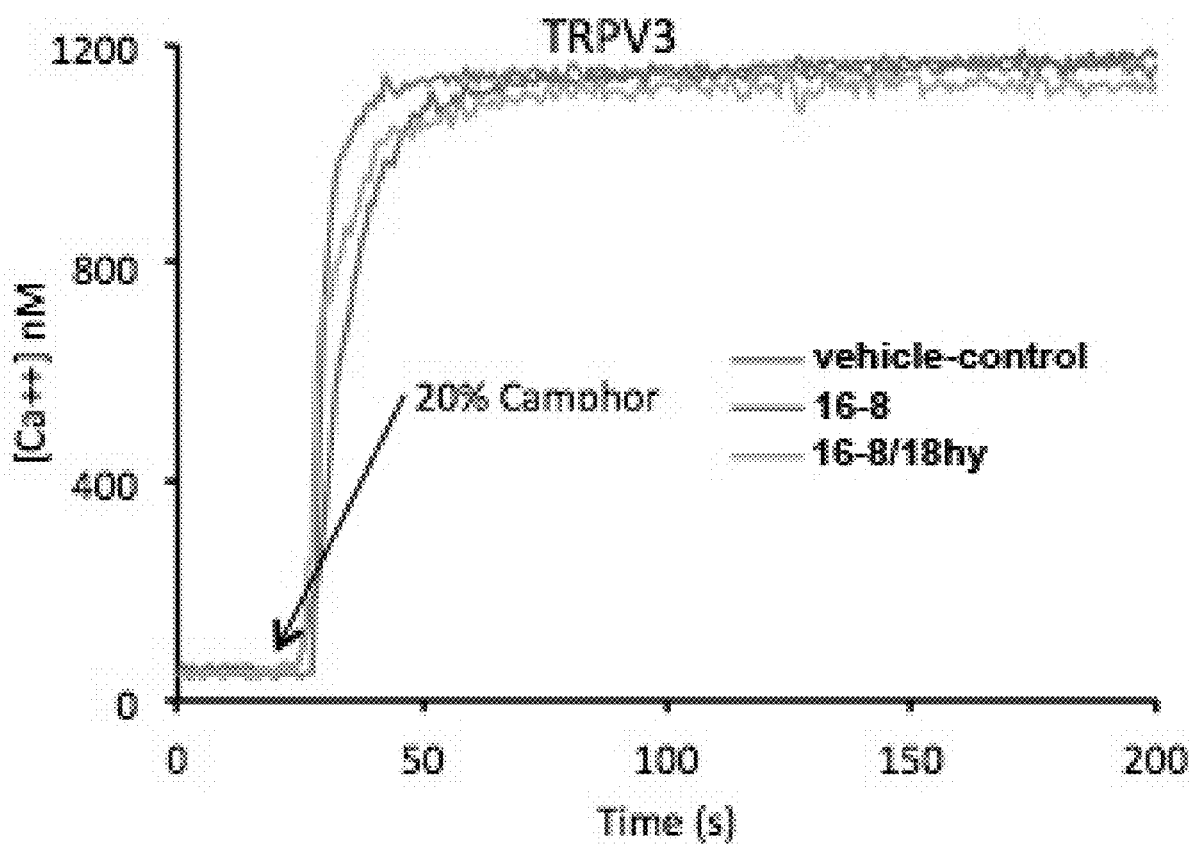

Results are shown in FIG. 24, which shows the Ca2+ signals for specific stimulation of TRPV1, TRPV2, and TRPV3. Control-transfected N2a cells did not respond to capsaicin (TRPV1 activation) or camphor (TRPV3 activation). For TRPV1, TRPV2, and TRPV3, Ca2+ transience was not affected by administration of 16-8 or 16-8/18hy. Therefore, compounds 16-8 and 16-8/18hy did not affect TRPV1, TRPV2, and TRPV3.

Example 19

Proteomics Methodology

Samples were supplemented with 1% Acid-Labile-Surfactant I (ALS-I) in 50 mM ammonium bicarbonate and subjected to dithiothreitol reduction and iodoacetamide cysteine alkylation prior to an overnight trypsin digestion at 37° C. (Promega). Resulting peptides were cleaned using a 1 cc Oasis MCX cartridge (Waters) following the manufacturer's recommended protocol, lyophilized to dryness and resuspended in 10 uL of 0.2% formic acid/2% acetonitrile. Samples were subjected to nanoscale capillary LC-MS/MS analysis on a nanoAcquity UPLC system (Waters Corp) coupled to a Thermo QExactive Plus high resolution accurate mass tandem mass spectrometer (Thermo) via a nanoelectrospray ionization source. Briefly, the sample was first trapped on a Symmetry C18 300 mm×180 mm trapping column for 3 min 5 µL/min (99.9/0.1 v/v water/acetonitrile 0.1% formic acid), after which the analytical separation was performed on a 1.7 µm Acquity BEH130 C18 75 mm×250 mm column (Waters Corp). Peptides were separated on a linear gradient from 5 to 40% acetonitrile with 0.1% formic acid over 90 min at a flow rate of 400 nanoliters/minute (nL/min) with a column temperature of 55° C. Data collection on the QExactive Plus mass spectrometer was performed in a data-dependent acquisition (DDA) mode of acquisition with a r=70,000 (@ m/z 200) full MS scan from m/z 375-1600 with a target automated gain control (AGC) value of 1e6 ions followed by 10 MS/MS scans at r-17,500 (@ m/z 200) at a target AGC value of 5e4 ions. A 20 sec dynamic exclusion was employed to increase depth of coverage. Mass spectra were searched using Mascot at 5 ppm precursor and 0.02 Da product mass tolerances against a SwissProt database with the human and mouse taxonomies selected. Searched spectra were loaded into Scaffold (Proteome Software) and annotated at a 1% protein false discovery rate. Procedures were as described in Zhang et al. (Curr. Protoc. Mol. Biol., 2014, 108, 10211-102130) and Domon et al. (Science, 2006, 312, 212-217).

Example 20

Analytical Methodology

Sample Processing.

20 µL plasma or tissue homogenate and 40 µL acetonitrile containing appropriate internal standard (see below) were vigorously mixed in a Fast-Prep (Thermo-Savant) agitator at speed #4 for 20 s and centrifuged at 13,000 g for 5 min. In case of brain and fat tissue, an additional delipidation step was necessary: 20 µL sample was added to 100 µL water+ 300 µL chloroform mixture, agitated in Fast-Prep as described above, centrifuged, 250 µL of chloroform layer evaporated to dryness, and reconstituted in 60 µL 0.1% formic acid/acetonitrile, 50/50 mixture. Pooled mouse plasma or homogenate from non-treated mouse organs was used to prepare calibration samples in the appropriate concentration range. Typical range for plasma was 0.5-10 nM, whereas the range for tissues was adjusted as appropriate. The calibration samples were analyzed along the study samples as a single analytical batch.

Liquid Chromatography Tandem-Mass Spectrometry (LC-MS/MS).

The analysis was performed on Shimadzu 20A series LC system coupled with Applied Biosciences/SCIEX API 4000 QTrap MS/MS. Column: Phenomenex, C18 4×3 mm, AJ0-4287 at 35° C. Solvent A: 0.1% formic acid in MS-grade water. Solvent B: MS-grade acetonitrile. Elution gradient at 1 µL/min: 0-1 min 30-90% B, 1-1.3 min 90% B, 1.3-1.31 min 90-30% B. Run time: 4 min. Injection volume: 30 µL. Autosampler temperature: 4° C. The MS/MS parameters (declustering, collision cell, and quadrupole voltages, gas flow, and ionization chamber voltage and temperature) were optimized by infusion of 100 ng/mL of GSK-205, compounds 16-8 and 16-19 at 10 µL/min. The MRM transitions (m/z), i.e. parent ion/fragment ion, for quantification of the standard (measured analyte) and appropriate internal standard were as follows: GSK-205 (std.) 401.2/280.2, 16-16 (int. std.) 387.1/280.2; compound 16-8 400.1/279.1, 16-16 (int. std.) 387.1/280.2; compound 16-19 (std.) 414.2/278.8, 16-8 (int. std.) 400.1/279.1. Procedures were as described in Ye et al. (Cell, 2012, 151, 96-110).

Example 21

Figure 25:
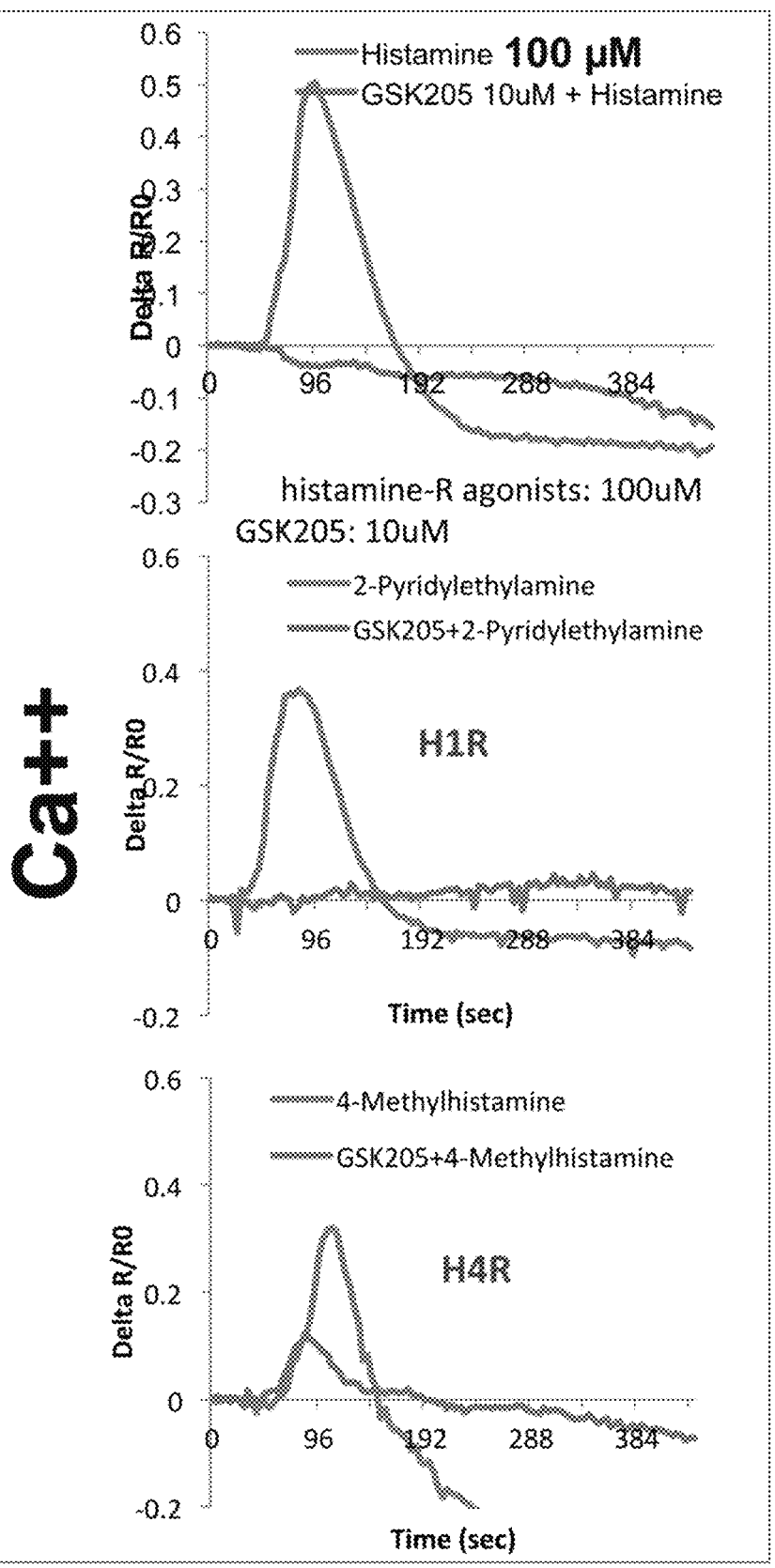
FIG. 25: Shown are graphs of calcium transience in mammalian epidermal keratinocytes in the presence of activators for histamine receptors, with (bottom curves) or without (top curves) the TRPV4 inhibitor GSK205.

Keratinocyte Histamine Stimulation and Block of the Resulting Ca++ Transient by Use of TRPV4 Blockers FIG. 25 shows Histamine-mediated Ca++ transients in mammalian epidermal keratinocytes depend on TRPV4. Mouse primary keratinocytes were prepared as described in Moore et al. (Proc Natl Acad Sci USA, 2013, 110, E3225-3416). Cells were pre-treated, for 10 min with 10 µM GSK205. Then 100 µM of each, histamine, 2-Pyridylethylamine (selective activator for H1R), and 4-Methylhistamine (selective activator for H4R; both H1R and H4R known to be expressed in rodent and human keratinocytes), were applied, and fura-2 loaded keratinocytes were imaged ratiometrically, as described (Moore et al. Proc Natl Acad Sci USA, 2013, 110, E3225-3416; Li, et al. Environ Health Perspect, 2011, 119, 784-9316). Shown in blue (top curve) is the average signal of ≥75 cells. Note the robust signal for histamine, and in response to selective activator of H1R, less prominent for H4R, in keeping with previous findings on expression levels of these channels in keratinocytes. The histamine-Ca++ response and the response to activation of H1R could be eliminated completely with GSK205. The response to H4R could be significantly attenuated when blocking with TRPV4.

Example 22

Pruritogenic or Algo-Genic

Periostin has a role in chronic allergic skin inflammation and also pathologic-fibrotic remodeling of the skin. Periostin was injected into mice's footpad to address the question whether it is pruritogenic or algo-genic. There were no behavioral responses in terms of nocifensive or scratching behavior of the injected mice when compared to vehicle-control injected animals within the next 30 min, a reasonable time-frame when examining effects down-stream of the classic pruritogen, histamine.

Example 23

Concentration of TRPV4 Inhibitors in Skin after Topical Application to Skin

Inhibiting TRPV4 can readily be accomplished by topical application of TRPV4-inhibitory compounds. The data show a concentration several times the ED50 after topical application, using analytical chemical detection by liquid chromatography and by mass-spectrometry (Ye, et al. Cell, 2012, 151, 96-110). The TRPV4 inhibitory compound 16-19 at 6.2 µM was found in their epidermis/dermis preparation (+/− 0.83 SEM). For this experiment, 5 C57BL6/j mice were subjected to facial skin exposure by applying 25 microliter solution to their whisker-pad with a cotton swab. This solution contained 50 µM compound. Animals were euthanized 120 minutes after compound application, their whiskerpad skin was carefully prepared as epidermis/dermis sample, and stored in liquid nitrogen until analyzed by LC-MS/MS analytical method. For comparison, intra-peritoneal application of 10 mg/kg bodyweight, in 250 microL vehicle, led to a concentration in skin of 2.9 µM (+/−0.3) after 6 h and 1.49 µM (+/−0.33) after 24 h. Likely these values under-represent the epidermal and directly sub-epidermal concentration of compound because of modest contamination of the preparation by dermal and sub-cutaneous tissue, also by superficial epidermal layers which are not vital cells.

It was also tested whether compounds are readily broken down in systemic fluid, for which serum was used. A 3 h and 12 h incubation in serum at 37° C. did not change the concentration of a fixed spiked amount of compounds 16-8, 16-18, and 16-19.

Example 24

Hepatic and Renal Function after Administration of TRPV4-Inhibitory Compounds

The hepatic and renal function of mice treated with 10 mg/kg body-weight of all three compounds was tested. Hepatic damage marker ALT and creatinine in serum, drawn at 2 h, 12 h, and 24 h after compound exposure did not differ significantly from vehicle-control treated mice. All measured concentrations were within normal range for mice, n=6 mice per group (C57BL6/j).

```
SEQUENCES
                                               (SEQ ID NO: 1)
     5'-CCTGCTGGTCACCTACATCA (SEQ ID NO: 2)
     5'-CTCAGGAACACAGGGAAGGA
```

The invention claimed is:

1. A method of reducing periostin release from keratinocytes in a subject in need thereof, the method comprising administering to the subject an effective amount of a TRPV4 and TRPA1 inhibitor, wherein the TRPV4 and TRPA1 inhibitor is according to Formula I:

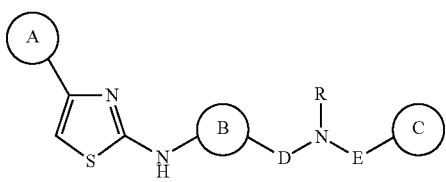

(I)

wherein A, B, and C are independently selected from aromatic, heteroaromatic, cycloalkenyl, and heterocycloalkenyl groups;
D is $C_1$-$C_3$ alkylene;
E is a bond, or $C_1$-$C_2$ alkylene; and
R is selected from hydrogen, hydroxyl, amino, alkyl, alkenyl, heteroalkyl, aromatic ring, or heteroaromatic ring, and
wherein periostin release from keratinocytes in the subject is inhibited upon administration of the TRPV4 and TRPA1 inhibitor.

2. The method of claim 1, wherein the inhibitor does not inhibit TRPV1, TRPV2, or TRPV3.

3. The method of claim 1, wherein the TRPV4 and TRPA1 inhibitor is selected from the following:

GSK205

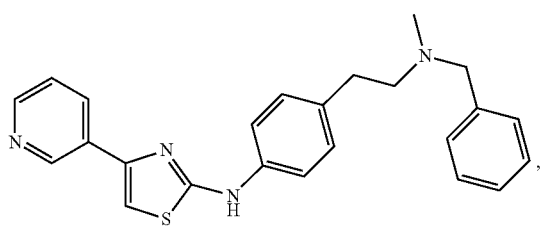

16-18

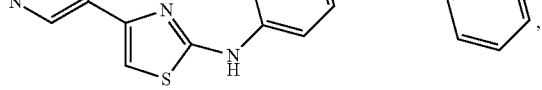

16-8

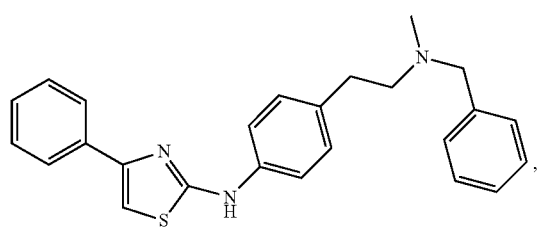

-continued 16-12c

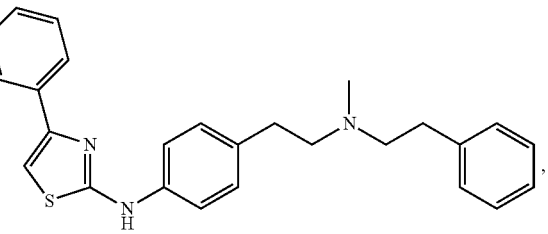

16-13

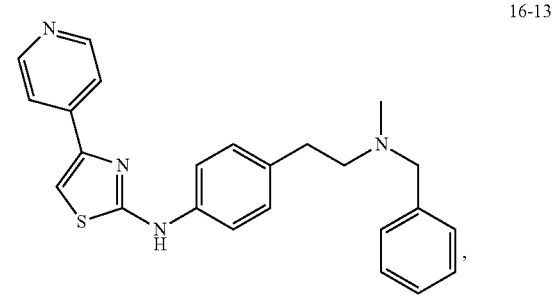

16-14

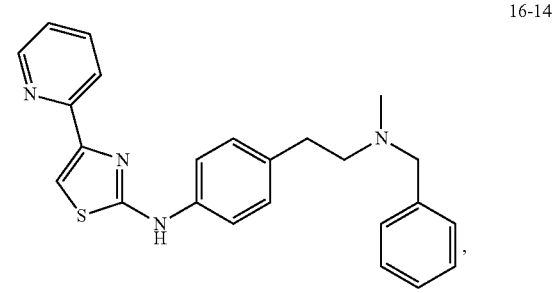

16-16

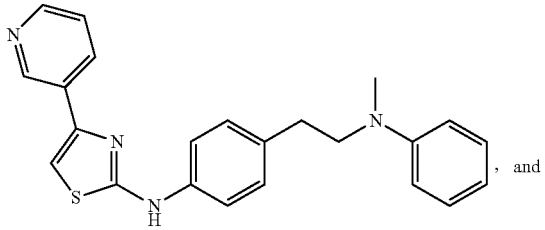

, and 16-8/18hy (16-19)

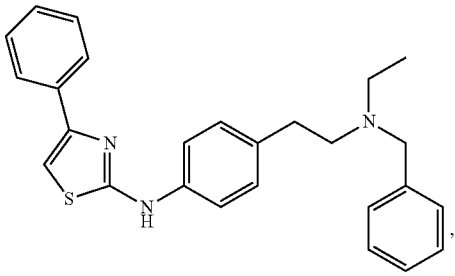

or any combination thereof.

4. The method of claim 1, wherein B is phenyl.
5. The method of claim 1, wherein C is phenyl.
6. The method of claim 1, wherein B is phenyl and C is phenyl.
7. The method of claim 1, wherein A is selected from phenyl and pyridine.
8. The method of claim 1, wherein R is selected from hydrogen, hydroxyl, amino, alkyl, and alkenyl.

9. The method of claim 1, wherein R is selected from hydrogen and alkyl.

10. The method of claim 1, wherein D is $C_1$ alkylene.

11. The method of claim 1, wherein E is $C_1$ alkylene.

12. The method of claim 1, wherein E is $C_2$ alkylene.

13. The method of claim 1, wherein administration of the TRPV4 and TRPA1 inhibitor to the subject thereby treats a fibrotic skin disease in the subject, and wherein the fibrotic skin disease comprises at least one disorder or condition selected from scleroderma, scar formation, keloid formation, atopic dermatitis, and skin fibrosis.

14. The method of claim 1, wherein administration of the TRPV4 and TRPA1 inhibitor to the subject thereby treats a fibrotic skin disease in the subject, and wherein the fibrotic skin disease comprises at least one disorder or condition selected from keloid formation, chemical or actinic injury, a pathologic response to skin irradiation ("radio-derm"), psoriasis, chronic atopic dermatitis, chronic UV-dermatitis, scleroderma, conditions characterized by a chronic maladaptive injury response to an ongoing noxious insult to the skin, and scar formation.

15. A method of reducing periostin release from keratinocytes in a subject in need thereof, the method comprising administering to the subject an effective amount of a TRPV4 and TRPA1 inhibitor, wherein the TRPV4 and TRPA1 inhibitor is according to the below:

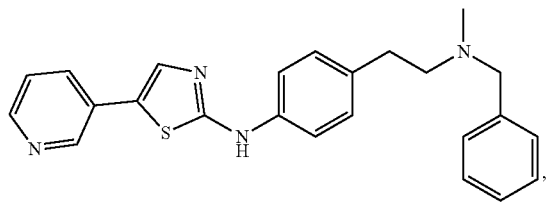

and
wherein periostin release from keratinocytes in the subject is inhibited upon administration of the TRPV4 and TRPA1 inhibitor.

16. The method of claim 15, wherein the inhibitor does not inhibit TRPV1, TRPV2, or TRPV3.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cctgctggtc acctacatca                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ctcaggaaca cagggaagga                                              20
```